(12) United States Patent
Perera et al.

(10) Patent No.: US 7,518,034 B2
(45) Date of Patent: Apr. 14, 2009

(54) COMPOSITIONS AND METHODS FOR THE MODIFICATION OF GENE EXPRESSION

(75) Inventors: Ranjan Perera, Overland Park, KS (US); Stephen Rice, Auckland (NZ); Clare Eagleton, Auckland (NZ); Marion Wood, Auckland (NZ); Elizabeth Visser, Auckland (NZ)

(73) Assignees: ArborGen LLC, Summerville, SC (US); Rubicon Forests Holdings Limited, Auckland (NZ)

( * ) Notice: Subject to any disclaimer, the term of this patent is extended or adjusted under 35 U.S.C. 154(b) by 233 days.

(21) Appl. No.: 10/927,641

(22) Filed: Aug. 27, 2004

(65) Prior Publication Data

US 2005/0244968 A1 Nov. 3, 2005

Related U.S. Application Data

(63) Continuation of application No. 10/137,036, filed on Apr. 30, 2002, now Pat. No. 7,211,711, which is a continuation-in-part of application No. 09/724,624, filed on Nov. 28, 2000, now abandoned, which is a continuation-in-part of application No. 09/598,401, filed on Jun. 20, 2000, now Pat. No. 6,596,925, which is a continuation-in-part of application No. 09/276,599, filed on Mar. 25, 1999, now Pat. No. 6,380,459.

(30) Foreign Application Priority Data

| Feb. 24, 2000 | (WO) | PCT/NZ00/00018 |
| Jun. 20, 2001 | (WO) | PCT/NZ01/00115 |
| Apr. 30, 2003 | (WO) | PCT/NZ03/00076 |

(51) Int. Cl.
*C12N 15/09* (2006.01)
*C12N 15/63* (2006.01)
*C12N 15/82* (2006.01)
*A01H 5/00* (2006.01)
*A01H 5/10* (2006.01)

(52) U.S. Cl. ............... 800/287; 800/298; 435/320.1; 435/419; 536/23.1; 536/24.1

(58) Field of Classification Search ............... 536/23.1, 536/24.1; 800/287, 290, 298
See application file for complete search history.

(56) References Cited

U.S. PATENT DOCUMENTS

| 5,412,087 A | 5/1995 | McGall et al. |
| 5,510,474 A | 4/1996 | Quail et al. |
| 5,545,451 A | 8/1996 | Huang et al. |
| 5,639,952 A | 6/1997 | Quail et al. |
| 5,656,496 A | 8/1997 | Quail et al. |
| 5,750,385 A | 5/1998 | Shewmaker et al. |
| 5,910,415 A | 6/1999 | Hodges et al. |
| 6,054,574 A | 4/2000 | Quail et al. |
| 6,225,529 B1 | 5/2001 | Lappegard et al. |

| 2005/0026162 A1 | 2/2005 | Perera et al. |

FOREIGN PATENT DOCUMENTS

| NZ | WO 03/09347 A1 * | 4/2003 |
| WO | WO 95/00450 | 1/1995 |
| WO | WO 97/47756 | 12/1997 |
| WO | WO 00/58474 | 10/2000 |

OTHER PUBLICATIONS

Benfey et al., Science 250:959-966, 1990.*
Kim Y. et al. Plant Molecular Biology, 1994, vol. 24, pp. 105-117.*
Szczyglowski K. et al. The Plant Cell, 1994, vol. 6, pp. 317-332.*
Ellis J. et al., EMBO Journal, 1987, vol. 6, No. 1, pp. 11-16.*
Aronen, Tuija, Genetic transformation of Scots pine (*Pinus sylvestris* L.), Dissertation Metsäntutkimuslaitoksen tiedonantoja 595, 1996, pp. 8-53.
Ellis et al., "Stable transformation of *Picea glauca* by Particle Acceleration," Biotechnology, vol. 11, Jan. 1993, pp. 84-89.
Baker, S. S., et al., "The 5'—region of *Arabidopsis thaliana* cor15a has cis-acting elements that confer cold-, drought- and ABA-regulated gene expression," Plant Molecular Biology, 1994, pp. 701-713, vol. 24.
Baranowskij, N., et al., "A novel DNA binding protein with homology to Myb oncoproteins containing only one repeat can function as a transcriptional activator," The EMBO Journal, 1994, pp. 5383-5392, vol. 13, No. 22.
Baumann, K., et al., "The DNA Binding Site of the Dof Protein NtBBF1 Is Essential for Tissue-Specific and Auxin-Regulated Expression of the rolB Oncogene in Plants," The Plant Cell, Mar. 1999, pp. 323-333, vol. 11.
Bevan, M., Binary Agrobacterium vectors for plant transformation, Nucleic Acids Research, 1984, pp. 8711-8721, vol. 12, No. 22.
Bilang, R., et al., "PEG-mediacted direct gene transfer and electroporation," Plant Molecular Biology Manual, 1994, pp. 1-16, A1.
Bradford, M., "a Rapid and Sensitive Method for the Quantitation of Microgram Quantities of Protein Utilizing the Principle of Protein-Dye Binding," Analytical Biochemistry, 1976, pp. 248-254, vol. 72.
Campisi, L., et al., "Generation of enhancer trap lines in *Arabidopsis* and characterization of expression patterns in the inflorescence," The Plant Journal, 1999, pp. 699-707, vol. 17(6).
De Carvalho Niebel, F., et al., Post-Transcriptional Cosuppression of β-1,3-Glucanase Genes Does Not Affect Accumulation of Transgene Nuclear mRNA., The Plant Cell, Mar. 1995, pp. 347-358, vol. 7.
Dunstan, D. I., et al., "12. Somatic Embryogenesis in Woody Plants," In Vitro Embryogenesis in Plants, 1995, pp,. 471-538.
Forde, B. G., et al., "Nuclear Factors Interact with Conserved A/T-Rich Elements Upstream of a Nodule-Enhanced Glutamine Synthetase Gene from French Bean," The Plant Cell, Sep. 1990, pp. 925-939, vol. 2.

(Continued)

*Primary Examiner*—Russell Kallis
(74) *Attorney, Agent, or Firm*—Cooley Godward Kronish LLP

(57) ABSTRACT

Novel isolated plant polynucleotide promoter sequences are provided, together with genetic constructs comprising such polynucleotides. Methods for using such constructs in modulating the transcription of DNA sequences of interest are also disclosed, together with transgenic plants comprising such constructs.

11 Claims, 19 Drawing Sheets

OTHER PUBLICATIONS

Grotewold, E., et al., "The myb-Homologous P Gene Controls Phlobaphene Pigmentation in Maize Floral Organs by Directly Activating a Flavonoid Biosynthetic Gene Subset," Cell Press, Feb. 11, 1994, pp. 543-553, vol. 76.

Iwasaki, T., et al., Identification of a cis-regulatory region of a gene in *Arabidopsis thaliana* whose induction by dehydration is mediated by abscisic acid and requires protein synthesis., Mol. Gen. Genet, 1995, pp. 391-398, vol. 247.

Kawasaki, H., et al., "Specific Regulation of Gene Expression by Antisense Nucleic Acids: A Summary of Methodologies and Associated Problems," Artificial Organs, 1996, pp. 836-848, vol. 20(8).

Kunkel, T. A., "Rapid and efficient site-specific mutagenesis without phenotypic selection," Proc. Natl. Acad. Sci. USA, Jan. 1985, pp. 488-492, vol. 82.

Lam, E., et al., "Binding site requirements and differential representation of TGA factors in nuclear ASF-1 activity," Nucleic Acids Research, 1995, pp. 3778-3785, vol. 23, No. 18.

Li, Y., et al., "An Auxin-Inducible Element in Soybean SAUR Promoters[1]," Plant Physiol., 1994, pp. 37-43, vol. 106.

McIntyre, C. L., et al., " Strategies for the suppression of peroxidase gene expression in tobacco. I. Designing efficient ribozymes," Transgenic Research, 1996, pp. 257-262, vol. 5.

Meier, I., et al., "Novel conserved sequence motifs in plant G-box binding proteins and implications for interactive domains," Nucleic Acids Research, 1994, pp. 470-478, vol. 22, No. 3.

Menkens, A. E., et al., "Isolation and characterization of a fourth *Arabidopsis thaliana* G-box-binding factor, which has similarities to Fos oncoportein," Proc. Natl. Acad. Sci. USA, Mar. 1994, pp. 2522-2526, vol. 91.

Merrifield, R. B., "Solid Phase Peptide Synthesis. I. The Synthesis of a Tetrapeptide[1]," Synthesis of a Tetrapeptide, Jul. 20, 1963, pp. 2149-2154, vol. 85.

Min, G., et al., "Long-Distance Genome Walking Using the Long and Accurate Polymerase Chain Reaction," BioTechniques, Mar. 1998, pp. 398-400, vol. 24.

Napoli, C., et al., "Introduction of a Chimeric Chalcone Synthase Gene into Petunia Results in Reversible Co-Suppression of Homologous Genes in trans," The Plant Cell, Apr. 1990, pp. 279-289, vol. 2.

Nordin, K., et al., "Differential expression of two related, low-temperature-induced genes in *Arabidopsis thaliana* (L.) Heynh.," Plant Molecular Biology, 1993, pp. 641-653, vol. 21.

Pearson, W. R., "[5] Rapid and Sensitive Sequence Comparison with FASTP and FASTA," Methods in Enzymology, Apr. 1988, pp. 63-99, vol. 183.

Pearson, W. R., et al., "Improved tools for biological sequence comparison," Proc. Natl. Acad. Sci. USA, 1988, pp. 2444-2448, vol. 85.

Roberts, D. R., et al., "Somatic Embryogenesis Of Spruce," Synseeds, 1993, pp. 427-450, Chapter 23.

Robinson-Benion, C., et al., "[23] Antisense Techniques," Methods in Enzymology, 1995, pp. 363-375, vol. 254.

Rogers, J. C., et al., "Definition and Functional Implications of Gibberellin and Abscisic Acid cis-Acting Hormone Response Complexes," The Plant Cell, Nov. 1992, pp. 1443-1451, vol. 4.

Shen, W H., et al., "Protein complexes binding to cis elements of the plant histone gene promoters: multiplicity, phosphorylation and cell cycle alteration," Plant Molecular Biology, 1997, pp. 367-379, vol. 33.

Ulmasov, T., et al., "ARF1, a Transcription Factor That Binds to Auxin Response Elements," Science, Jun. 20, 1997, pp. 1865-1868, vol. 276.

Valvekens, D., et al., "*Agrobacterium tumefaciens*-mediated transformation of *Arabidopsis thaliana* root explants by uising kanamycin selection," Proc. Natl. Acad. Sci. USA, Aug. 1988, pp. 5536-5540, vol. 85.

Vicente-Carbajosa, J., et al., "A maize zinc-finger protein binds the prolamin box in zein gene promoters and interacts with the basic leucine zipper transcriptional activator Opaque2," Proc. Natl. Acad. Sci. USA, Jul. 1997. pp. 7685-7690, vol. 94.

Asamizu et al., "Structural Analysis of *Arabidopsis thaliana* Chromosone 5.VIII. Sequence Features of the Regions of 1,081,958 bp Covered by Seventeen Physically assigned P1 and TAC Clones," DNA Research, 1998, pp. 379-391, vol. 5.

Belknap, W. R., et al., "The role of Ubiquitin in plant senescence and stress responses," Trends in Plant Science, Oct. 1996, pp. 331-335, vol. 1, No. 10.

Benfey et al., Science, 1990, pp. 959-966, vol. 250.

Callis et al., "Ubiquitin extension proteins of *Arabidopsis thaliana*," JBC, 1990, pp. 12486-12493, vol. 265.

Christensen et al., "Maize polyubiquitin genes: structure, thermal perturbation of expression and transcript splicing, and promoter activity following transfer to protoplasts by electroporation," Plant Molecular Biology, 1992, pp. 675-689, vol. 18.

Curie et al., "The activation process of *Arabidopsis thaliana* A1 gene encoding the translation elongation factor EF-1α is conserved among angiosperms," Plant Molecular Biology, 1992, pp. 1083-1089, vol. 18.

Ellis et al., EMBO Journal, 1987, pp. 11-16. vol. 1, No. 1.

EMBL Accession No. D10851 (ATHCDC2BG), Apr. 14, 2000.
EMBL Accession No. D63396 (NTBY2A, TOBBY12A), Feb. 13, 1999.
EMBL Accession No. U12012 (PTU12012), Mar. 23, 1996.
GenBank Accession No. 1838898, Feb. 10, 1997.
GenBank Accession No. AB016885, Dec. 27, 2000.
GenBank Accession No. AF041463, Jan. 6, 1998.
GenBank Accession No. AF075270, Sep. 24, 1998.
GenBank Accession No. AF077743, Jul. 13, 1998.
GenBank Accession No. AF139445, Jun. 1, 1999.
GenBank Accession No. AJ012552 (VFA012552), Nov. 13, 1998.
GenBank Accession No. L41658 (SCFPOLY), Nov. 28, 1995.
GenBank Accession No. M55147 X51434, Dec. 21, 1995.
GenBank Accession No. U53418 (GMU53418), May 28, 1997.
GenBank Accession No. U90350 (PRU90350), Oct. 10, 1997.
GenBank Accession No. U90350, Feb. 24, 1997.
GenBank Accession No. X53043 (LEEF1A), May 9, 1995.
GenBank Accession No. X74814 (TGOMTRN), Sep. 22, 1994.
GenBank Accession No. X74814, Aug. 27, 1993.
GenBank Accession No. Z14990 (ATUBC9), May 18, 1993.
GenBank Accession No. U73588, Oct. 7, 1996.
GenPept Accession No. AAA68878, Jun. 23, 1995.
GenPept Accession No. AAB21993, May 7, 1993.
GenPept Accession No. CAA10056, Nov. 12, 1998.
GenPept Accession No. CAA63531, Nov. 9, 1995.
GepPept Accession No. AAD56019 (AF181491_1), Sep. 22, 1999.

Girod et al., "Homologs of the essential ubiquitin conjugating enzymes UBC1, 4 and 5 in yeast are encoded by a multigene family in *Arabidopsis thaliana*," Plant Journal, 1993, pp. 545-552, vol. 3, No. 4.

Imajuku et al., "Exon-intron organization of the *Arabidopsis thaliana* protein kinase genes *CDC2a* and *CDC2b*," FEBS Letters, 1992, pp. 73-77, vol. 304, No. 1.

Kim et al., Plant Molecular Biology, 1994, pp. 105-117, vol. 24.

Kumagai et al., "The Involvement of Protein Synthesis Elongation Factor 1α in the Organization of Microtubules on the Perinuclear Region during the Cell Cycle Transition from M Phase to G1 Phase in Tobacco BY-2 Cells," Bot. Acta., 1995, pp. 467-473, vol. 108.

Liaud et al., Proc. Nat'l Acad. Sci., 1990. pp. 8918-8922, vol. 87, No. 22.

Poeydomenge et al., "A cDNA Encoding S-Adenosyl-L-Methionine: Carreic Acid 3-O-Methyltransferase from *Eucalyptus*," Plant Physiology, 1994, pp. 749-750, vol. 105.

Scharf et al., "Heat Stress Promoters and Transcription Factors," Results Probl Cell Differ, 1994, pp. 125-162, vol. 20.

Swiss-Prot Accession No. O24493 (MC1 PINRA), Jul. 15, 1999.

Szczglowski et al., The Plant Cell, 1994, pp. 317-332, vol. 6.

Tenhaken et al., "Cloning of an Enzyme that Synthesizes a Key Nucleotide-Sugar Precursor of Hemicellulose Biosynthesis from Soybean: UDP-Glucose Dehydroegnase," Plant Physiology, 1996, pp. 1127-1134, vol. 112.

Voo et al., "4-Coumarate:Coenzyme A Ligase from Loblolly Pine Xylem. Isolation, Characterization, and Complementary DNA Cloning," Plant Physiology, 1995, pp. 85-97, vol. 108.

Walden et al,. "Genes expressed in *Pinus radiate* Male Cones Include Homologs to Anther-Specific and Pathogenesis Response Genes," Plant Physiology, 1999, pp. 1103-1116, vol. 121.

* cited by examiner

```
AAAACCCCTCACAAATACATAAAAAAAATTCTTTATTTAATTATCAAACTCTCCACTACC        60
    13            36           3           7      6
TTTCCCACCAACCGTTACAATCCTGAATGTTGGAAAAAACTAACTACATTGATATAAAAA       120
     25         20                                  11
AACTACATTACTTCCTAAATCATATCAAAATTGTATAAATATATCCACTCAAAGGAGTCT       180
                                           35
AGAAGATCCACTTGGACAAATTGCCCATAGTTGGAAAGATGTTCACCAAGTCAACAAGAT       240
                                                    31
TTATCAATGGAAAAATCCATCTACCAAACTTACTTTCAAGAAAATCCAACGATTATAGAG       300
    20                                 29     32
TAAAAAATCTATGTATTATTAAGTCAAAAAGAAAACCAAAGTGAACAAATATTGATGTAC       360
                              29    33
AAGTTTGAGAGGATAAGACATTGGAATCGTCTAACCAGGAGGCGGAGGAATTCCCTAGAC       420
         11,16,8              23
AGTTAAAAGTGGCCGGAATCCCGGTAAAAAGATTAAAATTTTTTTGTAGAGGGAGTGCT        480
        12
TGAATCATGTTTTTTATGATGGAAATAGATTCAGCACCATCAAAAACATTCAGGACACCT      540
AAAATTTTGAAGTTTAACAAAATAACTTGGATCTACAAAAATCCGTATCGGATTTTCTC       600
              24
TAAATATAACTAGAATTTTCATAACTTTCAAAGCAACTCCTCCCCTAACCGTAAAACTTT      660
                                          13
TCCTACTTCACCGTTAATTACATTCCTTAAGAGTAGATAAAGAAATAAAGTAAATAAAAG      720
                                  11    29
TATTCACAAACCAACAATTTATTTCTTTTATTTACTTAAAAAAACAAAAAGTTTATTTAT      780
       33    31
TTTACTTAAATGGCATAATGACATATCGGAGATCCCTCGAACGAGAATCTTTTATCTCCC      840
TGGTTTTGTATTAAAAAGTAATTTATTGTGGGGTCCACGCGGAGTTGGAATCCTACAGAC      900
                             12       14
GCGCTTTACATACGTCTCGAGAAGCGTGACGGATGTGCGACCGGATGACCCTGTATAACC      960
           4       15      10                              9
CACCGACACAGCCAGCGCACAGTATACACGTGTCATTTCTCTATTGGAAAATGTCGTTGT     1020
 22                     4
TATCCCCGCTGGTACGCAACCACCGATGGTGACAGGTCGTCTGTTGTCGTGTCGCGTAGC     1080
   13                                                     19
GGGAGAAGGGTCTCATCCAACGCTATTAAATACTCGCCTTCACCGCGTTACTTCTCATCT     1140
    15          27        2                              5
TTTCTCTTGCGTTGTATAATCAGTGCGATATTCTCAGAGAGCTTTTCATTCAAAGGTATG     1200
  1            1         11
GAGTTTTGAAGGGCTTTACTCTTAACATTTGTTTTTCTTTGTAAATTGTTAATGGTGGTT     1260
                                                      12
TCTGTGGGGGAAGAATCTTTTGCCAGGTCCTTTTGGGTTTCGCATGTTTATTTGGGTTAT     1320
   12                        30
TTTTCTCGACTATGGCTGACATTACTAGGGCTTTCGTGCTTTCATCTGTGTTTTCTTCCC     1380
TTAATAGGTCTGTCTCTCTGGAATATTTAATTTTCGTATGTAAGTTATGAGTAGTCGCTG     1440
        18
TTTGTAATAGGCTCTTGTCTGTAAAGGTTTCAGCAGGTGTTTGCGTTTTATTGCGTCATG     1500
               17
TGTTTCAGAAGGCCTTTGCAGATTATTGCGTTGTACTTTAATATTTTGTCTCCAACCTTG     1560
                                  28      18   25
```

Fig. 6A

```
TTATAGTTTCCCTCCTTTGATCTCACAGGAACCCTTTCTTCTTTGAGCATTTTCTTGTGG    1620
                                                        12
CGTTCTGTAGTAATATTTTAATTTTGGGCCCGGGTTCTGAGGGTAGGTGATTATTCACAG    1680
TGATGTGCTTTCCCTATAAGGTCCTCTATGTGTAAGCTGTTAGGGTTTGTGCGTTACTAT    1740
                                                    34
TGACATGTCACATGTCACATATTTCTTCCTCTTATCCTTCGAACTGATGGTTCTTTTTC    1800
        26
TAATTCGTGGATTGCTGGTGCCATATTTTATTTCTATTGCAACTGTATTTTAGGGTGTCT    1860
      12                                                 18
CTTTCTTTTTGATTTCTTGTTAATATTTGTGTTCAGGTTGTAACTATGGGTTGCTAGGGT    1920
GTCTGCCCTCTTCTTTTGTCCTTCTTTCGCAGAATCTGTCCGTTGGTCTGTATTTGGGTG    1980
ATGAATTATTTATTCCTTGAAGTATCTGTCTAATTAGCTTGTGATGATGTGCAGGTATAT    2040
                                                21
TCGTTAGTCATATTTCAATTTCAAGATGCAGATCTTTGTCAAGACTCTCACCGGTAAGAC    2100
              20
CATCACTCTCGAGGTCGAGAGCTCTGACACCATTGACAATGTTAAAGCTAAGATCCAGGA    2160
CAAGGAAGGGATTCCCCCCGACCAGCAGCGTCTGATCTTCGCAGGAAAGCAGCTTGAGGA    2220
CGGCCGAACCCTTGCCGATTACAACATCCAGAAAGAATCTACCCTCCACCTTGTTCTCCG    2280
TTTGAGGGGTGGCATGCAAATCTTTGTAAAAACACTAACTGGAAAGACAATTACATTGGA    2340
AGTTGAGAGCTCGGACACCATTGACAACGTCAAGGCCAAGATCCAGGACAAGGAAGGAAT    2400
TCCCCCTGACCAGCAGAGGCTTATCTTCGCTGGTAAGCAGCTGGAGGATGGCAGGACCTT    2460
GGCTGATTACAATATTCAAAAGGAATCGACCCTGCATTTGGTGCTTCGTCTAAGAGGAGG    2520
CATGCAAATCTTTGTGAAAACCCTTACAGGTAAAACCATTACTCTGGAAGTGGAAAGCTC    2580
GGACACCATTGACAATGTGAAGGCTAAGATCCAGGACAAGGAGGGAATTCCACCTGACCA    2640
GCAGAGGTTGATCTTTGCCGGTAAGCAGCTGGAAGATGGTCGTACTCTCGCCGATTACAA    2700
TATTCAGAAGGAATCGACCCTTCACCTGGTGCTCCGTCTCCGCGGTGGCTTTTAGGTTTG    2760
GGTGTTATTTGTGGATAATAAATTCGGGTGATGTTCAGTGTTTGTCGTATTTCTCACGAA    2820
TAAATTGTGTTTATGTATGTGTTAGTGTTGTTTGTCTGTTTCAGACCCTCTTATGTTATA    2880
TTTTTCTTTTCGTCGGTCAGTTGAAGCCAATACTGGTGTCCTGGCCGGCACTGCAATACC    2940
ATTTCGTTTAATATAAAGACTCTGTTATCCGTTATGTAATTCCATGTTATGTGGTGAAAT    3000
GTGGATGAAATTCTTAGAAATTATTATTGTAATTTGAAACTTCCTTCGTCAATAATCTGC    3060
ACAACACATTTACCAAAAAAAAA                                        3084
```

Fig. 6B

```
CAT ACGT CTC GAGAAG CG TGACG GATGTGCGACCGGATGACCCTGTAT AACCCA CCGACA        60
    4       15      10                                  9      22
CAGCCAGCGCACAGTATA CACGTG TCATTTCTCTATTGGAAAATGTCGTTGTTAT CCCC G            120
                   4                                     13
CTGGTACGCAACCACCGATGGTGACAGGTCGTCTGTTGTCGTGTCGCGTAGCGG  GAGAAG              180
                                                19      15
GGTCT CATCCAACG C TATTAAA TACTCGCCTTCACCGCGTTACTTCTCA TCTTTTC TCTT           240
      27          2                                  5
GCGTTG TATAAT CAGTGC GATA TTCTCAGAGAGCTTTTCATTCAA                           300
       1             11
```

Fig. 7 - Superubiquitin construct without intron
SR52  195bp deletion (195 bp upstream of TATA box)

```
AATTTATTTCTTTTATTTACTTAAAAAAACAAAAAGTTTATTTATTTTACTTAAATGGCA        60

TAATGACATATCGGAGATCCCTCGAACGAGAATCTTTTATCTCCCTGGTTTTGTATTAAA       120

AAGTAATTTATT GTGG GGT CCACGCGG AGTTGGAATCCTACAGACGCGCTTTACAT ACGT    180
             12      14                                      4
CTC GAGAAG CG TGACG GATGTGCGACCGGATGACCCTGTAT AACCCA CCGACA CAGCCAG  240
    15        10                              9      22
CGCACAGTATA CACGTG TCATTTCTCTATTGGAAAATGTCGTTGTTAT CCCC GCTGGTAC    300
            4                                     13
GCAACCACCGATGGTGACAGGTCGTCTGTTGTCGTGTCGCGTAGCGG GAGAAG GGTCT CA    360
                                              19     15
TCCAACG C TATTAAA TACTCGCCTTCACCGCGTTACTTCTCA TCTTTTC TCTTGCGTTG T  420
27        2                                   5
ATAAT CAGTGC GATA TTCTCAGAGAGCTTTTCATTCAA                           480
1            11
```

Fig. 8 – Superubiquitin construct without intron
SR54  368bp deletion (368 bp upstream of TATA box)

TTTTCCTACTTCACCGTTAATTACATTCCTTAAGAGTA GATA AAGAAA TAAAGTAAATAA     60
                                                          11    29

AAGTATTCACA AACCAA CAATTTATTTCTTTTATTTACTTAAAAAAACAAAAAGTTTATT     120
               33   31

TATTTTACTTAAATGGCATAATGACATATCGGAGATCCCTCGAACGAGAATCTTTTATCT     180

CCCTGGTTTTGTATTAAAAAGTAATTTATT GTGG GGT CCACGCGG AGTTGGAATCCTACA     240
                                   12      14

GACGCGCTTTACAT ACGT CTC GAGAAG CG TGACG GATGTGCGACCGGATGACCCTGTAT A     300
                    4       15      10

ACCCA CCGACA CAGCCAGCGCACAGTATA CACGTG TCATTTCTCTATTGGAAAATGTCGT     360
9     22                                  4

TGTTAT CCCC GCTGGTACGCAACCACCGATGGTGACAGGTCGTCTGTTGTCGTGTCGCGT     420
       13

AGCGG GAGAAG GGTCT CATCCAACG C TATTAAA TACTCGCCTTCACCGCGTTACTTCTCA     480
   19      15        27          2

TCTTTTC TCTTGCGTTG TATAAT CAGTGC GATA TTCTCAGAGAGCTTTTCATTCAA     540
   5                   1           11

Fig. 9 - Superubiquitin construct without intron
SR53    446bp deletion (446 bp upstream of TATA box)

```
CAGGACACCTAAAATTTTGAAGTT TAACAAA AATAACTTGGATCTACAAAAATCCGTATC       60
                              24
GGATTTTCTCTAAATATAACTAGAATTTTCATAACTTTCAAAGCAACTCCT CCCC TAACC      120
                                                    13
GTAAAACTTTTCCTACTTCACCGTTAATTACATTCCTTAAGAGTA GATA AAGAAA TAAAG     180
                                               11    29
TAAATAAAAGTATTCACA AACCAA CAATTTATTTCTTTTATTTACTTAAAAAAACAAAAA      240
                    33 31
GTTTATTTATTTTACTTAAATGGCATAATGACATATCGGAGATCCCTCGAACGAGAATCT       300
TTTATCTCCCTGGTTTTGTATTAAAAAGTAATTTATT GTGG GGT CCACGCGG AGTTGGAA    360
                                       12      14
TCCTACAGACGCGCTTTACAT ACGT CTC GAGAAG CG TGACG GATGTGCGACCGGATGACC  420
                       4       15       10
CTGTAT AACCCA CCGACA CAGCCAGCGCACAGTATA CACGTG TCATTTCTCTATTGGAAA   480
        9     22                         4
ATGTCGTTGTTAT CCCC GCTGGTACGCAACCACCGATGGTGACAGGTCGTCTGTTGTCGT      540
               13
GTCGCGT AGCGG GAGAAG GGTCT CATCCAACG C TATTAAA TACTCGCCTTCACCGCGTTA 600
         19   15          27          2
CTTCTCA TCTTTTC TCTTGCGTTG TATAAT CAGTGC GATA TTCTCAGAGAGCTTTTCATT  660
         5                  1              11
CAA                                                                703

Fig. 10 - Superubiquitin construct without intron
         SR5S    573bp deletion (573 bp upstream of TATA box)
```

```
ATTGATGTACAAGTTTGAGAG GATAAG ACATTGGAATCGT CTAACCA GGAGGCGGAGGAA      60
                      11,16,8                23
TTCCCTAGACAGTTAAAA GTGG CCGGAATCCCGGTAAAAAGATTAAAATTTTTTGTAG         120
                   12
AGGGAGTGCTTGAATCATGTTTTTATGATGGAAATAGATTCAGCACCATCAAAAACATT         180
CAGGACACCTAAAATTTTGAAGTT TAACAAA AATAACTTGGATCTACAAAAATCCGTATC       240
                         24
GGATTTTCTCTAAATATAACTAGAATTTTCATAACTTTCAAAGCAACTCCT CCCC TAACC       300
                                                    13
GTAAAACTTTTCCTACTTCACCGTTAATTACATTCCTTAAGAGTA GATA AAGAAA TAAAG      360
                                              11   29
TAAATAAAAGTATTCACA AACCAA CAATTTATTTCTTTTATTTACTTAAAAAAACAAAAA       420
                   33 31
GTTTATTTATTTTACTTAAATGGCATAATGACATATCGGAGATCCCTCGAACGAGAATCT        480
TTTATCTCCCTGGTTTTGTATTAAAAAGTAATTTATT GTGG GGT CCACGCGG AGTTGGAA    540
                                      12      14
TCCTACAGACGCGCTTTACAT ACGT CTC GAGAAG CG TGACG GATGTGCGACCGGATGACC   600
                      4       15       10
CTGTAT AACCCA CCGACA CAGCCAGCGCACAGTATA CACGTG TCATTTCTCTATTGGAAA   660
       9     22                         4
ATGTCGTTGTTAT CCCC GCTGGTACGCAACCACCGATGGTGACAGGTCGTCTGTTGTCGT       720
              13
GTCGCGTAGCGG GAGAAG GGTCT CATCCAACG C TATTAAA TACTCGCCTTCACCGCGTTA  780
             19      15                 2
CTTCTCA TCTTTTC TCTTGCGTTG TATAAT CAGTGC GATA TTCTCAGAGAGCTTTTCATT   840
        5                 1             11
CAA                                                                  883
```

Fig. 11 - Superubiquitin construct without intron
SR56   753bp deletion (753 bp upstream of TATA box)

```
CAT ACGT CTC GAGAAG CG TGACG GATGTGCGACCGGATGACCCTGTAT AACCCA CCGACA      60
    4       15      10                                 9     22
CAGCCAGCGCACAGTATA CACGTG TCATTTCTCTATTGGAAAATGTCGTTGTTAT CCCC G          120
                    4                                            13
CTGGTACGCAACCACCGATGGTGACAGGTCGTCTGTTGTCGTGTCGCGT AGCGG  GAGAAG           180
                                                   19     15
GGTCT CATCCAACG C TATTAAA TACTCGCCTTCACCGCGTTACTTCTCA TCTTTTC TCTT         240
       27         2                                    5
GCGTTG TATAAT CAGTGC GATA TTCTCAGAGAGCTTTTCATTCAAAGGTATGGAGTTTTG           300
        1            11
AAGGGCTTTACTCTTAACATTTGTTTTTCTTTGTAAATTGTTAATG GTGG TTTCT GTGG G          360
                                                12       12
GGAAGAATCTTTTGCCAGGT CCTTTT GGGTTTCGCATGTTTATTTGGGTTATTTTCTCG            420
                      30
ACTATGGCTGACATTACTAGGGCTTTCGTGCTTTCATCTGTGTTTTCTTCCCTTAATAGG             480

TC TGTCTC TCTGGAATATTTAATTTTCGTATGTAAGTTATGAGTAGTCGCTGTTTGTAAT           540
    18
AGGCTCTTGTC TGTAAAG GTTTCAGCAGGTGTTTGCGTTTTATTGCGTCATGTGTTTCAG           600
             17
AAGGCCTTTGCAGATTATTGCGTTGT ACTTTA ATATTT TGTCTC CAACCTTGTTATAGTT         660
                            28            18     25
TCCCTCCTTTGATCTCACAGGAACCCTTTCTTCTTTGAGCATTTTCTT GTGG CGTTCTGT           720
                                                  12
AGTAATATTTTAATTTTGGGCCCGGGTTCTGAGGGTAGGTGATTATTCACAGTGATGTGC             780

TTTCCCTATAAGGTCCTCTATGTGTAAGCTGTTAGGGTTTGTGCGT TACTATT GACATGT           840
                                                 34
CACATG TCACATATTTTCTTCCTCTTATCCTTCGAACTGATGGTTCTTTTTCTAATTC GT           900
 26                                                               12
GG ATTGCTGGTGCCATATTTTATTTCTATTGCAACTGTATTTTAGGG TGTCTC TTTCTTT          960
                                                   18
TTGATTTCTTGTTAATATTTGTGTTCAGGTTGTAACTATGGGTTGCTAGGGTGTCTGCCC            1020

TCTTCTTTTGTGCTTCTTTCGCAGAATCTGTCCGTTGGTCTGTATTTGGGTGATGAATTA           1080

TTTATTCCTTGAAGTATCTGTCTAATTAGCTTGTGATGATG TGCAGG TATATTCGTTAGT         1140
                                            21
CATATTT CAAT TTCAAGATGCAGA                                              1164
         20
```

Fig. 12 Superubiquitin construct with the intron
SR52    195bp deletion (195 bp upstream of TATA box)

| | |
|---|---|
| AATTTATTTCTTTTATTTACTTAAAAAAACAAAAAGTTTATTTATTTTACTTAAATGGCA | 60 |
| TAATGACATATCGGAGATCCCTCGAACGAGAATCTTTTATCTCCCTGGTTTTGTATTAAA | 120 |
| AAGTAATTTATT GTGG GGT CCACGCGG AGTTGGAATCCTACAGACGCGCTTTACAT ACGT | 180 |
|                 12          14                                                4 | |
| CTC GAGAAG CG TGACG GATGTGCGACCGGATGACCCTGTAT AACCCA CCGACA CAGCCAG | 240 |
|    15       10                                             9     22 | |
| CGCACAGTATA CACGTG TCATTTCTCTATTGGAAAATGTCGTTGTTAT CCCC GCTGGTAC | 300 |
|            4                                                  13 | |
| GCAACCACCGATGGTGACAGGTCGTCTGTTGTCGTGTCGCGTAGCGG GAGAAG GGTCT CA | 360 |
|                                                       19      15 | |
| TCCAACG C TATTAAA TACTCGCCTTCACCGCGTTACTTCTCA TCTTTTC TCTTGCGTTG T | 420 |
|  27        2                                                     5 | |
| ATAAT CAGTGC GATA TTCTCAGAGAGCTTTTCATTCAAAGGTATGGAGTTTTGAAGGGCT | 480 |
|  1         11 | |
| TTACTCTTAACATTTGTTTTTCTTTGTAAATTGTTAATG GTGG TTTCT GTGG GGGAAGAA | 540 |
|                                              12          12 | |
| TCTTTTGCCAGGT CCTTTT GGGTTTCGCATGTTTATTTGGGTTATTTTCTCGACTATGG | 600 |
|               30 | |
| CTGACATTACTAGGGCTTTCGTGCTTTCATCTGTGTTTCTTCCCTTAATAGGTC TGTCT | 660 |
|                                                       18 | |
| G TCTGGAATATTTAATTTTCGTATGTAAGTTATGAGTAGTCGCTGTTTGTAATAGGCTCT | 720 |
| TGTC TGTAAAG GTTTCAGCAGGTGTTTGCGTTTTATTGCGTCATGTGTTTCAGAAGGCCT | 780 |
|     17 | |
| TTGCAGATTATTGCGTTGT ACTTTA ATATTT TGTCTC CAACCTTGTTATAGTTTCCCTCC | 840 |
|                        28           18       25 | |
| TTTGATCTCACAGGAACCCTTTCTTCTTTGAGCATTTTCTT GTGG CGTTCTGTAGTAATA | 900 |
|                                                12 | |
| TTTTAATTTTGGGCCCGGGTTCTGAGGGTAGGTGATTATTCACAGTGATGTGCTTTCCCT | 960 |
| ATAAGGTCCTCTATGTGTAAGCTGTTAGGGTTTGTGCGT TACTATT GACATGT CACATG T | 1020 |
|                                               34            26 | |
| CACATATTTTCTTCCTCTTATCCTTCGAACTGATGGTTCTTTTTCTAATTC GTGG ATTGC | 1080 |
|                                                               12 | |
| TGGTGCCATATTTTATTTCTATTGCAACTGTATTTTAGGG TGTCTC TTTCTTTTTGATTT | 1140 |
|                                                    18 | |
| CTTGTTAATATTTGTGTTCAGGTTGTAACTATGGGTTGCTAGGGTGTCTGCCCTCTTCTT | 1200 |
| TTGTGCTTCTTTCGCAGAATCTGTCCGTTGGTCTGTATTTGGGTGATGAATTATTTATTC | 1260 |
| CTTGAAGTATCTGTCTAATTAGCTTGTGATGATG TGCAGG TATATTCGTTAGTCATATTT | 1320 |
|                                         21 | |
| CAAT TTCAAGATGCAGA | 1337 |
| 20 | |

Fig. 13 Superubiquitin construct with the intron
SR54 368bp deletion (368 bp upstream of TATA box)

```
TTTTCCTACTTCACCGTTAATTACATTCCTTAAGAGTA GATA AAGAAA TAAAGTAAATAA          60
                                           11   29
AAGTATTCACA AACCAA CAATTTATTTCTTTTATTTACTTAAAAAAACAAAAAGTTTATT          120
            33  31
TATTTTACTTAAATGGCATAATGACATATCGGAGATCCCTCGAACGAGAATCTTTTATCT           180
CCCTGGTTTTGTATTAAAAAGTAATTTATT GTGG GGT CCACGCGG AGTTGGAATCCTACA        240
                               12      14
GACGCGCTTTACAT ACGT CTC GAGAAG CG TGACG GATGTGCGACCGGATGACCCTGTAT A     300
               4    15         10                                1
ACCCA CCGACA CAGCCAGCGCACAGTATA CACGTG TCATTTCTCTATTGGAAAATGTCGT        360
9     22                        4
TGTTAT CCCC GCTGGTACGCAACCACCGATGGTGACAGGTCGTCTGTTGTCGTGTCGCGT          420
       13
AGCGG GAGAAG GGTCT CATCCAACG C TATTAAA TACTCGCCTTCACCGCGTTACTTCTCA      480
19                 27            2
TCTTTTC TCTTGCGTTG TATAAT CAGTGC GATA TTCTCAGAGAGCTTTTCATTCAAAGGT       540
5                  1            11
ATGGAGTTTTGAAGGGCTTTACTCTTAACATTTGTTTTCTTTGTAAATTGTTAATG GTG            600
                                                          12
G TTTCT GTGG GGGAAGAATCTTTTGCCAGGT CCTTTT GGGTTTCGCATGTTTATTTGGGT       660
  12     12                         30
TATTTTCTCGACTATGGCTGACATTACTAGGGCTTTCGTGCTTTCATCTGTGTTTTCTT            720
CCCTTAATAGGTC TGTCTC TCTGGAATATTTAATTTTCGTATGTAAGTTATGAGTAGTCG          780
               18
CTGTTTGTAATAGGCTCTTGTC TGTAAAG GTTTCAGCAGGTGTTTGCGTTTTATTGCGTC         840
                       17
ATGTGTTTCAGAAGGCCTTTGCAGATTATTGCGTTGT ACTTTA ATATTT TGTCTC CAACC       900
                                      28           18     25
TTGTTATAGTTTCCCTCCTTTGATCTCACAGGAACCCTTTCTTCTTTGAGCATTTTCTT G           960
TGG CGTTCTGTAGTAATATTTTAATTTTGGGCCCGGGTTCTGAGGGTAGGTGATTATTCA          1020
12
CAGTGATGTGCTTTCCCTATAAGGTCCTCTATGTGTAAGCTGTTAGGGTTTGTGCGT TAC          1080
TATT GACATGT CACATG TCACATATTTTCTTCCTCTTATCCTTCGAACTGATGGTTCTTT        1140
34           26
TTCTAATTC GTGG ATTGCTGGTGCCATATTTTATTTCTATTGCAACTGTATTTTAGGG TG        1200
          12
TCTC TTTCTTTTTGATTTCTTGTTAATATTTGTGTTCAGGTTGTAACTATGGGTTGCTAG         1260
18
GGTGTCTGCCCTCTTCTTTTGTGCTTCTTTCGCAGAATCTGTCCGTTGGTCTGTATTTGG          1320
GTGATGAATTATTTATTCCTTGAAGTATCTGTCTAATTAGCTTGTGATGATG TGCAGG TA        1380
                                                     21
TATTCGTTAGTCATATTT CAAT TTCAAGATGCAGA                                 1415
                   20
```

Fig. 14 Superubiquitin construct with the intron
SR53 446bp deletion (446 bp upstream of TATA box)

CAGGACACCTAAAATTTTGAAGTT TAACAAA AATAACTTGGATCTACAAAAATCCGTATC    60
                         24
GGATTTTCTCTAAATATAACTAGAATTTTCATAACTTTCAAAGCAACTCCT CCCC TAACC   120
                                                     13
GTAAAACTTTTCCTACTTCACCGTTAATTACATTCCTTAAGAGTA GATA AAGAAA TAAAG  180
                                               11    29
TAAATAAAAGTATTCACA AACCAA CAATTTATTTCTTTTATTTACTTAAAAAAACAAAAA   240
                   33   31
GTTTATTTATTTTACTTAAATGGCATAATGACATATCGGAGATCCCTCGAACGAGAATCT    300

TTTATCTCCCTGGTTTTGTATTAAAAAGTAATTTATT GTGG GGT CCACGCGG AGTTGGAA 360
                                       12       14
TCCTACAGACGCGCTTTACAT ACGT CTC GAGAAG CG TGACG GATGTGCGACCGGATGACC 420
                       4       15     10
CTGTAT AACCCA CCGACA CAGCCAGCGCACAGTATA CACGTG TCATTTCTCTATTGGAAA  480
        9    22                         4
ATGTCGTTGTTAT CCCC GCTGGTACGCAACCACCGATGGTGACAGGTCGTCTGTTGTCGT  540
              13
GTCGCGTA GCGG GAGAAG GGTCT CATCCAACG C TATTAAA TACTCGCCTTCACCGCGTTA 600
          19    15          27         2
CTTCTCA TCTTTTC TCTTGCGTTG TATAAT CAGTGC GATA TTCTCAGAGAGCTTTTCATT 660
         5                 1            11
CAAAGGTATGGAGTTTTGAAGGGCTTTACTCTTAACATTTGTTTTTCTTTGTAAATTGTT  720

AATG GTGG TTTCT GTGG GGGAAGAATCTTTTGCCAGGT CCTTTT GGGTTTCGCATGTTTA 780
      12      12                            30
TTTCGGTTATTTTTCTCGACTATGGCTGACATTACTAGGGCTTTCGTGCTTTCATCTGTG  840

TTTTCTTCCCTTAATAGGTC TGTCTC TCTGGAATATTTAATTTTCGTATGTAAGTTATGA  900
                      18
GTAGTCGCTGTTTGTAATAGGCTCTTGTC TGTAAAG GTTTCAGCAGGTGTTTGCGTTTTA  960
                               17
TTGCGTCATGTGTTTCAGAAGGCCTTTGCAGATTATTGCGTTGT ACTTTA ATATTT TGTC 1020
                                              28        18
TC CAACCTTGTTATAGTTTCCCTCCTTTGATCTCACAGGAACCCTTTCTTCTTTGAGCAT 1080
25
TTTCTT GTGG CGTTCTGTAGTAATATTTTAATTTTGGGCCCGGGTTCTGAGGGTAGGTGA 1140
        12
TTATTCACAGTGATGTGCTTTCCCTATAAGGTCCTCTATGTGTAAGCTGTTAGGGTTTGT  1200

GCGT TACTATT GACATGT CACATG TCACATATTTTCTTCCTCTTATCCTTCGAACTGATG 1260
      34             26

Fig. 15A Superubiquitin construct with the intron
SR55    573bp deletion (573 bp upstream of TATA box)

```
GTTCTTTTTCTAATTC GTGG ATTGCTGGTGCCATATTTTATTTCTATTGCAACTGTATTT      1320
                  12
TAGGG TGTCTC TTTCTTTTTGATTTCTTGTTAATATTTGTGTTCAGGTTGTAACTATGGG      1380
      18
TTGCTAGGGTGTCTGCCCTCTTCTTTTGTGCTTCTTTCGCAGAATCTGTCCGTTGGTCTG       1440

TATTTGGGTGATGAATTATTTATTCCTTGAAGTATCTGTCTAATTAGCTTGTGATGATG T      1500

GCAGG TATATTCGTTAGTCATATTT CAAT TTCAAGATGCAGA                      1542
21                         20
```

Fig. 15B Superubiquitin construct with the intron
SR55   573bp deletion (573 bp upstream of TATA box)

ATTGATGTACAAGTTTGAGAG GATAAG ACATTGGAATCGT CTAACCA GGAGGCGGAGGAA       60
                      11,16,8                23
TTCCCTAGACAGTTAAAA GTGG CCGGAATCCCGGTAAAAAAGATTAAAATTTTTTGTAG          120
                   12
AGGGAGTGCTTGAATCATGTTTTTTATGATGGAAATAGATTCAGCACCATCAAAAACATT          180

CAGGACACCTAAAATTTTGAAGTT TAACAAA AATAACTTGGATCTACAAAAATCCGTATC         240
                         24
GGATTTTCTCTAAATATAACTAGAATTTTCATAACTTTCAAAGCAACTCCT CCCC TAACC         300
                                                    13
GTAAAACTTTTCCTACTTCACCGTTAATTACATTCCTTAAGAGTA GATA AAGAAA TAAAG        360
                                              11   29
TAAATAAAAGTATTCACA AACCAA CAATTTATTTCTTTTATTTACTTAAAAAAACAAAAA         420
                   33 31
GTTTATTTATTTTACTTAAATGGCATAATGACATATCGGAGATCCCTCGAACGAGAATCT          480

TTTATCTCCCTGGTTTTGTATTAAAAAGTAATTTATT GTGG GGT CCACGCGG AGTTGGAA       540
                                      12       14
TCCTACAGACGCGCTTTACAT ACGT CTC GAGAAG CG TGACG GATGTGCGACCGGATGACC     600
                      4       15        10
CTGTAT AACCCA CCGACA CAGCCAGCGCACAGTATA CACGTG TCATTTCTCTATTGGAAA      660
       9      22                       4
ATGTCGTTGTTAT CCCC GCTGGTACGCAACCACCGATGGTGACAGGTCGTCTGTTGTCGT         720
              13
GTCGCGT AGCGG GAGAAG GGTCT CATCCAACG C TATTAAA TACTCGCCTTCACCGCGTTA    780
        19    15          27            2
CTTCTCA TCTTTTC TCTTGCGTTG TATAAT CAGTGC GATA TTCTCAGAGAGCTTTTCATT     840
        5                 1      11
CAAAGGTATGGAGTTTTGAAGGGCTTTACTCTTAACATTTGTTTTTCTTTGTAAATTGTT          900

AATG GTGG TTTCT GTGG GGGAAGAATCTTTTGCCAGGT CCTTTT GGGTTTCGCATGTTTA     960
     12         12                        30
TTTGGGTTATTTTTCTCGACTATGGCTGACATTACTAGGGCTTTCGTGCTTTCATCTGTG          1020

TTTTCTTCCCTTAATAGGTC TGTCTC TCTGGAATATTTAATTTTCGTATGTAAGTTATGA        1080
                     18
GTAGTCGCTGTTTGTAATAGGCTCTTGTC TGTAAAG GTTTCAGCAGGTGTTTGCGTTTTA       1140
                              17
TTGCGTCATGTGTTTCAGAAGGCCTTTGCAGATTATTGCGTTGT ACTTTA ATATTT TGTC      1200
                                             28         18
TC CAACCTTGTTATAGTTTCCCTCCTTTGATCTCACAGGAACCCTTTCTTCTTTGAGCAT         1260

TTTCTT GTGG CGTTCTGTAGTAATATTTTAATTTTGGGCCCGGGTTCTGAGGGTAGGTGA        1320
       12
TTATTCACAGTGATGTGCTTTCCCTATAAGGTCCTCTATGTGTAAGCTGTTAGGGTTTGT         1380

Fig. 16A Superubiquitin construct with the intron
SR56 753bp deletion (753 bp upstream of TATA box)

```
GCGTTACTATTGACATGTCACATGTCACATATTTTCTTCCTCTTATCCTTCGAACTGATG         1440
    34           26
GTTCTTTTTCTAATTCGTGGATTGCTGGTGCCATATTTTATTTCTATTGCAACTGTATTT         1500
                12
TAGGGTGTCTCTTTCTTTTTGATTTCTTGTTAATATTTGTGTTCAGGTTGTAACTATGGG         1560
     18
TTGCTAGGGTGTCTGCCCTCTTCTTTTGTGCTTCTTTCGCAGAATCTGTCCGTTGGTCTG         1620

TATTTGGGTGATGAATTATTTATTCCTTGAAGTATCTGTCTAATTAGCTTGTGATGATG T        1680

GCAGGTATATTCGTTAGTCATATTTCAATTTCAAGATGCAGA                           1722
  21                        20
```

Fig. 16B Superubiquitin construct with the intron
SR56 753bp deletion (753 bp upstream of TATA box)

ID NO: 63-80, 87 and 130; polypeptide variants of those

SEQUENCE LISTING

```
<160> NUMBER OF SEQ ID NOS: 143

<210> SEQ ID NO 1
<211> LENGTH: 3083
<212> TYPE: DNA
<213> ORGANISM: Pinus radiata
<220> FEATURE:
<221> NAME/KEY: 5'UTR
<222> LOCATION: (1)...(2064)
```

```
<220> FEATURE:
<221> NAME/KEY: intron
<222> LOCATION: (1196)...(2033)
<220> FEATURE:
<221> NAME/KEY: CDS
<222> LOCATION: (2065)...(2751)
<220> FEATURE:
<221> NAME/KEY: 3'UTR
<222> LOCATION: (2755)...(3083)

<400> SEQUENCE: 1
```

| | | | | | |
|---|---|---|---|---|---|
| aaaaccctc | acaaatacat | aaaaaaaatt | ctttatttaa | ttatcaaact | ctccactacc | 60 |
| tttcccacca | accgttacaa | tcctgaatgt | tggaaaaaac | taactacatt | gatataaaaa | 120 |
| aactacatta | cttcctaaat | catatcaaaa | ttgtataaat | atatccactc | aaaggagtct | 180 |
| agaagatcca | cttggacaaa | ttgcccatag | ttggaaagat | gttcaccaag | tcaacaagat | 240 |
| ttatcaatgg | aaaaatccat | ctaccaaact | tactttcaag | aaaatccaag | gattatagag | 300 |
| taaaaaatct | atgtattatt | aagtcaaaaa | gaaaaccaaa | gtgaacaaat | attgatgtac | 360 |
| aagtttgaga | ggataagaca | ttggaatcgt | ctaaccagga | ggcggaggaa | ttccctagac | 420 |
| agttaaaagt | ggccggaatc | ccggtaaaaa | agattaaaat | ttttttgtag | agggagtgct | 480 |
| tgaatcatgt | tttttatgat | ggaaatagat | tcagcaccat | caaaaacatt | caggacacct | 540 |
| aaaattttga | agtttaacaa | aaataacttg | gatctacaaa | aatccgtatc | ggattttctc | 600 |
| taaatataac | tagaattttc | ataactttca | aagcaactcc | tcccctaacc | gtaaaacttt | 660 |
| tcctacttca | ccgttaatta | cattcctaa | gagtagataa | agaaataaag | taaataaaag | 720 |
| tattcacaaa | ccaacaattt | atttctttta | tttacttaaa | aaaacaaaaa | gtttatttat | 780 |
| tttacttaaa | tggcataatg | acatatcgga | gatccctcga | acgagaatct | tttatctccc | 840 |
| tggttttgta | ttaaaaagta | atttattgtg | gggtccacgc | ggagttggaa | tcctacagac | 900 |
| gcgctttaca | tacgtctcga | gaagcgtgac | ggatgtgcga | ccggatgacc | ctgtataacc | 960 |
| caccgacaca | gccagcgcac | agtatacacg | tgtcatttct | ctattggaaa | atgtcgttgt | 1020 |
| tatccccgct | ggtacgcaac | caccgatggt | gacaggtcgt | ctgttgtcgt | gtcgcgtagc | 1080 |
| gggagaaggg | tctcatccaa | cgctattaaa | tactcgcctt | caccgcgtta | cttctcatct | 1140 |
| tttctcttgc | gttgtataat | cagtgcgata | ttctcagaga | gctttcatt | caaaggtatg | 1200 |
| gagttttgaa | gggctttact | cttaacattt | gttttttcttt | gtaaattgtt | aatggtggtt | 1260 |
| tctgtggggg | aagaatcttt | tgccaggtcc | ttttgggttt | cgcatgttta | tttgggttat | 1320 |
| ttttctcgac | tatggctgac | attactaggg | ctttcgtgct | ttcatctgtg | ttttcttccc | 1380 |
| ttaataggtc | tgtctctctg | gaatatttaa | ttttcgtatg | taagttatga | gtagtcgctg | 1440 |
| tttgtaatag | gctcttgtct | gtaaaggttt | cagcaggtgt | ttgcgtttta | ttgcgtcatg | 1500 |
| tgtttcagaa | ggcctttgca | gattattgcg | ttgtacttta | atattttgtc | tccaaccttg | 1560 |
| ttatagtttc | cctcctttga | tctcacagga | accctttctt | ctttgagcat | tttcttgtgg | 1620 |
| cgttctgtag | taatattttta | attttgggcc | cgggttctga | gggtaggtga | ttattccagt | 1680 |
| gatgtgcttt | ccctataagg | tcctctatgt | gtaagctgtt | agggtttgtg | cgttactatt | 1740 |
| gacatgtcac | atgtcacata | ttttcttcct | cttatccttc | gaactgatgg | ttcttttttct | 1800 |
| aattcgtgga | ttgctggtgc | catattttat | ttctattgca | actgtatttt | agggtgtctc | 1860 |
| tttctttttg | atttcttgtt | aatatttgtg | ttcaggttgt | aactatgggt | tgctagggtg | 1920 |
| tctgccctct | tcttttgtgc | ttcttttcgca | gaatctgtcc | gttggtctgt | atttgggtga | 1980 |
| tgaattattt | attccttgaa | gtatctgtct | aattagcttg | tgatgatgtg | caggtatatt | 2040 |

```
cgttagtcat atttcaattt caag atg cag atc ttt gtc aag act ctc acc         2091
                          Met Gln Ile Phe Val Lys Thr Leu Thr
                            1               5 ggt aag acc atc act ctc gag gtc gag agc tct gac acc att gac aat         2139
Gly Lys Thr Ile Thr Leu Glu Val Glu Ser Ser Asp Thr Ile Asp Asn
 10              15                  20                  25 gtt aaa gct aag atc cag gac aag gaa ggg att ccc ccc gac cag cag         2187
Val Lys Ala Lys Ile Gln Asp Lys Glu Gly Ile Pro Pro Asp Gln Gln
             30                  35                  40 cgt ctg atc ttc gca gga aag cag ctt gag gac ggc cga acc ctt gcc         2235
Arg Leu Ile Phe Ala Gly Lys Gln Leu Glu Asp Gly Arg Thr Leu Ala
         45                  50                  55 gat tac aac atc cag aaa gaa tct acc ctc cac ctt gtt ctc cgt ttg         2283
Asp Tyr Asn Ile Gln Lys Glu Ser Thr Leu His Leu Val Leu Arg Leu
     60                  65                  70 agg ggt ggc atg caa atc ttt gta aaa aca cta act gga aag aca att         2331
Arg Gly Gly Met Gln Ile Phe Val Lys Thr Leu Thr Gly Lys Thr Ile
 75                  80                  85 aca ttg gaa gtt gag agc tcg gac acc att gac aac gtc aag gcc aag         2379
Thr Leu Glu Val Glu Ser Ser Asp Thr Ile Asp Asn Val Lys Ala Lys
 90                  95                 100                 105 atc cag gac aag gaa gga att ccc cct gac cag cag agg ctt atc ttc         2427
Ile Gln Asp Lys Glu Gly Ile Pro Pro Asp Gln Gln Arg Leu Ile Phe
             110                 115                 120 gct ggt aag cag ctg gag gat ggc agg acc ttg gct gat tac aat att         2475
Ala Gly Lys Gln Leu Glu Asp Gly Arg Thr Leu Ala Asp Tyr Asn Ile
         125                 130                 135 caa aag gaa tcg acc ctg cat ttg gtg ctt cgt cta aga gga ggc atg         2523
Gln Lys Glu Ser Thr Leu His Leu Val Leu Arg Leu Arg Gly Gly Met
     140                 145                 150 caa atc ttt gtg aaa acc ctt aca ggt aaa acc att act ctg gaa gtg         2571
Gln Ile Phe Val Lys Thr Leu Thr Gly Lys Thr Ile Thr Leu Glu Val
 155                 160                 165 gaa agc tcg gac acc att gac aat gtg aag gct aag atc cag gac aag         2619
Glu Ser Ser Asp Thr Ile Asp Asn Val Lys Ala Lys Ile Gln Asp Lys
170                 175                 180                 185 gag gga att cca cct gac cag cag agg ttg atc ttt gcc ggt aag cag         2667
Glu Gly Ile Pro Pro Asp Gln Gln Arg Leu Ile Phe Ala Gly Lys Gln
             190                 195                 200 ctg gaa gat ggt cgt act ctc gcc gat tac aat att cag aag gaa tcg         2715
Leu Glu Asp Gly Arg Thr Leu Ala Asp Tyr Asn Ile Gln Lys Glu Ser
         205                 210                 215 acc ctt cac ctg gtg ctc cgt ctc cgc ggt ggc ttt taggtttggg             2761
Thr Leu His Leu Val Leu Arg Leu Arg Gly Gly Phe
     220                 225 tgttatttgt ggataataaa ttcgggtgat gttcagtgtt tgtcgtattt ctcacgaata       2821
aattgtgttt atgtatgtgt tagtgttgtt tgtctgtttc agaccctctt atgttatatt       2881
tttcttttcg tcggtcagtt gaagccaata ctggtgtcct ggccggcact gcaataccat       2941
ttcgtttaat ataaagactc tgttatccgt tatgtaattc catgttatgt ggtgaaatgt       3001
ggatgaaatt cttagaaatt attattgtaa tttgaaactt ccttcgtcaa taatctgcac       3061
aacacattta ccaaaaaaaa aa                                                3083

<210> SEQ ID NO 2
<211> LENGTH: 2064
<212> TYPE: DNA
<213> ORGANISM: Pinus radiata
```

```
<220> FEATURE:
<221> NAME/KEY: 5'UTR
<222> LOCATION: (1)...(2064)
<220> FEATURE:
<221> NAME/KEY: intron
<222> LOCATION: (1196)...(2033)

<400> SEQUENCE: 2 aaaaccccctc acaaatacat aaaaaaaatt ctttatttaa ttatcaaact ctccactacc      60
tttcccacca accgttacaa tcctgaatgt tggaaaaaac taactacatt gatataaaaa     120
aactacatta cttcctaaat catatcaaaa ttgtataaat atatccactc aaaggagtct     180
agaagatcca cttggacaaa ttgcccatag ttggaaagat gttcaccaag tcaacaagat     240
ttatcaatgg aaaaatccat ctaccaaact tactttcaag aaaatccaag gattatagag     300
taaaaaatct atgtattatt aagtcaaaaa gaaaaccaaa gtgaacaaat attgatgtac     360
aagtttgaga ggataagaca ttggaatcgt ctaaccagga ggcggaggaa ttccctagac     420
agttaaaagt ggccggaatc ccggtaaaaa agattaaaat ttttttgtag agggagtgct     480
tgaatcatgt tttttatgat ggaaatagat tcagcaccat caaaaacatt caggacacct     540
aaaattttga agtttaacaa aaataacttg gatctacaaa aatccgtatc ggattttctc     600
taaatataac tagaattttc ataactttca aagcaactcc tcccctaacc gtaaaacttt     660
tcctacttca ccgttaatta cattccttaa gagtagataa agaaataaag taaataaaag     720
tattcacaaa ccaacaattt atttctttta tttacttaaa aaaacaaaaa gtttatttat     780
tttacttaaa tggcataatg acatatcgga gatccctcga acgagaatct tttatctccc     840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga gctttcatt caaaggtatg    1200 gagttttgaa gggctttact cttaacattt gttttttcttt gtaaattgtt aatggtggtt    1260
tctgtggggg aagaatcttt tgccaggtcc ttttgggttt cgcatgttta tttgggttat    1320
ttttctcgac tatggctgac attactaggg ctttcgtgct ttcatctgtg ttttcttccc    1380
ttaataggtc tgtctctctg gaatatttaa ttttcgtatg taagttatga gtagtcgctg    1440
tttgtaatag gctcttgtct gtaaaggttt cagcaggtgt ttgcgttta ttgcgtcatg    1500 tgtttcagaa ggccttttgca gattattgcg ttgtacttta atattttgtc tccaaccttg    1560
ttatagtttc cctcctttga tctcacagga acccttctt ctttgagcat tttcttgtgg    1620
cgttctgtag taatatttta attttgggcc cgggttctga gggtaggtga ttattccagt    1680
gatgtgcttt ccctataagg tcctctatgt gtaagctgtt agggtttgtg cgttactatt    1740
gacatgtcac atgtcacata ttttcttcct cttatccttc gaactgatgg ttctttttct    1800
aattcgtgga ttgctggtgc catatttat ttctattgca actgtatttt agggtgtctc    1860 tttcttttg atttcttgtt aatatttgtg ttcaggttgt aactatgggt tgctagggtg    1920
tctgccctct tcttttgtgc ttctttcgca gaatctgtcc gttggtctgt atttgggtga    1980
tgaattattt attccttgaa gtatctgtct aattagcttg tgatgatgtg caggtatatt    2040
cgttagtcat atttcaattt caag                                           2064
```

```
<210> SEQ ID NO 3
<211> LENGTH: 1226
<212> TYPE: DNA
<213> ORGANISM: Pinus radiata
<220> FEATURE:
<221> NAME/KEY: 5'UTR
<222> LOCATION: (1)...(1266)

<400> SEQUENCE: 3 aaaaccccctc acaaatacat aaaaaaaatt ctttatttaa ttatcaaact ctccactacc      60
tttcccacca accgttacaa tcctgaatgt tggaaaaaac taactacatt gatataaaaa     120
aactacatta cttcctaaat catatcaaaa ttgtataaat atatccactc aaaggagtct     180
agaagatcca cttggacaaa ttgcccatag ttggaaagat gttcaccaag tcaacaagat     240
ttatcaatgg aaaaatccat ctaccaaact tactttcaag aaaatccaag gattatagag     300
taaaaaatct atgtattatt aagtcaaaaa gaaaaccaaa gtgaacaaat attgatgtac     360
aagtttgaga ggataagaca ttggaatcgt ctaaccagga ggcggaggaa ttccctagac     420
agttaaaagt ggccggaatc ccggtaaaaa agattaaaat ttttttgtag agggagtgct     480
tgaatcatgt tttttatgat ggaaatagat tcagcaccat caaaaacatt caggacacct     540
aaaattttga agtttaacaa aaataacttg gatctacaaa aatccgtatc ggattttctc     600
taaatataac tagaattttc ataactttca aagcaactcc tcccctaacc gtaaaacttt     660
tcctacttca ccgttaatta cattccttaa gagtagataa agaaataaag taaataaaag     720
tattcacaaa ccaacaattt atttctttta tttacttaaa aaaacaaaaa gtttatttat     780
tttacttaaa tggcataatg acatatcgga gatccctcga acgagaatct tttatctccc     840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga gcttttcatt caaaggtata    1200
ttcgttagtc atatttcaat ttcaag                                         1226

<210> SEQ ID NO 4
<211> LENGTH: 485
<212> TYPE: DNA
<213> ORGANISM: Pinus radiata
<220> FEATURE:
<221> NAME/KEY: 5'UTR
<222> LOCATION: (1)...(431)
<220> FEATURE:
<221> NAME/KEY: TATA_signal
<222> LOCATION: (350)...(356)
<220> FEATURE:
<221> NAME/KEY: CAAT_signal
<222> LOCATION: (326)...(333)

<400> SEQUENCE: 4
agtaaaattg gcccatgtag gactaagtca aaatcaaaat tccatctcta aaagcggaac      60
tttgtcccct gaaaattttg actaatttcc aaccaaaaaa aagtgggga aaatataaaa     120 ctctaactaa taaacaata atcaccaaaa atctatcacc aaaaatgaaa aaagattttg     180
aatactaggc catatgagct acacaaattt caaaagtatc ttacacttat tacgcacccg     240
gatgtcccca ctttcgaaaa accgtttcca agcctttcac gaaagtccaa cggtcagaaa     300
```

```
attcaaaatg actgtttgag gcagagccaa tctaggacca cgctccattt atatatggcc    360
tctgcttctc tcgacccctta gagtcctctg ctctgcgaat cttgttgtta gttactgtgt    420
acgctgtaac aatggatgcc tatgagaagt tggagaaggt gggagaagga acctatggga    480
aggtg                                                                 485
```

```
<210> SEQ ID NO 5
<211> LENGTH: 246
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (185)...(191)

<400> SEQUENCE: 5
```

```
tgagaacatg ataagctgtg taaattcatg ctagtcacca taactttct cattgctttt     60 catccacact gttgattcat tcattatata agatcagatt cgtatgatat acaggcaacc    120
atagaaacaa ccagcaaagt tactagcagg aaatccaact aggtatcatg aagactacca    180
acgcaggctc gataatgttg gtgctcatta ttttgggtg ctgtttcatt ggggtcatag     240
ctacat                                                                246
```

```
<210> SEQ ID NO 6
<211> LENGTH: 600
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (471)...(477)
<220> FEATURE:
<221> NAME/KEY: CAAT_signal
<222> LOCATION: (444)...(451)

<400> SEQUENCE: 6
```

```
caccaattta atgggatttc agatttgtat cccatgctat tggctaagcc attttttctta    60 ttgtaatcta accaattcca atttccaccc tggtgtgaac tgactgacaa atgcggcccg    120
aaaacagcga atgaaatgtc tgggtgatcg gtcaaacaag cggtgggcga gagaacgcgg    180
gtgttggcct agccgggatg ggggtaggta gacggcgtat taccggcgag ttgtccgaat    240
ggagttttcg gggtaggtag taacgtagac gtcaatggaa aaagtcataa tctccgtcaa    300
aaatccaacc gctccttcac accgcagagt tggtggccac gggaccctcc acccactcac    360
tcaatcgatc gcctgccgtg gttgcccatt attcaaccat acgccacttg actcttcacc    420
aacaattcca ggccggcttt cgagacaatg tactgcacag gaaaatccaa tataaaaggc    480
cggcctccgc ttccttctca gtagccccca gctcattcaa ttcttcccac tgcaggctac    540
atttgtcaga cacgttttcc gccatttttc gcctgtttct gcggagaatt tgatcaggtt    600
```

```
<210> SEQ ID NO 7
<211> LENGTH: 591
<212> TYPE: DNA
<213> ORGANISM: Eucalyptus grandis
<220> FEATURE:
<221> NAME/KEY: 5'UTR
<222> LOCATION: (1)...(591)
```

```
<220> FEATURE:
<221> NAME/KEY: TATA_signal
<222> LOCATION: (432)...(437)

<400> SEQUENCE: 7
agtttggaat gtgttgtgtg tgatgtgatg gagagtatca gcattccaaa catgacatgg      60
ttttaactta tctgcaatgg tttcttttt attcagcgaa ctcgatggct gatgctgaga     120
gaaatgaatt gggaagtcga tcgacaatgg cagctcaact caatgatcct caggtataag    180 cattttttg gcagctctgg tcattgtgtc ttcaactttt agatgagagc aaatcaaatt     240
gactctaata ccggttatgt gatgagtgaa tcatttgctt ttagtagctt taatttatgc    300
ccccatctta gttgggtata aaggttcaga gtgcgaagat tacatctatt ttggttcttg    360
caggacacag ggattcatgc tagacacatc agcagtgttt ctacgttgga tagtggtatg    420
tacttagcta ctataaagga aattttgata gatatgtttg atatggtgct tgtacagatc    480
tatttaatgt caatgtattt gaaactatct tgtctcataa cttcttgaa gaatacaatg     540 atgagactgg gaaccctatc tggaagaata gagtggagag ctggaaggac a             591

<210> SEQ ID NO 8
<211> LENGTH: 480
<212> TYPE: DNA
<213> ORGANISM: Eucalyptus grandis
<220> FEATURE:
<221> NAME/KEY: 5'UTR
<222> LOCATION: (1)...(480)

<400> SEQUENCE: 8
atgctgagag aaatgaattg ggaagtcgat cgacaatggc agctcaactc aatgatcctc      60
aggtataagc attttttgg cagctctggt cattgtgtct tcaacttta gatgagagca      120 aatcaaattg actctaatac cagttatgtg atgagtgaat catttgcttt tagtagcttt    180
aatttatgcc cccatcttag ttgggtataa aggttcagag tgcgaagatt acatctatttt   240 tggttcttgc aggacacagg gattcatgct agacacatca gcagtgtttc tacgttggat    300
agtggtatgt acttagctac tataaaggaa attttgatag atatgtttga tatggtgctt    360
gtacagatct atttaatgcc aatgtatttg aaactatctt gtctcataac tttcttgaag    420
aatacaatga tgagactggg aaccctatct ggaagaatag agtggagagc tggaaggaca    480

<210> SEQ ID NO 9
<211> LENGTH: 308
<212> TYPE: DNA
<213> ORGANISM: Eucalyptus grandis
<220> FEATURE:
<221> NAME/KEY: 5'UTR
<222> LOCATION: (1)...(259)

<400> SEQUENCE: 9
gcccatctca ggtgcaacgg tttaactgat gtttactaca cgcaaggggg aggtatccgg      60
aaagcttgca atcgggtaa aaacgaaaat gggcgacgtg gactcagcct gcccatgttt      120
tcggtctctc tcctggactt ccatgcccga taagggccgc caactctctc tctctctctc    180
tttttctctc acatctctct gcctgttcat gtcgcctgca agtgaagatt cgtcggagca    240
agaaggacga accgggcaca tggcggggtc ggcggtcgcg acggttctaa agggtctctt    300
cctggtgt                                                             308
```

```
<210> SEQ ID NO 10
<211> LENGTH: 300
<212> TYPE: DNA
<213> ORGANISM: Eucalyptus grandis
<220> FEATURE:
<221> NAME/KEY: 5'UTR
<222> LOCATION: (1)...(251)

<400> SEQUENCE: 10
gcccatctca ggtgcaacgg tttaactgat gtttactaca cgcaagggggg aggtatccgg      60 aaagcttgca atcgggtaaa aacgaaaat gggcgacgtg gactcagcct gcccatgttt       120
tcggtccctc tcctggactt ccatgcccga taaaggccgc caactctctc tcttttttctc     180 tcacatctct ctgcctgttc atgtcgcctg caagtgaaga ttcgtcggag caagaaggac      240
gaactgggca tatggcgggg tcggcggtcg cgacggttct aaagggtctc ttcctggtgt     300

<210> SEQ ID NO 11
<211> LENGTH: 297
<212> TYPE: DNA
<213> ORGANISM: Eucalyptus grandis

<400> SEQUENCE: 11
gtgcaacggt ttaactgatg tttactacac gcaagggggga ggtatccgga aagcttgcaa      60
atcgggtaaa aacgaaaatg ggcgacgtgg actcagcctg cccatgtttt cggtctctct     120
cctggacttc catgcccgat aagggccgcc aactctctct ctctctctct ttttctctca    180
catctctctg cctgttcatg tcgcctgcaa gtgaagattc gtcggagcaa gaaggacgaa     240
ctgggcatat ggcggggtcg gcggtcgcga cggttctaaa gggtctcttc ctggtgt        297

<210> SEQ ID NO 12
<211> LENGTH: 661
<212> TYPE: DNA
<213> ORGANISM: Eucalyptus grandis

<400> SEQUENCE: 12
ctgagccatt taattcgaga gcacatcgcc caaaattatt cttcttgctg ccataactgt      60
cgaattttct cttttaggta agtaaccaat gatgcatcat gttgacaaaa aggctgatta    120
gtatgatctt ggagttgttg gtgcaaattt gcagctgac gatggcccct cagggaaatt      180
aaggcgccaa cccagattgc aaagagcaca agagcacga tccaaccttt ccttaacaag    240
atcatcacca gatcggccag taagggtaat attaatttaa caaatagctc ttgtaccggg     300
aactccgtat ttctctcact tccataaacc cctgattaat ttggtgggaa agcgacagcc     360
aacccacaaa aggtcagatg tcatcccacg agagagagag agagagagag agagagagag     420
agagttttct ctctatattc tggttcaccg gttggagtca atggcatgcg tgacgaatgt     480
acatattggt gtagggtcca atatttgcg ggagggttgg tgaaccgcaa agttcctata     540
tatcgaacct ccaccaccat acctcacttc aatccccacc atttatccgt tttatttcct    600
ctgctttcct ttgctcgagt ctcgcggaag agagagaaga gaggagagga gagaatgggt     660
t                                                                    661

<210> SEQ ID NO 13
<211> LENGTH: 336
<212> TYPE: DNA
<213> ORGANISM: Pinus radiata
```

```
<400> SEQUENCE: 13
actagtgatt tgttgagaat gagtaggcat tgctacaccc atcatcacaa gcatcatcat    60
gaggagaaga agatccattt ctcactctat tactcgaact tccttcagat taggctgtgt   120
atttctcact ctaccactcc aacttccttc aaatgctgtg agttttttgtt gtaattgccc   180 cgtctattta aatcgcagc agcactcgta tataaagac ccgtgtgtgt gaacaacaac     240
caagtgattt gaattggaaa tgaagagcga gaatggcggt gtcatgaccg ggagcaacca   300
gcccgggccg tcgaccacgc gtgccctata gtaatc                             336

<210> SEQ ID NO 14
<211> LENGTH: 763
<212> TYPE: DNA
<213> ORGANISM: Pinus radiata

<400> SEQUENCE: 14
actagtgatt tgttgagaat gagtaggcat tgctacaccc atcatcacaa gcatcaacat    60
gaagagaaga agacgatcca tttctcactc tatcactcca acttccttca gattaggctg   120
tgtatttctc actctaccac tccaactacc actccaactt attgccgcaa agagagagg    180 ttcccaaact ctgtcggaat tctcccactc aaagcattaa aggaaagatc taattgctgc   240
aaaaaagaga gattcccaat atatttctca actcccttca aatgatttct cactctacca   300
ctccaactcc cttcaaatga tttctcactc taccactcca acttccttca aatgctgtga   360 gttttttgttg taattgcccc gtctatttat aatcgcagca gcactcgtca tataaagacc   420
cgtgcgtgtg aacaacaatg gcggtgtctt gactgggagc aaccgcataa agaaagtggg    480
cttcatacat taaaaaaatc tgtaaatttt acggatttgg aaaaaggaag agcaggaggg    540
acctcccgac ttgacccgag aatggcggtg tcttgaccgc gtaaagaaag tggtcttctg    600
tacccgactt gacccgaaaa aagaggaaac gttgaacgag acaatctctg ggaacttcat    660
cgaaatgaac ctcacgactt gactctttcg attgtactgt tttcattgtt cccgcgtaaa    720
acgaccagcc cgggccgtcg accacgcgtg ccctatagta atc                      763

<210> SEQ ID NO 15
<211> LENGTH: 40
<212> TYPE: DNA
<213> ORGANISM: Artificial Sequence
<220> FEATURE:
<223> OTHER INFORMATION: Made in a lab

<400> SEQUENCE: 15
acggataaca gagtctttat attaaacgaa atggtattgc                            40

<210> SEQ ID NO 16
<211> LENGTH: 51
<212> TYPE: DNA
<213> ORGANISM: Artificial Sequence
<220> FEATURE:
<223> OTHER INFORMATION: Made in a lab

<400> SEQUENCE: 16
tgacgcggcc gcgaccgacg aaaagaaaaa tataacataa gagagtctga a               51

<210> SEQ ID NO 17
<211> LENGTH: 27
<212> TYPE: DNA
<213> ORGANISM: Artificial Sequence
<220> FEATURE:
<223> OTHER INFORMATION: Made in a lab
```

<400> SEQUENCE: 17
tatagcggcc gcggggggggg ggggggg                                           27

<210> SEQ ID NO 18
<211> LENGTH: 30
<212> TYPE: DNA
<213> ORGANISM: Artificial Sequence
<220> FEATURE:
<223> OTHER INFORMATION: Made in a lab

<400> SEQUENCE: 18
cggagaacaa ggtggagggt agattctttc                                         30

<210> SEQ ID NO 19
<211> LENGTH: 31
<212> TYPE: DNA
<213> ORGANISM: Artificial Sequence
<220> FEATURE:
<223> OTHER INFORMATION: Made in a lab

<400> SEQUENCE: 19
tctgcatctt gaaattgaaa tatgactaac g                                       31

<210> SEQ ID NO 20
<211> LENGTH: 363
<212> TYPE: DNA
<213> ORGANISM: Eucalyptus grandis

<400> SEQUENCE: 20
aatcgggtga aaataggggcc gccctaaatt agaattgaca catttcttg ggcaaagtta         60 atgtaagtta catgaaaaaa aaaaaaaagg atagtttgtt ggaagtaatg gagcatttgt        120
attgtgaaat tcacgataga gctaacaaaa ataaggtag ttggtgggtt aacccagtta        180
aaaaagaaca ataatttgaa gagaggagag agagagagag gaggggggaga gcatttcgat        240 aaattcacta gaaaaaatgc gtgttttagt ataaatgaga gtggaaatag ggccatctag        300
ggaacgatcg atcgcccctg cacccggcca tctggagagt ctgtttatac ttctctccgg        360
ctt                                                                     363

<210> SEQ ID NO 21
<211> LENGTH: 839
<212> TYPE: DNA
<213> ORGANISM: Pinus radiata
<220> FEATURE:
<221> NAME/KEY: misc_feature
<222> LOCATION: (1)...(839)
<223> OTHER INFORMATION: n = A,T,C or G

<400> SEQUENCE: 21
gtatggagtt ttgaagggct ttactcttaa catttgtttt tctttgtaaa ttgttaatgg         60
tggtttctgt gggggaagaa tcttttgcca ggtccttttg ggtttcgcat gtttatttgg        120 gttattttc tcgactatgg ctgacattac tagggctttc gtgctttcat ctgtgttttc        180
ttcccttaat aggtctgtct ctctggaata tttaattttc gtatgtaagt tatgagtagt        240 cgctgttttgt aataggctct tgtctgtaaa ggtttcagca ggtgtttgcg ttttattgcg        300
tcatgtgttt cagaaggcct ttgcagatta ttgcgttgta ctttaatatt ttgtctccaa        360
ccttgttata gtttccctcc tttgatctca caggaaccct ttcttctttg agcatttttct        420 tgtggcgttc tgtagtaata tttttaatttt gggcccgggt tctgagggta ggtgattatt        480
cncagtgatg tgctttccct ataaggtcct ctatgtgtaa gctgttaggg tttgtgcgtt        540

```
actattgaca tgtcacatgt cacatatttt cttcctctta tccttcgaac tgatggttct      600
ttttctaatt cgtggattgc tggtgccata ttttatttct attgcaactg tattttaggg      660
tgtctctttc tttttgattt cttgttaata tttgtgttca ggttgtaact atgggttgct      720
agggtgtctg ccctcttctt ttgtgcttct ttcgcagaat ctgtccgttg gtctgtattt      780
gggtgatgaa ttatttattc cttgaagtat ctgtctaatt agcttgtgat gatgtgcag      839
```

<210> SEQ ID NO 22
<211> LENGTH: 881
<212> TYPE: DNA
<213> ORGANISM: Eucalyptus grandis

<400> SEQUENCE: 22

```
acgtgacgat gctcgagtct cgcgttctcc tctctcttgt tctgcaaaac agaaaagaga       60
gaatggaggt tggcctctct caattacgtg dacgccaatg agataactca ggtgggcgac      120
aaaacaaacg cctcttgatt tcctcaaacc ccaaaccgaa tccctcgtca aggggcaagg      180
cttttggtcc cgcggcccca cggatcgctc gttcccgtct cgccacgtcg cgtcgcagcg      240
tgtcgagcaa acagaggggt ccgagcgact ataaaatccc gacgccatcg acaccacagt      300
ccatcgaaaa ccttgttcaa ttcccaagtg aaagtgagta actgtgaacg aagagttgaa      360
ctttgcatct cggcgtgtgg attcaagagg aagcagcaaa gtggaaatgg acaactccaa      420
gatgggcttc aatgcagggc aggccaaggg ccagactcag gagaagagca accagatgat      480
ggataaggca tccaacactg ctcaatctgc aagggattcc atgcaagaga ctggtcagca      540
gatgaaggcc aaagcccagg gtgctgctga tgcagtgaag aatgccaccg ggatgaacaa      600
atgaagagct caagacatga atgaataaat aattaagctc tggttatcat ttgcttttcc      660
ggtcgtttgt tgtcctgttt ttccttgtca agagcttatt atgagggtcc ttttgctctt      720
tccttagttc tttttgtttc ttggttgttc catgaagaga gcaactctct gtgtttgaga      780
gtactcatct cgcttcataa ggtctcagta tgtagttgcc tttcgagaat gttatgttct      840
ctctcataat gctattctga ttttataaaa aaaaaaaaa a                          881
```

<210> SEQ ID NO 23
<211> LENGTH: 350
<212> TYPE: DNA
<213> ORGANISM: Eucalyptus grandis

<400> SEQUENCE: 23

```
ctatagggca cgcgtggtcg acggcccggg ctggtccttt cttacaaaaa gcaaaattct       60
tataattttt tttgatataa taaaaatgat ccataaactt tgcttaatg tgcaacgtaa       120 accataatat attcaacgtg atgcttaaac tttaatcgag tatgcaatgt agtccataat      180
atattcaata tgatccttca atccaattga agtgtgcaat gtggtcgcta gattttttta      240
tgtattcaac ttagtcttta agctaccaac cttccaataa tttatgtttt agaaataata      300
tcgaacatct tttatattat tcaaggaata aaacgaacat gcatcaaaag                 350
```

<210> SEQ ID NO 24
<211> LENGTH: 49
<212> TYPE: DNA
<213> ORGANISM: Eucalyptus grandis

<400> SEQUENCE: 24

```
actatagggc acgcgtggtc gacggcccgg gctggtactt ttttttttct                   49
```

<210> SEQ ID NO 25
<211> LENGTH: 909
<212> TYPE: DNA
<213> ORGANISM: Eucalyptus grandis

<400> SEQUENCE: 25

```
cagggtaaag aaaatggaat atttgcttgg ccccccagct ttgaaagttg ctgtaagaac      60
acactcacct tgcatttata cgatggttgt gagcagtgca ggctggtggt gctgcaaatt     120
tatgatgctg atgtgatagg cagatgaatg gcagttgagc taagttaaag ccctcataca     180
tagatcagag caggaggagt agtatatata ggcatcttgg caagtcccta aaagagcggc     240
ttcgtgtatt cccacatatt cctctctcgt tagaacgttc agaaatgggt ggcccttttga    300
ctcttgatgc agaggttgag gttaagtctc ctgcagacaa gttctgggtg agcgtgagag     360
actccaccaa actgttccca agatcttcc cggaccagta caagaatatt gaagtccttg      420
agggagatgg gaaggctcct ggctcagttc gcctcttcac gtatggtgaa ggttctccac     480
ttgttaaagt atcaaaggag aagattgatg gtgtggacga agcagacaag gtcgtgacct     540
acagcgttat agacggtgat ctcctgaagt actacaagaa tttcaatggc agcatcaagg     600
taattcctaa aggagacgga agcttggtga atggtcgtg tgggtttgag aaggcaagcg      660
atgaaattcc tgatcccac gtaatcaagg acttcgcaat ccagaatttc aaagagcttg      720
atgagttcat cctcaaggca tagatgccgc caatcgtcta tccggatttg cactaaatat     780
caataaaata atgcggagct ggactccgca cttctatatg catctagtat gagagtcccc     840
tgctgtctct gtttgtattc acttgaaggg ttttctatta agctctcttt actgcctccg     900
aaaaaaaaa                                                              909
```

<210> SEQ ID NO 26
<211> LENGTH: 430
<212> TYPE: DNA
<213> ORGANISM: Eucalyptus grandis

<400> SEQUENCE: 26

```
tggagcttga gatagatcga ccgagagatc ccagcggaaa tagaagattt cctgatacca     60
tcgatccttc ttctccaatg gctgcgaatt cgtcattcc gaccaaaatg aaggcttggg     120
tgtaccgtga gcacggaaac gtcgccgacg tattgggatt ggacccggaa ctcaaggtcc    180
ctgaattgca agaaggccaa gtgctggtta agttcttgc cgcagcgctc aatccagtcg     240
acgccgcgag aatgaagggg gttatcaagc tcccgggctt ttctctaccg gccgtgccag    300
gttacgatct cgccggcgtt gtggtaaagg tgggccgcga agtgaaggag ctcaagatcg    360
gggacgaggt atatggattt atgtttcacg ccaagaaaga cgggacgctg gctgagtacg    420
cagccgtgga                                                           430
```

<210> SEQ ID NO 27
<211> LENGTH: 1253
<212> TYPE: DNA
<213> ORGANISM: Eucalyptus grandis

<400> SEQUENCE: 27

```
gcttgagata gatcgactga gagatcctag tggaaataga agatttcctg ataccatcga     60
tccattcttc tccaatggct gcgaatttcg tcattccaac caaaatgaag cttgggtgt    120
accgtgagca cggagacgtc gccaacgtat tgggattgga cccggaactc aaggtccctg    180
aattgcaaga aggccaagtg ctggttaaag ttcttgccgc ggcgctcaat ccaatcgaca    240
```

-continued

```
ccgcgagagt gaaggggtt atcaagctcc cgggcttttc tctaccggcc gtgccaggtt      300
acgatctcgc cggcgttgtg gtgaaggtgg gccgcgaagt gaaggagctc aaggtcgggg      360
acgaggtata tggatttatg tttcacgcca agaaagacgg gacgctggct gagtacgcag      420
ccgtggaaga gtcgttcttg gctttgaagc ccaagaagct gcgtttcggg gaggctgctt      480
ctctgccggt ggtcattcag accgccatg gaggccttga agagctggcc ctctctcatg       540
gcaagtccct cctcgtctta ggtggtgctg gtggcgtcgg cacactcata atacagctag      600
ctaaggaagt ttttggtgca tcaagagtag cagctacatc cagcactggg aagctagagt      660
tgttgaagag cttgggtgct gatctggcca ttgactacac caaagtcaac tttgaagacc      720
tcccagaaaa gtttgatgtt gtctacgata cagttgggga aattgagcgg cagcgaagg       780 ctgtgaagcc aggagggagc atcgtgacga tcgtaaaaca aaacaagaca ttaccccgc       840 ctgctttctt ttttgcagta acttcgaacc gttcgacctt ggagaagttg aagcccttct      900
tggagagcgg gaaggtgaag ccggtgatcg accccaagag cccgttccca ttttcgcaag      960
ccattgaggc cttctcgtat cttcaaaccc gccgggcaac tggaaaactc gtgattcacc     1020
ccgtcccatg atacacaaac gagaaagaaa taaagcgtcc acatggatct gccttaatca     1080
cgagtcctta attagtagtc gatggtgctt gctgtttgtc tccgtacatt cagcttctct     1140
ttgcatagta gtttctacat agtgcgtgta gagaagcaag tggatgtaca agtaaaataa     1200
ttactttttc tataaacaat attacaaact caaaaaaaaa aaaaaaaaa aaa             1253
```

<210> SEQ ID NO 28
<211> LENGTH: 99
<212> TYPE: DNA
<213> ORGANISM: Eucalyptus grandis

<400> SEQUENCE: 28

```
gatagatcga ccgagagatc ccagcggaaa tagaagattt cctgatacca tcgatccatt       60
cttctccaat ggctgcgaat tcgtcattc cgaccaaaa                               99
```

<210> SEQ ID NO 29
<211> LENGTH: 927
<212> TYPE: DNA
<213> ORGANISM: Eucalyptus grandis

<400> SEQUENCE: 29

```
cgacgtcgca tgctcccggc cgccatgcgg ccgcgggaat tcgattacta tagggcacgc       60
gtggtcgacg gcccgggctg gtactctcac taattcttta gttttccaat ttagcccctt      120
ctgtaattgc tcatcttctt taccaaattc tctaatttgg ccggcgaagg gctgacaagg      180
gattggtcat gtcaccctca ccaaaggttg ccgaaggtcc ggtgacctca gctgacggcc      240
acctacacca aatctagctc actagcagcc taagcccttc atcaactcta gtgaaaggtt      300
ttgagtattt tttaataaaa aatatttaaa aaatatatag cgagagctca ttacaaaaaa      360 atttttaaaaa aaaatctaaa cattacttga actcaaagtg actttataaa gagttttttac     420 caaaggatct tggtttcatc atttgcacta cacccaaaac ccaatttcta agttaaatca      480
aacccactgt ctaatagaga taaggtaaat gttataaacc aaattccaaa attccgaagc      540
actaaatata tttgctgatc ttataatcgc caattgagag ggtctcattc tccaagggat      600
tgtgacatat tagtaattga tagggtctca tccgtaggac tccgactcag ccgcgccacg      660
tgactggatc gctgaacggc gcggaaccag aggagcgtga ttacctaata ttttctccta      720
ccttggcctt gagattgaat ttcagaaaaa gaaaagaaa aaggaacaac ttcgccgact       780
```

```
gttctataaa atgcatgcgc caccccgacc cccacccacg catcacatcc atccagcctc    840
cacgacagac gcataaacac aacacacgtc ggttagagag agagagagag agagagagag    900
agagagagag atgcttggac agttgtc                                       927
```

```
<210> SEQ ID NO 30
<211> LENGTH: 411
<212> TYPE: DNA
<213> ORGANISM: Eucalyptus grandis

<400> SEQUENCE: 30
actatagggc acgcgtggtc gacggcccgg gctggtctga aactgtcgct cggcgatgca     60
taccaaaggc tgaaggtatc agaatctaat gcagcttatg taaaagcgcg atcaatttat    120 tgacccccgac gaccttgact ccatacttca cgcctcagct ttgtgttgga tggtcttgac    180
ctctctcacc ctaaaaggta gctcaaaaga atgagacttt ccgtcatact tataaaaccga   240 ccaccagcct cttttcacaac cgacatggga caacctcaaa tagaattttt aacaacaccc    300
ttgcacgctc tttctatcca ctttattatg ccatcacatg agcgttttcc acgcgtaaat    360
cggctaccac ccactttcac acggcggcga aacgagaaaa aggtcctacc t             411
```

```
<210> SEQ ID NO 31
<211> LENGTH: 178
<212> TYPE: DNA
<213> ORGANISM: Eucalyptus grandis

<400> SEQUENCE: 31
cgagtcagca gaaacccagt acactccgc ccaaacggaa gctaaacctg atgggccata      60
cgatttcttt cactgagcct cttgcttttc ctccggaatc tcacggcacc ggaatgccgg    120
aggaacttgg gaagaaccaa tgatgcctgg tcactgagtg atcgatgaat gcaatagt      178
```

```
<210> SEQ ID NO 32
<211> LENGTH: 178
<212> TYPE: DNA
<213> ORGANISM: Eucalyptus grandis

<400> SEQUENCE: 32
gtccaatgtc ctgtcaaagg aggaaagatg actatggccc ggcgccggc ggggactgca      60 tgggatttag tatgttgatt gagtacccgt cgccaccacc ttcaagtaaa tcaggagtca    120
gcagaaaccc agtacactcg ccaaacggag ctaaacctga tggccatacg atttcttt      178
```

```
<210> SEQ ID NO 33
<211> LENGTH: 178
<212> TYPE: DNA
<213> ORGANISM: Eucalyptus grandis

<400> SEQUENCE: 33
gcatgggatt tagtatgttg attgagtacc cgtcgccacc accttcaagt aaatcaggag     60
tcagcagaaa cccagtacac tcgccaaacg gagctaaacc tgatggccat acgatttctt    120
tcactgagcc tcttgctttt cctccggaat ctcacggcac cggaatgccg gaggcaac     178
```

```
<210> SEQ ID NO 34
<211> LENGTH: 1274
<212> TYPE: DNA
<213> ORGANISM: Eucalyptus grandis
```

<400> SEQUENCE: 34

```
ctatagggca cgcgtggtcg acggcccggg ctggtccttt cttacaaaaa gcaaaattct      60
tataatttt tttgatataa taaaaatgat ccataaactt ttgcttaatg tgcaacgtaa      120
accataatat attcaacgtg atgcttaaac tttaatcgag tatgcaatgt agtccataat     180
atattcaata tgatccttca attttaattg aatgtgcaat gtggtcgcta gatttttta     240
tgtattcaac ttagtcttta agctaccaac cttccaataa tttatgttta gaataatat     300
cgaacatctt ttatattatt caaggaataa acgaacatg catcaaaagt ttaaatatat     360
caaataaaat aaaattttaa gaattatatt acatattaaa attaaagttc atgattaaat    420
tgaaataaaa taaaattta aaaatcacgt tgtatgttgt gccgaaacaa aattcagtga     480
cttgtggtgt caattttctt aggtggagct ccacaagcat tgagatggag tgttccttcc    540
gccgaggttt tcattgcgtg gctcaaaacg gtggcgcgtt ttgcacgaca cgagatgcct    600
cgattgccgc atcgtgtagg cgacgcaacg gaaaaacgcg ttgccgtggc gtctatccgg    660
ggtttcgtct ccgatgcggc acgtagccta taatgcgca cgatctcccg gtctgccaat    720
tcgctatcga ttgcagaaga aaactcaaac cctaggcgct ctctctccgt tcgacctctc    780
gaagttctcc tctcttcgcg tcaagatgca aatctttgtg aaaaccctta ctggcaagac    840
aatcaccctc gaggtggaaa gctcggacac agtcgataat gtgaaagcaa aaatccagga    900
caaggaaggg atccctccgg accagcagag gcttatcttt gctggcaagc agctggaaga    960
tggccgaacc ttggccgatt ataacattca gaaggagtcc accctccact tggtgctccg   1020
tctcagggga ggcatgcaaa tttttgtgaa gactcttact ggcaagacaa tcaccctcga   1080
ggtggaaagc tccgacacag ttgataatgt gaaagcaaaa atccaggaca aggaagggat   1140
ccctccggac cagcagaggc ttatctttgc tggcaagcag ctggaagatg gccgaacctt   1200
ggccgattat aacattcaga aggagtccac cctccacttg gtgctccgtc tcaagggagg   1260
catgcaaatc tttg                                                    1274
```

<210> SEQ ID NO 35
<211> LENGTH: 795
<212> TYPE: DNA
<213> ORGANISM: Eucalyptus grandis

<400> SEQUENCE: 35

```
aaaaatacag gctttcgaaa gctagtgcgg tataaataac ctgggaaaag caagccgctt     60
gagctttagt ttcagtcagc catggccact cacgcagctc ttgctccctc aaccctcccc    120
gccaatgcca agttctctag caagagctcc tctcactcct tccccactca atgcttctct    180
aagaggctcg aggtggcgga attctcaggc cttcgtgctg atcgtgtgt gacttatgcg    240
aagaatgccg gggagggatc cttcttcgat gctgtggctg tcagctcac tcccaagact    300
tcagcaccag ctccagctaa gggagagact gtcgctaaac tgaaggtggc aatcaatggt    360
ttcggtcgca ttggtcggaa cttccttaga tgctggcacg ggagaaagaa ctcgcccctt    420
gatgtcattg ttgtcaatga cagcggtggt gtcaaaaatg cttcacattt gctgaagtat    480
gattccatgc tggggacttt caaagctgat gtgaaaattg tggacaatga gaccatcagc    540
gtcgatggga agcccgttaa ggtcgtctct aaccgggacc ctctcaagct cccctgggct    600
gagctcggca tcgacattgt cattgaggga actggagtct tcgtggatgg ccctggtgct    660
ggaaaacata ttcaagctgg tgccaagaaa gttatcatca ctgcaccagc aaaaggcgct    720
```

```
gatataccca cctacgtcta tggtgtgaat gagacagatt attcgcatga agttgctaac      780
ataatcagca atgct                                                       795
```

<210> SEQ ID NO 36
<211> LENGTH: 1200
<212> TYPE: DNA
<213> ORGANISM: Eucalyptus grandis

<400> SEQUENCE: 36

```
aaaatatcca tcgacagcat caccccgctt agagaacggt gtctcggctt ctcacaatgt       60 tatagccga atgtacaaaa tcggcataat gttctataat atagcggact ttacagatga      120
gcattcaaat acgtacgccg tactcgattc ccattcgatt gttcattcat ccgcatgcaa      180
atttcataga gataatatct gtgcacgtcc ttagattaag aacaaccaaa gagtatctgg      240
tggaagtttg aagcatgacc accgaagtca gatggaacaa acaaggtggg tggtggggat      300
atagtggaca aaggaacgag aggtgaatag gaaaaggaga aggcaagatg cgggagatag      360
gatttacgtg gcgagcggcg attgcacgca tggtccaccc caccctcaac ctcaaacttt      420
cgaaaatgca acgggcatca gggtggcgat gaaggagacg atggagatat tgttgctttc      480 tcccccaaa aaacatcatc caatccatcc ccattcctca tcttcaccac aaggagtctg      540
aagctctcct tcaccggtcc gtcgctttct ctcttatctt cttcttctcc ctcctcttct      600
cgttcttcct tcgaccgttc tctcggtatc gtgaatttat tgcggggtgg ttcgcatgct      660
ataaattcca cagcaacgag ggcccttgc cacaatgtcg acgtctccgg ttagcagctg      720
gtgcgccacc tccttctccc ctgcccattc ctcgctcaag agagccgccg gcctacggcc      780
ctctctctcc gcccgcctcg gcccttcctc ctcctcctcc tccgtctctc ctccgaccct      840
catccgtaac gagcccgttt cgccgcccc cgcccctgtc atcaacccca cttggacaga      900
agagatgggc aaggactatg acgaggccat tgaggctctc aagaaactcc tcagtgagaa      960
gggggacctg aaagccacag cagccgcaaa agtggagcaa ataactgcgg agttgcaaac     1020
tgcttcccca gacatcaagc catccagctc cgttgacaga atcaaaactg gcttcacctt     1080
cttcaagaag gagaaatacg acaagaaccc tgctttatat ggtgaactgg caaagcagag     1140
tccaaagttc atggtgtttg cttgctcgga ctcgagagtg tgcccatctc atgtgctgga     1200
```

<210> SEQ ID NO 37
<211> LENGTH: 648
<212> TYPE: DNA
<213> ORGANISM: Eucalyptus grandis

<400> SEQUENCE: 37

```
cgacggactc ctttcacgat atcgaaacga ggaaacggag gagaagcaga agaaagaaga       60
tgaagaaagg cagatggttg gtgatggatg aaactgtcgg gaagctggga gcttcaggga      120
gttctattta tggggcgaaa caggggaggg gaaaccgaat ttaccaagat gcccttcttg      180
gtgggattgg acatggagct gcacgaccgt cgtcccatca cgaagagtct tgctcttcgg      240
tacacatgca atcgtcggcg aaccgacctt atccgaccgg ttccaagctt gtcctggtaa      300
aaggtttcga accttggaaa aggcttaaga gatgtatcgg tgccttaacc attattccat      360
gttcacataa tatttggccc ggttttcagg tcaattttgg agtagcccgg ttcggttcta      420
gtcccgctcc cgattcaaaa attcattggg aacaaatttt gacactgtct ggtatttttg      480
gtctaagacc ctacccaatt ttagaactgt acacccttgc tttatcccaa aataaaattg      540
```

```
tcaattagtc aacttttcac acttgatgat cgattaagta gatggatgac atggtctttt      600
accagcccgg gccgtcgacc acgcgtgccc tatagtgagt cgtattac                   648

<210> SEQ ID NO 38
<211> LENGTH: 288
<212> TYPE: DNA
<213> ORGANISM: Eucalyptus grandis

<400> SEQUENCE: 38
gattgtaata cgactcacta tagggcacgc gtggtcgacg gcccgggctg gtatcgtgaa       60
agaagtccgt cgacgacaat ggccgagaag agcaaggtcc tgatcatcgg agagaagagc      120
aaggtcctga tcatcggaga aagagcaag gtcctgatca tcggagagaa gagcaagggtc     180 cttatcatcg gagaatcgaa ttcccgcggc cgccatggcg gccggagca tgcgacgtcg      240 ggcccaattc gccctatagt gagtcgtatt acaattcact ggccgtcg                   288

<210> SEQ ID NO 39
<211> LENGTH: 382
<212> TYPE: DNA
<213> ORGANISM: Eucalyptus grandis

<400> SEQUENCE: 39
acagcaatct catctgatga ttcttcagtt cggagctcag aggatacatc atctatagct       60
gaattgagct gtgcaatctt ctcggcaagc accttcctcg tttctgaaa atcatcagat      120 tttaaggtga atccatattt cgcagatggc catgttactg ctacactctc ttcacagcat      180
acatgaagga ggtcacatag caagcataca taggacctca tatacaaata tgacagcaga      240
ccagcccggg ccgtcgacca cgcgtgccct atagtagtag tggggaagga gtgagaggag      300
ctcttgatga ggaatgtcgg ctttttcttcc atcagttgat gttccgggtt cctagtcatt     360
atgccgatgg tggccactcc ag                                                382

<210> SEQ ID NO 40
<211> LENGTH: 986
<212> TYPE: DNA
<213> ORGANISM: Eucalyptus grandis

<400> SEQUENCE: 40
aaatacaaac tggtttaata ttcaactcag ataattacat gacaccacct aaataatgga       60
aagtcaagca aatagacata ttatccccac acataatcaa ctatattcat gactggagag      120
gtgctagatg gtatagagtc cctagttatt atttattttt ttgggcccga aagatcctg       180 atggatctat gctgtttgat actttcgat ttgttttgtc tacagctcaa ataaattagt       240
gcttgggttt tgatatatta tctaatctga tacaagtctt tgtcctggcc aattttgca       300 gagtttcctg caaaacagtg cactaaagct tccagaggac ctcatgccat gcccaagggc      360
accacctatg atggaacgga gaatcaaacc acagactgaa caggcgttga aatgccccag      420
atgtgattct acaaacacaa aattctgtta ctataacaac tacaatcttt cacaacctcg      480
ccatttctgc aagacctgca ggcgatactg gaccaaagga ggtgccttac gtaacgttcc      540
tgttggtggg ggttgcagaa agaataaacg agccaagcga gcagtagacc atcctgtctc      600
tgctcagaat gaagcatcca cctctgcagc cccaggcaac gaagtacctg accggtctcc      660
ctttgagcca ccatcttcaa aatccattta ctatggggga gaaaacatga acttaaccgg      720
tctccccttt agcagaattc agcaggaccg agctgcattg gcccactgca actcttcttc      780 cttttctagga atgtcatgtg gcacccaatc ggcctctctg gaaccacatc tttcggcttt      840
```

```
aaatacattt aattcattca agtctaacaa tcctggtctg gatttttccta gcttaagcac    900 agaccagaat tcactgtttg agaccagcca gccacaactg tcaagagcaa tggcatctgc    960
ccttttttct atgccaatgg ctcctg                                          986
```

<210> SEQ ID NO 41
<211> LENGTH: 313
<212> TYPE: DNA
<213> ORGANISM: Pinus radiata

<400> SEQUENCE: 41

```
aaaggaaaat tcaaagatct ttagccaatt tttgttgttg tgaccttgaa tttctaaaaa     60
atttaatgga ttcgttttct aaattcctga ttcgtcaaag gctgaagggc acgatagtaa   120
tagaaaatgg acggcagttt atcctttcat ggctggacac acagaatttg tggagggact   180
ctccattctg gtttatccgc cgttagttct ctctgtactc caccccttagt tctctttgta   240 ctcgagacct ttaatgatta gccctgctta tgctgtcatt actgaactca cttccagagc   300
cccaaaaatc tct                                                       313
```

<210> SEQ ID NO 42
<211> LENGTH: 713
<212> TYPE: DNA
<213> ORGANISM: Pinus radiata

<400> SEQUENCE: 42

```
taattcacaa gtagaaaatg agattttttgc aattttgtaa ctaacatttc ccggtctcct    60
ctgtatgttt tcaccccttta atgtaattga aatttgcacc cgggttagat tcaaagcgga   120
gaataacatc ggggccttgt tctagacaga gattttttcac aaataacagg ttcgaaggta   180
tgtgtagaca tctgggtagt tgtagaataa agacggagcc cattaggtga tccaatcgaa   240
gagctcagat gggaaaacag ataaaaatta tcgggtggac cttccttcac atgttaatta   300
tatatcaagt gtcgccaatc cttatgtgaa acatttagta aagcttcgcc agagcacttc   360
ttataggcat tctgtgggct ctgttgttgt ggttggaagt actcctttaa gggaggtatc   420
tgaatatttg caacagaagt cagttaaaca agtggttgac tgtctgtttg tacaagatgt   480
tactggcata cctgtgggct tgatagagac ttccaggcgc attgtgcatg taaatcattt   540
ggtgatgcag aagctagccg gagtagagtc tatagagccc actgaagcaa ttggtgtaat   600
caagcttcct agcagcttct acaacttgga atctcttgaa attcactcta gttcccagat   660
atggtgctcg tcgccacatc gtctgcttgt acttgatggc attcaggatc ctg            713
```

<210> SEQ ID NO 43
<211> LENGTH: 28
<212> TYPE: DNA
<213> ORGANISM: Pinus radiata

<400> SEQUENCE: 43

```
ccacctcaca tcaataaatt ttatacga                                        28
```

<210> SEQ ID NO 44
<211> LENGTH: 35
<212> TYPE: DNA
<213> ORGANISM: Pinus radiata

<400> SEQUENCE: 44

```
gctgtttcat tggggtcata gctacgtggt gctga                                35
```

<210> SEQ ID NO 45
<211> LENGTH: 1729
<212> TYPE: DNA
<213> ORGANISM: Pinus radiata

<400> SEQUENCE: 45

```
cttattgaca tataaaagca aagttggatc catctgttat tttgggtccc ctccagaagc    60
cttactaaat gcggacaaaa aatccacgta aagaacttct gaatttaccg tcatctgggc   120
tctgtaatta cgaatttagg gtttcctctg tcaatatctg gtagtgacaa acaaggttta   180
atggcagcct tagcaacaac tgaagtttgt gatacatatc cacgccttgt ggagaatggt   240
gagcttcgtg tcttgcaacc aattttccag atatatggtc gacgtcgagc tttctctgga   300
cctatagtta cactgaaggt ctttgaggac aatgtccttt tgcgggaatt ccttgaggag   360
agaggtaatg aagagttttt ggtagttgat ggaggaggaa gccttagatg tgccatactg   420
gggggcaatg tagttgtatc tgcccaaaac aatggttggt ctggaataat tgtcactggc   480
tgcataaggg acgttgatga aataaacaga tgtgacattg gtataagagc actgacatct   540
aacccactga aggccaacaa gaagggtgtg ggtgaaaaac atgcgcctat ttacattgct   600
ggtacccgca ttcttccggg ggaatggtgt tatgctgaca gtgatggtat tcttgtttca   660
cagcaagagt tatcactgtg agataataaa attcataagt ttcagattgt gactttcatg   720
tcctgtggaa catatatttg actcgagtta gattctaata ggattaattg atagattctg   780
aaaattgagg aatatctctg gtcatgaaaa tcttcttctc atgtgatctt ttatgctcag   840
cttttgagtac aggatgataa aagtttgtg catgtttgtc taaaggttta gcaagtatta   900
tcggaccatc ataagagata gattatggaa ctcagggact tgctattttt aatccaaaat   960
aacatttatt ctttgtgttt ttgccaaatt aacttttatt tcccttggca ccactagtga  1020
tttgcaatat ccagttgctg agaacataga agtgggcaac ggtgagagtt gcaacagtat  1080
ctagcataga tttaacaagt attgttggat cattataaga aaataaacta cagaaccaag  1140
ggaatctagt tgacaacata gttaaagtag gcatggtgct actgtatcga tacatcttca  1200
taaacagaaa aatatgaaca agctctaatg atgggagaaa ctccagcttg gtgttttgat  1260
taagcatcca tattcacacc taaaaggtta caagttccaa aataaaaatt ccaatgaatt  1320
tagccaatct aatcagacct tataagaaat acactaggca tctggggatc aaaatccagt  1380
agtttagaaa gtagttgtaa ataacccaga gacaaaaatc tcaatgatag cttgcttggg  1440
tcataggttt gataataatt gaaaacatag ttgaaaggag aatcctagca atggctagct  1500
tgaataatag atgtacagca aaattacagt agttgagaac aaagatggaa ggataatccc  1560
aacgatagct agcttggaca gtaggatgat tacatcaaaa tcatagcagt tgagaacata  1620
gttggaagga gaatccttat gatggctacg ttggataata ggcgtgatta tcgtaggtag  1680
attagagcac aagatcaaac taatagctgg cgcagctatc gactattttt              1729
```

<210> SEQ ID NO 46
<211> LENGTH: 1038
<212> TYPE: DNA
<213> ORGANISM: Pinus radiata

<400> SEQUENCE: 46

```
tgattactat agggcacgcg tggtcgacgg cccgggctgg taaatgagaa catgataagc    60
tgtgtaaatt catgctagtc accataactt ttctcattgc ttttcatcca cactgttgat   120
tcattcatta tataagatca gattcgtatg atatacaggc aaccatagaa acaaccagca   180
```

```
aagttactag caggaaatcc aactaggtat catgaagact accaacgcag gctcgataat      240
gttggtgctc attattttg ggtgctgttt cattggggtc atagctacat cttttgattt      300
ctattacttc gttcaacagt ggcctggttc atactgcgat actcgtagag gatgctgtta    360
ccctcgcacg ggaaggcctg cttccgaatt ttccattcat ggcctctggc ccaactacaa    420
gaccggtaaa tggccacagt tctgtggttc ctccgaagaa ttcgactact caaagatctc    480
agatctggag gaggagctga acaggtattg gggttcgtta agctgtccaa gcagcgatgg    540
acaggaattt tggggacacg agtgggagaa acatggcact tgctctctca atcttgatga    600
gcattcatac tttgagaagg ctctctcctt gagacaaaat atagacattc ttggggctct    660
taaaactgca ggtattaaac ccgatggaag ccaatacagt ttgagcgata tcaaggaagc    720
cattaaacaa acactgggc agctcccagg aatcgattgc aacacgagcg cagagggaga    780
gcatcaacta tatcaggtgt atgtgtgtgt tgataaatcc gatgcttcca ctgttattga    840
atgccccatt tatccacaca gcaattgccc atccatggtt gtgtttcctc cttttgggga    900
ggatcaggag gaccgagatg gttacacaga aggaatgtac gagctgtaga tctggacaaa    960
cagcatttct tctctccgca tttgatttt atcaatgaaa tttccgattc caacattttg    1020
taaaaaaaaa aaaaaaaa                                                   1038

<210> SEQ ID NO 47
<211> LENGTH: 91
<212> TYPE: DNA
<213> ORGANISM: Pinus radiata

<400> SEQUENCE: 47
aattttccat tcatgcctct gcccaactac aagaccggta aatggccaca gttctgtggt     60
tcctccgaag aattcgatat caagcttatc g                                    91

<210> SEQ ID NO 48
<211> LENGTH: 91
<212> TYPE: DNA
<213> ORGANISM: Pinus radiata

<400> SEQUENCE: 48
gcttttcatc cacactggtg cctcattcat tatataagat cagattcgtg tgatatacag     60
gcaaccatag aaacaaccgg caaagttact a                                    91

<210> SEQ ID NO 49
<211> LENGTH: 809
<212> TYPE: DNA
<213> ORGANISM: Pinus radiata

<400> SEQUENCE: 49
tgatatatat aacttctagc agaatgacac gcgacttgta tatctttca tttttttaacc     60 catgaaaacc gattagggta ttgcaaatta gggcattgcc attcaaataa ttctcagatg   120
aaagattctc tctaacaatt acaaatgatt atttttttcc atgagtgttg catgttcgaa    180
cggtctgccc agtctgtgag agagcataga gaaccctccc tgcccaattt gttagagcat    240
agagaaccct actgcatgag tagtaagaaa atattcggt ctcaattcgg caaagaccac    300
ctcgaatgga tgacttcaac gacaatctca tgatagtgtt ctgatcagca ccagttcacc    360
tatatatttt atctagggtt tagtttgcat gtatcaatcc tctggtgcac taggtaattc    420
tttcccagta tcatatatcc ttaatactgt tttgtctttt aatccatggc taccatcaga    480
acaagctcaa agcagaataa gggagcatca gccatcctct tgcttatcgc gattgcaggg   540
```

```
ttagtaaatg cgtgcaacgc tgtgggtatt gagccaatgt gcgacactgt ggtgtcgagt    600
cttctgaggc ttctgccatg caggacggct gttgatccct caattgccgc cattccactt    660
ccaagctgct gcaacgcggt tgagtcagct gggcttcaat gcctctgtct cgtcgttaac    720
ggccctcctt ttccaggggt cgaccgcggc ctcgcaatga agctgcctgc caaatgccat    780
ctcacccttc ctccctgtaa cagttagtt                                      809
```

<210> SEQ ID NO 50
<211> LENGTH: 428
<212> TYPE: DNA
<213> ORGANISM: Eucalyptus grandis

<400> SEQUENCE: 50

```
tttcttgtga ctattcattt tcctcctgat tatccattca agcccccgaa ggttgcattt     60
aggactaaag ttttccaccc aaatataaat aacaatggaa gtatctgcct tgacatcttg    120
aaggaacagt ggagtcctgc tttgacaatc tccaaggttt tgctctcaat ttgctctttg    180
ttgacggatc caaacccaga tgatcctctt gtaccagaga ttgctcatat gtacaagact    240 gatagggggca atatgagtc cactgcacgg agttggactc agaaatatgc aatgggttaa    300 cttttaaaaac tatatatcag tgatggaact ttatccctaa gttggaatct cttcgaatca    360
atgacttgtt tgcttgtaag aaatgtttcc ttaagataag tggcttttcct caaaacttga    420 ttgaagtg                                                             428
```

<210> SEQ ID NO 51
<211> LENGTH: 525
<212> TYPE: DNA
<213> ORGANISM: Pinus radiata

<400> SEQUENCE: 51

```
cccttctttg ccttcaacta atcctgctca tcctctcctg cccccattcc caaagatggc     60
tgcacccaga tcatccgcta aattgggtgc acttttggca atactgctca tagttgcggc    120
agcgcaggct caagattgct caaatgccat ggacaaattg gctccatgca cttcagcagt    180
gggactgtct agcaatggag tgaagccctc atctgagtgc tgtgatgccc tcaaaggaac    240
cagtactggc tgcgtctgca agtctgtgag agcagtgata tcacttcctg ctaagtgcaa    300
tctcccagcc ataacctgct ctggatctcg ctgaaggctc tctgttatgg cgattctcag    360
atcgtggatc tctttaagat tttcagcaag caagtgatag aataaattct cagattttga    420
gatatctata tagcgatttt cagtatcaga ttgtctatag tactcatata tttaagtgat    480
tgaatagcat tctccgattc cgagttggaa acacagacac aatga                    525
```

<210> SEQ ID NO 52
<211> LENGTH: 1126
<212> TYPE: DNA
<213> ORGANISM: Pinus radiata

<400> SEQUENCE: 52

```
actagtgatt actataggc acgcgtggtc gacggcccgg gctggtaaat acccaactta     60
atttaattgt tattgagcca gagagatgcg tagtcgctca tgtcacttgt gtttaccaaa    120
aagacataca taaacacctg cacctaaaag ttataatgat aacatgcata caaccctaca    180
acgtacgtag tcatgcgcgg ctagaactta aaccccctacc acaaacatag ccacctgcac    240
ccagaagtta taataataac atacatgaa cccttacaat aaaaaaagtt atctccaatg    300
attattaatc tactgcaggc cagccatact cagcttgaac gtgaaaattc gcattgtaag    360
```

```
catggcgcca cattaaaata acctcggcaa tattttcatg tccaagtggc cggccagcca      420
cgctcctcgc actctgagaa tactctattc atccacttgt tctgccccg caactcatat      480 aaatgtggcc aacccaagca ccatatccat gttcattaat cccctctttg ccttcaacta     540
atcctgctca tccctcttg ccccaattcc caaagatggc tgcacccaga tcatccgcta     600
aatcggctgc acttttcgca atactgctca tagttgcggc agtacaggct gaagattgct     660
caaatgccat ggacaaattg gctccatgca cttcagcagt gggactgtct agcaatggag     720
tgaagccctc atctgagtgc tgtgatgccc tcaaaggaac cagtactggc tgcgtctgca     780
aatctgtgag agcagtgata tcacttcctg ctaagtgcaa tctcccagcc ttaacctgct     840
ctggatctcg ctgaaggctc tctgttatgg cgattctcag atcgtggatc tctttaagat     900
tttcaggaag caagtgatag aataaattct cagatgttga gatatctata tagcgatttt     960
cagtatcaga ttgtctacag taccaatata tttaagtgat tgaatggaat tctcggattc    1020
tgagatagaa ataggcac agaatgtggc cggaggaatg ttcgaattcg agaatgataa      1080
taaataataa atgattgatt tctctctgca aaaaaaaaaa aaaaaa                   1126
```

<210> SEQ ID NO 53
<211> LENGTH: 454
<212> TYPE: DNA
<213> ORGANISM: Pinus radiata

<400> SEQUENCE: 53

```
atcctgctca tcctctcctg cccccattcc caaagatggc tgcacccaga tcatccgcta      60 aatgggtgc acttttggca atactgctca tagttgcggc agcgcaggct caagattgct      120
caaatgccat ggacaaattg gctccatgca cttcagcagt gggactgtct agcaatggag     180
tgaagccctc atctgagtgc tgtgatgccc tcaaaggaac cagtactggc tgcgtctgca     240
agtctgtgag agcagtgata tcacttcctg ctaagtgcaa tctcccagcc ataacctgct     300
ctggatctcg ctgaaggctc tctgttatgg cgattctcag atcgtggata tctttaagat     360
tttcagcaag tgatagaata aattctcaga ttttgagata tctatatagc gattttcagt     420
atcagattgt ctatagtact catatattta agtg                                 454
```

<210> SEQ ID NO 54
<211> LENGTH: 335
<212> TYPE: DNA
<213> ORGANISM: Pinus radiata

<400> SEQUENCE: 54

```
agaagcacct gttaaaaagg aggcctgctc tttgttcatg agcttataga taagccctag      60
tctgcaagga ttattgccct gtagttattt ggaagtagat cattttcaca ggcccagatg     120
cattatattc taatgcagtt gtttgttaat tgaagtgcaa atagttccaa atgtttaca     180 tgaatcaata gtgaacaaat ccctctgttt tatatcatat tgatggatta ttcgatttt     240 tggtgacgtg gcgcgaaact gcttttcgaa ctcatggaaa tagtaattgt tataatccat     300
aggcatgaga ttcttgttaa tcgtgcacaa ggttt                                335
```

<210> SEQ ID NO 55
<211> LENGTH: 336
<212> TYPE: DNA
<213> ORGANISM: Pinus radiata

```
<400> SEQUENCE: 55
aaaccttgtg cacgattaac aagaatctca tgcctatgga ttataacaat tactatttcc      60
atgagttcga aaagcagttt cgcgccacgt caccaaaaaa tcgaataatc catcaatatg     120
atataaaaca gagggatttg ttcactattg attcatgtaa acattttgga actatttgca     180
cttcaattaa caaacaactg cattagaata taatgcatct ggtgcctgtg aaaatgatct     240
acttccaaat aactacaggg caataatcct tgcagactag gcttatcta taagctcatg      300 aacaaagagc aggcctcctt tttaacaggt gcttct                              336

<210> SEQ ID NO 56
<211> LENGTH: 532
<212> TYPE: DNA
<213> ORGANISM: Pinus radiata

<400> SEQUENCE: 56
cgttcgttcc cttcccttc cattgttgcg tttaagccct ccaatttct tttggcgtcc       60 cgttttttggg gctcccttga agatctcctc ttcatttcgg gatttcctgc cttcgccgcg    120
ccatttgaag ttcttttttct gagagaagaa tttagacatg gctgatcgca tgttgactcg    180
aagccacagc cttcgcgagc gtttggacga gaccctctct gctcaccgca acgatattgt    240
ggccttcctt tcaagggttg aagccaaggg caaaggcatc ttgcagcgcc accagatttt    300
tgctgagttt gaggccatct ctgaggagag cagagcaaag cttcttgatg ggccttttgg    360
tgaagtcctc aaatccactc aggaagcgat tgtgtcgcct ccatggggttg ctcttgctgt    420 tcgtccaagg ccgggcgtgt gggagcacat ccgtgtgaac gtccatgcgc ttgttcttga    480
gcaattggag gttgctgagt atctgcactt caaagaagag cttgctgatg ga            532

<210> SEQ ID NO 57
<211> LENGTH: 3103
<212> TYPE: DNA
<213> ORGANISM: Eucalyptus grandis

<400> SEQUENCE: 57
gggtgaaaac aattaatgag atcatttgaa ttaaggaaag tggaaaggcg gttttctgat      60
tggtacactg aaacaacagg aaggtggtgg aggccgcaat gatggaattt atccacttta    120
atcattttat gaaatcgata cactaacctt tgtttctcct aaacccaaag gcattaatcc    180
ctgtcctcct cactcgatct cgaaggccag aaggggagg ccgagcctct tgcttttttt    240
cgtgtataaa agggcctccc ccattcctca ttttcacca tcctccgttc gttcgttccc     300 ttcccttttcc attgttgcgt ttaagccctc aatttctct tttggcgtccc gttttttgggg  360 ctcccttgaa gatctcctct tcatttcggg atttcctgcc ttcgccgcgc catttgaagt    420
tctttttctg agagaagaat ttagacatgg ctgatcgcat gttgactcga agccacagcc    480
ttcgcgagcg tttggacgag accctctctg ctcaccgcaa cgatattgtg gccttccttt    540
caagggttga agccaagggc aaaggcatct tgcagcgcca ccagattttt gctgagtttg    600
aggccatctc tgaggagagc agagcaaagc ttcttgatgg ggcctttggt gaagtcctca    660
aatccactca ggaagcgatt gtgtcgcctc catgggttgc tcttgctgtt cgtccaaggc    720
cgggcgtgtg ggagcacatc cgtgtgaacg tccatgcgct tgttcttgag caattggagg    780
ttgctgagta tctgcacttc aaagaagagc ttgctgatgg aagcttgaat ggtaactttg    840
tgcttgagct tgactttgag ccattcactg cctcttttcc gcgccgact ctttccaagt    900 ctattggcaa tggcgtcgag tttctcaatc gccatctctc cgctaagctc ttccatgaca    960
```

```
aggaaagctt gcaccctctg cttgaattcc tccaagtcca ctgctacaag gggaagaaca    1020
tgatggtgaa tgccagaatc cagaatgtgt tctccctcca acatgtcctg aggaaggcgg    1080
aggagtatct gacctcgctc aaacccgaga ccccgtactc ccagttcgag cacaagttcc    1140
aggagatcgg gctcgagcgg gggtggggtg acacggctga gcgcgtcctc gagatgatcc    1200
agctcctgtt ggatctcctt gaggctcccg accgtgcac tctcgagaag ttcttggata    1260
gggttcccat ggtcttcaac gtcgtgatca tgtctcccca cggatacttt gctcaggacg    1320
acgtccttgg ttatccggat accggtggcc aggttgttta catcctggat caagttcgtg    1380
ccctagagga agaaatgctt caccgcatta agcaacaagg actggatatt actcctcgga    1440
ttctcattat cactcggctt cttccagacg cggttggaac cacctgtggc cagcgccttg    1500
agaaagtttt tgggaccgag tactcccaca ttcttcgcgt ccccttcaga aatgagaagg    1560
gagtcgtccg caagtggatt tcccggttcg aggtgtggcc ctatttggaa agatacactg    1620
aggatgtcgc gagcgaactt gctggagagt gcaggggaa gcctgatctg atcatcggaa    1680
actacagtga tggaaacatt gttgcttcct tgttagcaca taaattaggt gttacacagt    1740
gtacaatagc ccatgccctc gagaagacga agtacccaga gtcagacata tactggaaga    1800
aatttgagga aaagtaccac ttctcttgcc agttcactgc tgatctcatc gccatgaacc    1860
acaccgactt cattatcacc agcaccttcc aagaaattgc tggaagcaag gatacagtgg    1920
ggcagtatga gagtcacatg aacttcactc ttcctggact ctaccgagtt gtccacggga    1980
tcgacgtctt cgacccgaag ttcaacattg tttcaccagg tgctgacatg agcatctact    2040
ttgcttacac cgaacaggag cggcggttga aatccttcca ccctgagatc gaggaactcc    2100
tcttcagcga tgttgagaac aaggaacact tgtgtgtgtt gaaagataag aagaagccta    2160
ttattttcac catggcaagg ctggaccgtg tcaagaactt gacagggctt gttgagtggt    2220
atggcaagaa ctccaagttg agggaactcg ccaacttggt cgtggttgga ggtgacagga    2280
ggaaggattc gaaggacttg gaagagcagt ctgagatgaa gaaaatgtac gacctcatcg    2340
aaaagtacaa gctgaatggc cagttcaggt ggatttcctc ccagatgaac cgggtgagga    2400
atggagagct ctaccgctac atctgtgaca cgaagggagt cttcgttcaa ccggctatct    2460
atgaagcttt cgggttgacc gtggttgagg ccatgacttg tggattgcca acctttgcca    2520
cttgcaatgg tggaccagct gagatcattg tgcatggcaa atcgggctac acattgatc    2580 cttaccatgg tgaccaggcg gccgagcttc ttgtagactt cttcaacaag tgcaagattg    2640
accagtccca ctgggacgag atctcaaagg gtgccatgca gagaattgaa gagaagtata    2700
catggaaaat atattctgag aggctgttga acctgactgc cgtgtatggc ttctggaagc    2760
atgtgactaa ccttgatcgg cgcgagagtc gccggtacct tgaaatgttc tatgccctca    2820
agtatcgccc actggcacag tctgttcctc cggctgtcga gtaaacaaag agacagattg    2880
ttaccagaag acggaagcat tggacttttg aagtttcaa ggaataaaca ttggaaattg    2940
tttgaatttg ggattgccaa gagcgatctt tttcgtttcc ttttttttggt ccttttctc    3000 ttctttgttt ccattccgcg aatgtttgca ttttgggtt tgtacccatc aattcagtaa    3060
atggttcatt ttcttttcaa aaaaaaaaaa aaaaaaaaa aaa                      3103
```

<210> SEQ ID NO 58
<211> LENGTH: 326
<212> TYPE: DNA
<213> ORGANISM: Eucalyptus grandis

```
<400> SEQUENCE: 58
ctcgaaaccg agacgctgac tgtgggttga gctctaacca atgggagtga tgtctctctt    60
acgtgcctgc cgtgggcccc agtgacgggc cccaaaagtg taaacgaagg aagctcccgg   120
ggatctgatt ggccgcgacg tccgcctctg acgtggcacc accgacgatt ttttttaat    180 atcttggtca agtcctaatt taactatggg gtccagatta aagcttatc cactatggat    240 taaattaaat caaatgggaa ttaaattaaa ttaaaatcat cgtgcggagg tgcacgagat   300
gcacgagatc cgacggcgca gagcag                                        326

<210> SEQ ID NO 59
<211> LENGTH: 311
<212> TYPE: DNA
<213> ORGANISM: Eucalyptus grandis

<400> SEQUENCE: 59
attactatag ggcacgcgtg gtcgacggcc cgggctggta ctctcactaa ttctttagtt    60
ttccaattta gccccttctg taattgctca tcttctttac caaattctct aatttggccg   120
gcgaagggct gacaagggat tggtcatgtc accctcacca aaggttgccg aaggtccggt   180
gacctcagct gacggccacc tacaccaaat ctagctcact agcagcctaa gcccttcatc   240
aactctagtg aaaggttttg agtatttttt aataaaaaat atttaaaaaa tatatagcga   300
gagctcatta c                                                        311

<210> SEQ ID NO 60
<211> LENGTH: 2096
<212> TYPE: DNA
<213> ORGANISM: Eucalyptus grandis

<400> SEQUENCE: 60
gattactata gggcacgcgt ggtcgacggc ccgggctggt ctgagccatt taattcgaga    60
gcacatcgcc caaaattatt cttcttgctg ccataactgt cgaatttttct cttttaggta  120 agtaaccaat gatgcatcat gttgacaaaa aggctgatta gtatgatctt ggagttgttg   180
gtgcaaattt gcaagctgac gatggcccct cagggaaatt aaggcgccaa cccagattgc   240
aaagagcaca aagagcacga tccaaccttt ccttaacaag atcatcacca gatcggccag   300
taagggtaat attaatttaa caaatagctc ttgtaccggg aactccgtat ttctctcact   360
tccataaacc cctgattaat ttggtgggaa agcgacagcc aacccacaaa aggtcagatg   420
tcatcccacg agagagagag agagagagag agagagagag agagttttct ctctatattc   480
tggttcaccg gttggagtca atggcatgcg tgacgaatgt acatattggt gtagggtcca   540
atattttgcg ggagggttgg tgaaccgcaa agttcctata tatcgaacct ccaccaccat   600
acctcacttc aatccccacc atttatccgt tttatttcct ctgctttcct ttgctcgagt   660
ctcgcggaag agagagaaga gaggagagga gagaatgggt tcgaccggat ccagacccca   720
gatgaccccg acccaagtct cggacgagga ggcgaacctc ttcgccatgc agctggcgag   780
cgcctccgtg ctccccatgg tcctcaaggc cgccatcgag ctcgacctcc tcgagatcat   840
ggccaaggcc gggccggggcg cgttcctctc cccgggggaa gtcgcggccc agctcccgac   900
ccagaacccc gaggcacccg tcatgctcga ccggatcttc cggctgctgg ccagctactc   960
cgtgctcacg tgcaccctcc gcgacctccc cgatggcaag gtcgagcggc tctacggctt  1020
agcgccggtg tgcaagttct tggtcaagaa cgaggacggg gtctccatcg ccgcactcaa  1080
cttgatgaac caggacaaaa tcctcatgga aagctggtat tacctgaaag atgcggtcct  1140
```

```
tgaaggcgga atcccattca acaaggcgta cgggatgacc gcgttcgagt atcatggcac      1200
cgacccgcga ttcaacaaga tctttaaccg gggaatgtct gatcactcca ccattactat      1260
gaagaagata ctggaaacat acaagggctt cgagggcctc gagaccgtgg tcgatgtcgg      1320
aggcggcact ggggccgtgc tcagcatgat cgttgccaaa tacccatcaa tgaaagggat      1380
caacttcgac cgcccccaacg gattgaagac gccccacccc ttcctggtgt caagcacgtc      1440
ggaggcgaca tgttcgtcag cgttccaaag ggagatgcca ttttcatgaa gtggatatgc      1500
catgactgga gtgacgacca ttgcgcgaag ttcctcaaga actgctacga tgcgcttccc      1560
aacaatggaa aggtgatcgt tgcagagtgc gtactccctg tgtacccaga cacgagccta      1620
gcgaccaaga atgtgatcca catcgactgc atcatgttgg cccacaaccc aggcgggaaa      1680
gagaggacac agaaggagtt cgaggcattg gccaaagggg ccggatttca gggcttccaa      1740
gtcatgtgct gcgctttcgg cactcacgtc atggagttcc tgaagaccgc ttgatctgct      1800
cctctgtggt gatgttcatg gttccttggat ttgaaaggtc gtgaaggagc ccttttctca      1860
cagttggctt cggcatacca agttcttctc ataaaaggaa acaataagaa gcgactgtat      1920
gatggcgcaa gtggaagtta caagatttgt tgtttttatgt ctataaagtt ttgagtcttc      1980
tgcatactga tttcacagaa tgtgtaacga aacggcgtat atggatgtgc ctgaatgatg      2040
gaaattgtga tattctgtct tcttttttcag taaatcactt cgaacaaaaa aaaaaa         2096

<210> SEQ ID NO 61
<211> LENGTH: 522
<212> TYPE: DNA
<213> ORGANISM: Eucalyptus grandis

<400> SEQUENCE: 61
ctaaaacgct aatcctgccc tgcccttccc ttctgctgct gctgctcgtc acctctctct       60
ccctctcgcg gccagctgcg agatctgccg agtttaagcc tcgtacatca aaatgggtaa      120
ggagaagatt cacatcagca ttgtggtcat tggccatgtc gattctggga agtcaaccac      180
aactggccac ttgatataca agctcggagg aatcgacaag cgtgtgattg agagattcga      240
gaaggaagct gctgagatga acaagagatc gttcaagtat gcttgggtgc ttgacaagct      300
caaggccgag cgcgagcgcg gtattaccat tgatattgcc ttgtggaagt tcgagaccac      360
caagtactac tgcactgtca ttgatgctcc tggacatcgt gactttatta agaatatgat      420
tactggaacc tcccaggccg actgtgctgt ccttatcatt gattccacca ctggtggttt      480
cgaagctggt atttccaagg atggccagac ccgtgaacat gc                         522

<210> SEQ ID NO 62
<211> LENGTH: 420
<212> TYPE: DNA
<213> ORGANISM: Eucalyptus grandis

<400> SEQUENCE: 62
tttgatacgc taacaaacaa aacatgtgaa aagcttaatt atggcaatta tcataaatag       60
aaaaaaatta gaaaaaaaga gaggaaatgg gccattattt aaattgcaat cgaaagattg      120
agggcaattc tgtttctcta gtgtaaataa gggtgtattt aataattgag ggatggaaat      180
agcatggtca ctcggtaatt atcaggaaa gcaagaataa aaatgaaaaa aaaaaaaaa        240 aaagcttgaa gaggccaatg tcgaaattat gagcgcgaga tgaggacact cctgggaaac      300
gaaaaatggc attcgcgggg ggtgctatat aaagcctcgt gtaagggtgc gttcctcact      360
ctcaaaccct aatcctgccc ttcccttctg ctgctgctgc tcgtcacctc tctcctccct      420
```

<210> SEQ ID NO 63
<211> LENGTH: 65
<212> TYPE: PRT
<213> ORGANISM: Eucalyptus grandis

<400> SEQUENCE: 63

Met Asp Asn Ser Lys Met Gly Phe Asn Ala Gly Gln Ala Lys Gly Gln
1               5                   10                  15

Thr Gln Glu Lys Ser Asn Gln Met Met Asp Lys Ala Ser Asn Thr Ala
            20                  25                  30

Gln Ser Ala Arg Asp Ser Met Gln Glu Thr Gly Gln Gln Met Lys Ala
        35                  40                  45

Lys Ala Gln Gly Ala Ala Asp Ala Val Lys Asn Ala Thr Gly Met Asn
    50                  55                  60

Lys
65

<210> SEQ ID NO 64
<211> LENGTH: 152
<212> TYPE: PRT
<213> ORGANISM: Eucalyptus grandis

<400> SEQUENCE: 64

Met Gly Gly Pro Leu Thr Leu Asp Ala Glu Val Glu Val Lys Ser Pro
1               5                   10                  15

Ala Asp Lys Phe Trp Val Ser Val Arg Asp Ser Thr Lys Leu Phe Pro
            20                  25                  30

Lys Ile Phe Pro Asp Gln Tyr Lys Asn Ile Glu Val Leu Glu Gly Asp
        35                  40                  45

Gly Lys Ala Pro Gly Ser Val Arg Leu Phe Thr Tyr Gly Glu Gly Ser
    50                  55                  60

Pro Leu Val Lys Val Ser Lys Glu Lys Ile Asp Gly Val Asp Glu Ala
65                  70                  75                  80

Asp Lys Val Val Thr Tyr Ser Val Ile Asp Gly Asp Leu Leu Lys Tyr
                85                  90                  95

Tyr Lys Asn Phe Asn Gly Ser Ile Lys Val Ile Pro Lys Gly Asp Gly
            100                 105                 110

Ser Leu Val Lys Trp Ser Cys Gly Phe Glu Lys Ala Ser Asp Glu Ile
        115                 120                 125

Pro Asp Pro His Val Ile Lys Asp Phe Ala Ile Gln Asn Phe Lys Glu
    130                 135                 140

Leu Asp Glu Phe Ile Leu Lys Ala
145                 150

<210> SEQ ID NO 65
<211> LENGTH: 117
<212> TYPE: PRT
<213> ORGANISM: Eucalyptus grandis

<400> SEQUENCE: 65

Met Ala Ala Asn Phe Val Ile Pro Thr Lys Met Lys Ala Trp Val Tyr
1               5                   10                  15

Arg Glu His Gly Asn Val Ala Asp Val Leu Gly Leu Asp Pro Glu Leu
            20                  25                  30

Lys Val Pro Glu Leu Gln Glu Gly Gln Val Leu Val Lys Val Leu Ala
        35                  40                  45

Ala Ala Leu Asn Pro Val Asp Ala Ala Arg Met Lys Gly Val Ile Lys
    50                  55                  60

```
Leu Pro Gly Phe Ser Leu Pro Ala Val Pro Gly Tyr Asp Leu Ala Gly
 65                  70                  75                  80

Val Val Val Lys Val Gly Arg Glu Val Lys Glu Leu Lys Ile Gly Asp
                 85                  90                  95

Glu Val Tyr Gly Phe Met Phe His Ala Lys Lys Asp Gly Thr Leu Ala
            100                 105                 110

Glu Tyr Ala Ala Val
        115
```

<210> SEQ ID NO 66
<211> LENGTH: 318
<212> TYPE: PRT
<213> ORGANISM: Eucalyptus grandis

<400> SEQUENCE: 66

```
Met Ala Ala Asn Phe Val Ile Pro Thr Lys Met Lys Ala Trp Val Tyr
  1               5                  10                  15

Arg Glu His Gly Asp Val Ala Asn Val Leu Gly Leu Asp Pro Glu Leu
                 20                  25                  30

Lys Val Pro Glu Leu Gln Glu Gly Gln Val Leu Val Lys Val Leu Ala
             35                  40                  45

Ala Ala Leu Asn Pro Ile Asp Thr Ala Arg Val Lys Gly Val Ile Lys
 50                  55                  60

Leu Pro Gly Phe Ser Leu Pro Ala Val Pro Gly Tyr Asp Leu Ala Gly
 65                  70                  75                  80

Val Val Val Lys Val Gly Arg Glu Val Lys Glu Leu Lys Val Gly Asp
                 85                  90                  95

Glu Val Tyr Gly Phe Met Phe His Ala Lys Lys Asp Gly Thr Leu Ala
            100                 105                 110

Glu Tyr Ala Ala Val Glu Glu Ser Phe Leu Ala Leu Lys Pro Lys Lys
            115                 120                 125

Leu Arg Phe Gly Glu Ala Ala Ser Leu Pro Val Val Ile Gln Thr Ala
130                 135                 140

Tyr Gly Gly Leu Glu Arg Ala Gly Leu Ser His Gly Lys Ser Leu Leu
145                 150                 155                 160

Val Leu Gly Gly Ala Gly Gly Val Gly Thr Leu Ile Ile Gln Leu Ala
                165                 170                 175

Lys Glu Val Phe Gly Ala Ser Arg Val Ala Ala Thr Ser Ser Thr Gly
            180                 185                 190

Lys Leu Glu Leu Leu Lys Ser Leu Gly Ala Asp Leu Ala Ile Asp Tyr
        195                 200                 205

Thr Lys Val Asn Phe Glu Asp Leu Pro Glu Lys Phe Asp Val Val Tyr
210                 215                 220

Asp Thr Val Gly Glu Ile Glu Arg Ala Ala Lys Ala Val Lys Pro Gly
225                 230                 235                 240

Gly Ser Ile Val Thr Ile Val Lys Gln Asn Lys Thr Leu Pro Pro Pro
                245                 250                 255

Ala Phe Phe Phe Ala Val Thr Ser Asn Arg Ser Thr Leu Glu Lys Leu
            260                 265                 270

Lys Pro Phe Leu Glu Ser Gly Lys Val Lys Pro Val Ile Asp Pro Lys
        275                 280                 285

Ser Pro Phe Pro Phe Ser Gln Ala Ile Glu Ala Phe Ser Tyr Leu Gln
    290                 295                 300

Thr Arg Arg Ala Thr Gly Lys Leu Val Ile His Pro Val Pro
305                 310                 315
```

<210> SEQ ID NO 67
<211> LENGTH: 156
<212> TYPE: PRT
<213> ORGANISM: Eucalyptus grandis

<400> SEQUENCE: 67

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Met Gln Ile Phe
65                  70                  75                  80

Val Lys Thr Leu Thr Gly Lys Thr Ile Thr Leu Glu Val Glu Ser Ser
                85                  90                  95

Asp Thr Val Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Lys Gly Gly Met Gln Ile Phe
145                 150                 155

<210> SEQ ID NO 68
<211> LENGTH: 238
<212> TYPE: PRT
<213> ORGANISM: Eucalyptus grandis

<400> SEQUENCE: 68

Met Ala Thr His Ala Ala Leu Ala Pro Ser Thr Leu Pro Ala Asn Ala
1               5                   10                  15

Lys Phe Ser Ser Lys Ser Ser Ser His Ser Phe Pro Thr Gln Cys Phe
            20                  25                  30

Ser Lys Arg Leu Glu Val Ala Glu Phe Ser Gly Leu Arg Ala Gly Ser
        35                  40                  45

Cys Val Thr Tyr Ala Lys Asn Ala Gly Glu Gly Ser Phe Phe Asp Ala
    50                  55                  60

Val Ala Ala Gln Leu Thr Pro Lys Thr Ser Ala Pro Ala Pro Ala Lys
65                  70                  75                  80

Gly Glu Thr Val Ala Lys Leu Lys Val Ala Ile Asn Gly Phe Gly Arg
                85                  90                  95

Ile Gly Arg Asn Phe Leu Arg Cys Trp His Gly Arg Lys Asn Ser Pro
            100                 105                 110

Leu Asp Val Ile Val Val Asn Asp Ser Gly Gly Val Lys Asn Ala Ser
        115                 120                 125

His Leu Leu Lys Tyr Asp Ser Met Leu Gly Thr Phe Lys Ala Asp Val
    130                 135                 140

Lys Ile Val Asp Asn Glu Thr Ile Ser Val Asp Gly Lys Pro Val Lys
145                 150                 155                 160

Val Val Ser Asn Arg Asp Pro Leu Lys Leu Pro Trp Ala Glu Leu Gly
                165                 170                 175

Ile Asp Ile Val Ile Glu Gly Thr Gly Val Phe Val Asp Gly Pro Gly
            180                 185                 190

Ala Gly Lys His Ile Gln Ala Gly Lys Lys Val Ile Ile Thr Ala
            195                 200                 205

Pro Ala Lys Gly Ala Asp Ile Pro Thr Tyr Val Tyr Gly Val Asn Glu
        210                 215                 220

Thr Asp Tyr Ser His Glu Val Ala Asn Ile Ile Ser Asn Ala
225                 230                 235

<210> SEQ ID NO 69
<211> LENGTH: 168
<212> TYPE: PRT
<213> ORGANISM: Eucalyptus grandis

<400> SEQUENCE: 69

Met Ser Thr Ser Pro Val Ser Ser Trp Cys Ala Thr Ser Phe Ser Pro
1               5                   10                  15

Ala His Ser Ser Leu Lys Arg Ala Ala Gly Leu Arg Pro Ser Leu Ser
            20                  25                  30

Ala Arg Leu Gly Pro Ser Ser Ser Ser Ser Val Ser Pro Pro Thr
        35                  40                  45

Leu Ile Arg Asn Glu Pro Val Phe Ala Ala Pro Ala Pro Val Ile Asn
    50                  55                  60

Pro Thr Trp Thr Glu Glu Met Gly Lys Asp Tyr Asp Glu Ala Ile Glu
65                  70                  75                  80

Ala Leu Lys Lys Leu Leu Ser Glu Lys Gly Asp Leu Lys Ala Thr Ala
                85                  90                  95

Ala Ala Lys Val Glu Gln Ile Thr Ala Glu Leu Gln Thr Ala Ser Pro
            100                 105                 110

Asp Ile Lys Pro Ser Ser Val Asp Arg Ile Lys Thr Gly Phe Thr
        115                 120                 125

Phe Phe Lys Lys Glu Lys Tyr Asp Lys Asn Pro Ala Leu Tyr Gly Glu
    130                 135                 140

Leu Ala Lys Gln Ser Pro Lys Phe Met Val Phe Ala Cys Ser Asp Ser
145                 150                 155                 160

Arg Val Cys Pro Ser His Val Leu
                165

<210> SEQ ID NO 70
<211> LENGTH: 214
<212> TYPE: PRT
<213> ORGANISM: Eucalyptus grandis

<400> SEQUENCE: 70

Met Pro Cys Pro Arg Ala Pro Pro Met Met Glu Arg Arg Ile Lys Pro
1               5                   10                  15

Gln Thr Glu Gln Ala Leu Lys Cys Pro Arg Cys Asp Ser Thr Asn Thr
            20                  25                  30

Lys Phe Cys Tyr Tyr Asn Asn Tyr Asn Leu Ser Gln Pro Arg His Phe
        35                  40                  45

Cys Lys Thr Cys Arg Arg Tyr Trp Thr Lys Gly Gly Ala Leu Arg Asn
    50                  55                  60

Val Pro Val Gly Gly Gly Cys Arg Lys Asn Lys Arg Ala Lys Arg Ala
65                  70                  75                  80

Val Asp His Pro Val Ser Ala Gln Asn Glu Ala Ser Thr Ser Ala Ala
                85                  90                  95

```
Pro Gly Asn Glu Val Pro Asp Arg Ser Pro Phe Glu Pro Pro Ser Ser
            100                 105                 110

Lys Ser Ile Tyr Tyr Gly Glu Asn Met Asn Leu Thr Gly Leu Pro
            115                 120                 125

Phe Ser Arg Ile Gln Gln Asp Arg Ala Ala Leu Ala His Cys Asn Ser
            130                 135                 140

Ser Ser Phe Leu Gly Met Ser Cys Gly Thr Gln Ser Ala Ser Leu Glu
145                 150                 155                 160

Pro His Leu Ser Ala Leu Asn Thr Phe Asn Ser Phe Lys Ser Asn Asn
                165                 170                 175

Pro Gly Leu Asp Phe Pro Ser Leu Ser Thr Asp Gln Asn Ser Leu Phe
                180                 185                 190

Glu Thr Ser Gln Pro Gln Leu Ser Arg Ala Met Ala Ser Ala Leu Phe
                195                 200                 205

Ser Met Pro Met Ala Pro
            210

<210> SEQ ID NO 71
<211> LENGTH: 166
<212> TYPE: PRT
<213> ORGANISM: Pinus radiata

<400> SEQUENCE: 71

Met Ala Ala Leu Ala Thr Thr Glu Val Cys Asp Thr Tyr Pro Arg Leu
1               5                   10                  15

Val Glu Asn Gly Glu Leu Arg Val Leu Gln Pro Ile Phe Gln Ile Tyr
            20                  25                  30

Gly Arg Arg Arg Ala Phe Ser Gly Pro Ile Val Thr Leu Lys Val Phe
        35                  40                  45

Glu Asp Asn Val Leu Leu Arg Glu Phe Leu Glu Glu Arg Gly Asn Gly
    50                  55                  60

Arg Val Leu Val Val Asp Gly Gly Ser Leu Arg Cys Ala Ile Leu
65                  70                  75                  80

Gly Gly Asn Val Val Val Ser Ala Gln Asn Asn Gly Trp Ser Gly Ile
                85                  90                  95

Ile Val Thr Gly Cys Ile Arg Asp Val Asp Glu Ile Asn Arg Cys Asp
            100                 105                 110

Ile Gly Ile Arg Ala Leu Thr Ser Asn Pro Leu Lys Ala Asn Lys Lys
            115                 120                 125

Gly Val Gly Glu Lys His Ala Pro Ile Tyr Ile Ala Gly Thr Arg Ile
            130                 135                 140

Leu Pro Gly Glu Trp Cys Tyr Ala Asp Ser Asp Gly Ile Leu Val Ser
145                 150                 155                 160

Gln Gln Glu Leu Ser Leu
                165

<210> SEQ ID NO 72
<211> LENGTH: 236
<212> TYPE: PRT
<213> ORGANISM: Pinus radiata

<400> SEQUENCE: 72

Met Leu Val Leu Ile Ile Phe Gly Cys Cys Phe Ile Gly Val Ile Ala
1               5                   10                  15

Thr Ser Phe Asp Phe Tyr Tyr Phe Val Gln Gln Trp Pro Gly Ser Tyr
            20                  25                  30
```

-continued

Cys Asp Thr Arg Arg Gly Cys Cys Tyr Pro Arg Thr Gly Arg Pro Ala
            35                  40                  45

Ser Glu Phe Ser Ile His Gly Leu Trp Pro Asn Tyr Lys Thr Gly Lys
    50                  55                  60

Trp Pro Gln Phe Cys Gly Ser Ser Glu Glu Phe Asp Tyr Ser Lys Ile
65                  70                  75                  80

Ser Asp Leu Glu Glu Glu Leu Asn Arg Tyr Trp Gly Ser Leu Ser Cys
                85                  90                  95

Pro Ser Ser Asp Gly Gln Glu Phe Trp Gly His Glu Trp Glu Lys His
                100                 105                 110

Gly Thr Cys Ser Leu Asn Leu Asp Glu His Ser Tyr Phe Glu Lys Ala
            115                 120                 125

Leu Ser Leu Arg Gln Asn Ile Asp Ile Leu Gly Ala Leu Lys Thr Ala
130                 135                 140

Gly Ile Lys Pro Asp Gly Ser Gln Tyr Ser Leu Ser Asp Ile Lys Glu
145                 150                 155                 160

Ala Ile Lys Gln Asn Thr Gly Gln Leu Pro Gly Ile Asp Cys Asn Thr
                165                 170                 175

Ser Ala Glu Gly Glu His Gln Leu Tyr Gln Val Tyr Val Cys Val Asp
            180                 185                 190

Lys Ser Asp Ala Ser Thr Val Ile Glu Cys Pro Ile Tyr Pro His Ser
    195                 200                 205

Asn Cys Pro Ser Met Val Val Phe Pro Pro Phe Gly Glu Asp Gln Glu
            210                 215                 220

Asp Arg Asp Gly Tyr Thr Glu Gly Met Tyr Glu Leu
225                 230                 235

<210> SEQ ID NO 73
<211> LENGTH: 92
<212> TYPE: PRT
<213> ORGANISM: Pinus radiata

<400> SEQUENCE: 73

Met Ala Ala Pro Arg Ser Ser Ala Lys Leu Gly Ala Leu Leu Ala Ile
1               5                   10                  15

Leu Leu Ile Val Ala Ala Ala Gln Ala Gln Asp Cys Ser Asn Ala Met
            20                  25                  30

Asp Lys Leu Ala Pro Cys Thr Ser Ala Val Gly Leu Ser Ser Asn Gly
            35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Ile Thr Cys Ser Gly Ser Arg
                85                  90

<210> SEQ ID NO 74
<211> LENGTH: 92
<212> TYPE: PRT
<213> ORGANISM: Pinus radiata

<400> SEQUENCE: 74

Met Ala Ala Pro Arg Ser Ser Ala Lys Ser Ala Ala Leu Phe Ala Ile
1               5                   10                  15

Leu Leu Ile Val Ala Ala Val Gln Ala Glu Asp Cys Ser Asn Ala Met
            20                  25                  30

```
Asp Lys Leu Ala Pro Cys Thr Ser Ala Val Gly Leu Ser Ser Asn Gly
            35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Leu Thr Cys Ser Gly Ser Arg
                85                  90

<210> SEQ ID NO 75
<211> LENGTH: 92
<212> TYPE: PRT
<213> ORGANISM: Pinus radiata

<400> SEQUENCE: 75

Met Ala Ala Pro Arg Ser Ser Ala Lys Leu Gly Ala Leu Leu Ala Ile
1               5                   10                  15

Leu Leu Ile Val Ala Ala Ala Gln Ala Gln Asp Cys Ser Asn Ala Met
            20                  25                  30

Asp Lys Leu Ala Pro Cys Thr Ser Ala Val Gly Leu Ser Ser Asn Gly
            35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Ile Thr Cys Ser Gly Ser Arg
                85                  90

<210> SEQ ID NO 76
<211> LENGTH: 125
<212> TYPE: PRT
<213> ORGANISM: Eucalyptus grandis

<400> SEQUENCE: 76

Met Ala Asp Arg Met Leu Thr Arg Ser His Ser Leu Arg Glu Arg Leu
1               5                   10                  15

Asp Glu Thr Leu Ser Ala His Arg Asn Asp Ile Val Ala Phe Leu Ser
            20                  25                  30

Arg Val Glu Ala Lys Gly Lys Gly Ile Leu Gln Arg His Gln Ile Phe
            35                  40                  45

Ala Glu Phe Glu Ala Ile Ser Glu Glu Ser Arg Ala Lys Leu Leu Asp
    50                  55                  60

Gly Ala Phe Gly Glu Val Leu Lys Ser Thr Gln Glu Ala Ile Val Ser
65                  70                  75                  80

Pro Pro Trp Val Ala Leu Ala Val Arg Pro Arg Pro Gly Val Trp Glu
                85                  90                  95

His Ile Arg Val Asn Val His Ala Leu Val Leu Glu Gln Leu Glu Val
            100                 105                 110

Ala Glu Tyr Leu His Phe Lys Glu Glu Leu Ala Asp Gly
            115                 120                 125

<210> SEQ ID NO 77
<211> LENGTH: 805
<212> TYPE: PRT
<213> ORGANISM: Eucalyptus grandis
```

<400> SEQUENCE: 77

```
Met Ala Asp Arg Met Leu Thr Arg Ser His Ser Leu Arg Glu Arg Leu
 1               5                  10                  15

Asp Glu Thr Leu Ser Ala His Arg Asn Asp Ile Val Ala Phe Leu Ser
             20                  25                  30

Arg Val Glu Ala Lys Gly Lys Gly Ile Leu Gln Arg His Gln Ile Phe
         35                  40                  45

Ala Glu Phe Glu Ala Ile Ser Glu Glu Ser Arg Ala Lys Leu Leu Asp
     50                  55                  60

Gly Ala Phe Gly Glu Val Leu Lys Ser Thr Gln Glu Ala Ile Val Ser
 65                  70                  75                  80

Pro Pro Trp Val Ala Leu Ala Val Arg Pro Arg Pro Gly Val Trp Glu
                 85                  90                  95

His Ile Arg Val Asn Val His Ala Leu Val Leu Glu Gln Leu Glu Val
            100                 105                 110

Ala Glu Tyr Leu His Phe Lys Glu Glu Leu Ala Asp Gly Ser Leu Asn
        115                 120                 125

Gly Asn Phe Val Leu Glu Leu Asp Phe Glu Pro Phe Thr Ala Ser Phe
130                 135                 140

Pro Arg Pro Thr Leu Ser Lys Ser Ile Gly Asn Gly Val Glu Phe Leu
145                 150                 155                 160

Asn Arg His Leu Ser Ala Lys Leu Phe His Asp Lys Glu Ser Leu His
                165                 170                 175

Pro Leu Leu Glu Phe Leu Gln Val His Cys Tyr Lys Gly Lys Asn Met
            180                 185                 190

Met Val Asn Ala Arg Ile Gln Asn Val Phe Ser Leu Gln His Val Leu
        195                 200                 205

Arg Lys Ala Glu Glu Tyr Leu Thr Ser Leu Lys Pro Glu Thr Pro Tyr
    210                 215                 220

Ser Gln Phe Glu His Lys Phe Gln Glu Ile Gly Leu Glu Arg Gly Trp
225                 230                 235                 240

Gly Asp Thr Ala Glu Arg Val Leu Glu Met Ile Gln Leu Leu Leu Asp
                245                 250                 255

Leu Leu Glu Ala Pro Asp Pro Cys Thr Leu Glu Lys Phe Leu Asp Arg
            260                 265                 270

Val Pro Met Val Phe Asn Val Ile Met Ser Pro His Gly Tyr Phe
        275                 280                 285

Ala Gln Asp Asp Val Leu Gly Tyr Pro Asp Thr Gly Gly Gln Val Val
    290                 295                 300

Tyr Ile Leu Asp Gln Val Arg Ala Leu Glu Glu Glu Met Leu His Arg
305                 310                 315                 320

Ile Lys Gln Gln Gly Leu Asp Ile Thr Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Phe Gly Thr Glu Tyr Ser His Ile Leu Arg Val Pro Phe Arg
        355                 360                 365

Asn Glu Lys Gly Val Val Arg Lys Trp Ile Ser Arg Phe Glu Val Trp
    370                 375                 380

Pro Tyr Leu Glu Arg Tyr Thr Glu Asp Val Ala Ser Glu Leu Ala Gly
385                 390                 395                 400

Glu Leu Gln Gly Lys Pro Asp Leu Ile Ile Gly Asn Tyr Ser Asp Gly
                405                 410                 415
```

```
Asn Ile Val Ala Ser Leu Leu Ala His Lys Leu Gly Val Thr Gln Cys
            420                 425                 430

Thr Ile Ala His Ala Leu Glu Lys Thr Lys Tyr Pro Glu Ser Asp Ile
        435                 440                 445

Tyr Trp Lys Lys Phe Glu Glu Lys Tyr His Phe Ser Cys Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Asn Phe Thr Leu Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Ser Ile Tyr Phe Ala Tyr Thr Glu Gln Glu Arg Arg Leu Lys Ser Phe
    530                 535                 540

His Pro Glu Ile Glu Glu Leu Leu Phe Ser Asp Val Glu Asn Lys Glu
545                 550                 555                 560

His Leu Cys Val Leu Lys Asp Lys Lys Pro Ile Ile Phe Thr Met
                565                 570                 575

Ala Arg Leu Asp Arg Val Lys Asn Leu Thr Gly Leu Val Glu Trp Tyr
            580                 585                 590

Gly Lys Asn Ser Lys Leu Arg Glu Leu Ala Asn Leu Val Val Val Gly
        595                 600                 605

Gly Asp Arg Arg Lys Asp Ser Lys Asp Leu Glu Glu Gln Ser Glu Met
    610                 615                 620

Lys Lys Met Tyr Asp Leu Ile Glu Lys Tyr Lys Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Cys Asp Thr Lys Gly Val Phe Val Gln Pro Ala Ile Tyr
            660                 665                 670

Glu Ala Phe Gly Leu Thr Val Val Glu Ala Met Thr Cys Gly Leu Pro
        675                 680                 685

Thr Phe Ala Thr Cys Asn Gly Gly Pro Ala Glu Ile Ile Val His Gly
    690                 695                 700

Lys Ser Gly Tyr His Ile Asp Pro Tyr His Gly Asp Gln Ala Ala Glu
705                 710                 715                 720

Leu Leu Val Asp Phe Phe Asn Lys Cys Lys Ile Asp Gln Ser His Trp
                725                 730                 735

Asp Glu Ile Ser Lys Gly Ala Met Gln Arg Ile Glu Glu Lys Tyr Thr
            740                 745                 750

Trp Lys Ile Tyr Ser Glu Arg Leu Leu Asn Leu Thr Ala Val Tyr Gly
        755                 760                 765

Phe Trp Lys His Val Thr Asn Leu Asp Arg Arg Glu Ser Arg Arg Tyr
    770                 775                 780

Leu Glu Met Phe Tyr Ala Leu Lys Tyr Arg Pro Leu Ala Gln Ser Val
785                 790                 795                 800

Pro Pro Ala Val Glu
                805
```

<210> SEQ ID NO 78
<211> LENGTH: 264
<212> TYPE: PRT
<213> ORGANISM: Eucalyptus grandis

<400> SEQUENCE: 78

Met Gly Ser Thr Gly Ser Glu Thr Gln Met Thr Pro Thr Gln Val Ser
1               5                   10                  15

Asp Glu Glu Ala Asn Leu Phe Ala Met Gln Leu Ala Ser Ala Ser Val
            20                  25                  30

Leu Pro Met Val Leu Lys Ala Ala Ile Glu Leu Asp Leu Leu Glu Ile
        35                  40                  45

Met Ala Lys Ala Gly Pro Gly Ala Phe Leu Ser Pro Gly Glu Val Ala
50                  55                  60

Ala Gln Leu Pro Thr Gln Asn Pro Glu Ala Pro Val Met Leu Asp Arg
65                  70                  75                  80

Ile Phe Arg Leu Leu Ala Ser Tyr Ser Val Leu Thr Cys Thr Leu Arg
                85                  90                  95

Asp Leu Pro Asp Gly Lys Val Glu Arg Leu Tyr Gly Leu Ala Pro Val
            100                 105                 110

Cys Lys Phe Leu Val Lys Asn Glu Asp Gly Val Ser Ile Ala Ala Leu
        115                 120                 125

Asn Leu Met Asn Gln Asp Lys Ile Leu Met Glu Ser Trp Tyr Tyr Leu
130                 135                 140

Lys Asp Ala Val Leu Glu Gly Gly Ile Pro Phe Asn Lys Ala Tyr Gly
145                 150                 155                 160

Met Thr Ala Phe Glu Tyr His Gly Thr Asp Pro Arg Phe Asn Lys Ile
                165                 170                 175

Phe Asn Arg Gly Met Ser Asp His Ser Thr Ile Thr Met Lys Lys Ile
            180                 185                 190

Leu Glu Thr Tyr Lys Gly Phe Glu Gly Leu Glu Thr Val Val Asp Val
        195                 200                 205

Gly Gly Gly Thr Gly Ala Val Leu Ser Met Ile Val Ala Lys Tyr Pro
210                 215                 220

Ser Met Lys Gly Ile Asn Phe Asp Arg Pro Asn Gly Leu Lys Thr Pro
225                 230                 235                 240

His Pro Phe Leu Val Ser Ser Thr Ser Glu Ala Thr Cys Ser Ser Ala
                245                 250                 255

Phe Gln Arg Glu Met Pro Phe Ser
            260

<210> SEQ ID NO 79
<211> LENGTH: 136
<212> TYPE: PRT
<213> ORGANISM: Eucalyptus grandis

<400> SEQUENCE: 79

Met Gly Lys Glu Lys Ile His Ile Ser Ile Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
50                  55                  60

```
Ala Glu Arg Glu Arg Gly Ile Thr Ile Asp Ile Ala Leu Trp Lys Phe
 65                  70                  75                  80

Glu Thr Thr Lys Tyr Tyr Cys Thr Val Ile Asp Ala Pro Gly His Arg
                 85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His
    130                 135

<210> SEQ ID NO 80
<211> LENGTH: 229
<212> TYPE: PRT
<213> ORGANISM: Eucalyptus grandis

<400> SEQUENCE: 80

Met Gln Ile Phe Val Lys Thr Leu Thr Gly Lys Thr Ile Thr Leu Glu
  1               5                  10                  15

Val Glu Ser Ser Asp Thr Ile Asp Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Gln Leu Glu Asp Gly Arg Thr Leu Ala Asp Tyr Asn Ile Gln Lys Glu
 50                  55                  60

Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 81
<211> LENGTH: 345
<212> TYPE: DNA
<213> ORGANISM: Eucalyptus grandis

<400> SEQUENCE: 81
taataaatga tgaatttatt ataaacgtat ccgtttgaga tttttgtggg tcataggtgt    60
atcaatttga aatctttgat agtaacaaaa ataatttag gtagtttatg tttttcatga   120
```

```
tataaacctt gaaagttaat gctactaaat tgttatatat atattaggca aattacaacc      180
ttaatgcaac agttaatgac gtgatactgt tcagattata gatacaatgg ttatccttga      240
atgaataaga agaagtccta agggcaagtg ctatgagctt gcacgactgc ttttgcgcca      300
tttttgttta ccagcccggg ccgtcgacca cgcgtgccct atagt                      345
```

```
<210> SEQ ID NO 82
<211> LENGTH: 72
<212> TYPE: DNA
<213> ORGANISM: Eucalyptus grandis

<400> SEQUENCE: 82
cagtagggga cttgttcccc caagggcacg tgtcgttggt gaagctctgg cggtggatga       60
accgcgtggg cc                                                           72
```

```
<210> SEQ ID NO 83
<211> LENGTH: 544
<212> TYPE: DNA
<213> ORGANISM: Eucalyptus grandis

<400> SEQUENCE: 83
actagtgatt tcgtcgtctt cgtcttcttc gtcttctgga acttcgttgc tccgagcttt       60
atcagaaccg gcgatggaaa tgaaaccctc gttctctctc cctcgctcct ctctttcttc      120
tatccaggag cgtttgtaca ctgggagtac agagcttctt gcgataccga aactacccctt     180 ggacgactgg cctttttgcc tcgcgccccc tctctgagcc ggggcgcaat tgtcccttt       240 cccagagcga agtgtcgatt tgtccttcc acgaggcttt acctactccc atcgcccgag      300
ccccaagccc aggcccaaat gcctgttcct tgtggccctg ccaacattcc ctttgaaatt      360
aaaaaattaa aaaaaactc tctgccaggc aaaagtaaag attaacacca ccaaaattta      420
taacaaattt atcattcatt aatttttcgtt aaattttatt ttcaaattac tgagtcgaat    480
tacatgtata aattcacgga tgtatcggtt cgagatttta tcctctaatt atcattagtg      540
tatg                                                                  544
```

```
<210> SEQ ID NO 84
<211> LENGTH: 515
<212> TYPE: DNA
<213> ORGANISM: Eucalyptus grandis

<400> SEQUENCE: 84
gattactata gggcacgcgt ggtcgacggc ccgggctggt ctgccttcct ttaactcccc       60 tttttttgtaa cttttaaaa tgtagtttta aatttaattt aattacttttt tatattaatt    120 atttaccaca tcagagacaa acaatgtct tttttgtatt ttctagtcac gtcaacatgc      180
aaaacaacgc cattttgcac tcaccttgcc ggaaaattgc cacgtcaaca atttggctag      240
agtggcgctt aagtgatcta ttttgctcca atttttggcac ttaagtgtca ttttcctaaa    300
ttttagcact taaagtattc ctctatgtca agttttgaca cttggggtgt actttgtcca      360
atcataaacc gtataagttc actttaaaca aaaatgcgc aaaagcagtc gtgcaagctc      420
atagcacttg cccttaggac ttcttcttat tcattcaagg ataaccattg tatctataat     480
ctgaacagta tcacgtcatt aactgttgca ttaag                                515
```

<210> SEQ ID NO 85
<211> LENGTH: 515
<212> TYPE: DNA
<213> ORGANISM: Eucalyptus grandis

<400> SEQUENCE: 85

```
actagtgatt tcgtcgtctt cgtcttcttc gtcttctgga acttcgttgc tccgagcttt      60
atcagaaccg gcgatggaaa tgaaaccctc gttctctctc cctcgctcct ctctttcttc     120
tatccaggag cgtttgtaca ctgggagtac agagcttctt gcgataccga aactacccct     180
ggacgactgg cctttttgcc tcgtgccccc tctctgagcc ggggcgcaat tgtcccttt     240
cccagagcga agtgtcgatt ttgtccttcc acgaggcttt acctactccc atcgcccgag     300
ccccaagccc aggcccaaat gcctgttcct tgtggccctg caacattcc ctttgaaatt      360
aaaaaattaa aaaaaactc tctgccaggc aaaagtaaag attaacacca ccaaaattta     420
taacaaattt atcattcatt aattttcgtt aaattttatt ttcaaattac tgagtcgaat    480
tacatgtata aattcacgga tgtatcggtt cgaga                                515
```

<210> SEQ ID NO 86
<211> LENGTH: 782
<212> TYPE: DNA
<213> ORGANISM: Eucalyptus grandis

<400> SEQUENCE: 86

```
gagggtttca tttccatcgc cggttctgat aaagctcgga gcaacgaagt tccagaagac      60
gaagaagacg aagacgacga cggcgacatg ccttgcttga acatctccac caacgtcagc    120
ctcgacggcc tcgacacctc cgccattctc tccgagacca cctccggcgt cgccaagctc    180
atcggcaagc ccgaggccta tgtgatgatt gtgttgaagg ggtcagtccc catggctttt    240
ggtgggactg agcaacctgc tgcctatggc gagttggtgt caatcggcgg tttgaacccc    300
gatgtgaaca agaagctgag tgctgcaatt gcttcaatcc tcgaaaccaa gctgtccatc    360
cccaagtcgc ggttcttcct gaaatttat gataccaagg gttccttctt tggatggaat     420
ggatccacct tctgagctgt tggtcgcatt ctcctcagtg tttaccatgt atttcggccc    480
taaactctac ttctaggcct gttaaaagtg tctttttaa ggtaattctg ctattacccc      540
tcttaagtgc atcttatcag taaacatgga atatcctgaa ctttgattat atgccggctc    600
gtggctgtgg aagcacttct ttatgttacc accagcttct caggtgaata taagctttgc    660
ccagtctgtt ctctggggga tttgcttggt gggtagtggc aatcagatgg ttttgtcact    720
tttgtgcata tttaagtagt aaatgtccac gacagcccaa agagtagcaa tccgggtgca    780
ct                                                                    782
```

<210> SEQ ID NO 87
<211> LENGTH: 115
<212> TYPE: PRT
<213> ORGANISM: Eucalyptus grandis

<400> SEQUENCE: 87

```
Met Pro Cys Leu Asn Ile Ser Thr Asn Val Ser Leu Asp Gly Leu Asp
 1               5                  10                  15

Thr Ser Ala Ile Leu Ser Glu Thr Thr Ser Gly Val Ala Lys Leu Ile
            20                  25                  30

Gly Lys Pro Glu Ala Tyr Val Met Ile Val Leu Lys Gly Ser Val Pro
        35                  40                  45
```

```
Met Ala Phe Gly Gly Thr Glu Gln Pro Ala Ala Tyr Gly Glu Leu Val
         50                  55                  60

Ser Ile Gly Gly Leu Asn Pro Asp Val Asn Lys Lys Leu Ser Ala Ala
 65                  70                  75                  80

Ile Ala Ser Ile Leu Glu Thr Lys Leu Ser Ile Pro Lys Ser Arg Phe
                 85                  90                  95

Phe Leu Lys Phe Tyr Asp Thr Lys Gly Ser Phe Gly Trp Asn Gly
            100                 105                 110

Ser Thr Phe
        115

<210> SEQ ID NO 88
<211> LENGTH: 1521
<212> TYPE: DNA
<213> ORGANISM: Pinus radiata

<400> SEQUENCE: 88
ccttcaaaga caacagagaa agttatgcaa tatgctggca gctagctctt gggataatct      60
atttagcgat gggtttgtcg agaagttggg agcattatt gtgaagcttc acagaaaaaa     120
tgtcgaatac atcaagcaca tgaagaagca atttgtgcca taggctatct ttagcctcat    180
ggatgttaaa ataatttctt tctttccttc cttcttcttt cttacccacc aaaacacaaa    240
ataatagttt caaattttga attttcaccc aattttatga gaggacaaaa ttacttagag    300
tctttcactc tttaatttat attctacata agtacctaaa gaggctctcc gacaatcata    360
tgataccata aaagtaacct cgattagaga gcgcctctcc atacaatcat ttgattttcg    420
agttaaatca aaattatagg ctatttccaa atcaatctat cgtccaactg aaaatttcaa    480
atgaatggaa ccagcacgga gtttcgtagg aaatagaagt aataggtgaa agaagcatt     540 gtcgaatttg aaagaatacc ctacgttttc atttcaaaaa ccatggtttt ttgtaagagg    600
gattaagttg actcaaggtt gtagaaggtt gacataacaa tagcatgcag gcacaggatg    660
catgtagtgc ccgtaatttg gaccaaccta gtaagattgt cacccgtttc aaatgactgc    720
ctacaagtgc atgcaaaggc catggaagtt gatggttagt gaaaagatcc ggagagacga    780
ttattccatc atgcaatgca catcgcacgc ttgctttatt actcacacga ccaacgttcc    840
cttcatccac ggaattaatt tctctaatcg atccaataaa ccgccttcga tgtcgatttc    900
caaatgaatt aaatcgttac atgcccaccc gacttcacac atgctccctg cacgtgcaac    960
caaatccatt acgcccaccg ggcccggccc tgctcacaca tcttgcatcg cccaactact   1020
ctgattttac atgaatatca atactattcc ctccacttat aaaatggcca acgccctgc    1080 ttagttctca aagcagatca gagcctttca agagcttccg caaagatttt ctttgcgagt   1140
aatttgatcg agaaggatgt ctgcatcgaa cggaactaat ggtgttgtcg cagtcaagtc   1200
tcgccgacag cacagacctg gaaaacgac agccatggcg ttcgggaggg cgtttccaga   1260
tcagctggtg atgcaggagt tcctcgtcga tggatatttc cgcaacacga attgccagga   1320
ccccgtcctc cgccagaagc tcgaaaggct ttgcaagacg acgacggtga agacgcgata   1380
cgtggtgatg tcggatgaaa tattggcgca gcatcctgag ctggcagtgg aaggttcggc   1440
caccgtccga cagcgactcg agatctcgaa cgtggccgtg accgacatgg cggtggacgc   1500
gtgccgtgac tgcctcaaag a                                              1521
```

<210> SEQ ID NO 89
<211> LENGTH: 2590
<212> TYPE: DNA
<213> ORGANISM: Eucalyptus grandis

<400> SEQUENCE: 89

| | | | | | |
|---|---|---|---|---|---|
| ctgaaactgt | cgctcggcga | tgcataccaa | aggctgaagg | tatcagaatc | taatgcagct | 60 |
| tatgtaaaag | cgcgatcaat | ttattgaccc | cgacgacctt | gactccatac | ttcacgcctc | 120 |
| agctttgtgt | tggatggtct | tgacctctct | caccctaaaa | ggtagctcaa | agaatgaga | 180 |
| ctttccgtca | tacttataaa | ccgaccacca | gcctctttca | caaccgacat | gggacaacct | 240 |
| caaatagaat | ttttaacaac | acccttgcac | gctctttcta | tccactttat | tatgccatca | 300 |
| catgagcgtt | ttccacgcgt | aaatcggcta | ccacccactt | tcacacggcg | gcgaaacgag | 360 |
| aaaaaggtcc | tacctttgac | tcccccgcg | tcccaaattc | tcactcccga | ccggtaaccg | 420 |
| agctcacaag | tttcagcctt | tcatcatcat | cactcgaagg | cagagagaag | gacatacact | 480 |
| aaagacaacg | aaacagtctc | tccatcccgc | catccgacac | gatccacatt | acggtacgga | 540 |
| acacatcccg | cggagcaacc | cgacgtccca | aactcttcgc | tgatcaaaac | cagtccggtc | 600 |
| gactccgttt | cgcgcggacg | caacgtgaga | gagggagaga | gagagagaga | gtaccggcga | 660 |
| ggggatgatg | ctgtgcggaa | gcgtcgtcgg | gcgctctccc | ggcgaacgcg | tctctacatt | 720 |
| ccggcgacgg | cgacggcgac | gaaggcgggg | agggaatgc | cgcggggttt | ctgcaacgac | 780 |
| ggaagctcac | ggcatttttc | agagagagag | agagagatgg | cacgtcgag | cgccattccc | 840 |
| ccacgcgacg | ttccgccttc | cggtattcct | tccgggagaa | aaagtgggca | aattgcaata | 900 |
| gacaaaaaaa | aaagaaaaa | aaagacggtc | acccaaatta | tttcttataa | cacaaaaaat | 960 |
| cgtacctata | taatatatct | atcactaact | tgtgcagtat | gacaaattta | cacatttacc | 1020 |
| tgaaactgtt | tttataacat | aaaaaattta | aacattttc | tgtgacaata | aatgttcaca | 1080 |
| caaatataaa | actgggattt | ttatttcaat | tacaaattta | gaataaatgc | gcaacataaa | 1140 |
| tacaaattta | tgattttcg | tgttggcaag | aaagtttgag | ataaatgtat | cattgtaggt | 1200 |
| aaagtttaga | gttttttttt | atggctttta | accaaaatgc | acattttagt | tccgagttct | 1260 |
| aaaagaaaaa | ttactatttt | cctttacatt | tacttatgta | ggtgtgtaat | tataaatatt | 1320 |
| aattctcttt | aggatttgta | acaattcttt | gagcttttgt | tttgccttta | ggccattaga | 1380 |
| attactaaaa | agttaataat | ataacatttt | tttcgaccac | ggtcaccatt | catacctaac | 1440 |
| ttctaattat | tgaaagattc | tcgcatttga | tcgaaatcca | tttactctca | taaatttgag | 1500 |
| gttttgaacg | gtatctacca | taagatcatg | gtttattaca | aaacacttat | ggcgggtggc | 1560 |
| gcggacctgg | cgagaatgtg | gctactttaa | tgatgaggat | ttgagatatt | ataccacgat | 1620 |
| ccataataat | aaaggagcgc | ggcaatcata | tcttttttca | tataaaggac | gatttatttt | 1680 |
| ctatgctgtg | agtatttgct | cttggaatta | taagatatta | gagatcaaac | ctatcaccaa | 1740 |
| cggtgatttg | aaattaaaga | agtccttgta | tcacttacaa | aaataaatat | ataaaaaag | 1800 |
| ctttcattgt | gcacttgaat | atttaaacat | aaattattag | tagtagataa | ttttttaatt | 1860 |
| taactaataa | tgagcactca | ttttagaaa | atagttttc | aaatcattca | ttttctactt | 1920 |
| aaaaaaacca | attgaccaac | taaattagta | tctctcattc | agttggtgaa | tgaatgactc | 1980 |
| gcactctaac | ccttcacttg | gcgagtcatt | ctgtgtagac | cagtctctgc | aaatctagcc | 2040 |
| atgctcatct | agcaactacc | ttcaagcgca | agtactttgt | catgtagacc | aaacgttgag | 2100 |
| caacacggaa | tgaatcctaa | cgcacttgga | aaacaatcaa | tccacgctac | gcaagctaat | 2160 |

```
gctcacacaa gcatcatgat acccgaagcc gaaaatacat gagtcgaaag acatcgaact    2220
ccgccgtcct cgcgaatcat ccgaatcgca tgtcacgccg ctcgacttgg tagcttaacg    2280
agccttccag tacctgctgt ttaaatgctt tgtcaatgtg attcgaatcc tttcaaagat    2340
cctgaaagtg cagcttcaaa aatggcgtcg accaaatggg cttgcgttgc tgcaatctcg    2400
ctcctactga gcctaggatc gagcgctgct cagaggtctc tccttatgag cagcgccaac    2460
tggcaagagg ccggtgagcc gacggatctg gacttacgtg gaggaattgc cggaaccctg    2520
gggtcatcaa gtgagggcgg caccatggcc agctccgaca tgggcggttt tggccaggac    2580
atgcctggtg                                                          2590

<210> SEQ ID NO 90
<211> LENGTH: 1172
<212> TYPE: DNA
<213> ORGANISM: Eucalyptus grandis

<400> SEQUENCE: 90
actctcacta attctttagt tttccaattt agcccttct gtaattgctc atcttcttta      60
ccaaattctc taatttggcc ggcgaagggc tgacaaggga ttggtcatgt caccctcacc    120
aaaggttgcc gaaggtccgg tgacctcagc tgacggccac ctacaccaaa tctagctcac    180
tagcagccta agcccttcat caactctagt gaaaggtttt gagtattttt taataaaaaa    240
tatttaaaaa atatatagcg agagctcatt acaaaaaaat tttaaaaaaa aatctaaaca    300
ttacttgaac tcaaagtgac tttataaaga gtttttacca aaggatcttg gtttcatcat    360
ttgcactaca cccaaaaccc aatttctaag ttaaatcaaa cccactgtct aatagagata    420
aggtaaatgt tataaaccaa attccaaaat tccgaagcac taaatatatt tgctgatctt    480
ataatcgcca attgagaggg tctcattctc caagggattg tgacatatta gtaattgata    540
gggtctcatc cgtaggactc cgactcagcc gcgccacgtg actggatcgc tgaacggcgc    600
ggaaccagag gagcgtgatt acctaatatt ttctcctacc ttggccttga gattgaattt    660
cagaaaaaga aaaagaaaaa ggaacaactt cgccgactgt tctataaaat gcatgcgcca    720
ccccgacccc cacccacgca tcacatccat ccagcctcca cgacagacgc ataaacacaa    780
cacacgtcgg ttagagagag agagagagag agagagagat gcttggacag                 840
ttgtcgcacg agacggaaat gaaggtggga gcaggcaaag catgggagct gtatggcacg    900
ctcaagctgg tcctgctggc caagcaggaa ttctctaata ccatctgcga cgtcttggaa    960
ggtgatggcg gcgttggcac cgtcatcaag ctcaattttg gaagtttatc ctatacagag    1020
aagtacacaa aggtggacca cgagcgccgc gtgaaagaaa cggaggcgat cgaaggtggg    1080
ttcctggaca tgggtctcg ctgtatcgat tgcgattcga agtgataggc aaggacgagg    1140
aggagtcgtt ccgttattaa agcccccccc cc                                  1172

<210> SEQ ID NO 91
<211> LENGTH: 446
<212> TYPE: DNA
<213> ORGANISM: Eucalyptus grandis

<400> SEQUENCE: 91
gggtgaaaac aattaatgag atcatttgaa ttaaggaaag tggaaaggcg gttttctgat     60
tggtacactg aaacaacagg aaggtggtgg aggccgcaat gatggaattt atccacttta    120
atcattttat gaaatcgata cactaacctt tgtttctcct aaaccaaag gcattaatcc     180 ctgtcctcct cactcgatct cgaaggccag aagggggagg ccgagcctct tgcttttttt    240
```

```
cgtgtataaa agggcctccc ccattcctca ttttcacca tcctccgttc gttcgttccc      300 ttcccttcc attgttgcgt ttaagccctc caattttctt ttggcgtccc gtttttgggg      360
ctcccttgaa gatctcctct tcatttcggg atttcctgcc ttcgccgcgc catttgaagt     420 tcttttctg agagaagaat ttagac                                          446
```

<210> SEQ ID NO 92
<211> LENGTH: 2119
<212> TYPE: DNA
<213> ORGANISM: Pinus radiata

<400> SEQUENCE: 92

```
atcttattcc cacctcacat caataaattt tatacgattt taacatcttt aaaattaaaa      60
gaatcaagaa ggcatccagg tgataaagcc acgtccaata taaatctcc tcggtggatc      120 ctttcaatcc agctacccaa tgcggcgaaa ataacgctga ttggactggg ctacactgta    180
atcacaaatt cccttccgtt tagatttcaa ctcgttgacc tacgagtatt ttatcgattt     240
aaaattatac aaaaaattgt ggaatgtttt acataagcaa aacttaaata atgtaaatag    300
cgatgatgct ttacttgtac ctaaaaattt cttccaaatt aaaccaaata tcaaatccta     360
gattgatgag ttccagtgga gtctgccatt ttatttcttt ctctctttca ttctttgcaa    420
cgaaaggaga aaatccttaa cacaattcga aaacgataat gattctggca aaagagaaaa    480
aaaacgtgaa gattagacac ttgttttgtt ttaaatgagc aatcacatgt gaatagagag    540
ggttttatgg gcctggtttt gtgtgcataa tttcttatga aagcgatgtg cctggagcgt    600
tgaagctcat agaacattgc aacaagagat cgagagtgtg ggttagaaaa ccgcaacaat    660
agtttgtgtc gtgttttct atattcgag gtgttgtgtg gtaaatatct ctggatttat      720
ctcgaatgcg tcacttttac agacacagaa gctcagcgga aaccctcaac gctttaaggg    780
ccataaattt gctcagtttt aaaaattgtt tgatttccca ggtttgaata ttttctttt    840 gttatcggaa gtggctctgc cttatgagta tcatgttctt ggttttgtgt tgggcgctta    900
ttgattcagg tatgtattat ttctagtcct tttatcagc ataggtggaa tgttctgtat   960
tttatatttt ggggccatac acatggaacc gttgtcatta ccatgcttta tagataatgt    1020
ctctctgaat tgttttat aggcttttgc ctcctacgca gattttaaa ggaaaataca     1080 aagatattta gccaattttt gttgttgtga ccttgaattt ctaaaaaatt taatggattc    1140
gttttctaaa ttcctgattc gtcaaaggct gaagggcgcg atagtaatag aaaatggacg    1200
agagtttatc ttttcatggc tggacacaca gaatttgtgg aggggattct ccattctggt    1260
ttatccaccg ttagttctct ctgtactcca cccttagttc tctttgtact cgagaccttt   1320
aatgattaac cctgcttatg ctgtcagtac tgaactcact tccagagccc caaaaatctc    1380
tcccaagttt gccttattc ttaaaataat tcacaagtag aaaatgagat ttttgcaatt    1440
ttgtaactaa catttcccgg tctcctctgt atgttttcac cccttaatgt aattgaaatt    1500
tgcacccggg ttagattcaa agcggagaat aacatcgggg ccttgttcta gacagagatt    1560
tttcacaaat aacaggttcg aaggtatgtg tagacatctg ggtagttgta gaataaagac    1620
ggagcccatt aggtggatcc aatcgaagaa ctcagatggg aaaacagata aaaattatcg    1680
ggtggacctt cctccacatg ttaattatat atcaagtgtc gccaatcctt atgtgaaaca    1740
tttagtaaag cttcgccaga gcacttctta taggcattct gtgggctctg ttgttgtggt    1800
tggaagtact cctttaaggg aggtatctga atatttgcaa cagaagtcag taaaacaagt    1860
ggttgactgt ctgttgtac aagatgttac tggcatacct gtgggcttga tagagacttc    1920
```

```
caggcgcatt gtgcatgtaa atcatttggt gatgcagaag ctagccggag tagagtctat   1980
agagcccact gaagcaattg gtgtaatcaa gcttcctagc agcttctaca acttggaatc   2040
tcttgaaatc actctagttc ccagatatgg tgctcgtcgc cacatcgtct gcttgtactt   2100
gatggcattc aggatcctg                                                2119

<210> SEQ ID NO 93
<211> LENGTH: 2571
<212> TYPE: DNA
<213> ORGANISM: Eucalyptus grandis

<400> SEQUENCE: 93
aaggtaactg gttcagcaga gcgcagatac caaatacttg ttcttctagt gtagccgtag     60
ttaggccacc acttcaagaa ctctgtagca ccgcctacat acctcgctct gctaatcctg    120
ttaccagtgg ctgctgccag tggcgataag tcgtgtctta ccgggttgga ctcaagacga    180
tagttaccga taaggcgca gcggtcgggc tgaacggggg gttcgtgcac acagcccagc    240
ttggagcgaa cgacctacac cgaactgaga tacctacagc gtgagctatg agaaagcgcc    300
acgcttcccg aagggagaaa ggcggacagg tatccggtaa gcggcagggt cggaacagga    360
gagcgcacga gggagcttcc aggggggaaac gcctggtatc tttatagtcc tgtcgggttt    420
cgccacctct gacttgagcg tcgattttg tgatgctcgt cagggggggcg agcctatgg     480 aaaaacgcca gcaacgcggc ctttttacgg ttcctggcct tttgctggcc ttttgctcac    540
atgttctttc ctgcgttatc ccctgattct gtggataacc gtattaccgc ctttgagtga    600
gctgataccg ctcgccgcag ccgaacgacc gagcgcagcg agtcagtgag cgaggaagcg    660
gaagagcgcc caatacgcaa accgcctctc cccgcgcgtt ggccgattca ttaatgcagc    720
tggcacgaca ggtttcccga ctggaaagcg ggcagtgagc gcaacgcaat taatgtgagt    780
tagctcactc attaggcacc ccaggcttta cactttatgc ttccggctcg tatgttgtgt    840
ggaattgtga gcggataaca atttcacaca ggaaacagct atgaccatga ttacgccaag    900
ctatttaggt gacactatag aatactcaag ctatgcatcc aacgcgttgg gagctctccc    960
atatggtcga cctgcaggcg ccgcgaatt cactagtgat tggcccgggc tggtctggag   1020
tggccaccat cggcataatg actaggaacc cggaacatca actgatggaa gaaaagccga   1080
cattcctcat caagagctcc tctcactcct tccccactac tactataggg cacgcgtggt   1140
cgacggcccg gctggtctg ctgtcatatt tgtatatgag gtcctatgta tgcttgctat   1200
gtgacctcct tcatgtatgc tgtgaagaga gtgtagcagt aacatggcca tctgcgaaat   1260
atggattcac cttaaaatct gatgattttc agaaaacgag gaaggtgctt gccgagaaga   1320
ttgcacagct caattcagct atagatgatg tatcctctga gctccgaact gaagaatcat   1380
cagatgagat tgctgttgcc cctgatgaaa ttgaagctgc tgtttgatgg cccaaacctc   1440
ccaggcctac gatcatggtc atcttctgtt ttggtgcaat tggctctacc ttttttggtgg   1500 cctccatata acagaataat ggttcatatt gtaaatcttc tgtttatttt ctaaagacca   1560
atgcactcag tttctttttga tatgattgtc tcgattgagg aagtgcatca ttcgtggtat   1620
gattatgcag aataccattt aactcagcag actttgtacc gtatcatcgc agcttttccc   1680
ttcttgtgta tgcataaatc tagtccttca ttgaaggtga tcgccgttac agtctggata   1740
gtgtgtgcca tcagatggca ctacgattag tgtggttgac atggtgtcaa cttgaaagcc   1800
aattggtgac gatggtactt aatgtaagat tggcagatgg tgagaacgag attttgctcc   1860
agaatggcaa agcaaggcta agttgtagcg aatcaaatga tctacgaacc atcctagctg   1920
```

-continued

```
gctgtgtgac cacacactga agttctattg aactaagcca gttatggatg atatgggagg    1980
agaaaattga gaaatccatc agatggagtg ttggccgtgt tgggcttttg tcgcaggccg    2040
atacttcgaa ttcaggcgta ttttttattcc tgactgccgc ctctcccgga aagggaaggc    2100
ggatattatt ctctgaacga tttccaccat caactccaca tcgatctcca agccagaaat    2160
atacacaccc caattttctt ttaaatatat gggacatata tggtgtaggc tctcgcgcat    2220
gttaacacat aagctctctc aacaaaaatc tggctcgtgc ttttaaccga gaagttcacg    2280
agtcattgaa ggagtggcct taggggagg gagagagatg gattggtggt taaaatcagt     2340
ctgtggctca catttatacc gtggagatcc cccaacagca accttatccc attatatatc    2400
cccacaacac catattcacc actcgttcct tctaattggc ttccaaccat aattcacaga    2460
cacacatgta gtgaccaatg agaaaggaag aaaaatacag gctttcgaaa gctagtgcgg    2520
tataaataac ctgggaaaag caagccgctt gagctttagt ttcagtcagc c             2571
```

<210> SEQ ID NO 94
<211> LENGTH: 1406
<212> TYPE: DNA
<213> ORGANISM: Pinus radiata

<400> SEQUENCE: 94

```
aaagaggcgg aggaattgtc tagatggtca aaagtgaccg gaatctaagc aaaaaatttc      60
aaaaaatgtt gtaaaggtag cgtttgaatt gtgttttttga tggtggaaat ggattcaacg    120
ccatcaaaaa cgtctaagac acctaaaatt ttgaattttta acaactatat cttggattta    180
caaaaatcct tgccggattt tctctaaact ccttcacctt acgcaaaaga tatatatttt    240
tttgtgtgat gttgtgcatt ataagtttga tagtgaagta atgatatata tcctttatgt    300
gatggatgat tgaataatga atatattaaa tgaaataaat aatgatggga taatgaatat    360
attatatgaa ataaatataa agtaaaatgc tattttttaa tggtgttaat gatgaattag    420
tatcatcctt aaataatttg ttagtgaatt attaaaatga tgagttagca tggtcgttaa    480
ataaattgtt agtgaattat tatatttata tatttcctta ttagaaagtt ttttttttgt    540
aaaagttttc cttgaacttc acccatattt aattatcaat aatttatatt taataaatga    600
tatatataac ttctagcaga atgacacgcg acttgtatat cttttcattt tttaacccat    660
gaaaaccgat tagggtattg caaattaggg cattgccatt caaataattc tcagatgaaa    720
gattctctct aacaattaca aatgattatt ttttttccatg agtgttgcat gttcgaacgg    780
tctgcccagt ctgtgagaga gcatagagaa ccctccctgc ccaatttgtt agagcataga    840
gaaccctact gcatgagtag taagaaaaat attcggtctc aattcggcaa agaccacctc    900
gaatggatga cttcaacgac aatctcatga tagtgttctg atcagcacca gttcacctat    960
atattttatc tagggtttag tttgcatgta tcaatcctct ggtgcactag gtaattcttt    1020
cctagtatca tatatcctta atactgtttt gtctttttaat ccatggctac catcagaaca    1080
agctcaaagc agaaatcggg agcatcagcc atcctcttgc ttatcgcgct tgcagggtta    1140
gtaaatgcgt gcaacgctgt gggtattgag ccaatgtgcg cactgtggt gtcgagtctt     1200 ctgaggcttc tgccatgcag gacggctgtt gatccctcaa ttgccgccat tccacttcca    1260
agctgctgca acgcggttga gtcagctggg cttcaatgcc tctgtctcgt cgttaacggc    1320
cctccttttc caggggtcga ccgcggcctc gcaatgcagc tgcctgccaa atgccatctc    1380
acccttcctc cctgtaacag ttagtt                                         1406
```

<210> SEQ ID NO 95
<211> LENGTH: 2546
<212> TYPE: DNA
<213> ORGANISM: Pinus radiata

<400> SEQUENCE: 95

| | | | | | |
|---|---|---|---|---|---|
| ctggtagaac | aagcagctca | aggagcacca | aggcacgagc | ccactttgca | tgttgtagac | 60 |
| taacgaattt | tacattagaa | taaaatatgt | cgacaatatc | gaggagatct | tctccaaaat | 120 |
| ccaactcatt | aatctctatt | atgcacaaac | gagtgatgtg | tcgagactca | tctgccaaca | 180 |
| agccatcaac | atcaagaagg | gaacggaata | gagccaaagg | gaaccctaga | gaccctcatc | 240 |
| cacataataa | tgaaatattc | cacgtgtgtt | tttcaaaatt | tgaaaatttc | atgtatttt | 300 |
| tggttgattg | gttgtggtct | ggtttttttcc | aaattcaatc | tagttcaagt | ttttggagtc | 360 |
| gaccagttgg | gtaaccagtc | taattctggt | aacattgcat | tgtacttgat | ctcaataaaa | 420 |
| gcatatagga | tagaattatc | ttctgtcttg | atggtttcca | tgagaaccaa | ctgctatact | 480 |
| atgaaaaata | tcaatgttcc | acaatatttt | tgggacaagg | gaacacaaga | ttgagtcaac | 540 |
| agttcaggac | cccagaaaaa | ttattcctga | gttcgcagat | tattttccta | aaagtgaaca | 600 |
| attcaagacc | ctagccaaat | cattcccaag | tccaagttat | gtgacactgc | gactaacaag | 660 |
| gcaagttgga | agaaaccatc | aatcaatctc | ctagttaatg | acagtccttg | taagaagttc | 720 |
| aagaagatta | acaccagaag | aggtcatgct | gactgctttt | atccaattct | ctctgctctt | 780 |
| caccaacaga | aatagccaag | atggttgtac | ccattcccta | atctaattta | ttatatgaat | 840 |
| ttctctttat | ttttctacat | ataaaaaaca | aaaacttttc | ttgatggtca | aacagaaaag | 900 |
| gcagttcgat | tggatttaaa | catccaaata | cctcccacag | attgagaagg | ccaagcccca | 960 |
| atccaacagt | ccatgatata | atatttattc | aatcacactc | aagataatgc | aatgaaggtg | 1020 |
| caccacgcta | ttagattctg | cacagaactc | agatgactgt | aattatcaac | tttaaccagg | 1080 |
| agtaatttaa | aaactcaatt | gtgcttcagc | tatgtggaaa | actttggca | ctggaaatgg | 1140 |
| tataaatgtt | gttgaataag | caaacatttt | tcaagcactg | aattcaaagt | caagtcaaag | 1200 |
| gaacatctta | cttgggctgt | acaggaaatc | tgaagtacaa | aattagcgaa | aaacaggag | 1260 |
| aaagagagta | gtcattacat | gttataacat | taccatatag | gattttgtaa | tacttcttga | 1320 |
| tatttcaact | tcccgactga | tgaaatgtat | gccactacag | aacaggtcag | tcatgtatgt | 1380 |
| gagcaattag | ccaaactagg | tcctaaggtt | caaccagtgc | agacaacgct | gtaactgaaa | 1440 |
| caaatttgtg | ggacaattaa | aaattctcta | ccaggatagt | tgtaccagta | ggtgcccttt | 1500 |
| tcaaaccatg | atttaaaaca | aagggtggc | ttaccacttg | accaaatcat | ttaataacca | 1560 |
| accccctcgaa | catatcaaga | aagaaaacat | ctgcatataa | gtaaattgaa | agatgatatt | 1620 |
| taagaggcac | tgccttaaat | tttccatttg | gacaaatcca | cattgcttga | taagcataaa | 1680 |
| accttggtta | agagcaagtt | tagggaacca | tcaaatatttt | ctacatactt | tacaatagtg | 1740 |
| tgtttataaa | gctaatcaaa | tgcttctatt | taaatatata | gcaacctaca | caagaaattc | 1800 |
| actaggacag | caatcacttg | gccaatgtga | ttaccaatat | aaccatactt | gaagagcata | 1860 |
| cataaatcac | aaataatgat | tcaattagaa | atatcttaaa | gataaactat | tattcaatgt | 1920 |
| acatgttaca | aagaacctca | cctgtccgcc | tttgaggagc | aagtagacaa | ctaaaagcgg | 1980 |
| aggttacatc | ctgaactgaa | cttgttctcc | tctgttccaa | gaacttgcat | tgtatttga | 2040 |
| gtaacttcac | tcgtgccgaa | ttcggcacga | gaaaacactt | tgattgcttc | cgcgggtggg | 2100 |
| ttttactttc | tctggaatag | ttagttccgc | cgttttgga | agatttatca | gaatggccaa | 2160 |

-continued

```
aattcaggtg tcaaacggga gcgtcgtggt ggtggcggcg atgatattta tggtggcggt    2220
ggccatgcaa aaccatcacg tcgccgccca aagtgctgac tgcgcaccac cgcggagttg    2280
ctgagcccct cgcctcggc ggtgggaaac aacccgcaga ccccactccc gaatgctgtg    2340
ctgttctcca gaccgccgat gtcgactgca tctgcgccct cgtcgaatca accataaaat    2400
tgccttccga atgtggtctt gacaccccc agtgcccaag cgactagatt ctcaagaccg    2460
tgactgagtg ttggtttcag agccagtaaa cattcattct gctaataaat gagtgtatgg    2520
agctttaata ttggaaaatg cttcat                                         2546
```

<210> SEQ ID NO 96
<211> LENGTH: 4726
<212> TYPE: DNA
<213> ORGANISM: Pinus radiata

<400> SEQUENCE: 96

```
gattactata gggcacgcgt ggtcgacggc cctggctggt cctaggacac cgtaatatat      60
aacctcgaca tggcttacaa agctttgact tgcattctca ttgggcttac aatggtgctg     120
ccaaaaatga aaagtacat atgtacccct gttgaaatga gcagtaatag gcttgaacaa     180
tagtgaattg ctacaaaatt atgaatgcct ttctttgctt gaatgtgggc taaggagaag     240
tgggatttac atttgacttg caaatcctaa gacttgtcta gagctaagcc tccagaggag     300
gaaccatctt acatagtctt gagtctagag cggagaagat agccaaattt gaaaggaaac     360
ttttatttat ggggagaagg caaacaactt gaggggaag gatgatcaat aagtagggta     420
agggaatcca caacagaggg cactaaggaa atgggggtgt tagaattggc aactagggcc     480
aaattccacc ttgggatagc tctctggatg gagatgatga ttgcattaga ttcctctttt     540
cgagaggacc aagattgata taaagatcat ctcatttgga caagcatagg tatgattttg     600
aatttatacc cactcatgca caatttttt aggtccgcca catcatcatg taggctcatg     660
aagcccaacg gacatgactc ttcgcccta tcgtcttgta taaatacaag tgtcctccca     720
cctcatttgg catcttcatc tcttacagat tctctcttct tccctcattg gttcttgcat     780
cattgggcat tctctctctc ccacgtgtgg cacaaggagg atgaaattac aagaccgaaa     840
ataatagaaa ttttgcaatt tgaccagcat tgaccatgac cttccaagca tcattcgact     900 tcaattttt tgggttattt ttgtctcaac aagccgcata ttttggcaaa aaaatcgagg     960 cattctggc acttcgacta caaaccaaaa ttgtaggttg actgcaaatt tcaaatagtt    1020
tgactattga cattgtcact gttttcgatt gactttgacc tcctaattag gccgagtttg    1080
actaggggag gctgatttgt ttaaggaca tttgattgat gctttgacta gcattgactt    1140
ttatagttaa ggttgaagtt tgactacagt tgactgcata aatttgcaga gatgttttga    1200
ctttgaattg ggcaagtcaa tttgaatttt gtactatctc tctattttga acatttgata    1260
taataataag aagattcgat caagggttt tccccgcatt gggttttttc cctggcatcc    1320
gccaaatctg gtgttctctt gtctttgctt gtcttatgca ttttgtttca ttttctatct    1380
acttttactg tcaatgtgat tattgtcagt gttattggaa attggaaatt gtgattgggc    1440
tgctaaggaa cattgaagta aattgtgcta acaaagaac ataccattgt taacgaaaat    1500
taacaagggg gaaacacaga ggaatggttg caattgcaag attgtcattg attttgactt    1560
caagtgagga aggtcgcgtg gaggtcgcaa ggggagagga ataggagaga aggccctatc    1620
aacttgttca aggagagggg caatacaagg aatggaggaa ccctcaccaa tgaataatcc    1680
atgcacaaaa gtaatagaat gaacaaactt accacacgga agagcttcct tgttgccaaa    1740
```

```
agccttgcct ccgagacctg aatcctccaa tgcatcaaaa ttattgatca ttgaatcaac    1800
cacgattagg gccacttcct tggctaataa agcaattagt gtagcaaatt ctaaagctaa    1860
cttcaaagaa accttagctt tccaaaaaac aattgaaggg aggcaatgaa gatggcttat    1920
cacactaagc ctaaacatgc cccaccctat ggcatctaaa acatctaaaa gggattcact    1980
agtaatcgat cttttgtact tatgaaaaat tcccatgaac caattcgatc tcttccaaaa    2040
agccatctat gaggtcaacc tcaacctggc tctaatgttg attgagcttg taatcctagc    2100
cctactccaa tcttaagaac caaccaattt tatttccaat tgattcaagg accccctacac   2160 tccaaaagaa gcaagggaag gccaaggaga atgggccaaa cttgagcaga gaataaggat    2220
tctctgtgag ggtcgaaact aacatcccat tcacgtaaaa tcaaaccaga gagacctcaa    2280
ctccaactct tcttaatgat gaagcacaaa tattattttg agtgaaattt gaaaccaaga    2340
aaacctctca ctaatatatg gaagaggggc aatattcaac cattggtacc caaatcgcct    2400
caagacactt accaagggag ccaaccaaac aatcttacca caaaaccaac caacagtgtt    2460
tttacccaca agctcttgga tggaatccag gataatgtct tcaccaacaa ccatcttatg    2520
tctatccttg caagcacaaa tgcattgagc tttagatttg gagtgcataa atacaggggg    2580
gtatccaggg gggggagggg gtttgctaga accccagact caccaaggca tgaagacaaa    2640
atgaggagag agggatctag attggggat gcaagttgat gaagcatgaa aaggcaatcc    2700
atcaccctgc atggcatatt tacgaaggtt gttcagagga atgagaacta atggatgaac    2760
aacagctggt agaacaagca gctcaaggag cgccaaggca cgagcccact ttgcatgttg    2820
tagactaacg aattttacat tagaataaaa tatgtcgaca atatcgagga gatcttctcc    2880
aaaatccaac tcattaatct ctattatgca caaacgagtg atgtgtcgag actcatctgc    2940
caacaagcca tcaacatcaa gaagggaacg gaatagagcc aaagggaacc ctagagaccc    3000
tcatccacat aataatgaaa tattccacgt gtgtttttca aaatttggaa atttcatgta    3060
ttttttggtt gattgttgtg gtctggtttt ttccaaattc aatctagttc aagttttgg    3120 agtcgaccag ttgggtaacc agtctaattc tggtaacatt gcattgtact tgatctcaat    3180
aaaagcatat aggatagaat tatcttctgt cttgatggtt gccatgagaa ccaactgcta    3240
tactatgaaa aatatcaatg ttccacaata ttttttgggac aagggaacac aagattgagt    3300
caacagttca ggaccccaga aaaattattc ctgagtttgc agattatttt cctaaaagtg    3360
aacaattcaa gaccctagcc aaatcattcc caagtccaag ttatgtgaca ctgcgactaa    3420
caaggcaagt tggaagaaac catcaatcaa tctcctagtt aatgacagtc cttgtaagaa    3480
gttcaagaag attaacacca gaagaggtca tgctgactgc ttttatccaa ttctctctgc    3540
tcttcaccaa cagaaatagc caagatggtt gtacccattc cctaatctaa tttattatat    3600
gaatttctct ttattttct acatataaaa aacaaaaact tttcttgatg gtgaaacaga    3660
aaaggcagtt cgattggatt taaacatcca atacctccc acagattgag aaggccaagc    3720
cccaatccaa cagtccatga tataatattt attcaatcac actcaagata atgcaatgaa    3780
ggtgcaccac gctattagat tctgcacaga actcagatga ctgtaattat caactttaac    3840
caggagtaat ttaaaaactc aattgtgctt cagctatgtg gaaaactttt ggcactggaa    3900
atggtataaa tgttgttgaa taagcaaaca ttttagaaca ttttttcaagc actgaattca    3960 aagtcaagtc aaaggaacat cttacttggg ctgtacagga atctgaagt acaaaattag    4020 tgaaaaaaca ggagaaagag agtagtcatt acatgttata acattaccat ataggatttt    4080
gtaatacttc ttgatatttc aacttcccga ctgatgaaat gtataccact acagaacagg    4140
```

```
tcagtcatgt atgtgagcaa ttagccaaac taggtcctaa ggttcaacca gtgcagacaa    4200
cgctgtaact gaaacaaatt tgtgggacaa ttaaaaattc tctaccagga tagttgtgcc    4260
agtaggtgcc cttttcaaac catgatttaa aacacaaggg tggcttacca cttgaccaaa    4320
tcatttaata accaacccct cgaacatatc aagaagaaa  acatctgcat ataagtaaat    4380
tgaaagatga tatttaagag gcactgcctt aaattttcca tttggcaaat ccacattgct    4440
tgataagcat aaaaccttgg ttaagagcaa gtttagggaa ccatcaaata tttctacata    4500 cttttacaata gtgtgtttat aaagctaatc aaatgcttct atttaaatat atagcaacct    4560
acacaagaaa ttcactagga cagcaatcac ttggccaatg tgattaccaa tataaccata    4620
cttgaagagc atacataaat cacaaataat gattcaatta gaaatatctt aagataaac     4680 tattattcaa tgtacatgtt acaagaacc tcacctgtcc gccttt                    4726

<210> SEQ ID NO 97
<211> LENGTH: 635
<212> TYPE: DNA
<213> ORGANISM: Pinus radiata

<400> SEQUENCE: 97
aaattctatg aaaaaaatcc aatcatatta aaagtccaat tgattagcaa ttttatgaga     60
aaaatccaat tatgttaaaa gtcactgagt gtggccgaaa ttgtgaccga aattgaatgc    120
aataaccgag ggtttttcaa accaaggtta agcctctcat cattggggtg tgtatgaaaa    180
tgtaatgggc atcgataacc ttttattaca acttcacgaa aattgcctct attcaatggg    240
tgtggatgaa aatgtaagtg cgcatcgata atggaaagcg atatgcagca aaatcaataa    300
acctgacttc ccatgtgagt gatgatttga tcgtacaact gatggtgtga agttactttc    360
agcttcacct tcgggcataa tcagggaagt agggccaagt ttgcttagta tcactctaat    420
ccccaacacc gtgattacta tcttcatcaa caatggccac cttcgtcatt actttaactg    480
gtgggataca gctactttac aactgtaaat tgttgaggc agcctatcct cagcctatac    540
atactaatta ttgcagctcg attaggtatc tgctgtgaga atagctgtgt atctctgcgc    600
tggttgcagg atccaagttc ctctcagagc cctcc                              635

<210> SEQ ID NO 98
<211> LENGTH: 468
<212> TYPE: DNA
<213> ORGANISM: Pinus radiata

<400> SEQUENCE: 98
ctggtaaatt gagattccaa attattgatg cgaagcttcc tcgtggctgg tcggtgctgc     60
tggcatccaa accctaaatg aaaagaaaa aggtgtccgg acggattttt ttagtatttt     120
tttcttattt tttttatgaa ccgtcggatt cgagatcgga cggcgatccg aaactgcaag    180
cgtcggccgt cggatgcagc atcggacggc aaagaaggaa ccctaaaacg cattgcaacg    240
tgcttggtgg gtggagggtc tatggccagt atatgttgat aacaagggag aggaagtagt    300
cctcttcatc tagtgcgagt ctctctgctt ttctacgccg ctgcgaagct gttctgtggt    360
gtttctgatt ctccagactc aggcagtcgt ttttgtaaga gaatttagtt catcatggga    420
aaggagaaaa cccatatcaa cattgtggtt attggccatg tcgactcc                468

<210> SEQ ID NO 99
<211> LENGTH: 222
<212> TYPE: DNA
<213> ORGANISM: Pinus radiata
```

```
<400> SEQUENCE: 99
atccaaaccc taaatgaaaa agaaaaaggt gtccggacgg attttttttag tattttttttt    60 tcttattttt tttttatgaa ccgtcggatt cgagatcgga cggcgatccg aaactgcaag   120
cgtcggccgt cggatgcagc atcggacggc aagaaggaa ccctaaaacg cattgcaacg   180
tgcttggtgg gtggagggtc tatggccaga tatgttgtaa tc                      222

<210> SEQ ID NO 100
<211> LENGTH: 597
<212> TYPE: DNA
<213> ORGANISM: Pinus radiata

<400> SEQUENCE: 100
aaatgaggca gctaactatt tatttggttt tggcttcact gacttgttcc ttagtgtatt    60
aatgaacaat ctctttagac tcagagatgg tgagaaagat tctatgagaa atattcttgt   120
tattgcttcg actcatatcc cccaaagagt ggatccagct ctaatagctc caaatcgatt   180
agatagatcg atcaatattc gaatgcttgt tatcccacaa cgacaagggg aatttcctat   240
tcttttatgt agcaaaggat tatactcggg aaaatgtccc gatgaatttg gatctataac   300
catagattat gatgcacgag ctctattagc tcaggcctct ctgctgctcc ttggattgca   360
atctcattct ctgatttgcc gtgctgtttg ctctgctcac ttcagcccag atggagacct   420
tcttgttcac atcggagtct gtaaatgagg gacacccaga caaactctgt gaccagattt   480
ctgatgcagt gttggatgca tgcctcaccc aggaccccga cagcaaggta gcatgcgaga   540
cttgcactaa aacgaacatg gtcatggttt ttggtgaaat caccaccaag gccgatg      597

<210> SEQ ID NO 101
<211> LENGTH: 669
<212> TYPE: DNA
<213> ORGANISM: Pinus radiata

<400> SEQUENCE: 101
cctggaaatg ctatattaac tcaacaaagg attttcagcc aatcacaatt tgacaggttt    60
gaaatgaaag attacaggca tttccaatgg aacagaatat aattacttta ttccctcaaa   120
gtatcgtata aaataaatct tttgctccac acactttgga aaatacatttt tcaacaatgc   180 accgacaaac tttttctacc acgttatgga accatacaag ttaaatttaa acacgaatta   240
cgcgtatatt tctaataaat cgatggttga gattgaatgc cgtgggcgat tctcacgcgt   300
ccgattggga tcactagtcc atcactcatg gtctgcattg cctttaaatt ggcggggcga   360
ggaaagacca atgcgtcatt ggtgtagacg agctctatta gctcaggcct ctctgctgct   420
ccttggattg caatctcatt ctctgatttg ccgtgctgtt tgctctgctc acttcagccc   480
agatggagac cttcttgttc acatcggagt ctgtaaatga gggacaccca gacaaactct   540
gtgaccagat ttctgatgca gtgttggatg catgcctcac ccaggacccc gacagcaagg   600
tagcatgcga gacttgcact aaaacgaaca tggtcatggt ttttggtgaa atcaccacca   660
aggccgatg                                                           669

<210> SEQ ID NO 102
<211> LENGTH: 230
<212> TYPE: DNA
<213> ORGANISM: Pinus radiata
```

```
<400> SEQUENCE: 102
atccacctcg gaatgaaatc actatgcaca ctccaccttt tttttggctt cttttctcgt      60
tgcctttacc atcagaatca agcacgaaga gtaaatatca cccatgcttt acaagtgggt     120
tggtagcatt agcgattccc ttcaccaaat gaaccctttg ctggtgatga gtggacaacc     180
taaagttgtt tgctggtgat gagtggacaa ccagagtggg ggttggggaa                230

<210> SEQ ID NO 103
<211> LENGTH: 596
<212> TYPE: DNA
<213> ORGANISM: Eucalyptus grandis

<400> SEQUENCE: 103
actttgaaag ggtctcgagt caaagtgctc aaattgagag ggagaatttt agaacaaaat      60
cagatttgga gaatacatgc cattttaggg ggattttggg gatttcgcat atggcgtcgc     120
gtcgtcggcg ccttcttctt tacagattgt atcctcccat taaccgcgtg gacctgcact     180
gtaaccccga acggtgggg gccaatttcg tctttccgcc tcctccactc agcttcgtgg      240
aagattaaaa tcctcaccgt ccgtgcaaac gccacgtggc gcgttagttt gcgcgtggaa     300
aggtcctcac gaaccgtaaa gggcaaaaaa aagggaaaat aaaaaaggag gaggaggagg     360
gaggaggaag aattgtccga ttgaaaataa gagtgcggtg gtgtggtgtg ggtagatctt     420
gaattgaacg agctcaatcc gcgtatttaa acccgccccg cttcctcatt cttccttgtc     480
catttcaact ctccctctct ccctctcttc tgccctcga tcgatccagc gatcttccta     540
tttccggacg cggggagcag ctcctcttgt cgaaggttct aaattagtgt ggagag         596

<210> SEQ ID NO 104
<211> LENGTH: 653
<212> TYPE: DNA
<213> ORGANISM: Eucalyptus grandis

<400> SEQUENCE: 104
aaaattttcc tttatttct tttcattaaa aagataaata aataaaaaaa aaaagaagg       60 aaaacacatc gaggtgaggc ttaaaggtgc taggcaagga ccaccaagcc tacacaaggg     120
tcggcgaccc tcaccaatgc tggggcgagg gtgagcaacc ctcatccaaa tctggagagg     180
gttgtcactc gagaaagggt cactggccct cccctaaccg ctactaacat cgttggcctt     240
cgtcaccacc gcactaacaa tgggccacta ttttatatt tttcgtgata ttaatcctat      300
taaaaatgaa aatatctcct taattaatta agcttgtcag gaccgatgta aacaaaatta     360
atgtaaatgg acgcgccttt gacttgccaa caaactcgaa acgacgtttc ctccgtctga     420
taactatctc gcgacctccg acgacatccg acggtgcaga tcgggtcccg gtcaaccatc     480
cagatccacc cgattttctc ccggccctcg acaactccca ccaccactc tttcctccct      540 cttccttcc ttcctttctc accagatttt ccgagaaaaa tcacagagag agaaagaaaa     600
acctcaccgc ctagagagag aaagagagaa agagggaaga gagagagaga gag            653

<210> SEQ ID NO 105
<211> LENGTH: 342
<212> TYPE: DNA
<213> ORGANISM: Eucalyptus grandis

<400> SEQUENCE: 105
agttgggtaa ccagtctaat tctggtaaca ttgcattgta cttgatctca ataaaagcat      60
ataggataga attatcttct gtcttgatgg tttccatgag aaccaactgc tatactatga    120
```

```
aaaatatcaa tgttccacaa tattttggg acaagggaac acaagattga gtcaacagtt      180
caggacccca gaaaaattat tcctgagttc gcagattatt ttcctaaaag tgaacaattc      240
aagaccctag ccaaatcatt cccaagtcca agttatgtga cactgcgact aacaaggcaa      300
gttggaagaa accatcaatc aatctcctag ttaatgacag tc                        342

<210> SEQ ID NO 106
<211> LENGTH: 342
<212> TYPE: DNA
<213> ORGANISM: Eucalyptus grandis

<400> SEQUENCE: 106
ggtctggaag ctcatctctc caatttggtg aagattacag ctataagagg tagctatgat      60
gtgctggcca aatgcaagtg atgaaatacg tggaccacca agtgcgaagg cattcgaaga     120
acgagggtcg aatttatagt gggcgaagga tgattaggtg gaatatgaca agaaaatagg     180
tttgaaagag aaataaatat tatgatagtg aagggtcttc acatggttag tttgatctgt     240
ccgagggtgt ccacccttgt ctgatccgca attgctcttg gtcgtgctga attttagagt     300
gtagccaaag taagaatttt cctttcactg tccggacatt tc                        342

<210> SEQ ID NO 107
<211> LENGTH: 948
<212> TYPE: DNA
<213> ORGANISM: Eucalyptus grandis

<400> SEQUENCE: 107
ctgacaaatg caaatatcta aaccattgg ttgtttggtg cttgcaagtc tggattaccc       60
cactttatgt ttcaccttc aataatgaat aacaaggtac tcgggaaaaa aaggaaaggg     120
aaattcgcac aaccaaagtt gctatgcaga agtcaactca atcctaatca agttgatgag     180
agtgttgggc cctatttct gcagcaaaca tgaatctcga ttcatctccc tcgcaaaaga     240
taaggaagct gcaaaagctt cctcctaag tttgttggca agcaaattga ttttgtacca     300
gaaataaata caaagtgaaa cccaagcaat cacgcatggc ctgatttgtg ccatgtccat     360
ttgatctccc tctactattt ttcctgcttt ctcaagcaaa ctagttgctg taacagtgaa     420 tgatccccg gctctctctc tctctctctc tctctctctc catttattcc atccatgttt      480
ttgcttttcg cacaacactt atcattgagg tgctaactac tgaattcccc taactaaaaa     540
ttggaacctc tcacctaatt tcattttctc ccactttgat gagcaccact ctctttccca     600
gatttcaaat aaattgccac tctctccctc tcttttcctc acacaaccaa aagccttctt     660
caagtaccac ttcttcactg tcctctcttc acaatccccc tcttaccaag agcaaagcaa     720
aaaacatgat gaagagactg tcattctgc tcctactggt cctgctcttc caatgctcta     780
ccaccttggc tcagcctgcg gccgccccag ctccgcctgt gatagccccg gctgcacctg     840
ctacgcctgc cttaggcccg gctcctcctg tcttaggccc agctcctgca ggcccaaccg     900
acatcacgaa ggtcctcaag aaggtgagcc aatttacggt gctgctca                  948

<210> SEQ ID NO 108
<211> LENGTH: 362
<212> TYPE: DNA
<213> ORGANISM: Eucalyptus grandis

<400> SEQUENCE: 108
ccatcactca taatcaacaa ggatatctca tcatgtcttc caaccaaatt aaaccccaga      60
catctctaaa gcagtatgga aaagaaaaca gtccggaagt ctctagctca aaaactgtaa     120
```

```
cccgaccta attccggttg tctctgatta catcaattct tatgtcttaa cactccattc      180
gcacctccac aataaataga tcggcccttc atctccctt accatcgaat ccaatcccaa       240
aaacacttgc tcagacacca tcaaatcctt cgcaaagtct tttcttaca aaaaacaaac      300 gaaagcaacc atgaagcacc agttcattgt tctggctctc ttattcctca tcaacacagc      360
cc                                                                    362

<210> SEQ ID NO 109
<211> LENGTH: 326
<212> TYPE: DNA
<213> ORGANISM: Eucalyptus grandis

<400> SEQUENCE: 109
aaaaattaca atcaatggtt atcaatggat gttacaaagg gaggttacat atagaggtta       60
taaaagaggg ttacaaatag atgtctcaaa caattaccaa gcggttagat tgactccact     120
attttgacgg ttctcttgac tttactatct caacgattac tttatttcat catgttgacg     180
gttgcatcca tgattgttga cttcactttt tgtcgattcc ttcaagctgc tgattcttca     240
agttgccaat aattttattc ataaatgacg aaactctagc ctcatccatt aagtttgtta     300
cttgtccaca ataattaaat tcggta                                          326

<210> SEQ ID NO 110
<211> LENGTH: 296
<212> TYPE: DNA
<213> ORGANISM: Pinus radiata

<400> SEQUENCE: 110
tgctcccggt catgacaccg ccattctcgc tcttcatttc caattcaaat cacttggttg      60
ttgttcacac acacgggtct ttatatgacg agtgctgctg cgattataaa tagacggggc     120
aattacaaca aaaactcaca gcatttgaag gaagttggag tggtagagtg agaaatacac     180
agcctaatct gaaggaagtt cgagtaatag agtgagaaat ggatcttctt ctcctcatga     240
tgatgcttgt gatgatgggt gtagcaatgc ctactcattc tcaacaaatc actagt         296

<210> SEQ ID NO 111
<211> LENGTH: 723
<212> TYPE: DNA
<213> ORGANISM: Pinus radiata

<400> SEQUENCE: 111
cgttttacgc gggaacaatg aaaacagtac aatcgaaaga gtcaagtcgt gaggttcatt       60
tcgatgaagt tcccagagat tgtctcgttc aacgtttcct ctttttcgg gtcaagtcgg      120 gtacagaaga ccactttctt tacgcggtca agacaccgcc attctcgggt caagtcggga     180
ggtccctcct gctcttcctt tttccaaatc cgtaaaattt acagattttt ttaatgtatg     240
aagcccactt tctttatgcg gttgctccca gtcaagacac cgccattgtt gttcacacgc     300
acgggtcttt atatgacgag tgctgctgcg attataaata cgggcaa ttacaacaaa       360 aactcacagc atttgaagga agttggagtg gtagagtgag aaatcatttg aagggagttg     420
gagtggtaga gtgagaaatc atttgaaggg agttgagaaa tatattggga atctctcttt     480
tttgcagcaa ttagatcttt cctttaatgc tttgagtggg agaattccga cagagttggg     540
gaacctctct cttttgcggc aataagttgg agtggtagtt ggagtggtag agtgagaaat     600
acacagccta atctgaagga agttggagtg atagagtgag aaatggatcg tcttcttctc     660
```

```
ttcatgttga tgcttgtgat gatgggtgta gcaatgccta ctcattctca acaaatcact      720
agt                                                                   723

<210> SEQ ID NO 112
<211> LENGTH: 1301
<212> TYPE: DNA
<213> ORGANISM: Pinus radiata

<400> SEQUENCE: 112
actatagggc acgcgtggtc gacggccctg gctggtagcg acagagctgg ttcagtgacc       60
gttcgtgatt agccgcagta aaacaaaacc ctaaccgtaa ccctttcgcg cagattccat      120
ccttccccgt cctaccaaaa cccaaacttc ttgcccgaac tcaccttcta tgtattaatt      180
cttattatta tttaataata ataaatagtt aaacataaat ttataaatta attaattttt      240 atgatttta ttttagttta aaaatgtgac attgttatag attaatgctt atgaacgttt       300
attggccata attaccctaa ttaattataa ttaaaatata tagttataat taaaaaattg      360 tatatttat aaattgaatt aagaatttct gatgatattt catcattcaa ttccatctta      420
tcaaagttag agggaatagt taaccatgta ctagatctat tcatagctaa catttgccaa      480
gttcgtacta ggagacttgg atttttttta aaacataatt ttggcagtaa aaagtgaatt      540
ctattgtttt gaaaacaaaa caaaatacag gaagcgtgat tgtggggttg ttgttgaact      600
tgcccgggca aagaagaat gattagcggt agaggagtta gtagttacgt tcaactaaat      660
gcgtgactaa attatttatc ctccgccatg gaagcaggtg attcacacac aacttgctgc      720
acacattgct ctcaaacctt tcctataaat atccgtagca ggggctgcga tgatacacaa      780
cgcatttaat caaactactt tgattacttt ctgtgggttc tactttcttt gaatagtcag      840
ttctgctgtt tttagaagat ttataagaat ggccaaaatt caggtatcaa acgggaacgt      900
cgtggtggtg gctgcgatgt tatttatggt ggtggtggcc atgcaaaacc atcacgtcgc      960
cgcccaaagt gctgactgcg ccgccaccgc ggagtccctg agccctgcg cctcggcggt     1020 gggaaacaac ccacaggatc ccactcccga atgctgtgct gttcttcaga ccgctaatgt     1080
cgactgcatc tgcgccctcg tccaatcaac catgcaattg ccttccgaat gcggtcttga     1140
gactcctcag tgcccaagcg actagggtct caagaccgtg actgagtgct ggtttcagag     1200
acagtagaca ttctgcctaa taatgattg tatgagagct tttatatatg gaattgctca     1260
tatgctttcc tagatatgaa attattaaat tccatatgct t                         1301

<210> SEQ ID NO 113
<211> LENGTH: 3070
<212> TYPE: DNA
<213> ORGANISM: Eucalyptus grandis

<400> SEQUENCE: 113
agcaccatca gcaaaaaata gatgggatag agtgggacac cacctgttca gtttgattcc       60
cttgagatga cctacagtga tagcttgatg aataagatgg gataatagat tcaccagagg      120
gataaaaagg tagggagata ggggatctcc ccgtctgatg cctcgggtag gttgaaaata      180
aggcaaaagt tcgccgttga atttgacagc aaaagacacc gtcgttatgc attgcatgat      240
ccattgtacc catgtagggt gaaatcctag agtgaggaga tagtccttta gaaagtccca      300
ttccacccta tcataggctt tctgcatatc cattttaaga acagcccgga attgacgtct      360
acattttctg actttaaatt gatgtagaac ctcttagact attaaaatat tgtcctgaat      420
ttgacgtcca ctgacaaaag cgctttgctc ctggaaaata agtacaggca ggtagggctt      480
```

```
aaggcgattg gcaatcacct tagaaatgat cttatatgcg taattacaaa gactgatggg    540
gcggtattgg tctaattgtt caggatgtgg taccttgggt attagggcta tgatggttcg    600
attgagattc ggtggtatga tgccagaatt aaaaaagtgc tgcactgatg agaatagttc    660
atcctggagt atatcccaat gatgctggta gaagagtcca ttcaagccat ctggaccggg    720
ggccttggta agtcccagtt ggaaagtagc ctctctaact tccttcttgg taacaggagc    780
tattagggac atattcatct cattagtaac aacctaagga cactggttca gaataggcaa    840
gtagtctcga tgtcccactg tctgaaatag atgtgaaaag taacctatcg tcatcatctt    900
caaaatttca ggatcgcgca cccaagcttg attgtcatcc tgcaacatac taatcttgtt    960
tcgttgttgt ctttgtatag ttgttgcatg aaaaaattta gtattttgt ccccccagct   1020 gagccattta attcgagagc acatcgccca aaattattct tcttgctgcc ataactgtcg   1080
aattttctct tttaggtaag taaccaatga tgcgccatgt tgacaaaaag gctgattagt   1140
atgatcttgg agttgttggt gcaaatttgc aagctgacga tggcccctca gggaaattaa   1200
ggcgccaacc cagattgcaa agagcacaaa gagcacgacc caacctttcc ttaacaagat   1260
catcaccaga tcggccagta agggtaatat taatttaaca aatagctctt gtaccgggaa   1320 ctccgtatt ctctcacttc cataaacccc tgattaattt ggtgggaaag cgacagccaa   1380
cccacaaaag gtcagatgtc atcccacgag agagagagag agagagagag agagagagtt   1440
ttctctctat attctggttc accggttgga gtcaatggca tgcgtgacga atgtacatat   1500
tggtgtaggt tccaatattt tgcgggaggg ttggtgaacc gcaaagttcc tatatatcga   1560
acctccacca ccatacctca cttcaatccc caccatttat ccgttttatt tcctctgctt   1620
tcctttgctc gagtctcgcg gaagagagag aagagaggag aggagagaat gggttcgacc   1680
ggctccgaga cccagatgac cccgacccaa gtctcggacg acgaggcgaa cctcttcgcc   1740
atgcagctgg cgagcgcctc cgtgctcccc atggtcctaa aggccgccat cgagatcgac   1800
ctcctcgaga tcatggccaa ggacgggccg ggcgcgttcc tctccacggg ggaaatcgcg   1860
gcacagctcc cgacccagaa ccccgaggca cccgtcatgc tcgaccggat cttccggctg   1920
ctggccagct actccgtgct cacgtgcacc ctccgcgacc tccccgatgg caaggtcgag   1980
cggctctacg gcttagcgcc ggtgtgcaag ttcttggtca agaacgagga cggggtctcc   2040
atcgccgcac tcaacttgat gaaccaggac aaaatcctca tggaaagctg gtattacctg   2100
aaagatgcgg tccttgaagg cggaatccca ttcaacaagg cgtacgggat gaccgcgttc   2160
gagtatcatg gcaccgaccc gcgattcaac aagatcttta accggggaat gtctgatcac   2220
tccaccatta ctatgaagaa gatactggaa acatacaagg gcttcgaggg cctcgagacc   2280
gtggtcgatg tcggaggcgg cactgggggcc gtgctcagca tgatcgttgc caaataccca   2340
tcaatgaaag ggatcaactt cgaccgcccc aacggattga agacgcccca cccttcctg   2400 gtgtcaagca cgtcggaggc gacatgttcg tcagcgttcc aaagggagat gccattttca   2460
tgaagtggat atgccatgac tggagtgacg accattgcgc gaagttcctc aagaactgct   2520
acgatgcgct tccaacaat ggaaaggtga tcgttgcaga gtgcgtactc cctgtgtacc   2580
cagacacgag cctagcgacc aagaatgtga tccacatcga ctgcatcatg ttggcccaca   2640
acccaggcgg gaaagagagg acacagaagg agttcgaggc attggccaaa ggggccggat   2700
ttcagggctt ccaagtcatg tgctgcgctt tcggcactca cgtcatggag ttcctgaaga   2760
ccgcttgatc tgctcctctg tggtgatgtt catggttctt ggatttgaaa ggtcgtgaag   2820
gagccctttt ctcacagttg gcttcggcat accaagttct tctcataaaa ggaaacaata   2880
```

```
agaagcgact gtatgatggc gcaagtggaa gttacaagat ttgttgtttt atgtctataa    2940
agttttgagt cttctgcata ctgatttcac agaatgtgta acgaaacggc gtatatggat    3000
gtgcctgaat gatggaaatt gtgatattct gtcttctttt tcagtaaatc acttcgaaca    3060
aaaaaaaaaa                                                            3070
```

<210> SEQ ID NO 114
<211> LENGTH: 1227
<212> TYPE: DNA
<213> ORGANISM: Pinus radiata

<400> SEQUENCE: 114

```
aaatttcaag aggaagagat taattctttt aatttataaa attatataat aaaatattta      60
tatttaattt agatgataag tttatgaggt gtagaataga tagtgatggg tgtattattg     120
agttattccc ctaatgtgga gacaattgat tagaagttct atgagaaaaa tccaatcatg     180
ttaaagtgac ccctaatgtg aagacaattg attagaaatt ctatgaaaaa aatccaatca    240
tattaaaagt ccaattgatt agcaatttta tgagaaaaat ccaattatgt taaaagtcac    300
tgagtgtggc cgaaattgtg accgaaattg aatgcaataa ccgagggttt ttcaaaccaa    360
ggttaagcct ctcatcattg gggtgtgtat gaaaatgtaa tgggcatcga taacctttta    420
ttacaacttc acgaaaattg cctctattca atgggtgtgg atgaaaatgt aagtgcgcat    480
cgataatgga aagcgatatg cagcaaaatc aataaacctg acttcccatg tgagtgatga    540
tttgatcgta caactgatgg tgtgaagtta cttttcagctt caccttcggg cataatcagg    600
gaagtagggc caagtttgct tagtatcact ctaatcccca acaccgtgat tactatcttc    660
atcaacaatg gccaccttcg tcattacttt aactggtggg atacagctac tttacaactg    720
taaatttgtt gaggcagcct atcctcagcc tatacatact aattattgca gctcgattag    780
gtatctgctg tgagaatagc tgtgtatctc tgcgctggtt gcaggatcca agttcctctc    840
agagccctcc atggaagcgc agtcagtttc agttgttgag cagcgccccc atgccctact    900
attttcattt ccgttacagg gccacatcaa gcctttcatg aacttggcca agattttgtc    960
cagccggggc ttctatgtca ctttttgccag taccgaattt gttgtaaagc gcctcgcaga   1020
atgtggtgaa agtatcgccc atcgtgattc gatggtgtgc agcgagaacg atgatgtatg   1080
taacataaaa tttgaaacag tgcccgacgg actgcctccc caccacgatc gcagtactca   1140
gaatcttgcg gagctcttcc aatccatgga agagaacgct catattcact tccacaagtt   1200
gatggagaag ctccagaatc ttcggga                                         1227
```

<210> SEQ ID NO 115
<211> LENGTH: 1169
<212> TYPE: DNA
<213> ORGANISM: Eucalyptus grandis

<400> SEQUENCE: 115

```
ttcattatat gattattacg tcataatgat cgatttctag aaatttggag acatatgtaa     60
attcaggagg aatttcaaga aacgcgcgtt actttgaaag ggtctcgagt caaagtgctc    120
aaattgagag ggagaatttt agaacaaaat cagatttgga gaatacatgc catttaggg    180 ggatttgggg gatttcgcat atggcgtcgc gtcgtcggcg ccttcttctt tacagattgt    240
atcctcccat taaccgcgtg gacctgcata gggcacgcgt ggtcgacggc ccgggctggt    300
ttcattatat gattattacg tcataatgat cgatttctag aaatttggag acatatgtaa    360
attcaggagg aatttcaaga aacgcgcgtt actttgaaag ggtctcgagt caaagtgctc    420
```

```
aaattgagag ggagaattttt agaacaaaat cagatttgga gaatacatgc cattttaggg      480
ggattttggg gatttcgcat atggcgtcgc gtcgtcggcg ccttcttctt tacagattgt      540
atcctcccat taaccgcgtg gacctgcact gtaaccccga acggtgggg gccaatttcg      600 tctttccgcc tcctccactc agcttcgtgg aagattaaaa tcctcaccgt ccgtgcaaac      660
gccacgtggc gcgttagttt gcgcgtggaa aggtcctcac gaaccgtaaa gggcaaaaaa      720
aagggaaaat aaaaaggag gaggaggagg gaggaggaag aattgtccga ttgaaaataa      780
gagtgcggtg gtgtggtgtg ggtagatctt gaattgaacg agctcaattc gcgtatttaa      840
acccgccccg cttcctcatt cttccttgtc catttcaact ctccctctct ccctctcttc      900
tgcccctcga tcgatccagc gatcttccta tttccggacg cggggagcag ctcctcttgt      960
cgaaggttct aaattagtgt ggagagatgg tgaagatctg ctgcattggt gctggctatg     1020
tcggcgggcc tactatggcc gtgattgctc tcaagtgccc gtcagtagaa gttgcggtcg     1080
ttgatatttc tgtctctcgc atacaagcct ggaacagcga acagctccct atctatgaac     1140
caggccttga tgcggtggtg aagcaatgc                                        1169
```

<210> SEQ ID NO 116
<211> LENGTH: 947
<212> TYPE: DNA
<213> ORGANISM: Eucalyptus grandis

<400> SEQUENCE: 116

```
ggtctggaag ctcatctctc caatttggtg aagattacag ctataagagg tagctatgat       60
gtgctggcca aatgcaagtg atgaaatacg tggaccacca agtgcgaagg cattcgaaga      120
acgagggtcg aatttatagt gggcgaagga tgattaggtg gaatatgaca agaaaatagg      180
tttgaaagag aaataaatat tatgatagtg aagggtcttc acatggttag tttgatctgt      240
ccgagggtgt ccaccttgt ctgatccgca attgctcttg gtcgtgctga attttagagt      300
gtagccaaag taagaatttt cctttcactg tccggacatt tcgattgcta catggaccat      360
cccgtgtcta cccattcttg agaaccttcg agtggaaagc atgaataacc caccttgtac      420 tataggtt gccgaatatg cctagggcgc gaccatcatt gagacggagt tggggtgctc       480
cgctcggttc accaccacca ccaccaccac caccaccacc accaccattg ggcactgata      540
tagcgactcc accactaccc caaccgaggt tggcaaactc tagattgtac atgggatata      600
tcggagtagt tgaacatgat cagatcaatg gtagtggtta agactctaga aattattgaa      660
gcaatatgtt aaatcagata cgtgtgagaa agtgacttac taattgctat ggctttcatg      720
atacttaaac ttcaatgaat tggtaatgtg aagagcaatg tgatctccac aaatactact      780
agaaggccaa gtcctttct ttatgccgaa gtcctaaagt ttaatatttc aactctacct      840
atatcaaatt tgtatgcaaa ttgcataatc gcactgattt ctatggtttt attaatctag      900
ataagaactc tctccaagac attaactaat taagattgac cccattt                    947
```

<210> SEQ ID NO 117
<211> LENGTH: 1766
<212> TYPE: DNA
<213> ORGANISM: Eucalyptus grandis

<400> SEQUENCE: 117

```
atccagatcc ctacgaactg gattcacaca gtcactgctg taagctctgg ttttttttag       60
cttaggaagc aggttatgat caaacatgat taaaccatcg cgtgttcgcc agccatcaga      120
aatggaaagg caaatgttgt tatagtgatg gacagatcat gctgagatga ttgattatga      180
```

```
atcttactga tgactgtcat ttatgttatc gcactctgtg tgtgtgggtg tgtgtaatga        240
gtaatatcaa attaaccaga cgataggtgt tgaagattag ctgttgggcc accgtggcga        300
aaggtgtctt atacaagcca tcggcagtga cgcagaactg tagagaaccg ctgtaacaag        360
tcttcgaatg cattctttta atgtacagca cgacatgaag ggggttcgag tgtagcgaac        420
agttcgtgcg agaaagatca ttttcaatag cataaaagag tctgctttct gctgcaaaca        480
tggaaagaac ttacatttca atcattgagg agaagattat aacaaatcct aaatggttga        540
gattttagtt agtccattcg aactaaagtg gcgaagatgt cagttttttca agtggatgat        600 atttctcatg tatgttccgc agaggcaatc accttgtttg taactagaca tctagagaac        660
ctaacaagga ttgatgggggg tgaggtgaaa tgtctgtttc ctctttaata tggatccagc       720
gatgccttac agagcggatg gatggcactg gcaagtctta atccttagct cgaatgtttg        780
attggtaaca gatgcctttt ctttcttttc aatcacagct gacaaatgca aatatctaaa        840
accattggtt gtttggtgct tgcaagtctg gattacccca ctttatgttt cacctttcaa        900
taatgaataa caaggtactc gggaaaaaaa ggaagggaa attcgcacaa ccaaagttgc         960
tatgcagaag tcaactcaat cctaatcaag ctgatgagag tgttgggccc tattttctgc       1020
agcaaacatg aatctcgatt catctccctc gcaaagata aggaagctgc aaaagctttc        1080
ctcctaagtt tgttggcaag caaattgatt ttgtaccaga aataaataca aagtgaaacc       1140
caagcaatca cgcatggcct gatttgtgcc atgtccattt gatctccctc tactattttt       1200
cctgctttct caagcaaact agttgctgta acagtgaatg atcccccggc tctcccctc       1260 tctctctctc tctctctcca tttattccat ccatgttttt gcttttcgca caacacttat      1320
cattgaggtg ctaactactg aattcccta actaaaaatt ggaacctctc gcctaatttc       1380
attttctccc actttgatga gcaccactct cttcccaga tttcaaataa attgccactc       1440
tctccctcct ctttcctcac acaaccaaaa gccttcttca agtaccactt cttcactgtc       1500
ctctcttcac aatcccctc ttaccaagag caaagcaaaa acatgatga agagactgtc        1560 atttctgctc ctactggtcc tgctcttcca atgctctacc accttggctc agcctgcggc       1620
cgccccagct ccgcctgtga tagccccggc tgcacctgct acgcctgcct tagggcccggc     1680 tcctcctgtc ttaggcccag ctcctgcagg cccaaccgac atcacgaagg tcctcaagaa      1740
ggtgagccaa tttacggtgc tgctca                                           1766
```

<210> SEQ ID NO 118
<211> LENGTH: 1928
<212> TYPE: DNA
<213> ORGANISM: Eucalyptus grandis

<400> SEQUENCE: 118

```
ctggttccac gtcaagcacc tcctggagtg acaaggaaat gccaccggaa atcaagatt         60 gctgttttag gctcactttt ttcctgagct aagtgggtcg catttcaaga aacagtagaa       120
gttacgttct ccatggaaac tcgaaggat aaaaattaag aaacggaagc tccatgagaa       180
cgatgggggt cagcatcact cctattgtat tgtgctctca ttatctctgg cctacttgag      240
aagtgatctg ggattcgcta ttagtgaaaa caatcgcagg ctaactaaga tcttttatgc       300
taatcatatg gagaaatatc cctcttaagg gaagcatatg agttttttct taggatgact      360
acgcttattc aaaacctatc atacacgtca tgccaataat acccacttgt tgttcctta        420 ctcaggatcc tcgatagcca atactaattg gcaagaacct tgagtaacaa gctgaggtat      480
acataggcct atcattcatt tactagactc gattgcaagc acacatgatg cacatttata      540
```

```
tcagcaatca gcaatcatat ttccgaaaat tgtctctcag agaaaaagag agagagagag    600
agtccatagt atgtcatagc caaaagaaaa attagcaaca agatctcgag gtattgttga    660
aaggtagggc aatatcaaga attccattgt aattaatgtg tctagacaac atctaagaaa    720
aaaaagtgaa agaaaagagc tatatagtta ataatattta tacatgttgg agataaactt    780
gagttagagg tttatgacct cctagattga ttaaacagac caaatagtag taatcagggc    840
acttcttaaa tctactaata tattgttcaa acatgacttt taacctatct tgattagaaa    900
tgagtgttca agaaaacta atcatgcata tattttgtcg cccaatcacc ctagggtgga    960
aaaaaggcta tctactcaac aaatgctaaa attttacggc tacacgtggc cacagttgca    1020
gtacaattca tctcaaggaa ggactaaaac tgcaaagaga agaagactac ataggaaaaa    1080
ggaaaacaaa gaagccttga agtaaagagg agcataactc actcaactga gtgtgttcgc    1140
caatgtggca agaaaaagc ctctaagatc ctcacaaatg ccacgtgga ctcacacggc    1200
accctataca agtactacta ctactacagg actatgccag aaggagaagt gttagcgtga    1260
gtaccacgtg cgcacgcaga atctaagcct agcaaaaact atgctgagtc aagcagctcc    1320
cccacccatg aagatagtac tgtaatgtga ctcttgacag cgaaaccaaa cagtactcca    1380
agagaaaagc caaagcagca aaaatggggc ccgcagcaag aacctctgac tcgacctgga    1440
cccaccaaga caacagcca gccacaaaat aacgtaaaga ctttttgcgg ccactaactc    1500
ctcgacaagt ggcactgctt ggattccctt catcttgcct tcacttaacc cccaccctcc    1560
ctcacactgc attcacttca aacactcccc agtttcagag tttcattgag aaatatgttg    1620
aaggaagaca cgagtggcag cggcggcagc agcggcagcg gcagcggtgg taatagctgg    1680
gcacgtgtgt gtgacacttg ccgctcggca gcatgcaccg tgtactgccg tgccgacttg    1740
gcttacctat gctccagctg tgacgctcgt attcacgcag ccaccgtgtg gcctcgcgcc    1800
atgagcgcgt gtgggtgtgc gaagcgtgcg agcgcgcccc ggctgccttc ctctgcaagg    1860
ctgatgcagc atcactgtgc accgcctgcg atgcagacat acactcagcc aacccgcttg    1920
cgcgccgc                                                            1928

<210> SEQ ID NO 119
<211> LENGTH: 602
<212> TYPE: DNA
<213> ORGANISM: Eucalyptus grandis

<400> SEQUENCE: 119
attgggagga agtagagtgt gctgtgtgag attggtcgat gagctggctc ttgtggagat     60
ggcaagtgat tgtggcttct gtgatgcata tatataggca agggacgtga tgcggaggaa    120
gtatgtatca tcagcttata ataatgattg gtcagtttgt aagtgaatat taagggcctc    180
atgggtgttg gttcacggcc caaggcgggg cccactcacc gggggattta tcgtgtaagg    240
atacatccag ggtcagggtg tttggggaca cactttgcca tcttatgtgg gcatgatcag    300
attgagaaga atccgatcct tctttttcct aaaccattga acccaccatg agaatctttg    360
tttggaggga aaaataaaaa aatagattga gacgtattct aggagaggat agcaaaagaa    420
tgtgactttg tttgtttgtg tatcggattg atctaaggaa aaaagacact aaccgttcta    480
caatttcat acaactcttt catttaagca ccgtgacttc caaaaatcga tcatccttat    540
acggttggaa atcacacgtg gcattgctgt aaagaaata gttgatgggt ctcattgaag    600
at                                                                  602
```

<210> SEQ ID NO 120
<211> LENGTH: 1326
<212> TYPE: DNA
<213> ORGANISM: Pinus radiata

<400> SEQUENCE: 120

| | | |
|---|---|---|
| aaaaaaggga acattatac caaattttat gatatctttc aacaacatac tcttctatat | 60 |
| atggtgcctc ctctgatgga cccttgtcaa ctttctcttt ttatgtgtaa tgcctcaaga | 120 |
| gcccccactc acaagataat atcttttcca taatataata tatattccta ttgaagcagt | 180 |
| cttttgatgt accgagtaca ctactcatgg tgaaggccgt gtcttgcagc ttttcccatg | 240 |
| gtttattttg aaagtaatag tactggacct catttgcaac gacacataat attcttactg | 300 |
| acgacacttt gtttgatttc ttatagaaaa atgcaaggtg gcacaaaaag atggaaagcc | 360 |
| cgacctatca agcatacgaa gggtcatgtt cacaccctct gaaatcttca gagtctcacc | 420 |
| ctatgttgga cgctaatcaa tgggatcacg ctgaaacata tcgtaaatga cgaatcaatc | 480 |
| aatcaatcat tgaaaaatat accagataac tcctacgatg gaggggatta tttgcgtacc | 540 |
| ctccgcgtgg gtgggcacat tgggcaggtc ctttggtaag tcttggagac agagtcacgt | 600 |
| ttccataatt gaagtggaca tttatgaatc tttcgaaagt tgtagaactc ttaattttcg | 660 |
| acggaatagt ttgacacgtt ttgtacgatc tggttttttcc ggggaacgcc aattttggtt | 720 |
| tctgaaggac agcatttaca atattgtctg tcgttgacca ggacagctgg ctcggaactc | 780 |
| gggtttccga tgcgcaggaa gcgcattgaa atgagaatat aatctagttc tacctgtgga | 840 |
| gctatcacaa aatactaaaa ctggtggaca tacctcttgt ctgttctcga aatcggccaa | 900 |
| aatgggaaag aagagggtag agctgaaacg cattcaaaac cctagcagtc gacatgctac | 960 |
| tttctctaaa cgcaagaatg gattgctaaa aaaggcgttc gagctttctg tcctctgtga | 1020 |
| tgctgaagtc gctctcatca ttttctctga aactggcaag atttacgaat ttgcgagcaa | 1080 |
| taacgatatg gcagcaattc tgggaaaata ccgagtacac gaagaaggca ctgaaacgtc | 1140 |
| cagtccaaca tcgcttcaaa acgtaaagta tcatgaatca gggcttgaga aattgcaaga | 1200 |
| gaagttgacc gctttgcaaa agaaggaaaa gaacttgatt ggtgaagact ggaggtatt | 1260 |
| aacaatgaaa gaactgcaac ggcttgaaaa acagttacaa attggcataa aaggttagt | 1320 |
| gataga | 1326 |

<210> SEQ ID NO 121
<211> LENGTH: 1504
<212> TYPE: DNA
<213> ORGANISM: Eucalyptus grandis

<400> SEQUENCE: 121

| | | |
|---|---|---|
| atccactagt tatataaaaa taataataat atcaaatata tctcgtgatt tatgtatcta | 60 |
| tgaattatat atcataattt ggtaattaga catgtgggcc acttcaatgc atggacattt | 120 |
| agttcatctt gactcaatac tcaacctcaa cttaaataca tcctgattat tgatggcaac | 180 |
| cgaccaattt gacgtagagg ggacaaggat tgcaacttgg gtttgtgtgt tgggcaaagt | 240 |
| gagctcaaat aactcatgag ttcctcaact tgtttgtgtt gcccttgctc aacaatcata | 300 |
| acaaagctag ctaaacacaa atgaacaatc aagtatatcc acaaaaaaac aaaaacaaaa | 360 |
| aaacaagaaa acccaagcac tgataagaaa atctaaatttt ccaccaaaaa tgacaaatag | 420 |
| acattgccta ctctttcatt tgccgattat cgaaggaatt tacgcataga atgacccatt | 480 |
| tttttgacaa atgagatttg cataattatt caacggcatt tcgtggtata ttccatctgc | 540 |

```
atgggtgttc caaaaatagg catcgaatat tcttctggtg gaaaaaaagg ggcggggcgt      600
gaaaaatgaa agaaagaagc atcaagtggg actgaatcgc cgagtaaatc gtgccgagcc      660
gtacgtcaga agatacacac ttggctcaag tgggcgtcaa agcgatggcg cttgattggg      720
acctttgacc tttcgtcacc tccccatcct ccgtcctcct ccctgtcgcc cgttcattcc      780
ctccctccaa taaaaacaaa aaaacaaaaa aacaaaaaaa ctgtgctctc ttttactcgg      840
tcaaaacctt aaagaagcc ccccgcccac gcaaatccac ttgccacgtc accaaatcca      900
aatcccacac gtggcgcaca ctgaatcgca ttcaacttgg aacagctggc ggggttttac      960
ttggagtccc agtcacttag attctttgca gccatgacga tgacagtgac gctggctttt     1020
ctgcgtcctc tccgtaggaa ggaactccca gtacagactg gatcctccta atcccgtgtc     1080
ctcttcctga caatcccgt tcatataaag gaacccgaac tcactccctc cgctcccaat      1140
tcaagcacat gttctactcc accttcatct cacaataaaa accagcagtc cagcacgagc     1200
acattatcca cttccactcc agaactcaag cgcagacgta ctccaatgaa ccacttcttc     1260
tcttcttact ccgatcccag ctcctgcagc ctcgactttg ctgaagcgtc gtcctcctcg     1320
tcgccgctgt ccgatggcag gagtgctatg gtgcccggga acttttctga tgaggaggtg     1380
ctcctggcgt cgcaccagcc gaagaagcgc gccgggcgga agaagttcca ggagacgcgc     1440
caccccgtgt accgcggggt gcggcggcga agctcgggca gtgggtctg cgaggtccgc      1500 gagc                                                                  1504

<210> SEQ ID NO 122
<211> LENGTH: 1202
<212> TYPE: DNA
<213> ORGANISM: Pinus radiata

<400> SEQUENCE: 122
caataattat ctcaattaat atagtctaac acaatttgaa tttcaaaata aacttaccta       60
tcaaatttga aaattttcac acttgtccat tcgccatcct atctttacag ctgccaagaa      120
aaaaattgac aaatttgcaa actaatatct tttatctata ttggatgagg gcaaatcatc      180 caataaaag aaaacacaac aaaataaagg aatatccttt gaaaatactg ccagctgaat       240
ttccaattca actaaaactt tgaaccgtcc ggaatgagaa actcaattct cctctccgcg      300
tctttaggag taaactatgc tgtacaatcc gttaattcct gacacacaat tcctcacgat      360
aaaagaaaaa tctgtcagtc tatcgggtag ctggcggcac accgtttaac ggacgaccgg      420
tagctttgcc ctttagatcc accatccagt aactggcaat aggcggtggc ttactggccc      480
accttgagct tgccaattca ccgacatgaa cgcgtgtcag acggaagaag caacacaatt      540
ggacacagaa atacgactcg tttgcaacca caaggaacc atccgttgtc gtgtattaat       600
taaaaaatga gatgttaaaa attcaaaaaa tgatttataa tagaaaaatt atatatatat      660
ggatctgaat atgcttctcg ttgcttgttt cgtaggataa ttcagaggga gaagtcgctt      720
atattctata ctgacaccca ttccttgaag gaagcgctcc agtgttagag gccctggggt      780
ttgaaagctg attggtagca gggtcttcta tcagtgtacc tcctggttta atttttaattt     840 ctatgaatga catgcatcct tattaggaca agggggtttga tatatcaatt gcaaagggtt     900
tgagagaagc cagggtttgg tctttgtgtc aggcagaat tgttaatct ccagacgcca        960 tggacgctga attatgggcg gctcgtgtca cggcagcaaa gcgccatcac gcagttcatc     1020
attatcatca tcatacagat cggcagttta acttgatga attggaggc gatgatgaca      1080 tacgggcgga tttcacttgc ccatttttgtt ttgaggattt tgatatcgca ttgctctgct     1140
```

```
gccatcttga ggatgaacat tgcatcgaca caaaaaatgc gctatgtcct gtgtgcgcag    1200
ct                                                                    1202
```

<210> SEQ ID NO 123
<211> LENGTH: 1397
<212> TYPE: DNA
<213> ORGANISM: Eucalyptus grandis

<400> SEQUENCE: 123

```
ccttcctaaa gagctaccat ttctcctcat catccccgcc gccagaagaa gaagaagata      60
tttgcgatca tgaccatcag gatgatcatg atcgggtcag tggatttaag tggaagctca     120
agaggtcgat gaagggtttt aatgagtcgg cagcgggaat cgtaatggag gtccgtcgag     180
gactaacgtc ccagaggagg ctcaaaatca gggttttcag ggccaagctc aatcttcact     240
cttctttggt tgccttaacc acgagatgtt tcattccttg gtttagcaaa gttgagcatg     300
cgcagtgacc cacagttcaa ttagctttca ctccagaagt tctctatgtg aatatagttt     360
gaggttaaaa aaggttgcaa ccactctcct tctaagcacc atatgctcct gtcaatatcg     420
attgacctct tgtgagtttg gcaggaagta ctcatgtcca cagaatttct tgaaaataat     480
taacactttt gtcgtaaaga acgtagggta aaggagaaaa ttctacttct cgacatccta     540
cttttacctc ttcaaaatta tgcgattaat accatacgat acgtcttgac gatcctatct     600
cgcatggcac gtgttattgt caaggtatga attttgattt ttcgacaatc aaagcaacgt     660
caatccccat tcaagattga tgtactatgt cgaggaacca taaggatct gttctctctg      720
aggacggctc acccacatgg ggggtctgac cccaccaaag acttggtgga tgttgtggat     780
ttcatgcttt tgattcgggc caaaactcat atctccttat cttctctcgc cccttgactg     840
tccaccaaac actctcgggt atcttgccct caccaatcat ccacgcgcac aaacagacga     900
acgcaacaat atctctctga ccctcctctt tctttcattc tccctccacc tcttgatact     960
ctatttctct tgttctctta attgcgaaaa ttactcttga acttgtctgt tgtcctctc    1020
agcgtggcct gagatgggca ttttcaaaa ttaaacattg ctgcttggtt tagagacttc    1080
acttgatgag gttgataggt gaagaagaag aagaagaaga agaagaagaa gaagaagaag    1140
atgaagatac agtgtgatgt gtgcgagaga gcgccggcga cagtgatatg ttgcgcggat    1200
gaagctgcgc tgtgtgagaa atgtgatgtg gagattcacg cagcgaacaa actcgcgagc    1260
aagcaccaga ggcttctcct caactgcctc tccaacaaac tccctctctg tgacatttgc    1320
cgggagaagg ccgcgttcat cttctgtgtc gaagaccgag ctctcttctg tcaggactgt    1380
gatgaaccaa tccattc                                                  1397
```

<210> SEQ ID NO 124
<211> LENGTH: 1142
<212> TYPE: DNA
<213> ORGANISM: Pinus radiata

<400> SEQUENCE: 124

```
atctgataca attgtgaagg tgttattaat aatattttca tttctctgaa atctaggttt      60
agtcaattac atatttgata atttctttca tttccttacg caaatgattc catgaacgaa     120
attttgtttt tgattttttt tgtttcgttt atttctacca cgtgttgcat ttatatttga     180
aagcataagg agcacagtta gttttgatac ctgcaatgcc acgttttttc tgcaattcca     240
tcttccacca cacattcaaa gataatgtcg gtcatcacat tcttcagaac gcaatttgtc     300
atcaatgggt cacatgctgc catcagtatt ctgaattttc aaagcagaca aacccaaata     360
```

```
cacctggatt gcagtgggta cattatagtg acatgataaa tatcccacat cacattcttc      420
agaacgcaat ttgtcatcaa tgggtcacat actgccatca gtattccgaa tttcaaagt       480 agacaaaccc aaaatacaac tggagtgcag tgggtacatt atagtgacat gataaatatc     540
ccacatcaca ttcttccgaa tgcaatttgt catcaatagg tcacatactg ccatcagtat     600
tcttaatttt cacagtagac aaacccaaaa tacaactgga ttgcagtggg tacattatag     660
tgacatgata aatatcctac cgttttgata gtaaacttga gctgcaagta aactacatgt     720
gcactcatgg tggggcttgt gctgccaatt gccctttaaa atggagtcca tcaacatctt     780
tttaacataa gaattcttta gactgggagt tgatttgagc tttatttggg tgtatcatct     840
tgtagtctga aaagaagat tcacagtacc agcttaatta tttcatcatg gccactgcaa       900
ccttcataga tatcttgttg gccatacttc tgccaccttt gggagtcttt ctcaaatatg     960
agtgccattc tgaattctgg atatgtgtgc tgctgactct ttggggtgg ctaccaggga     1020 ttatatatgc cgtctatatt ctcaccaagt gaaaatgaat attctttgtt tggagcttgg    1080
tgccacttaa ttgtcatgag taaacataat tgaatttgtt tattcacttg tttttatgc      1140 at                                                                  1142

<210> SEQ ID NO 125
<211> LENGTH: 1489
<212> TYPE: DNA
<213> ORGANISM: Eucalyptus grandis

<400> SEQUENCE: 125
atcattgcac agatgctggc ctatcaagcg tccatcgatt aatgtcatga tgattcgtgt       60
catcaatttt tcccatagcga gtcagcgacc accgcatgca cgatgccgat gtcgccgtgc    120
gaaaaacatc gagcagacgg catgctaaag acatgcattt cggtcctctc tgatggtgaa     180
ttgcaatgca gaagagactc ggatggattt gatttcaaag tgacgacact gacttctgcg     240
cattcgttta tacatgcata ttcttcaaaa ggatgcttct gccacttctc ttttcagtg     300 gctttcagtt caagaaaccc cattaatttc aaaagagaaa gcaggtggct atctgcacgg    360
aagaatggtc tcattgttct atttaagcat ttccttttt cattgcacgt gtggtctaga       420
agagtttttc ctttcctcat atgaagccaa aataccatgt ccgagtttca cataatacaa    480
aacatttccc aggaagaaaa tgttcccaga gaccacatga gttctcttga aatctttgaa    540 attataacc ctgacccatg aaatcgggca agaaaaactg taatggcatc agcaggatgt     600
gaagagaatg gaggcggcgt acacctaatg cggttttacc gagtcggata tggttgtcgt    660
atggacaaca ggctgttgat ttggtaagtg tcggattttt tagggagaca aaagtccaac    720
ctatccccaa gcaaatccgg ggaattcgat ggtctcttga atatgtaaat gcttttgaac    780
ttcagtgact gagtccaaat gatcttcttc ttctgcaagc taactaacct tcggtccttc     840
tcttggctgc ttttgcaac tactactata ttattgcttt tagtaatggt ggtagttgca     900
atagaagtaa gcatagtgaa aaagtgttga tcggcaacaa acaaagaagc ttaattatta    960
ccgatccagc acaccttaat catctccaac tgttctctat tcttgcatct tcaaccgtaa   1020
tcagcagata atcctcgtca ttaatcatta ttctgaaaca acctgttgcc ccaccaaaga    1080
aaactcatag gtgactctgc tttgttctct tgcaatgcca tatataccc tgaaattctg     1140 atcgctctca ctcatctgtc gcattcaaag cctcaaagcc gcttgtttct gaactttgc     1200 cttggcttca aagaagaaag tcctcaaata gaagatcgac catatgggac tgaagatatt    1260
ctcagtcggc tttgctcttc tttgttgctt ctgttcactt ggcttctgtg atcaagacgg     1320
```

```
ttttctgagt ttagcttgtg gtggaactac caattacacg gattcatcca acatctggtg      1380
gattaccgac agtgatttca taagcacagg aaagactacc tatgttgaca atatcgaggg      1440
caattcatct ggtgtttcgc ttcggttctt cccagattcc aaagtccat                 1489
```

<210> SEQ ID NO 126
<211> LENGTH: 1273
<212> TYPE: DNA
<213> ORGANISM: Eucalyptus grandis

<400> SEQUENCE: 126

```
ttgtaaatta tgtgtgctta atagggtctt gttaatcaat gatcagtgta tttttttacgc      60 atgtgatgaa aaagtaattg cttttgagaa tatagttaca tcgaaaggac aatcaattcg     120
tttgacattg taatttttta tttgatagtt taacaagtgc ctcggaacac tcttcaacat     180
atcctttcac tttatttttgc atatttatgc ttgtacaaca acattttcaa ttgggtgatc     240
ataattcgta atatttataa ttttttgtta acaatgagta actctatact cctggattga     300
gcaaacatat ttgtaaagta gttatgagag tattacttat acttagacgt tgtgagatac     360
tcatgatcgt atcatatgtc cactagagga tatagattta cctagatgaa gccccttttct    420 tagaagtagg aaaaaaaaaa ctattatatt gacttgaacc catatcataa aaagtacgag     480
actcaaaatc caatcttaca tgtatatgtg tatatatata tgttcgcaaa tgataacaat     540
cttttcaaga atcaagacac cagaaaacca tattttcaat atccgtcaat gtcaatgtcc     600
tactcacatc gaacaggact gccgcgtaca caacaagttc cccagctaca gatttaccta     660
caattaggaa atgcaacccg aaaagacagg tctccatttc ttccttcact ttcccactca     720
tgaaaatgaa atatataatc acaaaatgcc tgagcgacac taaaggaacc aaagaacaac     780
gattccaact cagagagaga gagagagaga gagagaggca ctaattttttg gctgctcaac    840 aaaggaagca acttttattca aatccatttt gcttttagcgt gcccgtaatt ccaaccaaac    900
atatcctcaa agccctaata tatactccca aagcgcacc tcgtttccta cacacaagta     960
caaagcgtca acttcttctt cgctaaactg gtctcacaga cactcgcttg tccctcagtc     1020
cacactttgg cttagctcac agcaactatg gctgagacag cggaaccca gaagctggtc     1080 gagctcgaga aggtgcccga ccccgaggcc ggcgtgcccc cgaaaggaga ggaggcgccc    1140
ccagaacccc cacttccgcc cccagtgccg gcgccgccgg tggaaacttg cgtcttggtt    1200
gacgtggcac ttagggtttt gctcttcgca gcgacactga ccgctgtggt ggtgatggtc    1260
acggcgaacc aaa                                                        1273
```

<210> SEQ ID NO 127
<211> LENGTH: 3720
<212> TYPE: DNA
<213> ORGANISM: Eucalyptus grandis

<400> SEQUENCE: 127

```
cgaagttcag ctcccgcttc cctgatgttt tcaaatcttc tttcaagtta gaagtacata      60
tacagcaaac aagatccaac ccttttctta tcatgagccc ttacttccac aagtgacatt     120
tggcactagt cccacaattt aatcattcta tttccattct ctgtaaatgt accctattca     180
aagttgggac ataatgaccc ttttgaagcg ttaggatcac actttattaa aagggaacaa     240
caacattgac agcaaatgca cgcactttcg ataaagttca gacagtataa taagttctca     300
ttccaaaagg ccccaatgtg gaaggtacga cttctctaac cctgttttga tttgattttt     360
tcgcagagga aaaatcatca ccaaagactt ataaaaattg aagtagcaaa gaaaagaaaa     420
```

-continued

```
gcaagattag caaacagaga ggagaaagag aggggaagga gtgatgggcc aacagccatt      480
ctcccagaaa ccacataaaa aacaaacaca gaatgatcac ttgtgaagaa cacgcggagt      540
tccaagcaaa gcatctcgag aatcaatgtc gctctttctt cacaagcatt ggacagaaaa      600
aaagagcaag ctctaagttt tccagcgaaa gcccgaaaat taggacgaag ggcgacgaga      660
aaacgaaaaa ctagaaggaa acaaaaatca aataaaaaag gaaagagagg cctgtgcgag      720
taataacgat tgtaaggcaa gacgatgaac cggcaaagct tgattcctgg ttgcaaattg      780
gggacgaaga tggctcaaaa taggagtgac gggcggtgat tttaccgcga agcgaaacct      840
agaatgcaag gagcaaagaa gagggtggtg gcagaatcga cgccgacagt ggcagcagag      900
tcgacgccag cagcagcggc ggagtgtatg agcggagaag gcgtagtagc tgatggtggt      960
ggagtcgaca agaggagaag gcaagaagga agagtcgtcc ggaaccaatg tgtttggctt     1020
tgggtgtgga tgttttgtat tttggtgaga tgagagaacg tgtttgtttc attgtttaag     1080
attaataatg tgttcacgag ccgaacaatg tttcgacctt aacccgactc aaaacatggt     1140
tgtttgcttg ttttgtaatt gttacctaaa taatattaag acctaaaaca tcgtgttcgg     1200
gttgagtttt tggacactcc tacctgtgat agccaccgcg agcgtagact actggatttg     1260
atatttggaa gcacgaccac cttttattgc caattggaaa gataaaaacg aggcacgaat     1320
gggaccaaaa tgagcaagaa atacggtatc tttggatgcc atgtttgcca tttgtcacct     1380
tacgcagagt gctagtgtaa attctcaatc aaagagcacg ggatacgttt tgttcagaac     1440
ttcacaccat gagcaggctt ggaaaaggag gaccgtaaag gaaatcacca tattgtagat     1500
gttcaaaata agttaacgaa tcagaaaaag aatacccatt tagccgaatt taattaacgt     1560
aatctttacg tgggacaact aaagtggaaa ttttttttaac ttgtgctgat gttttagctt     1620
taaaatgcaa tcaccagcct aaaatatatc ttgattcatt atttgaaatc tcgaatgtaa     1680
attttagtag tatatcataa atatctccgt ttggcctact ttctaatgca gcatccgttt     1740
gatagggtgt cgacgactca actctacgta cgtaaaaaaa aaaaattaaa aaatgccata     1800
ttgactttat agtgtagcac gtcatcaaat tgggcgagca gtcgtcggat ggaattaaaa     1860
ttacatcaaa tggaaattgt tgttggttg cactttgggt caatttttttt tggactttga      1920 tgtaagtaat taagttaagt aatgatttcc attcactagg aagtcgaagc ccacacaacc     1980
ttgaaaaaaa aaaaaaaaaa agacatcagt ccatgcaaac aacgaattaa ctgaatttaa     2040
tgaagaatac gagaaacgta aaaacttgat aagtttatta acgatagga atgcatttta     2100 gattaatgta agtacaagta tctatagaga gttatacaaa tatatatata tatatatata     2160
tatatataat atttcagata gttttatgaa aatacttaaa attaaataga agaaaaaata     2220
tcaaactgat attgctctaa atgggattct acttttacta tcatagagat aataagctaa     2280
ggtataatta agtagaacta tcgtaatata tataatatca ataagataaa aaagtaaata     2340
gaaagatagc cacttttttt gttattgagg aaatggattg aaatgaaata atattacgaa     2400
atcaacaata gtgatagaag gaatgatttg acctagttat ggaatatcga gtgactaaat     2460
caggcaaatc gaaagtttaa gaatttaggt tgcacattta gctatgttta aagaccatat     2520
tgtatctgtc atgatagttt agagacttgc gactctctct cttgcgcatt caaacaaaag     2580
aagaacaaaa aatttaagaa tgacgttgtg cactcggtca gagttaaaga actattagtg     2640
tgattttttc attttttaagt aaacaaaaca cgatgtggga gatgtgggag attggaaaag     2700
tgatggctaa aatttggaag aaaaaatgaa atatgatcat gattgaagat ttataaaata     2760
aataatcatg gtacggactg aaactttaaa aaaatagtaa atgtactatg gtagacaaaa     2820
```

-continued

```
acaaattgag agtgtatatg gtaagggcaa cgctctttcc attccttata taactaaatt    2880
cacctaactc ttccaaaaat acaaagttgc atctatttta cattagtagt cccaaattta    2940
tttacttttt tttttttag tttttatatc tacataagat ttacttacca tagttaagaa    3000
tttatatgtt taatttagt taatttata ttttctatgt atattagagg cactatcttt    3060
cttttatccg ataatgcaat tttctttgat acgctaacaa acaaaacatg tgaaaagctt    3120
aattatggca attatcataa atagaaaaaa attagaaaaa aagagaggaa atgggccatt    3180
atttaaattg caatcgaaag attgagggca attctgtttc tctagtgtaa ataagggtgt    3240
atttaataat tgagggatgg aaatagcatg gtcactcggt aattatcaag gaaagcaaga    3300
ataaaaatgg aaaaaaaaaa aaaaaaagct tgaagaggcc aatgtcgaaa ttatgagcgc    3360
gagatgagga cactcctggg aaacgaaaaa tggcattcgc ggggggtgct atataaagcc    3420
tcgtgtaagg gtgcgttcct cactctcaaa ccctaatcct gcccttccct tctgctgctg    3480
ctgctcgtca cctctctcct ccctctcgcg gccagctgcg agatctgccg agtttaagcc    3540
tcgtacatca aaatgggtaa ggagaagatt cacatcagca ttgtggtcat tggccatgtc    3600
gattctggga agtcaaccac aactggccac ttgatataca agctcggagg aatcgacaag    3660
cgtgtgattg agagattcga gaaggaagct gctgagatga caagagatc gttcaagtat    3720
```

```
<210> SEQ ID NO 128
<211> LENGTH: 25
<212> TYPE: DNA
<213> ORGANISM: Eucalyptus grandis

<400> SEQUENCE: 128
tgagcggata acaatttcac acagg                                          25

<210> SEQ ID NO 129
<211> LENGTH: 25
<212> TYPE: DNA
<213> ORGANISM: Eucalyptus grandis

<400> SEQUENCE: 129
tcgagttttt tgatttcacg ggttg                                          25

<210> SEQ ID NO 130
<211> LENGTH: 54
<212> TYPE: PRT
<213> ORGANISM: Pinus radiata

<400> SEQUENCE: 130

Met Ala Thr Ala Thr Phe Ile Asp Ile Leu Leu Ala Ile Leu Leu Pro
1               5                   10                  15

Pro Leu Gly Val Phe Leu Lys Tyr Glu Cys His Ser Glu Phe Trp Ile
            20                  25                  30

Cys Val Leu Leu Thr Leu Leu Gly Trp Leu Pro Gly Ile Ile Tyr Ala
        35                  40                  45

Val Tyr Ile Leu Thr Lys
    50

<210> SEQ ID NO 131
<211> LENGTH: 285
<212> TYPE: DNA
<213> ORGANISM: Pinus radiata
```

<400> SEQUENCE: 131

```
catacgtctc gagaagcgtg acggatgtgc gaccggatga ccctgtataa cccaccgaca      60
cagccagcgc acagtataca cgtgtcattt ctctattgga aaatgtcgtt gttatccccg     120
ctggtacgca accaccgatg gtgacaggtc gtctgttgtc gtgtcgcgta gcgggagaag     180
ggtctcatcc aacgctatta aatactcgcc ttcaccgcgt tacttctcat ctttctctt     240
gcgttgtata atcagtgcga tattctcaga gagcttttca ttcaa                     285
```

<210> SEQ ID NO 132
<211> LENGTH: 458
<212> TYPE: DNA
<213> ORGANISM: Pinus radiata

<400> SEQUENCE: 132

```
aatttatttc ttttatttac ttaaaaaaac aaaaagttta tttatttac ttaaatggca      60
taatgacata tcggagatcc ctcgaacgag aatcttttat ctccctggtt ttgtattaaa    120
aagtaattta ttgtggggtc cacgcggagt tggaatccta cagacgcgct ttacatacgt    180
ctcgagaagc gtgacggatg tgcgaccgga tgaccctgta taacccaccg acacagccag    240
cgcacagtat acacgtgtca tttctctatt ggaaaatgtc gttgttatcc ccgctggtac    300
gcaaccaccg atggtgacag tcgtctgtt gtcgtgtcgc gtagcgggag aagggtctca    360
tccaacgcta ttaaatactc gccttcaccg cgttacttct catcttttct cttgcgttgt    420
ataatcagtg cgatattctc agagagcttt tcattcaa                             458
```

<210> SEQ ID NO 133
<211> LENGTH: 536
<212> TYPE: DNA
<213> ORGANISM: Pinus radiata

<400> SEQUENCE: 133

```
ttttcctact tcaccgttaa ttacattcct taagagtaga taaagaaata agtaaataa      60
aagtattcac aaaccaacaa tttatttctt ttatttactt aaaaaacaa aaagtttatt    120
tattttactt aaatggcata atgacatatc ggagatccct cgaacgagaa tcttttatct    180
ccctggtttt gtattaaaaa gtaatttatt gtggggtcca cgcggagttg gaatcctaca    240
gacgcgcttt acatacgtct cgagaagcgt gacggatgtg cgaccggatg accctgtata    300
acccaccgac acagccagcg cacagtatac acgtgtcatt tctctattgg aaaatgtcgt    360
tgttatcccc gctggtacgc aaccaccgat ggtgacaggt cgtctgttgt cgtgtcgcgt    420
agcgggagaa gggtctcatc caacgctatt aaatactcgc cttcaccgcg ttacttctca    480
tctttctct tgcgttgtat aatcagtgcg atattctcag agcttttc attcaa           536
```

<210> SEQ ID NO 134
<211> LENGTH: 663
<212> TYPE: DNA
<213> ORGANISM: Pinus radiata

<400> SEQUENCE: 134

```
caggacacct aaaatttga agtttaacaa aaataacttg gatctacaaa aatccgtatc      60
ggatttctc taaatataac tagaattttc ataactttca aagcaactcc tcccctaacc    120
gtaaaacttt tcctacttca ccgttaatta cattccttaa gagtagataa agaaataaag    180
taaataaaag tattcacaaa ccaacaattt atttctttta tttacttaaa aaacaaaaa    240
gtttatttat tttacttaaa tggcataatg acatatcgga gatccctcga acgagaatct    300
```

```
tttatctccc tggttttgta ttaaaaagta atttattgtg gggtccacgc ggagttggaa      360
tcctacagac gcgctttaca tacgtctcga gaagcgtgac ggatgtgcga ccggatgacc      420
ctgtataacc caccgacaca gccagcgcac agtatacacg tgtcatttct ctattggaaa      480
atgtcgttgt tatccccgct ggtacgcaac caccgatggt gacaggtcgt ctgttgtcgt      540
gtcgcgtagc gggagaaggg tctcatccaa cgctattaaa tactcgcctt caccgcgtta      600
cttctcatct tttctcttgc gttgtataat cagtgcgata ttctcagaga gcttttcatt      660
caa                                                                    663

<210> SEQ ID NO 135
<211> LENGTH: 843
<212> TYPE: DNA
<213> ORGANISM: Pinus radiata

<400> SEQUENCE: 135
attgatgtac aagtttgaga ggataagaca ttggaatcgt ctaaccagga ggcggaggaa       60
ttccctagac agttaaaagt ggccggaatc ccggtaaaaa agattaaaat ttttttgtag      120
agggagtgct tgaatcatgt tttttatgat ggaaatagat tcagcaccat caaaaacatt      180
caggacacct aaaattttga agtttaacaa aaataacttg gatctacaaa aatccgtatc      240
ggattttctc taaatataac tagaattttc ataactttca aagcaactcc tcccctaacc      300
gtaaaacttt tcctacttca ccgttaatta cattccttaa gagtagataa agaaataaag      360
taaataaaag tattcacaaa ccaacaattt atttctttta tttacttaaa aaaacaaaaa      420
gtttatttat tttacttaaa tggcataatg acatatcgga gatccctcga acgagaatct      480
tttatctccc tggttttgta ttaaaaagta atttattgtg gggtccacgc ggagttggaa      540
tcctacagac gcgctttaca tacgtctcga gaagcgtgac ggatgtgcga ccggatgacc      600
ctgtataacc caccgacaca gccagcgcac agtatacacg tgtcatttct ctattggaaa      660
atgtcgttgt tatccccgct ggtacgcaac caccgatggt gacaggtcgt ctgttgtcgt      720
gtcgcgtagc gggagaaggg tctcatccaa cgctattaaa tactcgcctt caccgcgtta      780
cttctcatct tttctcttgc gttgtataat cagtgcgata ttctcagaga gcttttcatt      840
caa                                                                    843

<210> SEQ ID NO 136
<211> LENGTH: 1164
<212> TYPE: DNA
<213> ORGANISM: Pinus radiata

<400> SEQUENCE: 136
catacgtctc gagaagcgtg acggatgtgc gaccggatga ccctgtataa cccaccgaca       60
cagccagcgc acagtataca cgtgtcattt ctctattgga aaatgtcgtt gttatccccg      120
ctggtacgca accaccgatg gtgacaggtc gtctgttgtc gtgtcgcgta gcgggagaag      180
ggtctcatcc aacgctatta aatactcgcc ttcaccgcgt tacttctcat cttttctctt      240
gcgttgtata atcagtgcga tattctcaga gagcttttca ttcaaaggta tggagttttg      300
aagggcttta ctcttaacat tgttttttct ttgtaaattg ttaatggtgg tttctgtggg      360
ggaagaatct tttgccaggt ccttttgggt ttcgcatgtt tatttgggtt attttctcg       420 actatggctg acattactag ggcttcgtg  ctttcatctg tgttttcttc ccttaatagg      480
tctgtctctc tggaatattt aattttcgta tgtaagttat gagtagtcgc tgtttgtaat      540
aggctcttgt ctgtaaaggt ttcagcaggt gtttgcgttt tattgcgtca tgtgtttcag      600
```

| | |
|---|---|
| aaggcctttg cagattattg cgttgtactt taatattttg tctccaacct tgttatagtt | 660 |
| tccctccttt gatctcacag gaacccttc ttctttgagc attttcttgt ggcgttctgt | 720 |
| agtaatattt taattttggg cccgggttct gagggtaggt gattattcac agtgatgtgc | 780 |
| tttccctata aggtcctcta tgtgtaagct gttagggttt gtgcgttact attgacatgt | 840 |
| cacatgtcac atattttctt cctcttatcc ttcgaactga tggttctttt tctaattcgt | 900 |
| ggattgctgg tgccatattt tatttctatt gcaactgtat tttagggtgt ctctttcttt | 960 |
| ttgatttctt gttaatattt gtgttcaggt tgtaactatg ggttgctagg gtgtctgccc | 1020 |
| tcttcttttg tgcttctttc gcagaatctg tccgttggtc tgtatttggg tgatgaatta | 1080 |
| tttattcctt gaagtatctg tctaattagc ttgtgatgat gtgcaggtat attcgttagt | 1140 |
| catatttcaa tttcaagatg caga | 1164 |

<210> SEQ ID NO 137
<211> LENGTH: 1337
<212> TYPE: DNA
<213> ORGANISM: Pinus radiata

<400> SEQUENCE: 137

| | |
|---|---|
| aatttatttc ttttatttac ttaaaaaaac aaaaagttta tttattttac ttaaatggca | 60 |
| taatgacata tcggagatcc ctcgaacgag aatcttttat ctccctggtt ttgtattaaa | 120 |
| aagtaattta ttgtggggtc cacgcggagt tggaatccta cagacgcgct ttacatacgt | 180 |
| ctcgagaagc gtgacggatg tgcgaccgga tgaccctgta taacccaccg acacagccag | 240 |
| cgcacagtat acacgtgtca tttctctatt ggaaaatgtc gttgttatcc ccgctggtac | 300 |
| gcaaccaccg atggtgacag tcgtctgtt gtcgtgtcgc gtagcgggag aagggtctca | 360 |
| tccaacgcta ttaaatactc gccttcaccg cgttacttct catctttct cttgcgttgt | 420 |
| ataatcagtg cgatattctc agagagcttt tcattcaaag gtatggagtt ttgaagggct | 480 |
| ttactcttaa catttgtttt tctttgtaaa ttgttaatgg tggtttctgt ggggggaagaa | 540 |
| tcttttgcca ggtcctttg ggtttcgcat gtttatttgg gttatttttc tcgactatgg | 600 |
| ctgacattac tagggctttc gtgctttcat ctgtgttttc ttcccttaat aggtctgtct | 660 |
| ctctggaata tttaattttc gtatgtaagt tatgagtagt cgctgtttgt aataggctct | 720 |
| tgtctgtaaa ggtttcagca ggtgtttgcg ttttattgcg tcatgtgttt cagaaggcct | 780 |
| ttgcagatta ttgcgttgta ctttaatatt ttgtctccaa ccttgttata gtttccctcc | 840 |
| tttgatctca caggaaccct tcttctttg agcatttct tgtggcgttc tgtagtaata | 900 |
| tttaatttt gggcccgggt ctgagggta ggtgattatt cacagtgatg tgctttccct | 960 |
| ataaggtcct ctatgtgtaa gctgttaggg tttgtgcgtt actattgaca tgtcacatgt | 1020 |
| cacatatttt cttcctctta tccttcgaac tgatggttct ttttctaatt cgtggattgc | 1080 |
| tggtgccata ttttatttct attgcaactg tattttaggg tgtctcttc ttttgattt | 1140 |
| cttgttaata tttgtgttca ggttgtaact atgggttgct agggtgtctg ccctcttctt | 1200 |
| ttgtgcttct ttcgcagaat ctgtccgttg gtctgtattt gggtgatgaa ttatttattc | 1260 |
| cttgaagtat ctgtctaatt agcttgtgat gatgtgcagg tatattcgtt agtcatattt | 1320 |
| caatttcaag atgcaga | 1337 |

<210> SEQ ID NO 138
<211> LENGTH: 1415
<212> TYPE: DNA
<213> ORGANISM: Pinus radiata

<400> SEQUENCE: 138

```
ttttcctact tcaccgttaa ttacattcct taagagtaga taaagaaata aagtaaataa      60
aagtattcac aaaccaacaa tttatttctt ttatttactt aaaaaaacaa aaagtttatt     120
tattttactt aaatggcata atgacatatc ggagatccct cgaacgagaa tcttttatct    180
ccctggtttt gtattaaaaa gtaatttatt gtggggtcca cgcggagttg aatcctaca     240
gacgcgcttt acatacgtct cgagaagcgt gacggatgtg cgaccggatg accctgtata    300
acccaccgac acagccagcg cacagtatac acgtgtcatt tctctattgg aaaatgtcgt    360
tgttatcccc gctggtacgc aaccaccgat ggtgacaggt cgtctgttgt cgtgtcgcgt    420
agcgggagaa gggtctcatc caacgctatt aaatactcgc cttcaccgcg ttacttctca    480
tcttttctct tgcgttgtat aatcagtgcg atattctcag agacttttc attcaaaggt    540
atggagtttt gaagggcttt actcttaaca tttgttttc tttgtaaatt gttaatggtg    600
gtttctgtgg gggaagaatc ttttgccagg tccttttggg tttcgcatgt ttatttgggt    660
tatttttctc gactatggct gacattacta gggctttcgt gctttcatct gtgttttctt    720
cccttaatag gtctgtctct ctggaatatt taattttcgt atgtaagtta tgagtagtcg    780
ctgtttgtaa taggctcttg tctgtaaagg tttcagcagg tgtttgcgtt ttattgcgtc    840
atgtgtttca gaaggccttt gcagattatt gcgttgtact ttaatatttt gtctccaacc    900
ttgttatagt ttccctcctt tgatctcaca ggaaccctt cttctttgag cattttcttg     960
tggcgttctg tagtaatatt ttaattttgg gcccgggttc tgagggtagg tgattattca    1020
cagtgatgtg ctttccctat aaggtcctct atgtgtaagc tgttagggtt tgtgcgttac    1080
tattgacatg tcacatgtca catatttct tcctcttatc cttcgaactg atggttcttt     1140
ttctaattcg tggattgctg gtgccatatt ttatttctat tgcaactgta ttttagggtg    1200
tctctttctt tttgatttct tgttaatatt tgtgttcagg ttgtaactat gggttgctag    1260
ggtgtctgcc ctcttctttt gtgcttcttt cgcagaatct gtccgttggt ctgtatttgg    1320
gtgatgaatt atttattcct tgaagtatct gtctaattag cttgtgatga tgtgcaggta    1380
tattcgttag tcatatttca atttcaagat gcaga                               1415
```

<210> SEQ ID NO 139
<211> LENGTH: 1542
<212> TYPE: DNA
<213> ORGANISM: Pinus radiata

<400> SEQUENCE: 139

```
caggacacct aaaatttga agtttaacaa aaataacttg gatctacaaa aatccgtatc      60
ggattttctc taaatataac tagaattttc ataactttca aagcaactcc tccctaacc    120
gtaaactttt tcctacttca ccgttaatta cattccttaa gagtagataa agaaataaag    180
taaataaaag tattcacaaa ccaacaattt atttcttta tttacttaaa aaacaaaaa     240
gtttattat tttacttaaa tggcataatg acatatcgga gatccctcga acgagaatct    300
tttatctccc tggttttgta ttaaaaagta atttattgtg gggtccacgc ggagttggaa    360
tcctacagac gcgctttaca tacgtctcga agcgtgac ggatgtgcga ccggatgacc     420
ctgtataacc caccgacaca gccagcgcac agtatacacg tgtcatttct ctattggaaa    480
atgtcgttgt tatccccgct ggtacgcaac caccgatggt gacaggtcgt ctgttgtcgt    540
gtcgcgtagc gggagaaggg tctcatccaa cgctattaaa tactcgcctt caccgcgtta    600
cttctcatct tttctcttgc gttgtataat cagtgcgata ttctcagaga cttttcatt    660
```

```
caaaggtatg agttttgaa gggctttact cttaacattt gttttctttt gtaaattgtt      720
aatggtggtt tctgtggggg aagaatcttt tgccaggtcc ttttgggttt cgcatgttta      780
tttgggttat ttttctcgac tatggctgac attactaggg ctttcgtgct ttcatctgtg      840
ttttcttccc ttaataggtc tgtctctctg gaatatttaa ttttcgtatg taagttatga      900
gtagtcgctg tttgtaatag gctcttgtct gtaaaggttt cagcaggtgt ttgcgtttta      960
ttgcgtcatg tgtttcagaa ggcctttgca gattattgcg ttgtacttta atattttgtc     1020
tccaaccttg ttatagtttc cctcctttga tctcacagga acctttctt ctttgagcat      1080 tttcttgtgg cgttctgtag taatatttta attttgggcc cgggttctga gggtaggtga     1140
ttattcacag tgatgtgctt tccctataag gtcctctatg tgtaagctgt tagggtttgt     1200
gcgttactat tgacatgtca catgtcacat attttcttcc tcttatcctt cgaactgatg     1260 gttcttttc taattcgtgg attgctggtg ccatattta tttctattgc aactgtattt      1320
tagggtgtct ctttctttt gatttcttgt taatatttgt gttcaggttg taactatggg      1380
ttgctagggt gtctgccctc ttcttttgtg cttctttcgc agaatctgtc cgttggtctg     1440
tatttgggtg atgaattatt tattccttga agtatctgtc taattagctt gtgatgatgt     1500
gcaggtatat tcgttagtca tatttcaatt tcaagatgca ga                         1542

<210> SEQ ID NO 140
<211> LENGTH: 1722
<212> TYPE: DNA
<213> ORGANISM: Pinus radiata

<400> SEQUENCE: 140
attgatgtac aagtttgaga ggataagaca ttggaatcgt ctaaccagga ggcggaggaa       60
ttccctagac agttaaaagt ggccggaatc ccggtaaaaa agattaaaat ttttttgtag      120
agggagtgct tgaatcatgt tttttatgat ggaaatagat tcagcaccat caaaaacatt      180
caggacacct aaaattttga agtttaacaa aaataacttg gatctacaaa aatccgtatc      240
ggattttctc taaatataac tagaattttc ataactttca aagcaactcc tcccctaacc      300
gtaaaacttt tcctacttca ccgttaatta cattccttaa gagtagataa agaaataaag      360
taaataaaag tattcacaaa ccaacaattt atttctttta tttacttaaa aaacaaaaa       420 gtttatttat tttacttaaa tggcataatg acatatcgga gatccctcga acgagaatct      480
tttatctccc tggttttgta ttaaaaagta atttattgtg gggtccacgc ggagttggaa      540
tcctacagac gcgctttaca tacgtctcga gaagcgtgac ggatgtgcga ccggatgacc      600
ctgtataacc caccgacaca gccagcgcac agtatacacg tgtcatttct ctattggaaa      660
atgtcgttgt tatccccgct ggtacgcaac caccgatggt gacaggtcgt ctgttgtcgt      720
gtcgcgtagc gggagaaggg tctcatccaa cgctattaaa tactcgcctt caccgcgtta      780
cttctcatct tttctcttgc gttgtataat cagtgcgata ttctcagaga cttttcatt      840 caaaggtatg gagttttgaa gggctttact cttaacattt gttttctttt gtaaattgtt      900
aatggtggtt tctgtggggg aagaatcttt tgccaggtcc ttttgggttt cgcatgttta      960
tttgggttat ttttctcgac tatggctgac attactaggg ctttcgtgct ttcatctgtg     1020
ttttcttccc ttaataggtc tgtctctctg gaatatttaa ttttcgtatg taagttatga     1080
gtagtcgctg tttgtaatag gctcttgtct gtaaaggttt cagcaggtgt ttgcgtttta     1140
ttgcgtcatg tgtttcagaa ggcctttgca gattattgcg ttgtacttta atattttgtc     1200
tccaaccttg ttatagtttc cctcctttga tctcacagga acctttctt ctttgagcat      1260
```

| | |
|---|---:|
| tttcttgtgg cgttctgtag taatattta attttgggcc cgggttctga gggtaggtga | 1320 |
| ttattcacag tgatgtgctt tccctataag gtcctctatg tgtaagctgt tagggtttgt | 1380 |
| gcgttactat tgacatgtca catgtcacat attttcttcc tcttatcctt cgaactgatg | 1440 |
| gttcttttc taattcgtgg attgctggtg ccatatttta tttctattgc aactgtattt | 1500 |
| tagggtgtct ctttcttttt gatttcttgt taatatttgt gttcaggttg taactatggg | 1560 |
| ttgctagggt gtctgccctc ttcttttgtg cttctttcgc agaatctgtc cgttggtctg | 1620 |
| tatttgggtg atgaattatt tattccttga agtatctgtc taattagctt gtgatgatgt | 1680 |
| gcaggtatat tcgttagtca tatttcaatt tcaagatgca ga | 1722 |

<210> SEQ ID NO 141
<211> LENGTH: 1193
<212> TYPE: DNA
<213> ORGANISM: Pinus radiata

<400> SEQUENCE: 141

| | |
|---|---:|
| aaaaccctc acaaatacat aaaaaaaatt ctttatttaa ttatcaaact ctccactacc | 60 |
| tttcccacca accgttacaa tcctgaatgt tggaaaaaac taactacatt gatataaaaa | 120 |
| aactacatta cttcctaaat catatcaaaa ttgtataaat atatccactc aaaggagtct | 180 |
| agaagatcca cttggacaaa ttgcccatag ttggaaagat gttcaccaag tcaacaagat | 240 |
| ttatcaatgg aaaaatccat ctaccaaact tactttcaag aaaatccaag gattatagag | 300 |
| taaaaaatct atgtattatt aagtcaaaaa gaaaaccaaa gtgaacaaat attgatgtac | 360 |
| aagtttgaga ggataagaca ttggaatcgt ctaaccagga ggcggaggaa ttccctagac | 420 |
| agttaaaagt ggccggaatc ccggtaaaaa agattaaaat tttttgtag agggagtgct | 480 |
| tgaatcatgt ttttatgat ggaaatagat tcagcaccat caaaaacatt caggacacct | 540 |
| aaaattttga agtttaacaa aaataacttg gatctacaaa aatccgtatc ggattttctc | 600 |
| taaatataac tagaattttc ataactttca aagcaactcc tcccctaacc gtaaaacttt | 660 |
| tcctacttca ccgttaatta cattcctaa gagtagataa agaaataaag taaataaaag | 720 |
| tattcacaaa ccaacaattt atttctttta tttacttaaa aaaacaaaaa gtttatttat | 780 |
| tttacttaaa tggcataatg acatatcgga gatccctcga acgagaatct tttatctccc | 840 |
| tggttttgta ttaaaaagta atttattgtg gggtccacgc ggagttggaa tcctacagac | 900 |
| gcgctttaca tacgtctcga gaagcgtgac ggatgtgcga ccggatgacc ctgtataacc | 960 |
| caccgacaca gccagcgcac agtatacacg tgtcatttct ctattggaaa atgtcgttgt | 1020 |
| tatccccgct ggtacgcaac caccgatggt gacaggtcgt ctgttgtcgt gtcgcgtagc | 1080 |
| gggagaaggg tctcatccaa cgctattaaa tactcgcctt caccgcgtta cttctcatct | 1140 |
| tttctcttgc gttgtataat cagtgcgata ttctcagaga ctttccatt caa | 1193 |

<210> SEQ ID NO 142
<211> LENGTH: 2077
<212> TYPE: DNA
<213> ORGANISM: Pinus radiata

<400> SEQUENCE: 142

| | |
|---|---:|
| aaaaccctc acaaatacat aaaaaaaatt ctttatttaa ttatcaaact ctccactacc | 60 |
| tttcccacca accgttacaa tcctgaatgt tggaaaaaac taactacatt gatataaaaa | 120 |
| aactacatta cttcctaaat catatcaaaa ttgtataaat atatccactc aaaggagtct | 180 |
| agaagatcca cttggacaaa ttgcccatag ttggaaagat gttcaccaag tcaacaagat | 240 |

```
ttatcaatgg aaaaatccat ctaccaaact tactttcaag aaaatccaag gattatagag    300
taaaaaatct atgtattatt aagtcaaaaa gaaaaccaaa gtgaacaaat attgatgtac    360
aagtttgaga ggataagaca ttggaatcgt ctaaccagga ggcggaggaa ttccctagac    420
agttaaaagt ggccggaatc ccggtaaaaa agattaaaat tttttttgtag agggagtgct    480 tgaatcatgt tttttatgat ggaaatagat tcagcaccat caaaaacatt caggacacct    540
aaaattttga agtttaacaa aaataacttg gatctacaaa aatccgtatc ggattttctc    600
taaatataac tagaattttc ataactttca aagcaactcc tcccctaacc gtaaaacttt    660
tcctacttca ccgttaatta cattccttaa gagtagataa agaaataaag taaataaaag    720
tattcacaaa ccaacaattt atttctttta tttacttaaa aaaacaaaaa gtttatttat    780
tttacttaaa tggcataatg acatatcgga gatccctcga acgagaatct tttatctccc    840
tggttttgta ttaaaaagta atttattgtg gggtccacgc ggagttggaa tcctacagac    900
gcgctttaca tacgtctcga gaagcgtgac ggatgtgcga ccggatgacc ctgtataacc    960
caccgacaca gccagcgcac agtatacacg tgtcatttct ctattggaaa atgtcgttgt   1020
tatccccgct ggtacgcaac caccgatggt gacaggtcgt ctgttgtcgt gtcgcgtagc   1080
gggagaaggg tctcatccaa cgctattaaa tactcgcctt caccgcgtta cttctcatct   1140
tttctcttgc gttgtataat cagtgcgata ttctcagaga gcttttcatt caaaggtatg   1200
gagttttgaa gggctttact cttaacattt gttttttcttt gtaaattgtt aatggtggtt   1260
tctgtggggg aagaatcttt tgccaggtcc ttttgggttt cgcatgttta tttgggttat   1320
ttttctcgac tatggctgac attactaggg ctttcgtgct ttcatctgtg ttttcttccc   1380
ttaataggtc tgtctctctg gaatatttaa ttttcgtatg taagttatga gtagtcgctg   1440
tttgtaatag gctcttgtct gtaaaggttt cagcaggtgt ttgcgtttta ttgcgtcatg   1500
tgtttcagaa ggccttttgca gattattgcg ttgtacttta atattttgtc tccaaccttg   1560
ttatagtttc cctcctttga tctcacagga acctttctt ctttgagcat tttcttgtgg    1620
cgttctgtag taatatttta attttgggcc cgggttctga gggtaggtga ttattcacag   1680
tgatgtgctt tccctataag gtcctctatg tgtaagctgt tagggtttgt gcgttactat   1740
tgacatgtca catgtcacat atttttcttcc tcttatcctt cgaactgatg gttcttttttc   1800 taattcgtgg attgctggtg ccatattta tttctattgc aactgtattt tagggtgtct    1860 ctttctttt gatttcttgt taatatttgt gttcaggttg taactatggg ttgctagggt   1920
gtctgccctc ttcttttgtg cttctttcgc agaatctgtc cgttggtctg tatttgggtg   1980
atgaattatt tattccttga agtatctgtc taattagctt gtgatgatgt gcaggtatat   2040
tcgttagtca tatttcaatt tcaagatgca gaaatca                            2077

<210> SEQ ID NO 143
<211> LENGTH: 3084
<212> TYPE: DNA
<213> ORGANISM: Pinus radiata

<400> SEQUENCE: 143
aaaacccctc acaaatacat aaaaaaaatt ctttatttaa ttatcaaact ctccactacc     60
tttcccacca accgttacaa tcctgaatgt tggaaaaaac taactacatt gatataaaaa    120
aactacatta cttcctaaat catatcaaaa ttgtataaat atatccactc aaaggagtct    180
agaagatcca cttggacaaa ttgcccatag ttggaaagat gttcaccaag tcaacaagat    240
ttatcaatgg aaaaatccat ctaccaaact tactttcaag aaaatccaag gattatagag    300
```

```
taaaaaatct atgtattatt aagtcaaaaa gaaaaccaaa gtgaacaaat attgatgtac    360
aagtttgaga ggataagaca ttggaatcgt ctaaccagga ggcggaggaa ttccctagac    420
agttaaaagt ggccggaatc ccggtaaaaa agattaaaat tttttttgtag agggagtgct   480 tgaatcatgt tttttatgat ggaaatagat tcagcaccat caaaaacatt caggacacct   540
aaaattttga agtttaacaa aaataacttg gatctacaaa aatccgtatc ggattttctc   600
taaatataac tagaattttc ataactttca aagcaactcc tccctaacc gtaaaacttt    660 tcctacttca ccgttaatta cattccttaa gagtagataa agaaataaag taaataaaag   720
tattcacaaa ccaacaattt atttctttta tttacttaaa aaaacaaaaa gtttatttat   780
tttacttaaa tggcataatg acatatcgga gatccctcga acgagaatct tttatctccc   840
tggttttgta ttaaaaagta atttattgtg gggtccacgc ggagttggaa tcctacagac   900
gcgctttaca tacgtctcga gaagcgtgac ggatgtgcga ccggatgacc ctgtataacc   960
caccgacaca gccagcgcac agtatacacg tgtcatttct ctattggaaa atgtcgttgt   1020
tatccccgct ggtacgcaac caccgatggt gacaggtcgt ctgttgtcgt gtcgcgtagc   1080
gggagaaggg tctcatccaa cgctattaaa tactcgcctt caccgcgtta cttctcatct   1140
tttctcttgc gttgtataat cagtgcgata ttctcagaga gcttttcatt caaaggtatg   1200
gagttttgaa gggctttact cttaacattt gttttttcttt gtaaattgtt aatggtggtt   1260
tctgtggggg aagaatcttt tgccaggtcc ttttgggttt cgcatgttta tttgggttat   1320 tttctcgac tatggctgac attactaggg ctttcgtgct ttcatctgtg ttttcttccc    1380
ttaataggtc tgtctctctg gaatatttaa ttttcgtatg taagttatga gtagtcgctg   1440
tttgtaatag gctcttgtct gtaaaggttt cagcaggtgt ttgcgttta ttgcgtcatg    1500 tgtttcagaa ggcctttgca gattattgcg ttgtacttta atattttgtc tccaaccttg   1560
ttatagtttc cctcctttga tctcacagga acctttctt cttgagcat ttcttgtgg     1620 cgttctgtag taatattta attttgggcc cgggtctga gggtaggtga ttattcacag    1680
tgatgtgctt tccctataag gtcctctatg tgtaagctgt tagggtttgt gcgttactat   1740
tgacatgtca catgtcacat attttcttcc tcttatcctt cgaactgatg gttcttttc    1800 taattcgtgg attgctggtg ccatatttta tttctattgc aactgtattt tagggtgtct   1860
cttttctttt gatttcttgt taatatttgt gttcaggttg taactatggg ttgctagggt   1920
gtctgccctc ttcttttgtg cttctttcgc agaatctgtc cgttggtctg tatttgggtg   1980
atgaattatt tattccttga agtatctgtc taattagctt gtgatgatgt gcaggtatat   2040
tcgttagtca tatttcaatt tcaagatgca gatctttgtc aagactctca ccggtaagac   2100
catcactctc gaggtcgaga gctctgacac cattgacaat gttaaagcta agatccagga   2160
caaggaaggg attcccccg accagcagcg tctgatcttc gcaggaaagc agcttgagga    2220
cggccgaacc cttgccgatt acaacatcca gaaagaatct accctccacc ttgttctccg   2280
tttgaggggt ggcatgcaaa tctttgtaaa aacactaact ggaaagacaa ttacattgga   2340
agttgagagc tcgacacca ttgacaacgt caaggccaag atccaggaca aggaaggaat    2400 tcccctgac cagcagaggc ttatcttcgc tggtaagcag ctggaggatg caggaccttt    2460
ggctgattac aatattcaaa aggaatcgac cctgcatttg gtgcttcgtc taagaggagg   2520
catgcaaatc tttgtgaaaa cccttacagg taaaaccatt actctggaag tggaaagctc   2580
ggacaccatt gacaatgtga aggctaagat ccaggacaag gagggaattc cacctgacca   2640
gcagaggttg atctttgccg gtaagcagct ggaagatggt cgtactctcg ccgattacaa   2700
```

-continued

| | | | | | | |
|---|---|---|---|---|---|---|
| tattcagaag | gaatcgaccc | ttcacctggt | gctccgtctc | cgcggtggct | tttaggtttg | 2760 |
| ggtgttattt | gtggataata | aattcgggtg | atgttcagtg | tttgtcgtat | ttctcacgaa | 2820 |
| taaattgtgt | ttatgtatgt | gttagtgttg | tttgtctgtt | tcagaccctc | ttatgttata | 2880 |
| tttttctttt | cgtcggtcag | ttgaagccaa | tactggtgtc | ctggccggca | ctgcaatacc | 2940 |
| atttcgttta | atataaagac | tctgttatcc | gttatgtaat | tccatgttat | gtggtgaaat | 3000 |
| gtggatgaaa | ttcttagaaa | ttattattgt | aatttgaaac | ttccttcgtc | aataatctgc | 3060 |
| acaacacatt | taccaaaaaa | aaaa | | | | 3084 |

COMPOSITIONS AND METHODS FOR THE MODIFICATION OF GENE EXPRESSION

CROSS REFERENCE TO RELATED APPLICATIONS

This application is a continuation of U.S. patent application Ser. No. 10/137,036, filed Apr. 30, 2002, now U.S. Pat. No. 7,211,711, the entire contents of which are incorporated herein by reference, which is a continuation-in-part of U.S. patent application Ser. No. 09/724,624, filed Nov. 28, 2000, now abandoned, which is a continuation-in-part of U.S. patent application Ser. No. 09/598,401, filed Jun. 20, 2000, now U.S. Pat. No. 6,596,925, which is a continuation-in-part of U.S. patent application Ser. No. 09/276,599, filed Mar. 25, 1999, now U.S. Pat. No. 6,380,459.

This application claims priority to International Patent Application No. PCT/NZ03/00076, filed Apr. 30, 2003; U.S. application Ser. No. 10/137,036, filed Apr. 30, 2002; International Patent Application No. PCT/NZ01/00115, filed Jun. 20, 2001; U.S. application Ser. No. 09/724,624 filed Nov. 28, 2000; U.S. patent application Ser. No. 09/598,401 filed Jun. 20, 2000; International Patent Application No. PCT/NZ00/00018, filed Feb. 24, 2000; U.S. Provisional Patent Application No. 60/146,591, filed Jul. 30, 1999; and U.S. patent application Ser. No. 09/276,599, filed Mar. 25, 1999.

TECHNICAL FIELD OF THE INVENTION

This invention relates to the regulation of polynucleotide transcription and/or expression. More specifically, this invention relates to polynucleotide regulatory sequences isolated from plants that are capable of initiating and driving the transcription of polynucleotides, and the use of such regulatory sequences in the modification of transcription of endogenous and/or heterologous polynucleotides and production of polypeptides. Polypeptide sequences are also disclosed.

BACKGROUND OF THE INVENTION

Gene expression is regulated, in part, by the cellular processes involved in transcription. During transcription, a single-stranded RNA complementary to the DNA sequence to be transcribed is formed by the action of RNA polymerases. Initiation of transcription in eukaryotic cells is regulated by complex interactions between cis-acting DNA motifs, located within the gene to be transcribed, and trans-acting protein factors. Among the cis-acting regulatory regions are sequences of DNA, termed promoters, to which RNA polymerase is first bound, either directly or indirectly. As used herein, the term "promoter" refers to the 5' untranslated region of a gene that is associated with transcription and which generally includes a transcription start site. Other cis-acting DNA motifs, such as enhancers, may be situated further up-and/or down-stream from the initiation site.

Both promoters and enhancers are generally composed of several discrete, often redundant elements, each of which may be recognized by one or more trans-acting regulatory proteins, known as transcription factors. Promoters generally comprise both proximal and more distant elements. For example, the so-called TATA box, which is important for the binding of regulatory proteins, is generally found about 25 basepairs upstream from the initiation site. The so-called CAAT box is generally found about 75 basepairs upstream of the initiation site. Promoters generally contain between about 100 and 1000 nucleotides, although longer promoter sequences are possible.

For the development of transgenic plants, constitutive promoters that drive strong transgene expression are preferred. Currently, the only available constitutive plant promoter that is widely used is derived from Cauliflower Mosaic Virus. Furthermore, there exists a need for plant-derived promoters for use in transgenic food plants due to public conceptions regarding the use of viral promoters. Few gymnosperm promoters have been cloned and those derived from angiosperms have been found to function poorly in gymnosperms. There thus remains a need in the art for polynucleotide promoter regions isolated from plants for use in modulating transcription and expression of polynucleotides in transgenic plants.

SUMMARY OF THE INVENTION

Briefly, isolated polynucleotide regulatory sequences from eucalyptus and pine that are involved in the regulation of gene expression are disclosed, together with methods for the use of such polynucleotide regulatory regions in the modification of expression of endogenous and/or heterologous polynucleotides in transgenic plants. The present invention provides polynucleotide promoter sequences from 5' untranslated, or non-coding, regions of plant genes that initiate and regulate transcription of polynucleotides placed under their control, together with isolated polynucleotides comprising such promoter sequences.

In a first aspect, the present invention provides isolated polynucleotide sequences comprising a polynucleotide selected from the group consisting of: (a) sequences recited in SEQ ID NO: 1-14, 20, 22-62, 81-86 and 88-127; (b) complements of the sequences recited in SEQ ID NO: 1-14, 20, 22-62, 81-86 and 88-127; (c) reverse complements of the sequences recited in SEQ ID NO: 1-14, 20, 22-62, 81-86 and 88-127; (d) reverse sequences of the sequences recited in SEQ ID NO: 1-14, 20, 22-62, 81-86 and 88-127; (e) sequences having either 40%, 60%, 75% or 90% identical nucleotides, as defined herein, to a sequence of (a)-(d); probes and primers corresponding to the sequences set out in SEQ ID NO: 1-14, 20, 22-62, 81-86 and 88-127; polynucleotides comprising at least a specified number of contiguous residues of any of the polynucleotides identified as SEQ ID NO: 1-14, 20, 22-62, 81-86 and 88-127; and extended sequences comprising portions of the sequences set out in SEQ ID NO: 1-14, 20, 22-62, 81-86 and 88-127; all of which are referred to herein as "polynucleotides of the present invention." The present invention also provides isolated polypeptide sequences identified in the attached Sequence Listing as SEQ ID NO: 63-80, 87 and 130; polypeptide variants of those sequences; and polypeptides comprising the isolated polypeptide sequences and variants of those sequences.

In another aspect, the present invention provides genetic constructs comprising a polynucleotide of the present invention, either alone, or in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a polynucleotide promoter sequence of the present invention, a polynucleotide to be transcribed, and a gene termination sequence. The polynucleotide to be transcribed may comprise an open reading frame of a polynucleotide that encodes a polypeptide of interest, or it may be a non-coding, or untranslated, region of a polynucleotide of interest. The open reading frame may be orientated in either a sense or antisense direction. Preferably, the gene termination sequence is functional in a host plant. Most preferably, the gene termination sequence is that of the gene of interest, but others generally used in the art, such as the *Agrobacterium tumefaciens* nopalin synthase terminator may be usefully employed in the present invention. The genetic construct may further include a marker for the identification of transformed cells.

In a further aspect, transgenic plant cells comprising the genetic constructs of the present invention are provided, together with organisms, such as plants, comprising such transgenic cells, and fruits, seeds and other products, derivatives, or progeny of such plants. Propagules of the inventive transgenic plants are included in the present invention. As used herein, the word "propagule" means any part of a plant that may be used in reproduction or propagation, sexual or asexual, including cuttings.

Plant varieties, particularly registerable plant varieties according to Plant Breeders' Rights, may be excluded from the present invention. A plant need not be considered a "plant variety" simply because it contains stably within its genome a transgene, introduced into a cell of the plant or an ancestor thereof.

In yet another aspect, methods for modifying gene expression in a target organism, such as a plant, are provided, such methods including stably incorporating into the genome of the organism a genetic construct of the present invention. In a preferred embodiment, the target organism is a plant, more preferably a woody plant, most preferably selected from the group consisting of eucalyptus and pine species, most preferably from the group consisting of *Eucalyptus grandis* and *Pinus radiata*.

In another aspect, methods for producing a target organism, such as a plant, having modified polypeptide expression are provided, such methods comprising transforming a plant cell with a genetic construct of the present invention to provide a transgenic cell, and cultivating the transgenic cell under conditions conducive to regeneration and mature plant growth.

In other aspects, methods for identifying a gene responsible for a desired function or phenotype are provided, the methods comprising transforming a plant cell with a genetic construct comprising a polynucleotide promoter sequence of the present invention operably linked to a polynucleotide to be tested, cultivating the plant cell under conditions conducive to regeneration and mature plant growth to provide a transgenic plant; and comparing the phenotype of the transgenic plant with the phenotype of non-transformed, or wild-type, plants.

In yet a further aspect, the present invention provides isolated polynucleotides that encode ubiquitin. In specific embodiments, the isolated polynucleotides comprise a polynucleotide selected from the group consisting of: (a) sequences recited in SEQ ID NO: 1 and 34; (b) complements of the sequences recited in SEQ ID NO: 1 and 34; (c) reverse complements of the sequences recited in SEQ ID NO: 1 and 34; (d) reverse sequences of the sequence recited in SEQ ID NO: 1 and 34; and (e) sequences having either 40%, 60%, 75% or 90% identical nucleotides, as defined herein, to a sequence of (a)-(d). Polypeptides encoded by such polynucleotides are also provided, together with genetic constructs comprising such polynucleotides, and host cells and transgenic organisms, for example plants, transformed with such genetic constructs. In specific embodiments, such polypeptides comprise a sequence provided in SEQ ID NO: 80 or 67.

In yet further aspects, the present invention provides isolated polynucleotides comprising the DNA sequence of SEQ ID NO: 21, or a complement, reverse complement or variant of SEQ ID NO: 21, together with genetic constructs comprising such polynucleotides and cells transformed with such sequences. As discussed below, removal of the sequence of SEQ ID NO: 21 from a polynucleotide that comprises the sequence of SEQ ID NO: 21 may enhance expression of the polynucleotide. Conversely, the inclusion of the sequence of SEQ ID NO: 21 in a genetic construct comprising a polynucleotide of interest may decrease expression of the polynucleotide.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

BRIEF DESCRIPTION OF THE DRAWINGS

FIGS. 6A and 6B show an annotated version of the full-length superubiquitin promoter, including the intron and the coding sequence (SEQ ID NO: 143). The intron is underlined and the coding sequence is in bold. Motifs are identified in boxes and described in the specification.

FIG. 7 shows an annotated superubiquitin construct without the intron identified and described as a 195 bp deletion (SEQ ID NO: 131).

FIG. 8 shows an annotated superubiquitin construct without the intron identified and described as a 368 bp deletion (SEQ ID NO: 132).

FIG. 9 shows an annotated superubiquitin construct without the intron identified and described as a 446 bp deletion (SEQ ID NO: 133).

FIG. 10 shows an annotated superubiquitin construct without the intron identified and described as a 573 bp deletion (SEQ ID NO: 134).

FIG. 11 shows an annotated superubiquitin construct without the intron identified and described as a 753 bp deletion (SEQ ID NO: 135).

FIG. 12 shows an annotated superubiquitin construct with the intron identified and described as a 195 bp deletion (SEQ ID NO: 136).

FIG. 13 shows an annotated superubiquitin construct with the intron identified and described as a 368 bp deletion (SEQ ID NO: 137).

FIG. 14 shows an annotated superubiquitin construct with the intron identified and described as a 446 bp deletion (SEQ ID NO: 138).

FIGS. 15A and B show an annotated superubiquitin construct with the intron identified and described as a 573 bp deletion (SEQ ID NO: 139).

FIGS. 16A and 16B show an annotated superubiquitin construct with the intron identified and described as a 753 bp deletion (SEQ ID NO: 140).

DETAILED DESCRIPTION OF THE INVENTION

Figure 1:
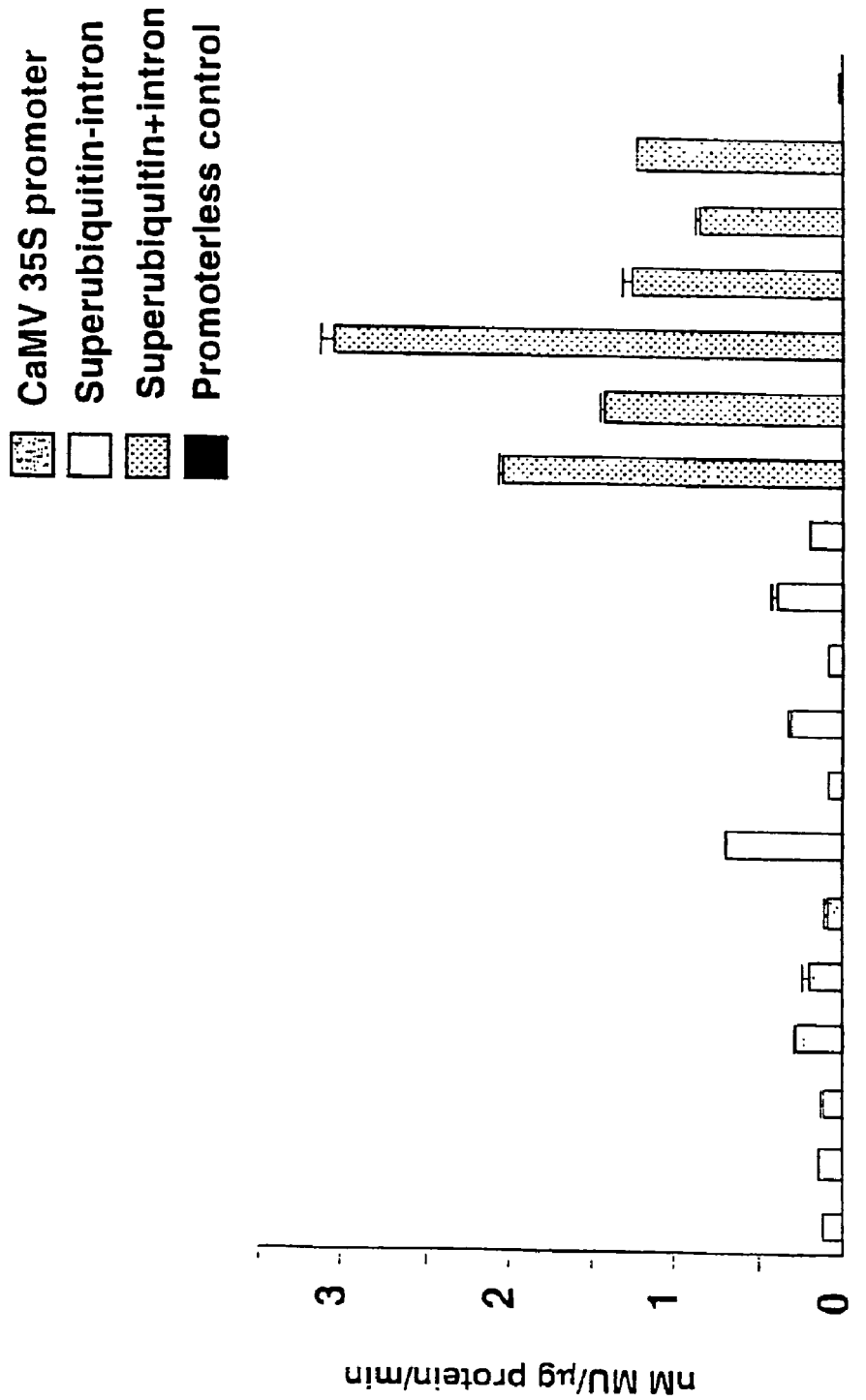
FIG. 1 shows the expression in *A. thaliana* of the GUS gene in promoter reporter constructs containing either the superubiquitin promoter with introns, the superubiquitin promoter without introns, or the CaMV 35S promoter. The GUS expression was measured by fluorimetric determination of 4-methyl-umbelliferone (MU) in protein extracts from these plants.

The present invention provides isolated polynucleotide regulatory regions that may be employed in the manipulation of plant phenotypes, together with isolated polynucleotides comprising such regulatory regions. More specifically, polynucleotide promoter sequences isolated from pine and eucalyptus are disclosed. As discussed above, promoters are components of the cellular "transcription apparatus" and are involved in the regulation of gene expression. Both tissue- and temporal-specific gene expression patterns have been shown to be initiated and controlled by promoters during the natural development of a plant. The isolated polynucleotide promoter sequences of the present invention may thus be employed in the modification of growth and development of plants, and of cellular responses to external stimuli, such as environmental factors and disease pathogens.

Using the methods and materials of the present invention, the amount of a specific polypeptide of interest may be increased or reduced by incorporating additional copies of genes, or coding sequences, encoding the polypeptide, operably linked to an inventive promoter sequence, into the genome of a target organism, such as a plant. Similarly, an increase or decrease in the amount of the polypeptide may be obtained by transforming the target plant with antisense copies of such genes.

The polynucleotides of the present invention were isolated from forestry plant sources, namely from *Eucalyptus grandis* and *Pinus radiata*, but they may alternatively be synthesized using conventional synthesis techniques. Specifically, isolated polynucleotides of the present invention include polynucleotides comprising a sequence selected from the group consisting of sequences identified as SEQ ID NO: 1-14, 20, 22-62, 81-86, 88-127 and 131-143; complements of the sequences identified as SEQ ID NO: 1-14, 20, 22-62, 81-86, 88-127 and 131-143; reverse complements of the sequences identified as SEQ ID NO: 1-14, 20, 22-62, 81-86, 88-127 and 131-143; at least a specified number of contiguous residues (x-mers) of any of the above-mentioned polynucleotides; extended sequences corresponding to any of the above polynucleotides; antisense sequences corresponding to any of the above polynucleotides; and variants of any of the above polynucleotides, as that term is described in this specification.

In another embodiment, the present invention provides isolated polypeptides encoded by the polynucleotides of SEQ ID NO: 63-80, 87 and 130.

The polynucleotides and polypeptides of the present invention were identified by DNA and polypeptide similarity searches. In the attached Sequence Listing, SEQ ID NOS. 1-14, 20, 22-62, 81-86, 88-127 and 131-143 are polynucleotide sequences, and SEQ ID NOS. 63-80, 87 and 130 are polypeptide sequences. The polynucleotides and polypeptides of the present invention are involved in regulation of transcription and/or expression in plants. The identity of each of the inventive polynucleotides is shown below in Table 1, together with the 5' untranslated region (5' UTR) or promoter region (identified by residue number).

TABLE 1

| Polynucleotide SEQ ID NO: | Polypeptide SEQ ID NO: | 5' UTR | IDENTITY |
|---|---|---|---|
| 1 | 80 | 1-2064 | Super Ubiquitin coding region and UTRs |
| 2 | — | 1-2064 | Super Ubiquitin promoter with intron |
| 3 | — | 1-1226 | Super Ubiquitin promoter without intron |
| 4 | — | 1-431 | Cell division control |
| 5 | — | 1-167 | Xylogenesis - specific |
| 6 | — | 1-600 | 4-Coumarate-CoA Ligase (4CL) |
| 7 | — | 1-591 | Cellulose synthase |
| 8 | — | 1-480 | 3' end, Cellulose synthase |
| 20 | — | 1-363 | 5' end, Cellulose synthase |
| 9 | — | 1-259 | Leaf specific |
| 10 | — | 1-251 | Leaf specific |
| 11 | — | 1-248 | Leaf specific |
| 12 | — | 1-654 | O-methyl transferase |
| 13 | — | 1-396 | Root specific |
| 14 | — | 1-763 | Root specific |
| 22 | 63 | 1-406 | Pollen coat protein |
| 23 | — | 1-350 | Pollen allergen |
| 24 | — | 1-49 | Pollen allergen |
| 25 | 64 | 1-284 | Pollen allergen |
| 26 | 65 | 1-77 | Auxin-induced protein |
| 27 | — | 1-74 | Auxin-induced protein |
| 28 | 66 | 1-99 | Auxin-induced protein |
| 29 | — | 1-927 | Flower specific |
| 30 | — | 1-411 | Flower specific |
| 31 | — | 1-178 | Flower specific |
| 32 | — | 1-178 | Flower specific |
| 33 | — | 1-178 | Flower specific |
| 34 | 67 | 1-805 | Ubiquitin |
| 35 | 68 | 1-81 | Glyceraldehyde-3-phosphate dehydrogenase |
| 36 | 69 | 1-694 | Carbonic anhydrase |
| 37 | — | 1-648 | Isoflavone reductase |
| 38 | — | 1-288 | Isoflavone reductase |
| 39 | — | 1-382 | Glyceraldehyde-3-phosphate dehydrogenase |
| 40 | 70 | 1-343 | Bud specific |
| 41 | — | 1-313 | Xylem-specific |
| 42 | — | 1-713 | Xylem-specific |
| 43 | — | 1-28 | Xylem-specific |
| 44 | — | 1-35 | Xylem-specific |
| 45 | 71 | 1-180 | Meristem-specific |
| 46 | 72 | 1-238 | Senescence-like protein |
| 47 | — | 1-91 | Senescence-like protein |
| 48 | — | 1-91 | Senescence-like protein |
| 49 | — | 1-809 | Pollen-specific |
| 50 | — | 1-428 | Pollen-specific |
| 51 | 73 | 1-55 | Pollen-specific |
| 52 | 74 | 1-575 | Pollen-specific |
| 53 | 75 | 1-35 | Pollen-specific |
| 54 | — | 1-335 | Nodulin homolog pollen specific |

TABLE 1-continued

| Polynucleotide SEQ ID NO: | Polypeptide SEQ ID NO: | 5' UTR | IDENTITY |
|---|---|---|---|
| 55 | — | 1-336 | Nodulin homolog pollen specific |
| 56 | 76 | 1-157 | Sucrose synthase |
| 57 | 77 | 1-446 | Sucrose synthase |
| 58 | — | 1-326 | Sucrose synthase |
| 59 | — | 1-311 | Flower specific |
| 60 | 78 | 1-694 | O-methyl transferase |
| 61 | 79 | 1-112 | Elongation factor A |
| 62 | — | 1-420 | Elongation factor A |
| 81 | — | — | MIF homologue |
| 82 | — | — | MIF homologue |
| 83 | — | — | MIF homologue |
| 84 | — | — | MIF homologue |
| 85 | — | — | MIF homologue |
| 86 | 87 | 1-87 | MIF homologue |
| 88 | — | 1-1156 | Chalcone synthase |
| 89 | — | 1-2590 | Unknown flower specific |
| 90 | — | 1-1172 | Unknown flower specific |
| 91 | — | 1-446 | Sucrose synthase |
| 92 | — | 1-2119 | Unknown xylem specific |
| 93 | — | 1-2571 | Glyceraldehyde-3-Phosphate dehydrogenase |
| 94 | — | 1-1406 | Unknown pollen specific |
| 95 | — | 1-2546 | *Pinus radiata* male-specific protein (PrMALE1) |
| 96 | — | 1-4726 | *Pinus radiata* male-specific protein (PrMALE1) |
| 97 | — | 1-635 | UDP glucose glycosyl-transferase |
| 98 | — | 1-468 | Elongation Factor A1 |
| 99 | — | 1-222 | Elongation Factor A1 |
| 100 | — | 1-410 | S-adenosylmethionine synthetase |
| 101 | — | 1-482 | S-adenosylmethionine synthetase |
| 102 | — | 1-230 | S-adenosylmethionine synthetase |
| 103 | — | 1-596 | UDP glucose 6 dehydrogenase |
| 104 | — | 1-653 | Hypothetical protein |
| 105 | — | 1-342 | Laccase 1 |
| 106 | — | 1-342 | Laccase 1 |
| 107 | — | 1-948 | Arabinogalactan-like 1 |
| 108 | — | 1-362 | Arabinogalactan-like 2 |
| 109 | — | 1-326 | Arabinogalactan like-2 |
| 110 | — | 1-296 | Root Receptor-like kinase |
| 111 | — | 1-723 | Root Receptor-like kinase |
| 112 | — | 1-1301 | *Pinus radiata* Lipid Transfer Protein 2 (PrLTP2) |
| 113 | — | 1-1668 | Caffeic acid O-methyl-transferase |
| 114 | — | 1-850 | UDP glucose glycosyl-transferase |
| 115 | — | 1-986 | UDP glucose 6 dehydrogenase |
| 116 | — | 1-947 | Laccase 1 |
| 117 | — | 1-1766 | Arabinogalactan like-1 |
| 118 | — | 1-1614 | Constans |
| 119 | — | 1-602 | Flowering Promoting Factor 1 (FPF1) |
| 120 | — | 1-901 | Agamous |
| 121 | — | 1-1,245 | Dreb 1A Transcription factor |
| 122 | — | 1-959 | Drought Induced Protein 19 |
| 123 | — | 1-1,140 | Salt Tolerance protein |
| 124 | 130 | 1-887 | Low Temperature Induced LTI-16 |
| 125 | — | 1-1,243 | Xylem specific receptor-like kinase |
| 126 | — | 1-1,047 | Root specific |
| 127 | — | 1-3,552 | Elongation Factor 1-alpha |
| 131 | — | 1- | Superubiquitin deletion sequence without intron including 195 bp upstream of TATA box |
| 132 | — | 1- | Superubiquitin deletion sequence without intron including 368 bp upstream of TATA box |
| 133 | — | 1- | Superubiquitin deletion sequence without intron including 446 bp upstream of TATA box |
| 134 | — | 1- | Superubiquitin deletion sequence without intron including 573 bp upstream of TATA box |
| 135 | — | 1- | Superubiquitin deletion sequence without intron including 753 bp upstream of TATA box |
| 136 | — | 1-1156 | Superubiquitin deletion sequence with intron including 195 bp upstream of TATA box |
| 137 | — | 1-1329 | Superubiquitin deletion sequence with intron including 368 bp upstream of TATA box |
| 138 | — | 1-1407 | Superubiquitin deletion sequence with intron including 446 bp upstream of TATA box |
| 139 | — | 1-1534 | Superubiquitin deletion sequence with intron including 573 bp upstream of TATA box |
| 140 | — | 1-1714 | Superubiquitin deletion sequence with intron including 753 bp upstream of TATA box |
| 141 | — | 1-1193 | Full length superubiquitin promoter |
| 142 | — | 1- | Full length superubiquitin promoter with intron |
| 143 | — | 1- | Full length superubiquitin promoter with intron and coding sequence and 3' UTR |

In one embodiment, the present invention provides polynucleotide sequences isolated from *Pinus radiata* and *Eucalyptus grandis* that have promoter activity and, in *Pinus radiata* and *Eucalyptus grandis* are associated with the coding region for a ubiquitin polypeptide. The ubiquitin promoter isolated from *Pinus radiata* and disclosed herein is referred to herein as "superubiquitin" as a consequence of its high level of promoter activity. Full-length sequences for the ubiquitin polynucleotide isolated from *Pinus radiata*, including the full-length superubiquitin promoter, an intron, the ubiquitin coding sequence and the 3' UTR are provided in SEQ ID NOS: 1 and 143, with sequence for the promoter region including an intron being provided in SEQ ID NOS: 2 and 142, and sequences for the promoter region excluding the intron being provided in SEQ ID NOS: 3 and 141. The sequences vary slightly in length and composition as a consequence of using different sequencing techniques and criteria.

An annotated version of the full-length ubiquitin polynucleotide of SEQ ID NO: 143, including the full-length superubiquitin promoter, an intron, the ubiquitin coding sequence and the 3'UTR, is shown in FIGS. 6A and 6B. In the figures, an intron is shown, underlined, at residues 1196-2035; the coding region for the ubiquitin protein is shown, in bold, at residues 2066-2755; the 3'UTR is shown at residues 2756-3084; and the full-length promoter is shown at residues 1-1193.

Polynucleotide motifs identified in the full-length ubiquitin polynucleotide of SEQ ID NO: 143 are shown in the annotations of FIGS. 6A and 6B.

Numerous forms and variations of the superubiquitin promoter have demonstrated promoter activity in experimental studies. Preliminary studies, performed by introducing constructs containing the GFP reporter gene operably linked to either the superubituitin promoter of SEQ ID NO: 2 (promoter with intron) or SEQ ID NO: 3 (promoter without intron) into Arabidopsis, are described below in Example 1. These preliminary studies showed that the superubiquitin promoter, both with and without the intron, demonstrated promoter activity, with the intron-less sequence showing higher levels of expression than the promoter sequence with the intron.

Subsequent studies are described in Examples 16, 17, 20 and 21. Experimental studies described in Example 16, done in Arabidopsis plants and quantitating GUS activity, demonstrated that a construct containing the superubiquitin promoter without the intron showed seven (7) times more GUS activity than the commercial CaMV 35S promoter, and the construct containing the superubiquitin promoter with the intron showed sixty-two (62) times more GUS activity than the CaMV 35S promoter. These follow-up studies thus confirmed that both the superubiquitin promoter sequence, with and without the intron, show high levels of promoter activity, with the superubiquitin sequence including the intron showing exceptionally high levels of promoter activity. Studies described in Example 17, done in tobacco protoplasts, demonstrated promoter activity of deletion constructs of the superubiquitin promoter, both with and without the intron. These studies confirmed that both the superubiquitin promoter sequence, with and without the intron, show high levels of promoter activity, with the superubiquitin sequence including the intron showing exceptionally high levels of promoter activity. Some of the deletion constructs demonstrated promoter activity, with greater activity in the longer constructs and no activity in the shortest constructs.

Experimental studies using superubiquitin deletion constructs, both with and without the intron, were repeated in Arabidopsis and tobacco plants, as described in Example 21. These experiments demonstrated that the partial superubiquitin promoter sequences of SEQ ID NOS: 132, 133, 134, 135, 137, 138, 139 and 140 showed constitutive promoter activity by GUS staining, in both Arabidopsis and tobacco plants. Only the shortest deletion constructs, SEQ ID NOS: 131 and 136, did not show constitutive promoter activity by GUS staining in the experimental studies described in Example 21.

Example 20 describes experimental work done to determine the effect of the 3'UTR superubiquitin sequences on gene expression in Arabidopsis. These studies showed that a construct containing the superubiquitin 3'UTR in the sense orientation and the intron-less superubiquitin promoter demonstrated high GUS expression levels, and enhanced the expression of the superubiquitin intron-less promoter to nearly the level of the superubiquitin promoter with the intron. This demonstrates that the combination of the superubiquitin promoter without the intron and the ubiquitin 3'UTR shows high levels of promoter activity.

The present invention thus contemplates a polynucleotide having promoter activity comprising a sequence of one of SEQ ID NOS: 2, 3, 132-135 and 137-142, as well as fragments and variants of such sequences having promoter activity. The present invention furthermore contemplates a polynucleotide having promoter activity comprising a sequence of one of SEQ ID NOS: 2, 3, 132-135 and 137-142, as well as fragments and variants of such sequences having promoter activity, in combination with a fragment of the 3'UTR ubiquitin sequence in the sense orientation. The 3'UTR ubiquitin sequence includes residues 2,755-3,073 of SEQ ID NO: 1 and is shown, in FIGS. 6A and 6B, as residues 2756-3084. A 250 bp fragment of the 3'UTR ubiquitin sequence, including residues 2,755-3,073 of SEQ ID NO: 1 is suitable and one of skill in the art would anticipate that smaller fragments and fragments from elsewhere within the ubiquitin 3'UTR would, in combination with a sequence of one of SEQ ID NOS: 2, 3, 132-135 and 137-142, as well as fragments and variants of such sequences, provide a sequence having promoter activity.

Numerous motifs have been identified in superubiquitin sequences, and in deletion constructs used to test the promoter activity of fragments of the superubiquitin promoter. Various of the motifs are described below in Table 2, and are identified in the sequences shown in FIGS. 6-16.

TABLE 2

| REFERENCE NUMBER | POLYNUCLEOTIDE MOTIF | DESCRIPTION |
| --- | --- | --- |
| 1 | TATAAT | −10 Mustard plastid box, also a Pribnow box, first TA and last T highly conserved |
| 2 | TATAAAA | (TATTAAA in SU promoter); a −35 Mustard plastid gene TATA box |
| 3 | TATTTWAT | (TATTTAAT in SU promoter); Nodule specific nuclear factor (NAT2, soybean). This sequence is important for protein recognition (Forde et al., Plant Cell 2:925-939, 1990) |
| 4 | CACGTG | G-box-binding factor (GBF) commonly found in many plant promoters which binds a subclass of bZIP DNA binding proteins. These elements are targets for nuclear DNA-binding factors, e.g. chlorophyll a/b binding proteins and chalcone synthase. ACGT is the core sequence and is also known as R-motif. Found in light-responsive genes, e.g., rbcS and chalcone synthase (chs), but also in other unrelated genes such as adh, Bz-2, Em, and chs. Binds with GBF (G box of rbcS), with GT-1 or with cG-1 (chs); ABA; UV; visible light; Factors groups 1, 2 and 3 have affinity for C-box; G-box is not essential for the elicitor responsiveness of the Str1 gene. GBF4 has similarities to Fos oncoprotein (Menkens and Cashmore, Proc. Natl. Acad. Sci. USA 91:2522-2526, 1994). The G-box is a cis-acting DNA sequence present in several plant promoters that are regulated by diverse signals such as UV irradiation, anaerobiosis, abscissic acid and light. Several basic/leucine zipper (bZIP) proteins from different plant species have been identified as high affinity G-box binding proteins. Although their capability to enhance transcription has been demonstrated, their precise function |

TABLE 2-continued

| REFERENCE NUMBER | POLYNUCLEOTIDE MOTIF | DESCRIPTION |
|---|---|---|
| | | in transcriptional activation is still unknown (Meier and Gruissem, Nucleic Acids Res. 22:470-478, 1994). |
| 5 | TCTTTTC (C/T CTTTT C/T) | Pyrimidine box sequence, amylase gene, is implied but not required for GA3 inducibility. |
| 6 | ACCTTTCC | If G is substituted for T, this motif is an 8 bp motif adjacent to wound inducible nuclear protein binding site. |
| 7 | TCTCCAC | Origin of genes and nuclear extract - Parsley PAL and 4CL genes |
| 8 | GATAAG | Origin of genes and nuclear extract - Lemna and Arabidopsis rbcS gene, tobacco cabE gene I-box, binding factor LRF-1 |
| 9 | AACCCA | Soybean embryo factor 3 (SEF3) binding site. Soybean B-conglycinin gene alpha subunit (embryo-specific) SEF-3, SEF-1 binding factors. Soybean (Glycine max) consensus sequence found in the 5' upstream region of beta-conglycinin (7S globulin) gene; AACCCA(-27 bp-)AACCCA. |
| 10 | TGACG | ASF-1 binding site in CaMV 35S promoter. ASF-1 binds to two TGACG motifs. The same motif is also found in HBP-1 binding site of wheat histone H3 gene. TGACG motifs are found in many promoters and are involved in transcriptional activation of several genes by auxin and/or salicylic acid and play a role in light regulation. It is also the binding site of tobacco TGA1a (TGA1a-sequence specific binding protein). Activating sequence factor 1 (ASF-1) is a nuclear DNA-binding activity that is found in monocots and dicots. It interacts with several TGACG-containing elements that have been characterized from viral and T-DNA genes, the prototypes of which are the as-1 element of the CaMV 35S promoter and the ocs element from the octopine synthase promoter. This class of cis-acting elements can respond to auxin and salicylic acid treatments (Lam and Lam, Nucleic Acids Res. 23:3778-3785, 1005). |
| 11 | GATA | Binding site, designated as-2 (activating sequence-2) at the −100 region of the cauliflower mosaic virus 35S promoter. These motifs are related to the I-boxes which bind nuclear factors. Similar to the GATA motif in CaMV 35S promoter. Binding with ASF-2; three GATA box repeats were found in the promoter of Petunia (P.h.) chlorophyll a/b binding protein, Cab22 gene; required for high level, light regulated, and tissue specific expression; Conserved in the promoter of all LHCII type I Cab genes. |
| 12 | GTGG | Maize Adh1 B1 G-box cis-acting DNA sequence elements are present in the promoter region of a number of signal-inducible plant genes and are essential for gene expression. |
| 13 | CCCC | Arabidopsis AdH interacts with GBF |
| 14 | CCAGCGG | The AT-1 binding site in cabE gene, tobacco, if C were a T. |
| 15 | GAGAAG | I-box binding GA-1 for tobacco cabE gene >IBOX "I box"; "I-box"; Conserved sequence upstream of light-regulated genes; Sequence found in the promoter region of rbcS of tomato and Arabidopsis; I box (Giuliano et al. 1988); Binding site of LeMYB1, which is a member of a novel class of myb-like proteins; LeMYBl act as a transcriptional activator GAGAA = >IBOXCORE "I box"; "I-box"; Conserved sequence upstream of light-regulated genes; Conserved sequence upstream of light-regulated genes of both monocots and dicots; See IBOX (S000124) |
| 16 | GGATA | MYBST1 core motif >MYBST1 Core motif of MybSt1 (a potato MYB homolog) binding site; core motif of MybSt1 (a potato MYB homolog) binding site; MybSt1 cDNA clone was isolated by using CaMV 35S promoter domain A as a probe (Baranowskij et al. 1994); The Myb motif of the MybSt1 protein is distinct from the plant Myb DNA binding domain described thus far. |
| 17 | TGTAAAG | Prolamin box or P Box is a highly conserved 7-bp sequence element found in the promoters of many cereal seed storage protein genes. Nuclear factors from maize endosperm specifically interact with the P-box present in maize prolamin genes (zeins). A prolamin-box binding factor (PBF) has been identified that encodes a member of the recently described Dof class of plant Cys2-Cys2 zinc-finger DNA binding proteins. PBF interacts in vitro with the basic leucine zipper protein Opaque2, a known transcriptional activator of zein gene expression. (Vicente-Carbajosa et al., Proc. Natl. Acad. Sci. USA 94:7685-7690, 1997). |
| 18 | TGTCTC | Occurs 3 times in intron: auxin response factor (ARF) binding site found in the promoters of primary/early auxin response genes of Arabidopsis thaliana. More than 10 ARFs have been identified in A. thaliana. This conserved sequence is the binding site of Arabidopsis ARF1 (Auxin response factor 1) in auxin response elements (Ulmasov et al., Science 276:1865-1868, 1997). The sequence is also found in the NDE element in soybean (Li et al., Plant Physiol. 106:37-43, 1994) 15A gene promoter. The NDE element is involved in auxin responsiveness in SAUR (Small Auxin-Up RNA) by conferring auxin inducibility to the SAUR promoters. |
| 19 | AGCGGG | BS1 (binding site 1) found in Eucalyptus gunnii Cinnamoyl-CoA reductase (CCR) gene promoter. Cinnamoyl-CoA reductase (CCR) catalyzes the first specific step in the biosynthesis of monolignols, the monomeric units of lignins. BS1 is a nuclear protein binding site that is required for vascular expression. |
| 20 | CAAT | CAAT promoter consensus sequence is found in legA gene of pea |
| 21 | TGCAGG | This motif is commonly found at the 3' of intron-exon splice junctions of plant introns and exons. |
| 22 | ACCGACA | Low temperature responsive element (LTRE) found in Arabidopsis thaliana low-temperature-induced (lti) genes. |

TABLE 2-continued

| REFERENCE NUMBER | POLYNUCLEOTIDE MOTIF | DESCRIPTION |
|---|---|---|
| | | This element is repeated four times in lti78 or cor78 and rd29A (Baker et al., Plant Mol. Biol. 24:701, 1994). The element is also found in the barley low temperature responsive genes blt4.2, blt4.6, blt4.9 (lipid transfer genes) and is cold inducible (Nordin et al., Plant Mol. Biol. 21:641-653, 1993). The core motif is CCGAC and is a portion of repeat-C (C-repeat), TGGCCGAC, which is repeated twice in con15a promoter. This element plays a role in cold-regulated gene expression of the cor15a gene and is also involved in drought and abscisic acid (ABA) responsiveness (Baker et al., Plant Mol. Biol. 24:701-713 1994). |
| 23 | CTAACCA | Binding site for MYB (ATMYB2) in the dehydration-responsive gene rd22, that is induced by ABA-induction (Iwasaki et al., Mol. Gen. Genet. 247:391-398, 1995). |
| 24 | TAACAAA | Central element of gibberellin (GA) response complex (GARC) in high-pI alpha-amylase gene in barley and similar to c-myb and v-myb consensus binding site. GAmyb binds specifically to the TAACAAA box in vitro and is the sole GA-regulated transcriptional factor required for transcriptional activation of the high-pI alpha-amylase (Rogers and Rogers, Plant Cell 4:1443-1451, 1992). |
| 25 | CCWACC | Core of consensus maize P (myb homolog) binding site where W could be A or T. Maize P gene specifies red pigmentation of kernel pericarp, cob, and other floral organs. (Grotewold et al., Cell 76:543-553 1994). |
| 26 | CACATG | Identified in SU intron. Binding site for MYC (rd22BP1) in *Arabidopsis* dehydration-resposive gene, rd22 rd22, that is induced by ABA-induction (Iwasaki et al., Mol. Gen. Genet. 247:391-398, 1995). |
| 27 | CATCCAACG | Nonamer motif found in promoter of wheat histone genes H3 and H4 (Shen and Gigot, Plant Mol. Biol. 33:367-379, 1997). |
| 28 | ACTTTA | Identified in SU intron - BBF1 (Dof protein from tobacco) binding site in *Agrobacterium rhizogenes* rolB oncogene and is required for tissue-specific expression and auxin induction of rolB (Baumann et al., Plant Cell 11:323-334, 1999). |
| 29 | AGAAA | AGAAA and TCCACCATA (S000246) are required for pollen specific expression in SU; TCCACCATA: one of two co-dependent regulatory elements responsible for pollen specific activation of tomato (L.e.) lat52 gene; Found at −72 to −68 region; See S000246 (POLLEN2LELAT52). |
| 30 | CCTTTT | In intron; pyrimidine box found in rice (O.s.) alpha-amylase (RAmy1A) gene; Gibberellin-response cis-element of GARE and pyrimidine box are partially involved in sugar repression. |
| 31 | CAACA | Binding consensus sequence of *Arabidopsis* (A.t.) transcription factor, RAV1; RAV1 specifically binds to DNA with bipartite sequence motifs of RAV1-A (CAACA) and RAV1-B (CACCTG); RAV1 protein contain AP2-like and B3-like domains; The AP2-like and B3-like domains recognize the CAACA and CACCTG motifs, respectively; The expression level of RAV1 were relatively high in rosette leaves and roots; See S000315(CACCTG). |
| 32 | AATCCAA | "rbcS general consensus sequence"; AATCCAA or AATCCAAC |
| 33 | AACCAA | 2 motifs present; "REalpha" found in *Lemna gibba* Lhcb21 gene promoter; Located at −134 to −129; Binding site of proteins of whole-cell extracts; The DNA binding activity is high in etiolated plants but much lower in green plants; Required for phytochrome regulation; See S000363 |
| 34 | TACTATT | In intron; one of SPBF binding site (SP8b); Found at −330, −220, and −200 of gSPO-B1 (sporamin) gene, and also at −80 of gB-Amy (beta-amylase) gene; SP8BF recognizes both SP8a and SP8b sequences; See also SP8BFIBSP8AIB (S000183); SP8BF activity is also found in tobacco; "SP8b" found in the 5' upstream region of three different genes coding for sporamin and beta-amylase; Binding site of SPF1; SPF1 also binds to the SP8b; See S000184. |
| 35 | TATCCAY | (TATCCAC in SU promoter); "TATCCAY motif" found in rice (O.s.) RAmy3D alpha-amylase gene promoter; Y = T/C; a GATA motif as its antisense sequence; TATCCAY motif and G motif (see S000130) are responsible for sugar repression (Toyofuku et al. 1998). |
| 36 | ATAAAAAAATT | The AT-1 binding site in cabE gene, tobacco, if A were a T. |

SEQ ID NO: 132 is the shortest fragment of the superubiquitin promoter for which promoter activity has been demonstrated experimentally. SEQ ID NO: 32 includes motifs 12, 14, 4, 15, 10, 9, 22, 4, 13, 19, 15, 27, 2, 5, 1 and 11, as described above in Table 2. It is expected that a sequence comprising at least ten (10), more preferably twelve (12), and most preferably fifteen (15) of the sixteen (16) motifs, selected from the group consisting of: motifs 12, 14, 4, 15, 10, 9, 22, 4, 13, 19, 15, 27, 2, 5, 1 and 11, as described above in Table 2, would exhibit promoter activity, and such sequences are contemplated by the present invention. Such sequences may also be combined with a 3'UTR fragment of the ubiquitin sequence comprising at least 50 consecutive bp, more preferably at least 100 or 150 consecutive bp, and most preferably at least 250 consecutive bp from the ubiquitin 3'UTR sequence identified as residues 2,755-3,073 of SEQ ID NO: 1. Additionally or alternatively, such sequences may also be combined with an intron, such as the intron identified as residues 1196-2034 of SEQ ID NO: 143 or 142. Fragments of the 3'UTR and intron sequences may also be combined with the sequences of SEQ ID NOS: 132-135 and 137-140 to provide promoters of the present invention. All of these sequences have features in common, in that they share ten or more common motifs, as described above, and more likely share sequence similarities over a substantial portion of the sequence.

The sequence for the ubiquitin polynucleotide isolated from *Eucalyptus grandis* is provided in SEQ ID NO: 34. In a related embodiment, the present invention provides isolated polypeptides encoded by the isolated polynucleotides of SEQ ID NO: 1 and 34, including polypeptides comprising the sequences of SEQ ID NO: 80 and 67.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Antisense polynucleotides and techniques involving anti-sense polynucleotides are well known in the art and are described, for example, in Robinson-Benion et al. "Antisense techniques," *Methods in Enzymol.* 254(23):363-375, 1995; and Kawasaki et al., in *Artific. Organs* 20(8):836-848, 1996.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

The definition of the terms "complement", "reverse complement" and "reverse sequence", as used herein, is best illustrated by the following example. For the sequence 5' AGGACC 3', the complement, reverse complement and reverse sequence are as follows:

```
Complement            3' TCCTGG 5'

Reverse complement    3' GGTCCT 5'

Reverse sequence      5' CCAGGA 3'
```

Some of the polynucleotides of the present invention are "partial" sequences, in that they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NO: 1-14, 20, 22-62, 81-86 and 88-127, or a variant thereof, or a portion of one of the sequences of SEQ ID NO: 1-14, 20, 22-62, 81-86 and 88-127, or a variant thereof, when the extended polynucleotide comprises an identified sequence or its variant, or an identified contiguous portion (x-mer) of one of the sequences of SEQ ID NO: 1-14, 20, 22-62, 81-86 and 88-127, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1-14, 20, 22-62, 81-86 and 88-127.

The polynucleotides identified as SEQ ID NO: 1-14, 20, 22-62, 81-86 and 88-127, and their extensions, may contain open reading frames ("ORFs") or partial open reading frames encoding polypeptides. Additionally, open reading frames encoding polypeptides may be identified in extended or full length sequences corresponding to the sequences set out as SEQ ID NO: 1-14, 20, 22-62, 81-86 and 88-127. Open reading frames may be identified using techniques that are well known in the art. These techniques include, for example, analysis for the location of known start and stop codons, most likely reading frame identification based on codon frequencies, etc. Suitable tools and software for ORF analysis include, for example, "GeneWise", available from The Sanger Center, Wellcome Trust Genome Campus, Hinxton, Cambridge, CB10 1SA, United Kingdom; "Diogenes", available from Computational Biology Centers, University of Minnesota, Academic Health Center, UMHG Box 43, Minneapolis Minn. 55455 and "GRAIL", available from the Informatics Group, Oak Ridge National Laboratories, Oak Ridge, Tenn. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The term "polypeptide", as used herein, encompasses amino acid chains of any length including full length proteins, wherein amino acid residues are linked by covalent peptide bonds. Polypeptides of the present invention may be isolated and purified natural products, or may be produced partially or wholly using recombinant techniques. The term "polypeptide encoded by a polynucleotide" as used herein, includes polypeptides encoded by a nucleotide sequence which includes the partial isolated DNA sequences of the present invention.

In a related aspect, polypeptides are provided that comprise at least a functional portion of a polypeptide having a sequence selected from the group consisting of sequences provided in SEQ ID NO: 63-80, 87 and 130, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below. A functional portion comprising an active site may be made up of separate portions present on one or more polypeptide chains and generally exhibits high substrate specificity.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain. (Merrifield, *J. Am. Chem. Soc.* 85: 2149-2154, 1963). Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82: 488-492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical residues in a specified region may be determined against other polynucleotide and polypeptide sequences, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN algorithm Version 2.0.4 [Feb.-24-1998], Version 2.0.6 [Sep.-16-1998] and Version 2.0.11 [Jan.-20-2000], set to the default parameters described in the documentation and distributed with the algorithm, are preferred for use in the determination of polynucleotide variants according to the present invention. The BLASTP algorithm, is preferred for use in the determination of polypeptide variants according to the present invention. The use of the BLAST family of algorithms, including BLASTN, BLASTP, and BLASTX, is described in the publication of Altschul, et al., "Gapped BLAST and PSI-BLAST: a new generation of protein database search programs," *Nucleic Acids Res.* 25: 3389-3402, 1997. The BLASTN software is available on the NCBI anonymous FTP server (ftp://ncbi.nlm.nih.gov) under /blast/executables/ and is available from the National Center for Biotechnology Information (NCBI), National Library of Medicine, Building 38A, Room 8N805, Bethesda, Md. 20894 USA.

The FASTA software package is available from the University of Virginia (University of Virginia, PO Box 9025, Charlottesville, Va. 22906-9025). Version 2.0u4, February, 1996, set to the default parameters described in the documentation and distributed with the algorithm, may be used in the determination of variants according to the present invention. The use of the FASTA algorithm is described in Pearson and Lipman, "Improved Tools for Biological Sequence Analysis," *Proc. Natl. Acad. Sci. USA* 85: 2444-2448, 1988; and Pearson, "Rapid and Sensitive Sequence Comparison with FASTP and FASTA," *Methods in Enzymol.* 183: 63-98, 1990.

The following running parameters are preferred for determination of alignments and similarities using BLASTN that contribute to the E values and percentage identity for polynucleotide sequences: Unix running command: blastall -p blastn -d embldb -e 10-G0 -E0 -r 1-v 30-b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0-E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E)

indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides of the present invention hybridize to the polynucleotide sequences recited in SEQ ID NO: 1-14, 20, 22-62, 81-86 and 88-127, or complements, reverse sequences, or reverse complements of those sequences under stringent conditions. As used herein, "stringent conditions" refers to prewashing in a solution of 6X SSC, 0.2% SDS; hybridizing at 65° C., 6X SSC, 0.2% SDS overnight; followed by two washes of 30 minutes each in 1X SSC, 0.1% SDS at 65° C. and two washes of 30 minutes each in 0.2X SSC, 0.1% SDS at 65° C.

The present invention also encompasses polynucleotides that differ from the disclosed sequences but that, as a consequence of the discrepancy of the genetic code, encode a polypeptide having similar activity to a polypeptide encoded by a polynucleotide of the present invention. Thus, polynucleotides comprising sequences that differ from the polynucleotide sequences recited in SEQ ID NO: 1-14, 20, 22-62, 81-86 and 88-127, or complements, reverse sequences, or reverse complements thereof, as a result of conservative substitutions are contemplated by and encompassed within the present invention. Additionally, polynucleotides comprising sequences that differ from the polynucleotide sequences recited in SEQ ID NO: 1-14, 20, 22-62, 81-86 and 88-127, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 63-80, 87 and 130, as a result of amino acid substitutions, insertions, and/or deletions totaling less than 10% of the total sequence length are contemplated by an encompassed within the present invention. In certain embodiments, variants of the inventive polypeptides and polynucleotides possess biological activities that are the same or similar to those of the inventive polypeptides or polynucleotides. Such variant polynucleotides function as promoter sequences and are thus capable of modifying gene expression in a plant.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5-nucleotide overhang. The next segment may then be synthesized in a similar fashion, with a 5-nucleotide overhang on the opposite strand. The "sticky" ends ensure proper ligation when the two portions are hybridized. In this way, a complete polynucleotide of the present invention may be synthesized entirely in vitro.

Polynucleotides of the present invention also comprehend polynucleotides comprising at least a specified number of contiguous residues (x-mers) of any of the polynucleotides identified as SEQ ID NO: 1-14, 20, 22-62, 81-86 and 88-127, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NO: 63-80, 87 and 130, and their variants. As used herein, the term "x-mer," with reference to a specific value of "x," refers to a sequence comprising at least a specified number ("x") of contiguous residues of any of the polynucleotides identified as SEQ ID NO: 1-14, 20, 22-62, 81-86 and 88-127, or the polypeptides identified as SEQ ID NO: 63-80, 87 and 130. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide or polypeptide identified as SEQ ID NO: 1-14, 20, 22-62, 81-86 and 88-127, and variants thereof.

As noted above, the inventive polynucleotide promoter sequences may be employed in genetic constructs to drive transcription and/or expression of a polynucleotide of interest. The polynucleotide of interest may be either endogenous or heterologous to an organism, for example a plant, to be transformed. The inventive genetic constructs may thus be employed to modulate levels of transcription and/or expression of a polynucleotide, for example gene, that is present in the wild-type plant, or may be employed to provide transcription and/or expression of a DNA sequence that is not found in the wild-type plant.

In certain embodiments, the polynucleotide of interest comprises an open reading frame that encodes a target polypeptide. The open reading frame is inserted in the genetic construct in either a sense or antisense orientation, such that transformation of a target plant with the genetic construct will lead to a change in the amount of polypeptide compared to the wild-type plant. Transformation with a genetic construct comprising an open reading frame in a sense orientation will generally result in over-expression of the selected polypeptide, while transformation with a genetic construct comprising an open reading frame in an antisense orientation will generally result in reduced expression of the selected polypeptide. A population of plants transformed with a genetic construct comprising an open reading frame in either a sense or antisense orientation may be screened for increased or reduced expression of the polypeptide in question using techniques well known to those of skill in the art, and plants having the desired phenotypes may thus be isolated.

Alternatively, expression of a target polypeptide may be inhibited by inserting a portion of the open reading frame, in either sense or antisense orientation, in the genetic construct. Such portions need not be full-length but preferably comprise at least 25 and more preferably at least 50 residues of the open reading frame. A much longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In further embodiments, the inventive genetic constructs comprise a polynucleotide including an untranslated, or non-coding, region of a gene coding for a target polypeptide, or a polynucleotide complementary to such an untranslated region. Examples of untranslated regions which may be usefully employed in such constructs include introns and 5'-untranslated leader sequences. Transformation of a target plant with such a genetic construct may lead to a reduction in the amount of the polypeptide expressed in the plant by the process of cosuppression, in a manner similar to that discussed, for example, by Napoli et al., *Plant Cell* 2:279-290, 1990 and de Carvalho Niebel et al., *Plant Cell* 7:347-358, 1995.

Alternatively, regulation of polypeptide expression can be achieved by inserting appropriate sequences or subsequences (e.g. DNA or RNA) in ribozyme constructs (McIntyre and Manners, *Transgenic Res.* 5(4):257-262, 1996). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The polynucleotide of interest, such as a coding sequence, is operably linked to a polynucleotide promoter sequence of the present invention such that a host cell is able to transcribe an RNA from the promoter sequence linked to the polynucleotide of interest. The polynucleotide promoter sequence is generally positioned at the 5' end of the polynucleotide to be transcribed. Use of a constitutive promoter, such as the *Pinus radiata* ubiquitin polynucleotide promoter sequence of SEQ ID NO: 2 and 3 or the *Eucalyptus grandis* ubiquitin polynucleotide promoter sequence contained within SEQ ID NO: 34, will affect transcription of the polynucleotide of interest in all parts of the transformed plant. Use of a tissue specific promoter, such as the leaf-specific promoters of SEQ ID NO: 9-11, the root-specific promoters of SEQ ID NO: 13 and 14, the flower-specific promoters of SEQ ID NO: 29-33, 59 and 89-90, the pollen-specific promoters of SEQ ID NO: 49-55 and 94, the bud-specific promoter of SEQ ID NO: 40 or the meristem-specific promoter of SEQ ID NO: 45, will result in production of the desired sense or antisense RNA only in the tissue of interest. Temporally regulated promoters, such as the xylogenesis-specific promoters of SEQ ID NO: 5, 41-44 and 92, can be employed to effect modulation of the rate of DNA transcription at a specific time during development of a transformed plant. With genetic constructs employing inducible gene promoter sequences, the rate of DNA transcription can be modulated by external stimuli, such as light, heat, anaerobic stress, alteration in nutrient conditions and the like.

The inventive genetic constructs further comprise a gene termination sequence which is located 3' to the polynucleotide of interest. A variety of gene termination sequences which may be usefully employed in the genetic constructs of the present invention are well known in the art. One example of such a gene termination sequence is the 3' end of the *Agrobacterium tumefaciens* nopaline synthase gene. The gene termination sequence may be endogenous to the target plant or may be exogenous, provided the promoter is functional in the target plant. For example, the termination sequence may be from other plant species, plant viruses, bacterial plasmids and the like.

The genetic constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds. *Methods for Plant Molecular Biology*, Academic Press Inc.: San Diego, Calif., 1988). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The genetic construct of the present invention may be linked to a vector having at least one replication system, for example *E. coli*, whereby after each manipulation, the resulting construct can be cloned and sequenced and the correctness of the manipulation determined.

The genetic constructs of the present invention may be used to transform a variety of target organisms including, but not limited to, plants. Plants which may be transformed using the inventive constructs include both monocotyledonous angiosperms (e.g., grasses, corn, grains, oat, wheat and barley) and dicotyledonous angiosperms (e.g., *Arabidopsis*, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:84-89, 1993), and larch (Huang et al., *In Vitro Cell* 27:201-207, 1991). In a preferred embodiment, the inventive genetic constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. Other species which may be usefully transformed with the genetic constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana*; other gymnosperms, such as *Abies amabilis, Abies balsamea, Abies concolor, Abies grandis, Abies lasiocarpa, Abies magnifica, Abies procera, Chamaecyparis lawsoniana, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata*; and *Eucalypts*, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni*; and hybrids of any of these species.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acids Res.* 12:8711-8721, 1984. Targets for the introduction of the genetic constructs of the present invention include tissues, such as leaf tissue, dissociated cells, protoplasts, seeds, embryos, meristematic regions; cotyledons, hypocotyls, and the like. The preferred method for transforming eucalyptus and pine is a biolistic method using pollen (see, for example, Aronen, *Finnish Forest Res. Papers*, Vol. 595, 53 pp, 1996) or easily regenerable embryonic tissues.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., "Somatic embryogenesis in woody plants," in Thorpe TA, ed., *In Vitro Embryogenesis of Plants* (Current Plant Science and Biotechnology in Agriculture Vol. 20), Chapter 12, pp. 471-540, 1995. Specific protocols for the regeneration of spruce are discussed by Roberts et al., "Somatic embryogenesis of spruce," in Redenbaugh K, ed., *Synseed: applications of synthetic seed to crop improvement*, CRC Press: Chapter 23, pp. 427-449, 1993). Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the polynucleotides incorporated into the genome of the target host. A target organism may be transformed with more than one genetic construct of the present invention, thereby modulating the activity of more than gene. Similarly, a genetic construct may be assembled containing more than one open reading frame coding for a polypeptide of interest or more than one untranslated region of a gene coding for such a polypeptide.

The isolated polynucleotides of the present invention also have utility in genome mapping, in physical mapping, and in positional cloning of genes. As detailed below, the polynucleotide sequences identified as SEQ ID NO: 1-14, 20, 22-62, 81-86 and 88-127, and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix (Santa Clara, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

An oligonucleotide probe or primer is described as "corresponding to" a polynucleotide of the present invention, including one of the sequences set out as SEQ ID NO: 1-14, 20, 22-62, 81-86 and 88-127, or a variant, if the oligonucleotide probe or primer, or its complement, is contained within one of the sequences set out as SEQ ID NO: 1-14, 20, 22-62, 81-86 and 88-127, or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Preferred techniques for designing PCR primers are disclosed in Dieffenbach, C W and Dyksler, GS. *PCR Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1-14, 20, 22-62, 81-86 and 88-120.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451; and PCT Publication No. WO 95/00450, the disclosures of which are hereby incorporated by reference.

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The following examples are offered by way of illustration and not by way of limitation.

EXAMPLE 1

Isolation and Characterization of a Ubiquitin Gene Promoter from *Pinus radiata*

*Pinus radiata* cDNA expression libraries were constructed and screened as follows. mRNA was extracted from plant tissue using the protocol of Chang et al., *Plant Molecular Biology Reporter* 11:113-116, 1993 with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

As described below, one of the most abundant sequences identified was a ubiquitin gene, hereinafter referred to as the "Super-Ubiquitin or SU" gene.

Isolation of cDNA Clones Containing the Ubiquitin Gene

Sequences of cDNA clones with homology to the ubiquitin gene were obtained from high-throughput cDNA sequencing as described above. Sequences from several independent clones were assembled in a contig and a consensus sequence was generated from overlapping clones. The determined nucleotide sequence of the isolated Super Ubiquitin clone, comprising the promoter region (including an intron), coding region and 3' untranslated region (UTR) is provided in SEQ ID NO: 1. The 5' UTR is represented by residues 1 to 2,064, the intron by residues 1,196 to 2,033, and the coding region of the gene, which contains three direct repeats, by residues 2,065 to 2,751. The 3' UTR is 328 residues long (residues 2,755 to 3,083). The nucleotide sequence of the Super Ubiquitin promoter region only, including the intron, is given in SEQ ID NO: 2. The nucleotide sequence of the Super Ubiquitin promoter region only, excluding the intron, is given in SEQ ID NO: 3. The predicted amino acid sequence for the *Pinus radiata* Super Ubiquitin is provided in SEQ ID NO: 80.

Ubiquitin proteins function as part of a protein degradation pathway, in which they covalently attach to proteins, thereby targeting them for degradation (for a review, see Belknap and Garbarino, *Trends in Plant Sciences* 1:331-335, 1996). The protein is produced from a precursor polypeptide, encoded by a single mRNA. The Super Ubiquitin mRNA contains three copies of the ubiquitin monomer.

Cloning of the Super Ubiquitin Promoter

Fragments of the Super Ubiquitin promoter were cloned by two different PCR-based approaches.

Method 1: Long Distance Gene Walking PCR

Using "Long Distance Gene Walking" PCR (Min and Powell, *Biotechniques* 24:398-400, 1998), a 2 kb fragment was obtained that contained the entire coding region of the ubiquitin gene, a 900 bp intron in the 5' UTR and approximately 100 bp of the promoter.

To generate this fragment, 2 nested primers were designed from the 3' UTR of the Super Ubiquitin cDNA sequence isolated from pine. Generally, the 5' UTR is used for primer design to amplify upstream sequence. However, the available 5' UTR of Super Ubiquitin was very short, and two initial primers derived from this region failed to amplify any fragments. Therefore, the primers of SEQ ID NO: 15 and 16 were designed from the 3' UTR.

The method involved an initial, linear PCR step with pine genomic DNA as template using the primer of SEQ ID NO: 15, and subsequent C-tailing of the single stranded DNA product using terminal transferase. The second PCR-step used these fragments as template for amplification with the primer of SEQ ID NO: 16 and primer AP of SEQ ID NO: 17. The AP primer was designed to bind to the polyC tail generated by the terminal transferase. Both primers (SEQ ID NO: 16 and 17) contained a 5'-NotI restriction site for the cloning of products into the NotI site of a suitable vector. The final PCR product contained fragments of different sizes. These fragments were separated by electrophoresis and the largest were purified from the gel, digested with restriction endonuclease NotI and cloned in the NotI site of expression vector pBK-CMV (Stratagene, La Jolla, Calif.). The largest of these clones contained the complete coding region of the gene (no introns were found in the coding sequence) and a 5' UTR which contained a 900 bp intron.

Method 2: "Genome Walker" Kit

The Super Ubiquitin gene promoter was cloned using a "Genome Walker" kit (Clontech, Palo Alto, Calif.). This is also a PCR-based method, which requires two PCR primers to be constructed, one of which must be gene-specific. Although the ubiquitin coding region is highly conserved, the 5' UTR from different ubiquitin genes is not conserved and could therefore be used to design a gene-specific primer. A 2.2 kb fragment was amplified and subcloned in pGEM-T-easy (Promega, Madison, Wis.). Analysis by PCR and DNA sequencing showed that the clone contained 5' UTR sequence of the Super Ubiquitin gene, including the 900 bp intron and approximately 1 kb of putative promoter region. An intron in the 5' UTR is a common feature of plant polyubiquitin genes and may be involved in determining gene expression levels.

The gene specific primers used for these PCR reactions are provided in SEQ ID NO: 18 and 19.

Expression of Super Ubiguitin

Using primers derived from the gene-specific 5' and 3' UTR sequences, expression levels of Super Ubiquitin in different plant tissues was examined by means of RT-PCR. Super Ubiquitin was found to be expressed in all plant tissues examined, including branch phloem and xylem, feeder roots, fertilized cones, needles, one year old cones, pollen sacs, pollinated cones, root xylem, shoot buds, structural roots, trunk phloem and trunk. Expression of Super Ubiquitin in plant tissues was also demonstrated in a Northern blot assay using a PCR probe prepared from the 5'UTR.

Functional Analysis of the Super Ubiguitin Promoter

To test the function of the Super Ubiquitin promoter in plants, *Arabidopsis thaliana* was transformed with constructs containing the reporter gene for Green Fluorescent Protein (GFP) operably linked to either the Super Ubiquitin promoter of SEQ ID NO: 2 or SEQ ID NO: 3 (i.e., either with or without the intron). Constructs lacking a promoter were used as a negative control, with a plant T-DNA vector carrying a CaMV 35S promoter cloned in front of GFP being used as a positive control. The constructs were introduced into *Arabidopsis* via *Agrobacterium*-mediated transformation.

All the plant culture media were according to the protocol of Valvekens and Van Montagu, *Proc. Natl. Acad. Sci. USA* 85:5536-5540, 1988 with minor modifications. For root transformation, sterilized seeds were placed in a line on the surface of germination medium, the plates were placed on their sides to facilitate root harvesting, and the seeds were grown for two weeks at 24° C. with a 16 h photoperiod.

Expression of the constructs was measured by determining expression levels of the reporter gene for Green Fluorescent Protein (GFP). Preliminary GFP expression (transient) was detected in early transgenic roots during T-DNA transfer. Transgenic roots that developed green callus, growing on shoot-inducing medium containing 50 μg/ml Kanamycin and 100 μg/ml Timentin, were further tested for GFP expression. After several weeks of stringent selection on Kanamycin medium, several independent transgenic *Arabidopsis* lines were engineered and tested for GFP expression.

Expression was seen both with the Super Ubiquitin promoter including intron and the Super Ubiquitin promoter without the intron. However, preliminary results indicated that the levels of expression obtained with the Super Ubiquitin intron-less promoter construct were significantly higher than those seen with the promoter including intron, suggesting that the intron may contain a repressor. The sequence of the intron is provided in SEQ ID NO: 21.

EXAMPLE 2

Isolation of a CDC Promoter from *Pinus radiata*

Plant polynucleotide sequences homologous to the Cell Division Control (CDC) protein gene were isolated from a *Pinus radiata* cDNA expression library as described in Example 1. Using the "Genome Walker" protocol described above and gene specific primers designed from these plant polynucleotide sequences, 5'UTR sequence containing the putative promoter of the *P. radiata* CDC gene was isolated from genomic DNA. The determined nucleotide sequence is given in SEQ ID NO: 4.

EXAMPLE 3

Isolation of a Xylogenesis-Specific Promoter from *Pinus radiata*

Plant polynucleotide sequences specific for plant xylogenesis were isolated from *Pinus radiata* cDNA expression libraries prepared from xylem, essentially as described in Example 1. Using the "Genome Walker" protocol described above and gene specific primers designed from these plant polynucleotide sequences, sequences containing putative *Pinus radiata* xylogenesis-specific promoters were isolated from genomic DNA. The determined nucleotide sequences are provided in SEQ ID NO: 5 and 41-44. An extended cDNA sequence for the clone of SEQ ID NO: 41-44 is provided in SEQ ID NO: 92.

EXAMPLE 4

Isolation of a 4-Coumarate-CoA Ligase Promoter from *Pinus radiata*

Plant polynucleotide sequences homologous to the 4-Coumarate-CoA Ligase (4CL) gene were isolated from a *Pinus radiata* cDNA expression library as described in Example 1. Using the "Genome Walker" protocol described above and gene specific primers designed from these plant polynucleotide sequences, sequences containing the putative promoter of the *P. radiata* 4CL gene was isolated from genomic DNA. The determined nucleotide sequence is given in SEQ ID NO: 6.

Genetic constructs comprising the reporter gene for Green Fluorescent Protein (GFP) or GUS reporter genes operably linked to the promoter of SEQ ID NO: 6 were prepared and used to transform *Arabidopsis thaliana* plants.

EXAMPLE 5

Isolation of a Cellulose Synthase Promoter from *Eucalyptus grandis*

Plant polynucleotide sequences homologous to the cellulose synthase gene were isolated from a *Eucalyptus grandis* cDNA expression library essentially as described in Example 1. Using the "Genome Walker" protocol described above and gene specific primers designed from these plant polynucleotide sequences, 5'UTR sequences containing the putative promoter of the *E. grandis* cellulose synthase gene were isolated from genomic DNA. Independent PCR experiments using different DNA bands as templates yielded two sequences which contained a number of base differences. One band was 750 bp in length and the nucleotide sequence of this band is given in SEQ ID NO: 7. The other band was 3 kb in length. The sequence of the 3' end of this band corresponded to the sequence given in SEQ ID NO: 7, with a number of base pair differences. The sequence of this 3' end is given in SEQ ID NO: 8. The sequence of the 5' end of this band is given in SEQ ID NO: 20.

EXAMPLE 6

Isolation of a Leaf-Specific Promoter from *Eucalyptus grandis*

Plant polynucleotide sequences specific for leaf were isolated from *Eucalyptus grandis* cDNA expression libraries prepared from leaf tissue, essentially as described in Example 1. Using the "Genome Walker" protocol described above and gene specific primers designed from these plant polynucleotide sequences, 5'UTR sequence containing a leaf-specific promoter of a novel *E. grandis* gene (of unknown function) was isolated from genomic DNA. Independent PCR experiments using different DNA bands as templates yielded three sequences which contained a number of base differences and deletions. The determined nucleotide sequences of the three PCR fragments are given in SEQ ID NO: 9-11.

EXAMPLE 7

Isolation of an O-Methyl Transferase Promoter from *Eucalyptus grandis*

Plant polynucleotide sequences homologous to an O-methyl transferase (OMT) gene were isolated from a *Eucalyptus grandis* cDNA expression library essentially as described in Example 1. Using the "Genome Walker" protocol described above and gene specific primers designed from these plant polynucleotide sequences, 5'UTR sequences containing the putative promoter of the *E. grandis* OMT gene was isolated from genomic DNA. The determined nucleotide sequence is given in SEQ ID NO: 12. This promoter sequence was extended by further sequencing. The extended cDNA sequences are given in SEQ ID NO: 60 and 113.

Genetic constructs comprising the reporter gene for Green Fluorescent Protein (GFP) operably linked to the promoter of SEQ ID NO: 12 were prepared and used to transform *Arabidopsis thaliana*.

EXAMPLE 8

Isolation of Root-Specific Promoters from *Pinus radiata*

Plant polynucleotide sequences homologous to the root-specific receptor-like kinase gene were isolated from a *Pinus radiata* cDNA expression library as described in Example 1. Using the "Genome Walker" protocol described above and gene specific primers designed from these plant polynucleotide sequences, 5'UTR sequence containing a putative *P. radiata* root-specific promoter was isolated from genomic DNA. Two independent PCR experiments yielded sequences that contained a number of base differences. The determined nucleotide sequences from the two experiments are given in SEQ ID NO: 13, 14, 110 and 111.

EXAMPLE 9

Isolation of an EF1-alpha Promoter from *Eucalyptus Grandis*

Plant polynucleotide sequences homologous to the *Eucalyptus Elongation* Factor-alpha (EF1-alpha) gene were isolated from a *Eucalyptus grandis* cDNA expression library and used to screen a *Eucalyptus grandis* genomic DNA library as follows.

The *Eucalyptus grandis* genomic DNA library was constructed using genomic DNA extracted from *Eucalyptus nitens xgrandis* plant tissue, according to the protocol of Doyle and Doyle, *Focus* 12:13-15, 1990, with minor modifications. Specifically, plant tissue was ground under liquid nitrogen and dissolved in 2X CTAB extraction buffer (2% CTAB, hexadecyltrimethylammonium bromide; 1.4 M NaCl, 20 mM EDTA pH 8.0, 100 mM Tris.HCl pH 8.0, 1% polyvinylpyrollidone). After extraction with chloroform: isoamylalcohol (24:1), 10% CTAB was added to the aqueous layer and the chloroform:isoamylalcohol extraction repeated. Genomic DNA was precipitated with isopropanol.

The resulting DNA was digested with restriction endonuclease Sau3A1 following standard procedures, extracted once with phenol:chloroform:isoamylalcohol (25:24:1) and ethanol precipitated. The digested fragments were separated on a sucrose density gradient using ultracentrifugation. Fractions containing fragments of 9-23 kb were pooled and ethanol precipitated. The resulting fragments were cloned into the lambda DASH II/BamHI vector (Stratagene, La Jolla, Calif.) following the manufacturer's protocol and packaged using a Gigapack II Packaging Extract (Stratagene). The library was amplified once.

The library was screened with radiolabeled EST fragments isolated from a *Eucalyptus grandis* library (as described in Example 1), that showed homology to the *Eucalyptus* EF1- alpha gene. Phage lysates were prepared from positive plaques and genomic DNA was extracted.

From this genomic DNA, the 5'UTR region containing the putative promoter of the *Eucalyptus* EF1-alpha gene was obtained using the ELONGASE Amplification System (Gibco BRL). A 10 kb fragment was amplified and restriction mapped. The putative promoter region of the *Eucalyptus* elongation factor A (EF1-alpha) gene was identified on a 4 kb fragment, which was subcloned into a pUC19 vector (Gibco BRL) containing an engineered NotI-site. The determined genomic DNA sequences of the isolated fragment containing the promoter region are provided in SEQ ID NO: 61 and 62, with the amino acid encoded by SEQ ID NO: 61 being provided in SEQ ID NO: 79. An extended sequence of the clone of SEQ ID NO: 61 is provided in SEQ ID NO: 127.

EXAMPLE 10

Isolation of Flower-Specific Promoters from *Eucalyptus grandis*

Plant polynucleotide sequences specific for flower-derived tissue were isolated from *Eucalyptus grandis* cDNA expression libraries prepared from flower tissue, essentially as described in Example 1. Using the "Genome Walker" protocol described above and gene specific primers designed from these plant polynucleotide sequences, several sequences, each containing a putative *Eucalyptus grandis* flower-specific promoter, were isolated from genomic DNA. The determined nucleotide sequences are given in SEQ ID NO: 29-33 and 59. An extended sequence of the clone of SEQ ID NO: 30-33 is provided in SEQ ID NO: 89. An extended sequence of the clone of SEQ ID NO: 29 is provided in SEQ ID NO: 90.

EXAMPLE 11

Isolation of Pollen-Specific Promoters from *Eucalyptus grandis* and *Pinus radiata*

Plant polynucleotide sequences specific for pollen were isolated from *Eucalyptus grandis* and *Pinus radiata* cDNA expression libraries prepared from pollen, essentially as described in Example 1. Using the "Genome Walker" protocol described above and gene specific primers designed from these plant polynucleotide sequences, several sequences, each containing a putative pollen-specific promoter, were isolated from genomic DNA. The determined nucleotide sequences isolated from *Pinus radiata* are given in SEQ ID NO: 49-53, with the predicted amino acid sequences encoded by SEQ ID NO: 51-53 being provided in SEQ ID NO: 73-75, respectively. An extended sequence for the clone of SEQ ID NO: 49 is provided in SEQ ID NO: 94.

EXAMPLE 12

Isolation of Bud-Specific and Meristem-Specific Promoter from *Pinus radiata*

Plant polynucleotide sequences specific for bud and meristem were isolated from *Pinus radiata* cDNA expression libraries prepared from bud and meristem, essentially as described in Example 1. Using the "Genome Walker" protocol described above and gene specific primers designed from these plant polynucleotide sequences, two sequences, one containing a putative bud-specific promoter and the other containing a putative meristem-specific promoter, were isolated from genomic DNA. The determined nucleotide sequences for these two promoters are given in SEQ ID NO: 40 and 45, respectively. The predicted amino acid sequences encoded by the DNA sequences of SEQ ID NO: 40 and 45 are provided in SEQ ID NO: 70 and 71, respectively.

EXAMPLE 13

Isolation of Promoters from *Eucalyptus grandis*

Plant polynucleotide sequences showing some homology to various known genes were isolated from *Eucalyptus grandis* cDNA expression libraries essentially as described in Example 1. Using the "Genome Walker" protocol described above and gene specific primers designed from these plant polynucleotide sequences, sequences containing the putative promoters for the following *E. grandis* genes were isolated from genomic DNA: auxin induced protein (SEQ ID NO: 26-28); carbonic anhydrase (SEQ ID NO: 36); isoflavone reductase (SEQ ID NO: 37 and 38); pollen allergen (SEQ ID NO: 23-25); pollen coat protein (SEQ ID NO: 22), sucrose synthase (SEQ ID NO: 56-58); ubiquitin (SEQ ID NO: 34); glyceraldehyde-3-phosphate dehydrogenase (SEQ ID NO: 35 and 39); O-methyl transferase (OMT; SEQ ID NO: 60); macrophage migration inhibition factor from mammals (MIF; SEQ ID NO: 81-86); UDP glucose 6-dehydrogenase (SEQ ID NO: 103); laccase 1 (SEQ ID NO: 105, 106 and 116); arabinogalactan-like 1 (SEQ ID NO: 107); arabinogalactan-like 2 (SEQ ID NO: 108, 109); a hypothetical protein (SEQ ID NO: 104); constans (SEQ ID NO: 118); Flowering Promoting Factor 1 (FPF1; SEQ ID NO: 119); transcription factor DREB-1 (SEQ ID NO: 121); salt tolerance protein (SEQ ID NO: 123); xylem-specific histidine kinase-like (SEQ ID NO: 125) and root specific (SEQ ID NO: 126). The amino acid sequences encoded by the DNA sequences of SEQ ID NO: 22, 25, 26, 28, 34, 35, 36, 56, 57, 60, 86 and 124 are provided in SEQ ID NO: 63, 64, 65, 66, 67, 68, 69, 76, 77, 78, 87 and 130, respectively. Extended cDNA sequences for the clones of SEQ ID NO: 58, 35, 60, 103, 106 and 107 are provided in SEQ ID NO: 91, 93, 113 and 115-117, respectively.

EXAMPLE 14

Isolation of Promoters from *Pinus radiata*

Plant polynucleotide sequences showing some homology to various known genes were isolated from *Pinus radiata* cDNA expression libraries essentially as described in Example 1. Using the "Genome Walker" protocol described above and gene specific primers designed from these plant polynucleotide sequences, sequences containing the putative promoters for the following *Pinus radiata* genes were isolated from genomic DNA: senescence-like protein (SEQ ID NO: 46-48); nodulin homolog pollen specific (SEQ ID NO: 54 and 55); chalcone synthase (SEQ ID NO: 88); PrMALE1 (SEQ ID NO: 95, 96); UDP glucose glycosyltransferase (SEQ ID NO: 97); elogation factor 1 alpha (SEQ ID NO: 98, 99); S-adenosylmethionine synthase (SEQ ID NO: 100-102); *Pinus radiata* lipid transfer protein 2 (PrLTP2; SEQ ID NO: 112); *Pinus radiata* agamous protein (SEQ ID NO: 120); Drought Induced DI-19 (SEQ ID NO: 122) and low temperature induced protein LTI (SEQ ID NO 124). The amino acid sequences encoded by the polynucleotide sequences of SEQ ID NOS: 46 and 124 are provided in SEQ ID NOS: 72 and 130. An extended cDNA sequence for the clone of SEQ ID NO: 97 is provided in SEQ ID NO: 114.

EXAMPLE 15

Polynucleotide and Amino Acid Analysis

The determined cDNA sequences described above were compared to and aligned with known sequences in the EMBL database (as updated to October 2000). Specifically, the polynucleotides identified in SEQ ID NOS: 22-62 and 88-120 were compared to polynucleotides in the EMBL database using the BLASTN algorithm Version 2.0.6 [Sep.-16-1998] and the polynucleotides identified in SEQ ID NOS: 121-127 were compared to polynucleotides in the EMBL database using the BLASTN algorithm Version 2.0.11 [Jan.-20-2000] set to the following running parameters: Unix running command: blastall -p blastn -d embldb -e 10 -G0 -E0 -r1 -v30 -b30 -i queryseq -o results. Multiple alignments of redundant sequences were used to build up reliable consensus sequences. Based on similarity to known sequences from other plant or non-plant species, the isolated polynucleotides of the present invention identified as SEQ ID NOS: 22-62 and 88-127 were putatively identified as having the functions shown in Table 1, above.

The cDNA sequences of SEQ ID NO: 1-22, 23, 25-42, 45-49, 57-59, 62, 88-99, 101-112 and 114-127 were determined to have less than 40% identity to sequences in the EMBL database using the computer algorithm BLASTN, as described above. The cDNA sequences of SEQ ID NO: 56 and 113 were determined to have less than 60% identity to sequences in the EMBL database using BLASTN, as described above. The cDNA sequences of SEQ ID NO: 43, 52, 60 and 61 were determined to have less than 75% identity to sequences in the EMBL database using BLASTN, as described above. The cDNA sequences of SEQ ID NO: 24, 51 and 100 were determined to have less than 90% identity to sequences in the EMBL database using BLASTN, as described above.

EXAMPLE 16

Modification of a Reporter Gene under Control of the Superubiquitin Promoter

Six independent *Arabidopsis thaliana* transgenic lines were transformed with *Pinus radiata* superubiquitin promoter constructs to demonstrate the relative expression of a GUS reporter gene under control of different superubiquitin promoter constructs. The reporter constructs in the plasmid pBI-101 contained the GUS (β-D-glucuronidase) reporter gene in frame with the superubiquitin promoter with the intron (SEQ ID NO: 2), the superubiquitin promoter without the intron (SEQ ID NO: 3), and the CaMV 35S promoter. A reporter gene construct without a promoter sequence was used as control.

Groups of six *Arabidopsis thaliana* plants were transformed with the reporter constructs described above, using *Agrobacterium tumefaciens* transformation protocols. *A. tumefaciens* was transformed with 100 ng of the plasmid DNA according to standard techniques, as described, for example, by Bevan (*Nucleic Acids Res.* 12:8711-8721, 1984). Fresh plant material was collected from each plant, protein extracted from the whole plant, and the protein concentration determined (Bradford, Anal. Biochem. 72:248-254, 1976). The protein samples were diluted with carrier bovine serum albumin to 100 ng protein to maintain readings on the fluorimeter in the linear part of the standard curve using 4-methylumbelliferone (MU). GUS activity was quantified by fluorimetric analysis, using a Victor$^2$ 1420 multi-label counter (Wallac, Turku, Finland) as described by Jefferson (Plant Mol. Biol. Rep. 5:387-405, 1987). As shown in FIG. 1, the construct containing the superubiquitin promoter without the intron showed seven times more GUS activity than the CaMV 35S promoter and the construct containing the superubiquitin promoter with the intron showed sixty two times more GUS activity than the CaMV 35S promoter. No activity was detected for the promoter-less control construct.

EXAMPLE 17

Determination of the Activity of Superubiguitin Promoter Constructs in Tobacco Plant Protoplasts Isolation of Protoplasts Protoplasts were isolated from sterile tobacco (*Nicotiana tabacum*) leaf tissue and transformed with superubiquitin promoter constructs. Mesophyll protoplasts were prepared according to the method of Bilang et al., *Plant Molecular Biology Manual* A1:1-16, 1994. A number of fully expanded leaves were removed from sterile wild type tobacco plants, sliced perpendicular to the midrib and submerged in a digestion enzyme solution containing 1.2% cellulase and 0.4% pectinase (Sigma, St. Louis Mo.). The leaves were left to incubate in the dark without agitation at 26° C. for approximately 18 hours. The leaf strips were then gently agitated for 30 min to release the protoplasts. Protoplasts were further purified by filtration through 100 μm nylon mesh. One ml of W5 solution (154 mM $MgCl_2$, 125 mM $CaCl_2$, 5 mM KCl, 5 mM glucose, pH 5.8-6) was carefully layered on top of the filtrate and centrifuged at 80×g for 10 min. The live protoplast layer was removed with a wide bore pipette, washed twice with 10 ml W5 solution using centrifugation at 70×g for 5 min, with final resuspension in 5 ml W5 solution. Protoplasts were counted in a hemocytometer and viability was determined under the microscope after staining with 5 mg/ml fluoroscein diacetate (FDA) in 100% acetone.

Transformation with Promoter Constructs

The isolated protoplasts were transformed with plasmid DNA using a polyethylene glycol protocol. After centrifugation of the purified protoplasts at 70×g for 5 min, they were resuspended in MMM solution (15 mM $MgCl_2$, 0.1% w/v 2 [N-morpholino]ethanesulfonic acid (MES), 0.5 M mannitol pH 5.8) to a density of 2×10$^6$ protoplasts/ml. Aliquots containing 5×10$^5$ protoplasts/ml in 250 μl were distributed to 15 ml tubes and mixed with 20 μg plasmid DNA. 250 μl polyethylene glycol-4000 (40%) was gently added and incubated for 5 minutes at room temperature. Ten ml W5 solution was slowly added, the protoplasts centrifuged at 70×g for 5 min and finally resuspended in 2 ml K3 medium (Bilang et al., *Plant Molecular Biology Manual* A1:1-16, 1994). The transformed protoplasts were incubated in the dark at 26° C. for 24 hours before protein was extracted for reporter enzyme assays using 4-methyl-umbelliferyl-glucuronide (MUG).

Protein was extracted from the protoplasts using the following protocol. Transformed protoplast suspensions were centrifuged at 70×g for 10 min, resuspended in 50 μl extraction buffer (Jefferson, *Plant Mol. Biol. Rep.* 5:387-405, 1987) and vigorously mixed using a vortex. The homogenate was cleared by centrifugation at 4,300 rpm for 5 min, the supernatant removed and used for protein assays (Bradford, *Anal. Biochem.* 72:248-254, 1976).

Figure 2:
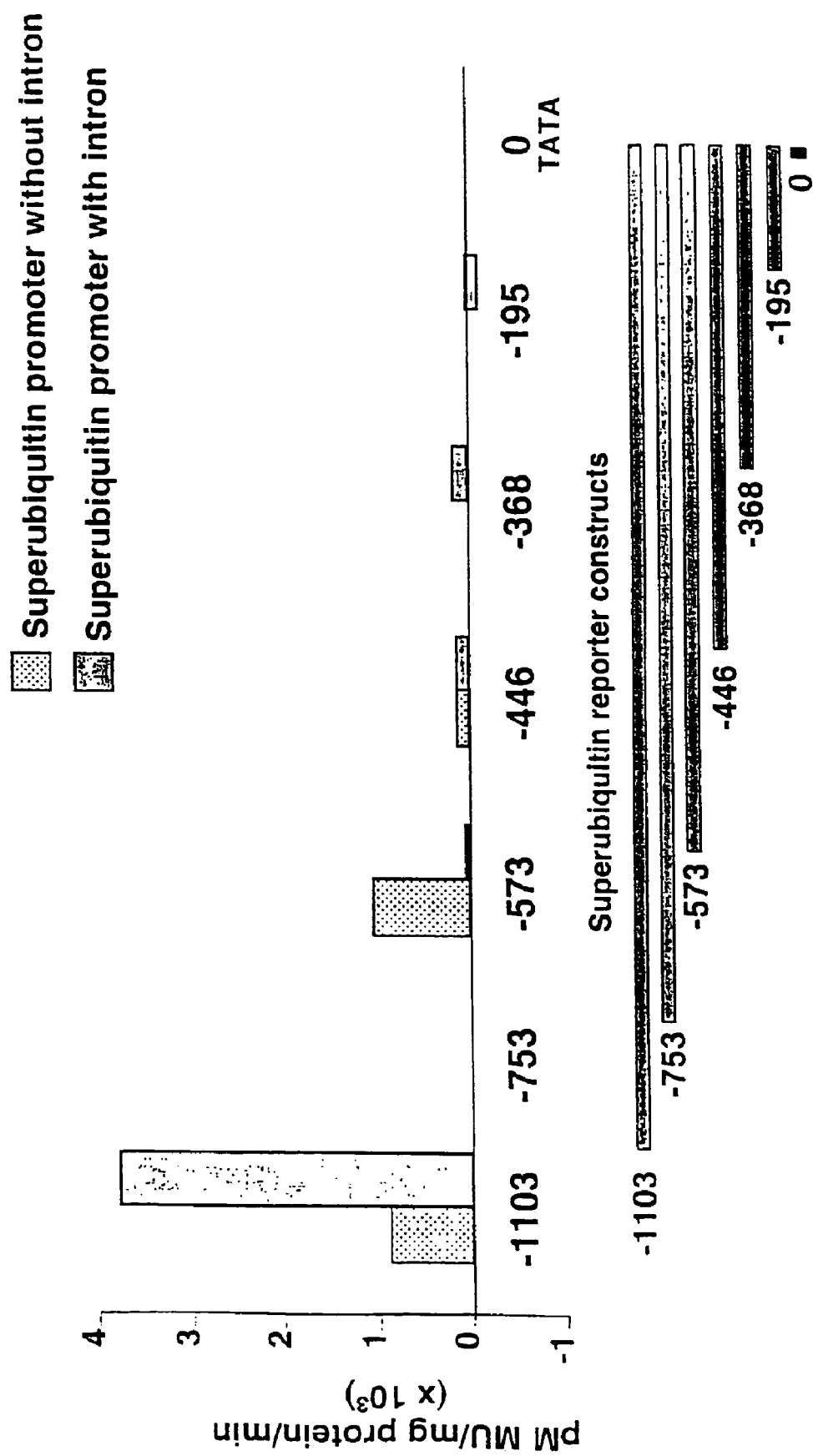
FIG. 2 shows the expression of the GUS gene in tobacco plant protoplasts by deletion constructs containing the superubiquitin promoter with or without the intron. The constructs contained 1,103; 753; 573; 446; 368; and 195 bp upstream of the TATA sequence (bp numbers 1,104-1,110 of SEQ ID NO: 2). The GUS expression was measured by fluorimetric determination of 4-methyl-umbelliferone (MU) in protein extracts from these protoplasts.

The results shown in FIG. 2 demonstrate the promoter activity of deletion constructs of the superubiquitin promoter without the intron (SEQ ID NO: 3) and the superubiquitin promoter with the intron (SEQ ID NO: 2) in tobacco plant protoplasts transformed as described above. The deletion constructs were made in plasmid pBI-101 that contained the GUS reporter gene, using Endonuclease III (Gibco BRL, Gaithersburg, Md.) according to the manufacturer's protocols. The deletion constructs contained 1,103; 753; 573; 446; 368 and 195 bp of superubiquitin promoter sequence, respectively, upstream of the TATA sequence (bp numbers 1,104-1, 110 of SEQ ID NO: 2). A control construct containing no sequence upstream of the TATA sequence was also made. These results show that the construct containing the entire superubiquitin promoter with the intron had the highest MU activity in the protoplasts.

Figure 3:
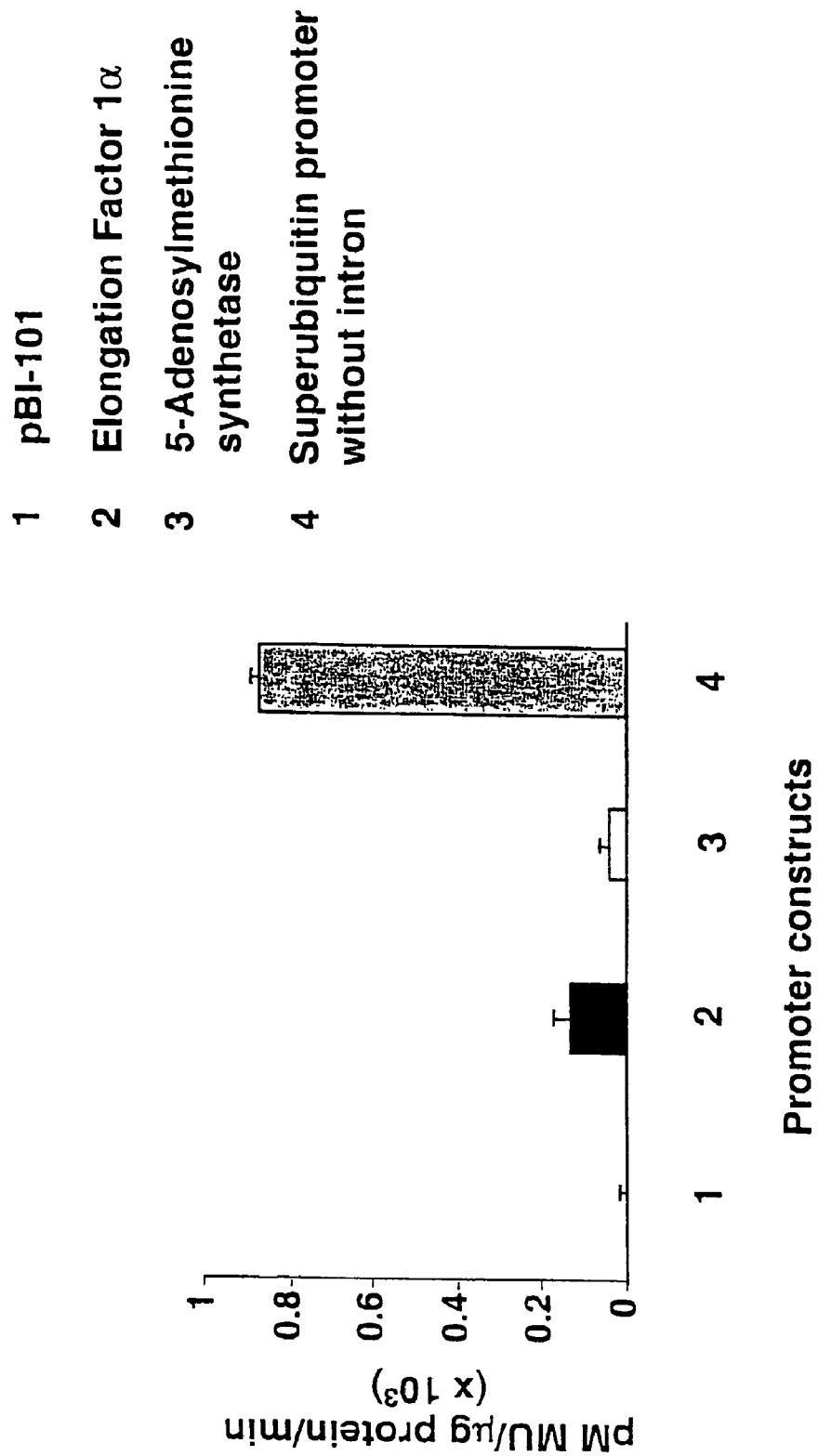
FIG. 3 shows the expression of the GUS gene in tobacco plant protoplasts by constructs containing *P. radiata* either the constitutive promoters Elongation factor-1 alpha, 5-adenosylmethionine synthetase or the superubiquitin promoter without the intron. The GUS expression was measured by fluorimetric determination of 4-methyl-umbelliferone (MU) in protein extracts from these protoplasts.

In FIG. 3, the tobacco protoplasts were transformed with four different promoter constructs in plasmid pBI-101 containing the GUS reporter gene. These included the superubiquitin promoter without the intron (SEQ ID NO: 3), an elongation factor 1α promoter (SEQ ID NO: 99) and a 5-adenosylmethionine synthetase promoter (SEQ ID NO: 100). A promoterless control was included in the experiment, and is referred to in FIG. 3 as pBI-101.

EXAMPLE 18

Determination of the Activity of *P. radiata* Pollen-Specific Promoter and *E. grandis* Pollen Specific Promoter Constructs in Transformed *Arabidopsis thaliana* cv Columbia

*Arabidopsis thaliana* transgenic lines were transformed with *A. tumefaciens* containing constructs of the *P. radiata* pollen specific promoter (SEQ ID NO: 94) and *E. grandis* pollen specific promoter (SEQ ID NO: 22) to demonstrate the relative expression of a GUS reporter gene under control of these promoter constructs. The promoter sequences were cloned into plasmid pBI-101 containing a GUS reporter gene.

*Agrobacterium tumefaciens* Transformation

*Agrobacterium tumefaciens* strain GV3101 was transformed with these constructs using electroporation. Electrocompetent *A. tumefaciens* cells were prepared according to the method of Walkerpeach and Velten, *Plant Mol. Biol. Man.* B1:1-19, 1994. Construct DNA (4 ng) was added to 40 μl competent *A. tumefaciens* GV3101 cells and electroporation was done using a BTX Electro Cell Manipulator 600 at the following settings: Mode: T 2.5 kV Resistance high voltage (HV), Set Capacitance: C (not used in HV mode), Set Resistance: R R5 (129 Ohm), Set charging voltage: S 1.44 kV, Desired field strength: 14.4 kV/cm and Desired pulse strength: t 5.0 msec. 400 μl YEP liquid media (20 g/l yeast, 20 g/l peptone and 10 g/l sodium chloride) was added to the cuvette and left to recover for one hour at room temperature. Transformed bacteria in YEP medium were spread out on solid YEP medium containing 50 mg/l kanamycin and 50 mg/l rifampicin and incubated at 29° C. for two days to allow colony growth.

Confirmation of Transformation of Constructs into *A. tumefaciens*

To confirm that the constructs have been transformed into *A. tumefaciens*, DNA from the *A. tumefaciens* colonies from the YEP plates were isolated using standard protocols and amplified using the polymerase chain reaction (PCR) with primers designed from the pBI-101 vector sequence. The primer sequences are given in SEQ ID NOS: 128 and 129. PCR reactions were set up following standard protocols and 30 PCR cycles were done with extension temperature of 72° C.

Transformation of *A. thaliana* with Transformed *A. tumefaciens*

The optical density of the *A. tumefaciens* bacterial culture was adjusted to 0.7 with infiltration medium (5% sucrose, 0.05% Silwett L-77 surfactant). *A. thaliana* cv. Columbia plants (6 punnets per construct and 10-12 plants per punnet) were pruned by removing secondary bolts. Pruned *A. thaliana* plants in punnets were dipped into infiltration solution and moved back and forth for 5 seconds. Punnets were put on their side to allow excess infiltration medium to drain covered with a top tray and wrapped in plastic wrap to maintain humidity. Plants were placed in a growth room at ambient conditions for 24 hours. After this period, the top tray and plastic wrap were removed and plants were set upright until siliques formed.

Seeds were harvested and sterilized with a 5% sodium hypochlorite solution to destroy any residual *A. tumefaciens* bacteria and fungal contamination.

Under sterile conditions, 100 μl seeds from the transformed *A. thaliana* plants were placed into an Eppendorf tube. One ml sterile water was added and the seeds left to imbibe the water for no longer than an hour. The water was remove by centrifugation, 1 ml 70% ethanol added to the seeds and gently mixed. This step was not allowed to last longer than one minute. The ethanol was removed by centrifugation, 1 ml 5% sodium hypochlorite solution was added to the seeds and gently mixed for up to 5 min. The sodium hypochlorite solution was removed by centrifugation and the seeds washed with sterile water for 1 min. The washing step was repeated three more times with centrifugation. Seeds were finally resuspended in sterile water. 500 μl of seeds in solution were pipetted onto half-strength Murashige and Skoog medium (MS; Gibco BRL) agar plates containing 50 mg/l kanamycin and 250 mg/l timentin and spread evenly with a flamed wireloop. The Petri dishes were placed in a refrigerator for 3 days to allow the seeds to stratify. Thereafter the plates were placed in growth room and grown under lights at 22° C. with a 14 hour photoperiod until germination. Putative transformant seedlings were selected as those growing on the antibiotic-containing medium, with large, healthy-looking dark green leaves and a strong root system. These transgenic plants were removed and placed into soil culture at 22° C. with a 12 hour photoperiod.

Staining of Plant Tissues

Tissue were taken from the flower, leaf, stem and root of *A. thaliana* transformed with constructs of *P. radiata* unknown pollen specific promoter and *E. grandis* pollen specific promoter and stained histochemically to determine the expression of the GUS gene under control of the pollen specific promoters. The GUS staining protocol is described by Campisi et al., *Plant J.* 17:699-707, 1999.

*A. thaliana* flower, leaf, stem and root tissue were immersed in staining solution (50 mM $NaPO_4$ pH 7.2; 0.5% Triton X-100; 1 mM X Glucuronide sodium salt (Gibco BRL)) for immunochemical staining. Vacuum was applied twice for 5 min to infiltrate the tissue with the staining solution. The tissue was left in the staining solution for 2 days (with agitation) at 37° for color development and then destained in 70% ethanol for 24 hours at 37° C. (with agitation). The tissues were examined for blue GUS staining using a light microscope. GUS expression was observed only in the flower buds of plants transformed with the *P. radiata* pollen specific promoter construct, and not in the leaf, stem or root tissue. With the *E. grandis* pollen specific promoter construct, Gus expression was observed in the floral buds as well as in the hydathodes of the leaves. No expression was observed in the stem or root tissues.

To determine in which cell layers the GUS gene was expressed, flower buds were fixed for thin sectioning. The flower buds were fixed with formaldehyde acetic acid (FAA) in an Eppendorf tube and vacuum was applied twice for 15 min. After incubation for 2 hours at room temperature, vacuum was again applied for 15 min and the tissue left overnight at 4° C. The tissues were then dehydrated using a series of ethanol and then passed into a xylene series. Paraffin wax (Sigma) was added slowly and the tissues left for 72 hours with wax changes every 12 hours. Sections of 8 to 10 µm thickness were prepared using a microtome.

The thin sections illustrated that GUS expression was restricted to the tapetum cell layer in the anther of the floral bud of *A. thaliana* transformed with the *P. radiata* construct (SEQ ID NO: 49). No staining was observed in other tissues from the floral bud. GUS expression was confined to the pollen grains within the flower bud of *A. thaliana* transformed with the *E. grandis* pollen specific promoter construct, with low levels of GUS expression in the fibrous and connective tissue of the anther. No GUS expression was observed in other organs of the floral bud.

EXAMPLE 19

Determination of the Activity of an *E. grandis* EF1 Alpha Promoter Deletion Construct in Transformed *Arabidopsis thaliana* cv Columbia Protoplasts from *Nicotiana tabacum* Bright Yellow 2 (BY-2) cell suspension were transformed with a deletion construct of the *E. grandis* EF1-alpha promoter to determine GUS expression. Base pairs 2,174 to 3,720 of SEQ ID NO: 127 were cloned into expression vector pART9, containing the reporter gene GUS and an OCS termination sequence.

Preparation of Protoplasts

Sterile *Nicotiana tabacum* Bright Yellow-2 (BY-2) suspension cultures were prepared as described in Example 17. After incubation for 3 to 5 days, 3 g of the *N. tabacum* BY-2 cell suspension were suspended in an enzyme solution containing 1% cellulase, 0.3% pectinase and 0.5% driselase in 0.4 M mannitol. These were left to digest in the dark, with agitation at 26° C., for 3-4 hours. Protoplasts were purified by filtration through a 63 µm nylon mesh. Protoplasts were centrifuged at 80×g for 5 min, washed twice with 10 ml FMS medium (Fukuda, Murashige and Skoog medium; Hasezawa & Syono, *Plant Cell Physiol.* 24:127-132, 1983) and finally resuspended in 5 ml FMS medium. Protoplasts were counted in a hemocytometer and viability determined by staining with 5 mg/ml FDA (fluorescein deacetate; Sigma St Louis Mich.) in 100% acetone by viewing under the fluorescent microscope.

Transformation of Protoplasts

Protoplasts were transformed according to the protocol described by Morgan and Ow (In: Methods in Plant Molecular Biology: a laboratory course manual, pp. 1-16. P. Maliga, D. Klessig, A. R. Cashmore, W. Gruissem, and J. E. Varner, eds. Cold Spring Harbor Laboratory, CSHP, NY). Briefly, the protocol is as follows. Following the counting step, protoplasts were centrifuged at 80×g for 5 min and resuspended in 1×MaMg solution (0.4 M manniotol, 15 mM $MgCl_2.6H_2O$, 0.1% 2-(N-Morpholino)ethane sulfonic acid (MES)) to a density of $5 \times 10^6$ protoplasts/ml. Aliquots of 100 µl ($0.5 \times 10^5$ protoplasts) were distributed to 15 ml tubes and washed with 5 ml ix MaMg (200 g, 5 min). Pelleted protoplasts were resuspended in 500 ul 1× MaMg solution, and heat shocked by placing at 45° C. for 5 minutes. After incubation at room temperature 5-10 minutes, the transforming DNA was added (10-20 µg DNA+10 µg carrier DNA). To this, 500 µl 40% PEG-3500 was gently added and incubated for 25 minutes at room temperature. 5 ml W5 (154 mM NaCl, 125 mM $CaCl_2.2H_2O$, 5 mM KCl, 5 mM Glucose) solution was slowly added stepwise followed by centrifugation at 200× g for 5 min. Pelleted protoplasts were resuspended in 1 ml K3AM medium at approximately $0.5 \times 10^5$ protoplasts/ml. Samples were transferred to 6-well plates and incubated in the dark at 26° C. for 48 hours.

To extract protein, protoplasts were centrifuged at 200×g for 5 min in a microfuge, resuspended in 100 µl GUS extraction buffer (50 mM $NaPO_4$ pH 7.2, 10 mM EDTA pH 8, 0.01% Sarcosyl, 0.1% Triton X-100) containing β-mercaptoethanol (Jefferson et al., *Plant Mol. Biol. Rep.* 5:387-405, 1987) and vortexed for 1 min. The homogenate was cleared by centrifugation at 5,000 rpm for 5 minutes. The supernatant containing the protein was transferred to a fresh tube and stored at −80° C. The protein concentrations were determined by BioRad protein assay kit (BioRad, Hercules, Calif.) following the manufacturer's protocols. Protein extracts were diluted 1/10 with extraction buffer.

Determination of GUS Expression

GUS expression in the protoplast extracts was determined using a MUG (4-methyl umbelliferyl β-D-glucuronide) assay. Protein samples, containing 1 µg protein made up to a total volume of 45 µl with extraction buffer, were aliquoted onto a microtitre plate and incubated at 37° C. To each sample, 5 µl of 10 mM MUG was added so that the final concentration of MUG was 1 mM. The plate was incubated at 37° C. for 30 min and terminated by adding 150 µl stop solution (0.2 M $Na_2CO_3$, pH 11.20), still keeping the plates at 37° C. Plates were read in a Victor² 1420 Multilabel counter with excitation set at 365 nm and emission at 455 nm. The concentration of 4-methyl-umbelliferone (MU) was calculated against a standard curve and the GUS expression calculated.

Figure 5:
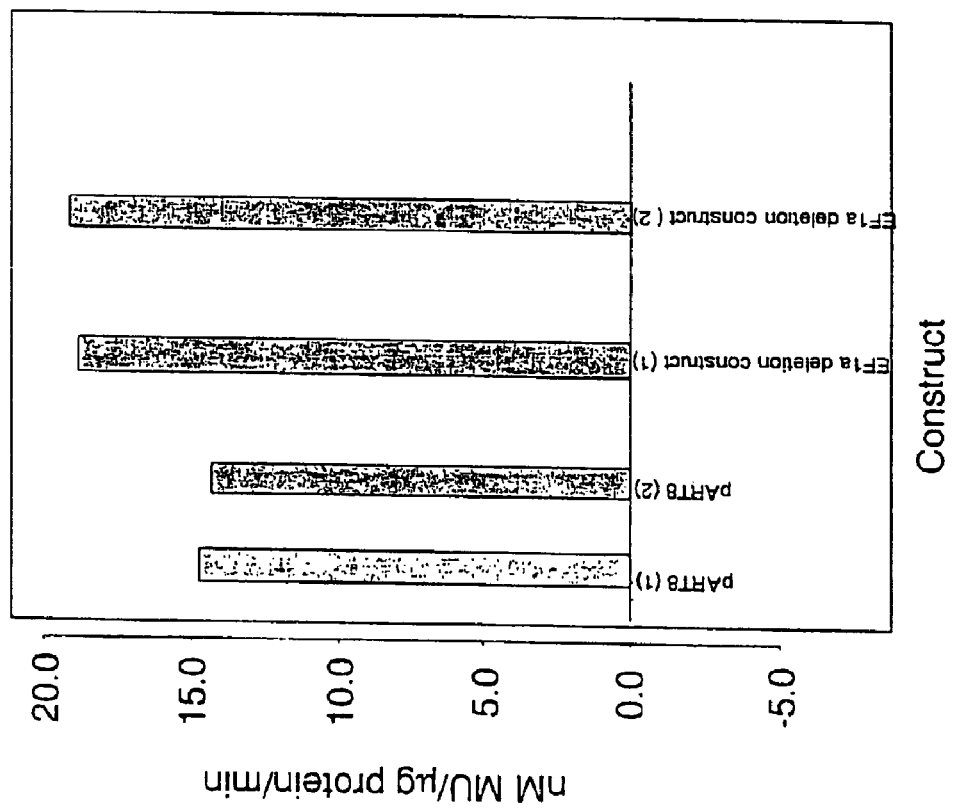
FIG. 5 shows the expression of the GUS gene in tobacco plant protoplasts by a deletion construct containing a fragment of the *E. grandis* constitutive promoter Elongation factor-1 alpha.

In FIG. 5, increased expression of the GUS reporter gene in *N. tabacum* BY-2 protoplasts transformed with an *E. grandis* EF1 alpha deletion construct was seen compared to the control plasmid without an insert.

EXAMPLE 20

Determination of the Effect of the 3'UTR Super-ubiquitin (SU) Sequences on Gene Expression in *Arabidopsis thaliana* cv Columbia In the polynucleotide sequences given in SEQ ID NO: 1 encoding *P. radiata* superubiquitin (SU) promoter and gene sequences, an 3' untranslated region (UTR) was identified (nucleotides 1,754 to 3,083). To determine the effect of this region on the expression of genes, 250 bp of the 3' UTR (nucleotides 2,755 to 3,073 from SEQ ID NO: 1) was cloned in the sense and antisense orientation into plasmid pBI-121 containing the GUS gene under control of the 35S CaMV promoter and plasmid pBI-101 containing the GUS gene under control of the *P. radiata* SU promoter (including the intron) given in SEQ ID NO: 2. For controls, constructs were made that contained the SU promoter without an intron (SEQ ID NO: 3) and without the SU 3' UTR sequence, the SU promoter with an intron (SEQ ID NO: 2) and without the SU 3' UTR sequence as well as a construct containing the 35S CaMV promoter but not the SU 3' UTR sequence.

*A. thaliana* cv Columbia were transformed with these constructs using the floral dip protocol described in Example 18.

Determining the Level of Gene Expression Using a MUG Assay

Six *A. thaliana* plants were harvested by trimming off the dried tissue and then harvesting the rest of the plant, including the roots. The roots were rinsed in tap water and the samples immersed in liquid nitrogen before storing at −80° C. Six plants from each construct were ground under liquid nitrogen and approximately 100 mg transferred to a microfuge tube. Five samples from each control were included in the assay. Extraction buffer (50 mM NaPO$_4$ pH 7.2, 10 mM EDTA pH 8, 0.01% Sarcosyl, 0.1% Triton X-100) was prepared. To 32 ml of extraction buffer, 8 ml methanol and 28 µl β-mercaptoethanol was added. Of this buffer, 200 µl was added to each sample, vortexed and stored on ice. Samples were spun at 4° C. at 15,000 rpm for 15 min. The supernatant was transferred to a fresh tube and diluted with 800 µl of extraction buffer. Protein concentration was determined using the BioRad Protein Assay Kit.

The expression of GUS by the four constructs was determined using a MUG assay, as follows. To 28 ml extraction buffer (as described in Example 18), 8 ml methanol, 56 µl β-mercaptoethanol and 4 ml of 10 mg/ml bovine serum albumin (BSA) were added. To microtitre plate wells, 100 and 10 ng of protein from each construct was added as well as 25 µl extraction buffer containing BSA and 5 µl 10 mM MUG. The plate was covered in foil and incubated at 37° C. for exactly 20 minutes. The reaction was terminated by adding 150 µl 0.2 M Na$_2$CO$_3$ pH 11.2. Plates were read with a Victor$^2$ 1420 Multilabel counter with excitation set at 365 nm and emission at 455 nm. GUS expression levels were determined against a MU standard curve.

Figure 4:
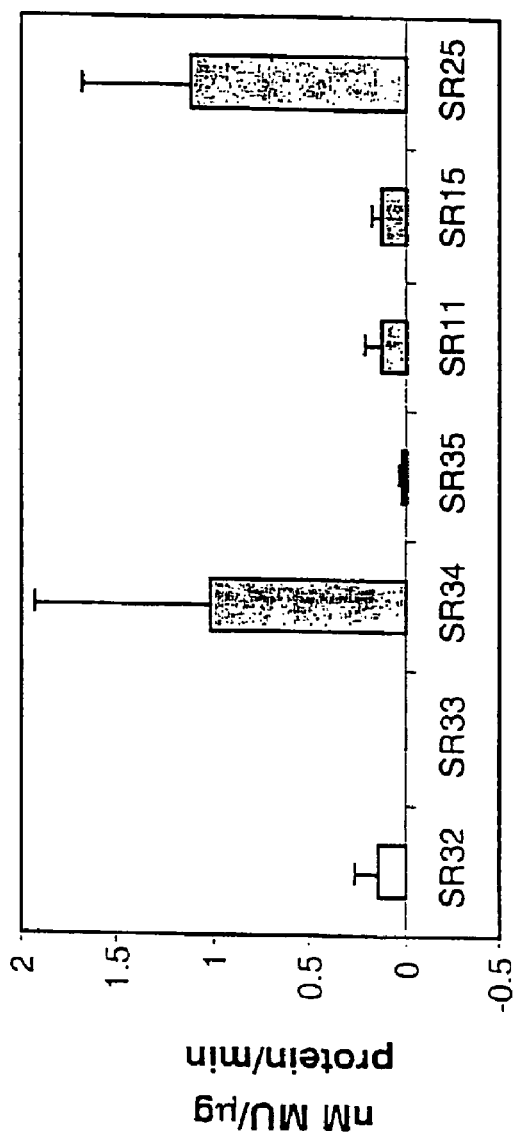
FIG. 4 shows the expression in *A. thaliana* of the GUS gene in promoter reporter constructs containing the 3' UTR of the superubiquitin promoter in sense or antisense orientation together with either the superubiquitin promoter with intron, the superubiquitin promoter without intron, or the CaMV 35S promoter. The GUS expression was measured by fluorimetric determination of 4-methyl-umbelliferone (MU) in protein extracts from these plants.

In FIG. 4, construct SR34 containing the SU 3'UTR in the sense orientation enhanced the expression of the SU without intron promoter almost to the level of the SU promoter with the intron. In constructs SR33 and SR35 containing the 3'UTR in the antisense orientation, promoter activity was reduced to basal levels.

EXAMPLE 21

Determination of the Activity of *P. radiata* Ubiquitin Promoter Constructs in Transformed *Arabidopsis thaliana* cv Columbia and Tobacco Plant Protoplasts A. Tobacco Plant Protoplasts 1. Isolation of Protoplasts Protoplasts were isolated from sterile tobacco (*Nicotiana tabacum*) leaf tissue and transformed with superubiquitin promoter constructs. Mesophyll protoplasts were prepared according to the method of Bilang et al., *Plant Molecular Biology Manual* A1:1-16, 1994. A number of fully expanded leaves were removed from sterile wild type tobacco plants, sliced perpendicular to the midrib and submerged in a digestion enzyme solution containing 1.2% cellulase and 0.4% pectinase (Sigma, St. Louis Mo.). The leaves were left to incubate in the dark without agitation at 26° C. for approximately 18 hours. The leaf strips were then gently agitated for 30 min to release the protoplasts. Protoplasts were further purified by filtration through 100 µm nylon mesh. One ml of W5 solution (154 mM MgCl$_2$, 125 mM CaCl$_2$, 5 mM KCl, 5 mM glucose, pH 5.8-6) was carefully layered on top of the filtrate and centrifuged at 80×g for 10 min. The live protoplast layer was removed with a wide bore pipette, washed twice with 10 ml W5 solution using centrifugation at 70×g for 5 min, with final resuspension in 5 ml W5 solution. Protoplasts were counted in a hemocytometer and viability was determined under the microscope after staining with 5 mg/ml fluoroscein diacetate (FDA) in 100% acetone.

2. Transformation with Promoter Constructs

The isolated protoplasts were transformed with plasmid BI-101 containing the GUS (β-D-glucuronidase) reporter gene in frame with the specified deletion constructs of the superubiquitin promoter, with and without the intron. The deletion constructs contained 753, 573, 446, 368 and 195 bp of superubiquitin promoter sequence, respectively, upstream of the TATA sequence (bp numbers 1104-1,110 of SEQ ID NO: 2. The constructs tested, and the results, are described in the table, below.

| Construct Ref. | Deletion construct | SEQ ID NO: | Annotated Fig. | GUS staining constitutive? |
|---|---|---|---|---|
| S38 | 195 bp | 131 | FIG. 7 | No |
| S39 | 368 bp | 132 | FIG. 8 | Yes |
| S40 | 446 bp | 133 | FIG. 9 | Yes |
| S41 | 573 bp | 134 | FIG. 10 | Yes |
| S48 | 753 bp | 135 | FIG. 11 | yes |
| S52 | 195 bp | 136 | FIG. 12 | No |
| S53 | 446 bp | 138 | FIG. 14 | Yes |
| S54 | 368 bp | 137 | FIG. 13 | Yes |
| S55 | 573 bp | 139 | FIG. 15 | Yes |
| S56 | 753 bp | 140 | FIGS. 16A, B | Yes |

Transformation was carried out using a polyethylene glycol protocol. After centrifugation of the purified protoplasts at 70×g for 5 min, they were resuspended in MMM solution (15 mM MgCl$_2$, 0.1% w/v 2[N-morpholino]ethanesulfonic acid (MES), 0.5 M mannitol pH 5.8) to a density of 2×10$^6$ protoplasts/ml. Aliquots containing 5×10$^5$ protoplasts/ml in 250 µl were distributed to 15 ml tubes and mixed with 20 µg plasmid DNA. 250 µl polyethylene glycol-4000 (40%) was gently added and incubated for 5 minutes at room temperature. Ten ml W5 solution was slowly added, the protoplasts centrifuged at 70×g for 5 min and finally resuspended in 2 ml K3 medium (Bilang et al., *Plant Molecular Biology Manual* A1:1-16, 1994).

For quantitation of GUS activity, the transformed protoplasts are incubated in the dark at 26° C. for 24 hours before protein is extracted for reporter enzyme assays using 4-methyl-umbelliferyl-glucuronide (MUG). GUS activity is quantified by fluorimetric analysis, as described by Jefferson (*Plant Mol. Biol. Rep.* 5: 387-405, 1987).

Protein is extracted from the protoplasts using the following protocol. Transformed protoplast suspensions were centrifuged at 70×g for 10 min, resuspended in 50 µl extraction buffer (Jefferson, *Plant Mol. Biol. Rep.* 5:387-405, 1987) and vigorously mixed using a vortex. The homogenate is cleared by centrifugation at 4,300 rpm for 5 min, the supernatant removed and used for protein assays (Bradford, *Anal. Biochem.* 72:248-254, 1976).

B. *Arabidopsis thaliana* Transgenic Lines

*Arabidopsis thaliana* plants were transformed with *A. tumefaciens* containing deletion constructs of the *P. radiate* ubiquitin promoter described above.

1. *Agrobacterium tumefaciens* Transformation

*Agrobacterium tumefaciens* strain GV3101 was transformed with the above-described deletion constructs using electroporation. The deletion constructs were prepared using restriction digestion and PCR. The deletion constructs were made in plasmid pBI-101 that contained the GUS reporter gene, using Endonuclease III (Gibco BRL, Gaithersburg, Md.) according to the manufacturer's protocols. A control construct containing no sequence upstream of the TATA sequence was also made.

Electrocompetent *A. tumefaciens* cells were prepared according to the method of Walkerpeach and Velten, *Plant Mol. Biol. Man. B*1:1-19, 1994. Construct DNA (4 ng) was added to 40 μl competent *A. tumefaciens* GV3101 cells and electroporation was done using a BTX Electro Cell Manipulator 600 at the following settings: Mode: T 2.5 kV Resistance high voltage (HV), Set Capacitance: C (not used in HV mode), Set Resistance: R R5 (129 Ohm), Set charging voltage: S 1.44 kV, Desired field strength: 14.4 kV/cm and Desired pulse strength: t 5.09 msec. 400 μl YEP liquid media (20 g/l yeast, 20 g/l peptone and 10 g/l sodium chloride) was added to the cuvette and left to recover for one hour at room temperature. Transformed bacteria in YEP medium were spread out on solid YEP medium containing 50 mg/l kanamycin and 50 mg/l rifampicin and incubated at 29° C. for two days to allow colony growth.

2. Confirmation of Transformation of Constructs into *A. tumefaciens*

To confirm that the constructs have been transformed into *A. tumefaciens*, DNA from the *A. tumefaciens* colonies from the YEP plates were isolated using standard protocols and amplified using the polymerase chain reaction (PCR) with primers designed from the pBI-101 vector sequence. The primer sequences are given in SEQ ID NOS: 128 and 129. PCR reactions were set up following standard protocols and 30 PCR cycles were done with extension temperature of 72° C.

3. Transformation of *A. thaliana* with Transformed *A. tumefaciens*

The optical density of the *A. tumefaciens* bacterial culture was adjusted to 0.7 with infiltration medium (5% sucrose, 0.05% Silwett L-77 surfactant). *A. thaliana* cv. Columbia plants (6 punnets per construct and 10-12 plants per punnet) were pruned by removing secondary bolts. Pruned *A. thaliana* plants in punnets were dipped into infiltration solution and moved back and forth for 5 seconds. Punnets were put on their side to allow excess infiltration medium to drain covered with a top tray and wrapped in plastic wrap to maintain humidity. Plants were placed in a growth room at ambient condition for 24 hours. After this period, the top tray and plastic wrap were removed and plants were set upright until siliques formed.

Seeds were harvested and sterilized with a 5% sodium hypochlorite solution to destroy any residual *A. tumefaciens* bacteria and fungal contamination.

Under sterile conditions, 100 μl seeds from the transformed *A. thaliana* plants were placed into an Eppendorf tube. One ml sterile water was added and the seeds left to imbibe the water for no longer than an hour. The water was remove by centrifugation, 1 ml 70% ethanol added to the seeds and gently mixed. This step was not allowed to last longer than one minute. The ethanol was removed by centrifugation, 1 ml 5% sodium hypochlorite solution was added to the seeds and gently mixed for up to 5 min. The sodium hypochlorite solution was removed by centrifugation and the seeds washed with sterile water for 1 min. The washing step was repeated three more times with centrifugation. Seeds were finally resuspended in sterile water. 500 μl of seeds in solution were pitpetted onto half-strength Murashige and Skoog medium (MS; Gibco BRL) agar plates containing 50 mg/l kanamycin and 250 mg/l timentin and spread evenly with a flamed wireloop. The Petri dishes were placed in a refrigerator for 3 days to allow the seeds to stratify. Thereafter the plates were placed in growth room and grown under lights at 22° C. with a 14 hour photoperiod until germination. Putative transformant seedlings were selected as those growing on the antibiotic-containing medium, with large, healthy-looking dark green leaves and a strong root system. These transgenic plants were removed and placed into soil culture at 22° with a 12 hour photoperiod.

4. Staining of Plant Tissues

Tissue were taken from the flower, leaf, stem and root of *A. thaliana* transformed with constructs of *P. radiata* ubiquitin promoter and stained histochemically to determine the expression of the GUS gene under control of the pollen specific promoters. The GUS staining protocol is described by Campisi et al., *Plant J* 17:699-707, 1999.

*A. thaliana* flower, leaf, stem and root tissue were immersed in a staining solution (50 mM $NaPO_4$ pH 7.2; 0.5% Triton X-100; 1 mM X Glucuronide sodium salt (Gibco BRL)) for immunochemical staining. Vacuum was applied twice for 5 min to infiltrate the tissue with the staining solution. The tissue was left in the staining solution for 2 days (with agitation) at 37° for color development and then destained in 70% ethanol for 24 hours at 37° C. (with agitation). The tissues were examined for blue GUS staining using a light microscope.

The results showed that constitutive expression was lost in the smallest deletion constructs (SEQ ID NOS: 131 AND 136) but was observed in all the other constructs tested, including both the intronless and intron-containing deletion constructs. These results demonstrate that the sequences described in SEQ ID NOS: 132-135 and 138-140 have constitutive promoter activity in both *Arabidopsis* and tobacco plants.

The invention claimed is:

1. An isolated polynucleotide comprising a sequence selected from the group consisting of:
   (a) a sequence recited in SEQ ID NO: 117, wherein the polynucleotide has arabinogalactan promoter activity;
   (b) a sequence recited in SEQ ID NO: 107, wherein the polynucleotide has arabinogalactan promoter activity; and
   (c) a sequence comprising the *E. grandis* arabinogalactan promoter contained in SEQ ID NO: 117 or SEQ ID NO: 107, wherein the polynucleotide has arabinogalactan promoter activity.

2. A genetic construct comprising a polynucleotide of claim 1.

3. A genetic construct comprising, in the 5'-3' direction:
   (a) a promoter sequence;
   (b) a DNA sequence of interest; and
   (c) a gene termination sequence, wherein the promoter sequence comprises an isolated polynucleotide of claim 1.

4. The genetic construct of claim 3, wherein the DNA sequence of interest comprises an open reading frame encoding a polypeptide of interest.

5. A transgenic plant cell comprising a genetic construct of claim 3.

6. A plant or a part or propagule or progeny thereof comprising a transgenic cell of claim 5.

7. A method for modifying gene expression in a target plant comprising stably incorporating into the genome of the plant a genetic construct according to claim 3.

8. A method for producing a plant having modified gene expression comprising:
   (a) transforming a plant cell with a genetic construct to provide a transgenic cell, wherein the genetic construct comprises: (i) a promoter sequence comprising a sequence of claim 1; (ii) a DNA sequence of interest; and (iii) a gene termination sequence; and
   (b) cultivating the transgenic cell under conditions conducive to regeneration and mature plant growth.

9. A method for modifying a phenotype of a target plant, comprising stably incorporating into the genome of the target plant a genetic construct comprising:
   (a) a promoter sequence of claim 1;
   (b) a DNA sequence of interest; and
   (c) a gene termination sequence.

10. An isolated polynucleotide comprising a sequence selected from the group consisting of:
    (a) complements of the entire length of the sequence recited in SEQ ID NO: 117 or 107; and
    (b) reverse complements of the entire length of the sequence recited in SEQ ID NO: 117 or 107.

11. A genetic construct comprising a polynucleotide of claim 10.

* * * * *